US012584128B2

(12) United States Patent
Freier

(10) Patent No.: US 12,584,128 B2
(45) Date of Patent: Mar. 24, 2026

(54) COMPOSITIONS FOR MODULATING ATAXIN 2 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 18/493,610

(22) Filed: Oct. 24, 2023

(65) Prior Publication Data

US 2024/0309374 A1 Sep. 19, 2024

Related U.S. Application Data

(60) Continuation of application No. 17/393,738, filed on Aug. 4, 2021, now Pat. No. 11,834,660, which is a continuation of application No. 16/387,308, filed on Apr. 17, 2019, now Pat. No. 11,111,494, which is a division of application No. 15/127,358, filed as application No. PCT/US2015/021608 on Mar. 19, 2015, now Pat. No. 10,308,934.

(60) Provisional application No. 61/982,131, filed on Apr. 21, 2014, provisional application No. 61/955,705, filed on Mar. 19, 2014.

(51) Int. Cl.
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/345* (2013.01); *C12N 2310/346* (2013.01)

(58) Field of Classification Search
CPC .............. C12N 15/113; C12N 2310/11; C12N 2310/315; C12N 2310/321; C12N 2310/345; C12N 2310/3231; C12N 2310/3341; A61P 25/28
See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,276,019 | A | 1/1994 | Cohen et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |

(Continued)

FOREIGN PATENT DOCUMENTS

| | | |
|---|---|---|
| EP | 0878543 A1 | 11/1998 |
| EP | 1752536 A1 | 2/2007 |

(Continued)

OTHER PUBLICATIONS

Ataxin-2 Wikipedia. Downloaded on Jul. 16, 2018 from http://en.wikipedia.org/wiki/Ataxin-2.

(Continued)

*Primary Examiner* — Terra C Gibbs
(74) *Attorney, Agent, or Firm* — McNeill PLLC

(57) ABSTRACT

Disclosed herein are antisense compounds and methods for decreasing Ataxin 2 mRNA and protein expression. Such methods, compounds, and compositions are useful to treat, prevent, or ameliorate Ataxin 2 associated diseases, disorders, and conditions. Such Ataxin 2 associated diseases include spinocerebellar ataxia type 2 (SCA2), amyotropic sclerosis (ALS), and parkinsonism.

23 Claims, No Drawings

Specification includes a Sequence Listing.

(56) References Cited

U.S. PATENT DOCUMENTS 5,399,676 A 3/1995 Froehler
5,403,711 A 4/1995 Walder et al.
5,405,938 A 4/1995 Sumerton et al.
5,405,939 A 4/1995 Suhadolnik et al.
5,432,272 A 7/1995 Benner
5,434,257 A 7/1995 Matteucci
5,446,137 A 8/1995 Maag et al.
5,453,496 A 9/1995 Caruthers et al.
5,455,233 A 10/1995 Spielvogel et al.
5,457,187 A 10/1995 Gmelner et al.
5,457,191 A 10/1995 Cook et al.
5,459,255 A 10/1995 Cook et al.
5,466,677 A 11/1995 Baxter et al.
5,466,786 A 11/1995 Burh et al.
5,470,967 A 11/1995 Huie et al.
5,476,925 A 12/1995 Letsinger et al.
5,484,908 A 1/1996 Froehler et al.
5,489,677 A 2/1996 Sanghvi et al.
5,491,133 A 2/1996 Walder et al.
5,502,177 A 3/1996 Matteucci et al.
5,508,270 A 4/1996 Baxter et al.
5,514,785 A 5/1996 Van Ness et al.
5,519,126 A 5/1996 Hecht
5,519,134 A 5/1996 Acevedo et al.
5,525,711 A 6/1996 Hawkins et al.
5,527,899 A 6/1996 Froehler
5,536,821 A 7/1996 Agrawal et al.
5,541,306 A 7/1996 Agrawal et al.
5,541,307 A 7/1996 Cook et al.
5,550,111 A 8/1996 Suhadolnik et al.
5,552,540 A 9/1996 Haralambidis
5,561,225 A 10/1996 Maddry et al.
5,563,253 A 10/1996 Agrawal et al.
5,565,350 A 10/1996 Kmiec
5,565,555 A 10/1996 Froehler et al.
5,567,811 A 10/1996 Mistura et al.
5,571,799 A 11/1996 Tkachuk et al.
5,576,427 A 11/1996 Cook et al.
5,587,361 A 12/1996 Cook et al.
5,587,469 A 12/1996 Cook et al.
5,587,470 A 12/1996 Cook et al.
5,591,722 A 1/1997 Montgomery et al.
5,594,121 A 1/1997 Froehler et al.
5,596,086 A 1/1997 Matteucci
5,596,091 A 1/1997 Switzer
5,597,909 A 1/1997 Urdea et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,065 A 4/1997 Cook et al.
5,623,070 A 4/1997 Cook et al.
5,625,050 A 4/1997 Beaton et al.
5,627,053 A 5/1997 Usman et al.
5,633,360 A 5/1997 Bishofberger et al.
5,639,873 A 6/1997 Barascut et al.
5,645,985 A 7/1997 Froehler et al.
5,646,265 A 7/1997 McGee
5,646,269 A 7/1997 Matteucci
5,652,355 A 7/1997 Metelev et al.
5,652,356 A 7/1997 Agrawal
5,663,312 A 9/1997 Chaturvedula
5,670,633 A 9/1997 Cook et al.
5,672,697 A 9/1997 Buhr et al.
5,677,437 A 10/1997 Teng et al.
5,677,439 A 10/1997 Weis et al.
5,681,941 A 10/1997 Cook et al.
5,698,685 A 12/1997 Summerton et al.
5,700,920 A 12/1997 Altmann et al.
5,700,922 A 12/1997 Cook
5,721,218 A 2/1998 Froehler
5,750,692 A 5/1998 Cook et al.
5,763,588 A 6/1998 Matteucci et al.
5,792,608 A 8/1998 Swaminathan et al.
5,792,847 A 8/1998 Burh et al.
5,801,154 A 9/1998 Baracchini et al.
5,808,027 A 9/1998 Cook et al.
5,830,653 A 11/1998 Froehler et al.
5,859,221 A 1/1999 Cook et al.
5,948,903 A 9/1999 Cook et al.
5,994,517 A 11/1999 Ts'O
6,005,087 A 12/1999 Cook et al.
6,005,096 A 12/1999 Matteucci et al.
6,166,199 A 12/2000 Cook et al.
6,300,319 B1 10/2001 Manoharan
6,426,220 B1 7/2002 Bennett et al.
6,525,191 B1 2/2003 Ramasamy
6,531,584 B1 3/2003 Cook et al.
6,582,908 B2 6/2003 Fodor et al.
6,600,032 B1 7/2003 Manoharan et al.
6,660,720 B2 12/2003 Manoharan
6,673,535 B1 1/2004 Pulst
6,770,748 B2 8/2004 Imanishi et al.
6,844,431 B1 1/2005 Pulst
7,015,315 B1 3/2006 Cook et al.
7,053,207 B2 5/2006 Wengel et al.
7,101,993 B1 9/2006 Cook et al.
7,262,177 B2 8/2007 Ts'o et al.
7,374,927 B2 5/2008 Palma et al.
7,399,845 B2 7/2008 Seth et al.
7,427,672 B2 9/2008 Imanishi et al.
7,491,805 B2 2/2009 Vargeese et al.
7,547,684 B2 6/2009 Seth et al.
7,569,686 B1 8/2009 Bhat et al.
7,666,854 B2 2/2010 Seth et al.
7,696,345 B2 4/2010 Allerson et al.
7,723,509 B2 5/2010 Manoharan et al.
7,741,457 B2 6/2010 Swayze et al.
7,750,131 B2 7/2010 Seth et al.
7,875,733 B2 1/2011 Bhat et al.
7,888,497 B2 2/2011 Bentwich et al.
7,939,677 B2 5/2011 Bhat et al.
8,022,193 B2 9/2011 Swayze et al.
8,030,467 B2 10/2011 Seth et al.
8,080,644 B2 12/2011 Wengel et al.
8,088,746 B2 1/2012 Seth et al.
8,088,904 B2 1/2012 Swayze et al.
8,106,022 B2 1/2012 Manoharan et al.
8,124,745 B2 2/2012 Allerson et al.
8,153,365 B2 4/2012 Wengel et al.
8,268,980 B2 9/2012 Seth et al.
8,278,283 B2 10/2012 Seth et al.
8,278,425 B2 10/2012 Prakash et al.
8,278,426 B2 10/2012 Seth et al.
8,440,803 B2 5/2013 Swayze et al.
8,501,805 B2 8/2013 Seth et al.
8,530,640 B2 9/2013 Seth et al.
8,546,556 B2 10/2013 Seth et al.
RE44,779 E 2/2014 Imanishi et al.
8,728,736 B2 5/2014 Leamon et al.
8,828,956 B2 9/2014 Manoharan et al.
9,005,906 B2 4/2015 Swayze et al.
9,012,421 B2 4/2015 Migawa et al.
9,127,276 B2 9/2015 Prakash et al.
9,290,760 B2 3/2016 Rajeev et al.
10,006,027 B2 6/2018 Bennett et al.
10,308,934 B2 6/2019 Freier
10,533,178 B2 1/2020 Bennett et al.
11,111,494 B2 9/2021 Freier
11,834,660 B2 12/2023 Freier et al.
11,926,825 B2 3/2024 Freier et al.
12,188,020 B2 1/2025 Rigo
2001/0053519 A1 12/2001 Fodor et al.
2003/0158403 A1 8/2003 Manoharan et al.
2003/0175906 A1 9/2003 Manoharan et al.
2003/0228597 A1 12/2003 Cowsert et al.
2004/0171570 A1 9/2004 Allerson et al.
2004/0220132 A1 11/2004 Kaemmerer
2005/0026164 A1 2/2005 Zhou
2005/0042646 A1 2/2005 Davidson et al.
2005/0100885 A1 5/2005 Crooke et al.
2005/0130923 A1 6/2005 Bhat et al.

(56) References Cited

U.S. PATENT DOCUMENTS

| | | | |
|---|---|---|---|
| 2005/0209178 | A1 | 9/2005 | Pulst |
| 2005/0244851 | A1 | 11/2005 | Blume et al. |
| 2005/0255487 | A1 | 11/2005 | Khvorova et al. |
| 2006/0148740 | A1 | 7/2006 | Platenburg |
| 2006/0270727 | A1 | 11/2006 | Melander et al. |
| 2007/0031844 | A1 | 2/2007 | Khvorova et al. |
| 2007/0224624 | A1 | 9/2007 | Pulst |
| 2008/0039618 | A1 | 2/2008 | Allerson et al. |
| 2008/0113351 | A1 | 5/2008 | Naito et al. |
| 2010/0190837 | A1 | 7/2010 | Migawa et al. |
| 2010/0197762 | A1 | 8/2010 | Swayze et al. |
| 2011/0054005 | A1 | 3/2011 | Naito et al. |
| 2011/0142789 | A1 | 6/2011 | Gitler et al. |
| 2013/0130378 | A1 | 5/2013 | Manoharan et al. |
| 2013/0172399 | A1 | 7/2013 | Corey et al. |
| 2013/0225659 | A1 | 8/2013 | Bennett et al. |
| 2014/0107330 | A1 | 4/2014 | Freier et al. |
| 2014/0303238 | A1 | 10/2014 | Linsley et al. |
| 2015/0018540 | A1 | 1/2015 | Prakash et al. |
| 2015/0141320 | A1 | 5/2015 | Krieg et al. |
| 2015/0184153 | A1 | 7/2015 | Freier et al. |
| 2015/0191727 | A1 | 7/2015 | Migawa et al. |
| 2015/0259679 | A1 | 9/2015 | Bennett et al. |
| 2015/0267195 | A1 | 9/2015 | Seth et al. |
| 2015/0275212 | A1 | 10/2015 | Albaek et al. |
| 2016/0053254 | A1 | 2/2016 | Kimpe et al. |
| 2016/0138014 | A1 | 5/2016 | Kordasiewicz et al. |
| 2017/0175113 | A1 | 6/2017 | Bennett et al. |
| 2017/0175114 | A1 | 6/2017 | Freier et al. |
| 2019/0002887 | A1 | 1/2019 | Rigo |
| 2019/0017047 | A1 | 1/2019 | Bennett et al. |
| 2020/0056179 | A1 | 2/2020 | Freier et al. |
| 2020/0087661 | A1 | 3/2020 | Freier |
| 2022/0064639 | A1 | 3/2022 | Freier et al. |
| 2022/0162615 | A1 | 5/2022 | Rigo |
| 2022/0195430 | A1 | 6/2022 | Freier et al. |
| 2024/0401039 | A1 | 12/2024 | Freier et al. |

FOREIGN PATENT DOCUMENTS

| | | | |
|---|---|---|---|
| EP | 2399611 | A2 | 12/2011 |
| WO | WO 1997/042314 | | 11/1997 |
| WO | WO 2000/015265 | | 3/2000 |
| WO | WO 2000/070039 | | 11/2000 |
| WO | WO 2001/083513 | | 11/2001 |
| WO | WO 2003/033741 | | 4/2003 |
| WO | WO 2004/003201 | | 1/2004 |
| WO | WO 2004/045543 | | 6/2004 |
| WO | WO 2004/047872 | | 6/2004 |
| WO | WO 2004/070062 | | 8/2004 |
| WO | WO 2005/116204 | | 12/2005 |
| WO | WO 2005/116212 | | 12/2005 |
| WO | WO 2006/021814 | | 3/2006 |
| WO | WO 2006/131925 | | 12/2006 |
| WO | WO 2007/106407 | | 9/2007 |
| WO | WO 2008/109379 | | 9/2008 |
| WO | WO 2008/109450 | | 9/2008 |
| WO | WO 2008/152636 | | 12/2008 |
| WO | WO 2009/046141 | | 4/2009 |
| WO | WO 2009/147684 | | 12/2009 |
| WO | WO 2010/014592 | | 2/2010 |
| WO | WO 2011/006121 | | 1/2011 |
| WO | WO 2011/073326 | | 6/2011 |
| WO | WO 2011/097641 | | 8/2011 |
| WO | WO 2012/012467 | | 1/2012 |
| WO | WO 2012/079578 | | 6/2012 |
| WO | WO 2012/149438 | | 11/2012 |
| WO | WO 2012/177639 | | 12/2012 |
| WO | WO 2013/081864 | | 6/2013 |
| WO | WO 2013/162363 | | 10/2013 |
| WO | WO 2013/173645 | | 11/2013 |
| WO | WO 2015/002971 | | 1/2015 |
| WO | WO 2015/072438 | | 5/2015 |
| WO | WO 2015/143245 | | 9/2015 |
| WO | WO 2015/143246 | | 9/2015 |
| WO | WO 2017/117496 | | 7/2017 |
| WO | WO 2020/023737 | | 1/2020 |

OTHER PUBLICATIONS

Bezprozvanny et al., "Therapeutic prospects for spinocerebellar ataxia type 2 and 3." Drugs Future (2009) 34(12):1-17.

Branch et al., "A good antisense molecule is hard to find," TIBS (1998) 23:45-50.

Burke et al., "Huntingtin and DRPLA proteins selectively interact with the enzyme GAPDH." Nat. Med. (1996) 2(3):347-350.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Ciosk et al., "ATX-2, the C. elegans ortholog of ataxin 2, functions in translational regulation in the germline." Development (2004) 131(19):4831-4841.

Corrado et al., "ATXN-2 CAG repeat expansions are interrupted in ALS patients." Hum. Genet. (2011) 130(4):575-580.

Crooke, St., et al., "Antisense Drug Technology" Second Edition, CRC Press (2008) Chapters 1-28.

Deleavy et al., "Designing chemically modified oligonucleotides for targeted gene silencing" Chem Biol (2012) 19(8):937-954.

Duvick et al., "SCA1-like disease in mice expressing wild-type ataxin-1 with a serine to aspartic acid replacement at residue 776." Neuron (2010) 67(6):929-935.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Elden et al., "Ataxin-2 intermediate-length polyglutamine expansions are associated with increased risk for ALS." Nature (2010) 466: 1069-1075.

European partial search report for 15765851.9 dated Oct. 25, 2017.

Evers et al., "Targeting Several CAG Expansion Diseases by a Single Antisense Oligonucleotide" PLoS One (2011) 6(9): e24308.

Extended Ep Search Report for 15765851.9 dated Jan. 30, 2018.

Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.

GenBank: BX410018.2, BX410018 *Homo sapiens* Fetal Brain *Homo sapiens* cDNA clone CSODF030YB07 5-Prime, mRNA sequence; (2003) (retrieved from the internet Jun. 28, 2017: https://www.ncbi.nlm.nih.gov/nucest/BX410018.2).

GenBank: NM_002973.3, *Homo sapiens* ataxin 2 (ATXN2), transcript variant 1, mRNA, NCBI Accession No. NM_002973 (2015) (retrieved from the internet Jun. 28, 2017: https://www.ncbi.nlm.nih.gov/nuccore/171543894/).

GenBank: NT_009775.17 (truncated from nucleotides 2465000 to 2616000) *Homo sapiens* chromosome 12 genomic contig, GRCh37.p13 Primary Assembly (2013) (retrieved from the internet Jun. 28, 2017: https://www.ncbi.nlm.nih.gov/nuccore/NT_009775.17?report=genbank).

Heuvel et al., "Taking a risk: a therapeutic focus on ataxin-2 in amyotrophic lateral sclerosis?" Trends Mol Med (2014) 20(1): 25-35.

Huynh et al., "Expansion of the polyQ repeat in ataxin-2 alters its Golgi localization, disrupts the Golgi complex and causes cell death." Hum. Mol. Genet. (2003) 12: 1485-1496.

Huynh et al., "Expression of ataxin-2 in brains from normal individuals and patients with Alzheimer's disease and spinocerebellar ataxia 2." Ann. Neurol. (1999) 45: 232-241.

International Search Report for application PCT/US2015/021607 dated Jun. 29, 2015.

International Search Report for application PCT/US2015/021608 dated Jul. 1, 2015.

International Search Report for application PCT/US2016/069406 dated Mar. 31, 2017.

(56) References Cited

OTHER PUBLICATIONS

Kim et al., "Importance of low-range CAG expansion and CAA interruption in SCA2 Parkinsonism." Arch. Neurol. (2007) 64(10): 1510-1518.
Koshy et al., "Spinocerebellar ataxia type-1 and spinobulbar muscular atrophy gene products interact with glyceraldehyde-3-phosphate dehydrogenase" Hum. Mol. Genet. (1996) 5(9): 1311-1318.
Lajoie et al., "Formation and toxicity of soluble polyglutamine oligomers in living cells." PLoS One (2010) 5(12): e15245 1-15.
Lou Gehrig's Disease (ALS): Prevention | Florida Hospital. Downloaded on Jul. 16, 2018 from https://www.floridahospital.com/lou-gehrigs-disease-als/prevention-lou-gehrigs-disease-als.
Lovett-Racke et al., Therapeutic Potential of Small Interfering RNA for Central Nervous System Diseases. Archives of Neurobiology (2005) 62:1810-1813.
Magana et al., "Spinocerebellar ataxia type 2: clinical presentation, molecular mechanisms, and therapeutic perspectives" Mol Neurobiol (2013) 47(1): 90-104.
Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.
New England Biolabs 1998/1999 Catalog (cover page and pp. 121 and 284).
Nonhoff et al., "Ataxin-2 interacts with the DEAD/H-box RNA helicase DDX6 and interferes with P-bodies and stress granules." Mol. Biol. Cell (2007) 18(4):1385-1396.
Nonis et al., "Ataxin-2 associates with the endocytosis complex and affects EGF receptor trafficking" Cell Signal (2008) 20(10):1725-1739.
Parkinson's Disease—Symptoms and causes—Mayo Clinic. Downloaded on Jul. 16, 2018 from https://www.mayoclinic.org/diseases-conditions/parkinsons-disease/symptoms-causes/syc-20376055.
Pulst S.M. (ed.) "Inherited Ataxias: An Introduction" Genetics of Movement Disorders. Elsevier, Inc., Amsterdam, published Oct. 3, 2002, pp. 19-34.
Pulst S.M., "Rare mendelian diseases: pathways to therapy development" Oral presentation, American Academy of Neurology Annual Meeting, Philadelphia, PA, Apr. 29, 2014.
Ramachandran, P. "RNA interference therapy for the Spinocerebellar ataxias." Thesis, May 2014, University of Iowa, pp. 1-140.
Reynolds et al., "Rational siRNA design for RNA interference" Nature Biotechnology (2004) 22(3):326-330.
Ross et al., "Ataxin-2 repeat-length variation and neurodegeneration." Hum. Mol. Genet. (2011) 20(16): 3207-3212.
Sanghvi et al., "Heterocyclic Base Modifications in Nucleic Acids and Their Applications in Antisense Oligonucleotides" Antisense Research and Applications (1993) pp. 273-288.
Satterfield et al., "Ataxin-2 and its *Drosophila homolog*, ATX2, physically assemble with polyribosomes." Hum. Mol. Genet. (2006) 15(16):2523-2532.
Scoles et al., Antisense oligonucleotides for the treatment of spinocerebellar ataxia type 2 (SCA2), 5th Ataxia Investigators Meeting (AIM) meeting abstract presented Mar. 20, 2014.
Scoles et al., "Antisense oligonucleotides for the treatment of spinocerebellar ataxia type 2 (SCA2)" AAN Annual Meeting abstract published online Feb. 26, 2015; Neurology (2015) 82(Meeting Abstracts): S32.002.
Scoles et al., "ATXN2 Is Regulated by a Promoter Associated Antisense Long Noncoding RNA (IncRNA)" Neurology (2013) 80: P05030.
Scoles et al., "ETS1 regulates the expression of ATXN2" Human Mol Genetics (2012) 21(23): 5048-65.
Scoles et al., "Treatment of Spinocerebellar Ataxia Type 2 (SCA2) with MOE Antisense Oligonucleotides." AAN Annual Meeting abstract published online Feb. 26, 2014; Neurology (2014) 82(10 Supplement): S47.006.
Seth et al., "Short Antisense Oligonucleotides with Novel 2'-4' Conformationally Restricted Nucleoside Analogues Show Improved Potency Without Increased Toxicity in Animals." J Med Chem (2009) 52:10-13.
Shen et al., "Research on (CAG)n mutation detection of Spinocerebellar ataxia type 2" Chinese J Int Med (2000) 39(4): 259-261.
Shibata et al., "A novel protein with RNA-binding motifs interacts with ataxin-2." Hum. Mol. Genet. (2000) 9(9): 1303-1313.
Van Damme et al., "Expanded ATXN2 Cag repeat size in ALS identifies genetic overlap between ALS and SCA2." Neurology (2011) 76(24):2066-2072.
Woolf et al. "Specificity of antisense oligonucleotides in vivo" PNAS (1992) 89:7305-7309.
Yamanaka et al., "Transcription factor sequestration by polyglutamine proteins." Methods Mol. Biol. (2010) 648:215-229.
Chiu et al., "Age-Dependent Penetrance of Disease in a Transgenic Mouse Model of Familial Amyotrophic Lateral Sclerosis," Mol and Cell Neurosci, 1995, 6:349-362.
Elden et al., "Ataxin-2 localization in ALS and FTLD-TDP and TDP-43 localization in SCA2" Nature (2010) 466: 1069-1075 (Supplementary Information).
Frey et al., "Early and Selective Loss of Neuromuscular Synapse Subtypes with Low Sprouting Competence in Motoneuron Diseases," J Neurosci, 2000, 20(7):2534-2542.
Grunweller et al. "Comparison of different antisense strategies in mammalian cells using locked nucleic acids, 2'-O-methyl RNA, phosphorothioates and small interfering RNA" Nucl Ac Res (2003) 31: 185-193.
Gurney et al., "Motor Neuron Degeneration in Mice that Express a Human Cu,ZN Superoxide Dismutase Mutation," Science (1994) 264:1772-1775.
Ito et al., "Treatment with edaravone, initiated at symptom onset, slows motor decline and decreases SOD1 deposition in ALS mice," Experimental Neurology, 2008, 213:448-455.
Philips et al., "Rodent Models of Amyotrophic Lateral Sclerosis," Curr Protoc Pharmacol, 2015, 69: 1-21.
Pun et al., "Selective Vulnerability and Pruning of Phasic Motoneuron Axons in Motoneuron Disease Alleviated by CTNF," Nat Neurosci, 2006, 9:408-419.
Takei et al., "Edaravone and its Clinical Development for Amyotrophic Lateral Sclerosis," Amyotrophic Lateral Sclerosis and Frontotemporal Degeneration, 2017, 18:5-10.
Van Blitterswijk et al., "Ataxin-2 as potential disease modifier in C9ORF72 expansion carriers" Neurobiology of Aging (2014) 35: e13-e17.
Zangemeister-Wittke et al., "A novel bispecific antisense oligonucleotide inhibiting both bcl-2 and bcl-xL expression efficiently induces apoptosis in tumor cells" Clin Cancer Res (2000) 6: 2547-2555.
Doherty "ALS vs. Parkinson's: What Are the Differences?" verywellhealth | downloaded Jan. 9, 2023 p. 1-16.
European partial search report for 21187734.5 dated Mar. 4, 2022.
Extended EP Search Report for 19841474.0 dated Apr. 18, 2023.
Extended EP Search Report for 21187734.5 dated Jul. 25, 2022.
O'Donnell Jr. "Neurodegenerative Disorders" Brain Institute | UT Southwestern Medical Center (utswmed.org) downloaded on Jan. 9, 2023 p. 1-7.

COMPOSITIONS FOR MODULATING ATAXIN 2 EXPRESSION

SEQUENCE LISTING

The present application is being filed along with a Sequence Listing in electronic format. The Sequence Listing is provided as a file entitled BIOL0239SEQ.xml created Oct. 23, 2023, which is 292 Kb in size. The information in the electronic format of the sequence listing is incorporated herein by reference in its entirety.

FIELD

Provided are compositions and methods for reducing expression of Ataxin 2 (ATXN2) mRNA and protein in an animal. Such methods are useful to treat, prevent, or ameliorate neurodegenerative diseases, including spinocerebellar ataxia type 2 (SCA2), amyotrophic lateral sclerosis (ALS), and parkinsonism by inhibiting expression of Ataxin 2 by inhibiting expression of Ataxin 2 in an animal.

BACKGROUND

Spinocerebellar ataxia type 2 (SCA2) is an autosomal dominant neurodegenerative disease characterized by progressive functional and cell loss of neurons in the cerebellum, brain stem and spinal cord. The cause of SCA2 is CAG expansion in the ATXN2 gene resulting in polyglutamine (polyQ) expansion in the ataxin-2 protein. Patients with SCA2 are characterized by progressive cerebellar ataxia, slow saccadic eye movements and other neurologic features such as neuropathy (Pulst, S. M. (ed.), *Genetics of Movement Disorders*. Elsevier, Inc., Amsterdam, 2003, pp. 19-34.). Moderate CAG expansion in the ATXN2 gene is also associated with parkinsonism or amyotrophic lateral sclerosis (ALS) indistinguishable from the idiopathic forms of these diseases (Kim et al., *Arch. Neurol.,* 2007, 64: 1510-1518; Ross et al., *Hum. Mol. Genet.,* 2011, 20: 3207-3212; Corrado et al., *Hum. Genet.,* 2011, 130: 575-580; Elden et al., *Nature,* 2010, 466: 1069-1075; Van Damme et al., *Neurology,* 2011, 76: 2066-2072).

The pathogenic functions of polyQ disease proteins that occur with polyQ expansion may be attributed to the gain of toxicity associated with the development of intranuclear inclusion bodies or with soluble toxic oligomers (Lajoie et al., *PLoS One,* 2011, 5: e15245). While SCA2 patient brains are characterized by loss of Purkinje cells, SCA2 Purkinje cells lack inclusion bodies indicating polyQ-expanded ataxin-2 may cause toxicity that is unrelated to inclusion body formation (Huynh et al., *Ann. Neurol.,* 1999, 45: 232-241). Functions gained in polyQ-expanded ataxin-2 may include anomalous accumulation in Golgi bodies (Huynh et al., *Hum. Mol. Genet.,* 2003, 12: 1485-1496), gain-of-normal functions (Duvick et al., *Neuron,* 2010, 67: 929-935) and sequestering of transcription factors (TFs) and glyceraldehyde-3-phosphate dehydrogenase like for other polyQ proteins (Yamanaka et al., *Methods Mol. Biol.,* 2010: 648, 215-229; Koshy et al., *Hum. Mol. Genet.,* 1996, 5: 1311-1318; Burke et al., *Nat. Med.,* 1996, 2: 347-350). Some normal functions of ataxin-2 have been characterized. Ataxin-2 is present in stress granules and P-bodies suggesting functions in sequestering mRNAs and protein translation regulation during stress (Nonhoff et al., *Mol. Biol. Cell,* 2007, 18: 1385-1396). Ataxin-2 overexpression interfered with the P-body assembly, while underexpression interfered with stress granule assembly (Nonhoff et al., *Mol. Biol. Cell,* 2007, 18: 1385-1396). Interactions with polyA-binding protein 1, the RNA splicing factor A2BP1/Fox1 and polyribosomes further support roles for ataxin-2 in RNA metabolism (Shibata et al., *Hum. Mol. Genet.,* 2000, 9: 1303-1313; Ciosk et al., *Development,* 2004, 131: 4831-4841; Satterfield et al., *Hum. Mol. Genet.,* 2006, 15: 2523-2532). Ataxin-2 is a regulator of EGF receptor internalization and signaling by the way of its interactions with SRC kinase and the endocytic protein CIN85 (Nonis et al., *Cell Signal.,* 2008, 20: 1725-1739). Ataxin-2 also interacts with the ALS-related protein TDP-43 in an RNA-dependent manner and familial and sporadic ALS associates with the occurrence of long normal CAG repeat expansion ATXN2 (Elden et al., *Nature,* 2010, 466: 1069-1075; Van Damme et al., *Neurology,* 2011, 76: 2066-2072).

Currently there is a lack of acceptable options for treating such neurodegenerative diseases. It is therefore an object herein to provide methods for the treatment of such diseases.

SUMMARY

Provided herein are methods, compounds, and compositions for modulating expression of Ataxin 2 (ATXN2) mRNA and protein. In certain embodiments, compounds useful for modulating expression of Ataxin 2 mRNA and protein are antisense compounds. In certain embodiments, the antisense compounds are modified oligonucleotides.

In certain embodiments, modulation can occur in a cell or tissue. In certain embodiments, the cell or tissue is in an animal. In certain embodiments, the animal is a human. In certain embodiments, Ataxin 2 mRNA levels are reduced. In certain embodiments, Ataxin 2 protein levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such Ataxin 2 related diseases, disorders, and conditions are neurodegenerative diseases. In certain embodiments, such neurodegenerative diseases, disorders, and conditions include spinocerebellar ataxia type 2 (SCA2), amyotrophic lateral sclerosis (ALS), and parkinsonism.

Such diseases, disorders, and conditions can have one or more risk factors, causes, or outcomes in common. Certain risk factors and causes for development of neurodegenerative disorder include growing older, having a personal or family history, or genetic predisposition. Certain symptoms and outcomes associated with development of a neurodegenerative disorder include but are not limited to: ataxia, speech and swallowing difficulties, rigidity, tremors, ophthalmoplegia, saccadic slowing, peripheral neuropathy, atrophy, dystonia, chorea, and dementia.

In certain embodiments, methods of treatment include administering an Ataxin 2 antisense compound to an individual in need thereof. In certain embodiments, methods of treatment include administering an Ataxin 2 modified oligonucleotide to an individual in need thereof.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and"

means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-$OCH_2CH_2$—$OCH_3$ and MOE) refers to an O-methoxy-ethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2-position of the furanose ring other than H or OH. In certain embodiments, 2' substituted nucleosides include nucleosides with bicyclic sugar modifications.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of Ataxin 2", it is implied that the Ataxin 2 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Ataxin 2" means the mammalian gene Ataxin 2 (ATXN2), including the human gene Ataxin 2 (ATXN2). Human Ataxin 2 has been mapped to human chromosome 12q24.1.

"Ataxin 2 associated disease" means any disease associated with any Ataxin 2 nucleic acid or expression product thereof. Such diseases may include a neurodegenerative disease. Such neurodegenerative diseases may include spinocerebellar ataxia type 2 (SCA2), amyotrophic lateral sclerosis (ALS), and parkinsonism.

"Ataxin 2 mRNA" means any messenger RNA expression product of a DNA sequence encoding Ataxin 2.

"Ataxin 2 nucleic acid" means any nucleic acid encoding Ataxin 2. For example, in certain embodiments, an Ataxin 2 nucleic acid includes a DNA sequence encoding Ataxin 2, an RNA sequence transcribed from DNA encoding Ataxin 2 (including genomic DNA comprising introns and exons), and an mRNA sequence encoding Ataxin 2. "Ataxin 2 mRNA" means an mRNA encoding an Ataxin 2 protein.

"Ataxin 2 protein" means the polypeptide expression product of an Ataxin 2 nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-$CH(CH_3)$—O-2'.

"Constrained ethyl nucleoside" (also cEt nucleoside) means a nucleoside comprising a bicyclic sugar moiety comprising a 4-$CH(CH_3)$—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g, saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having an Ataxin 2 associated disease" means identifying an animal having been diagnosed with an Ataxin 2 associated disease or predisposed to develop an Ataxin 2 associated disease. Individuals predisposed to develop an Ataxin 2 associated disease include those having one or more risk factors for developing an Ataxin 2 associated disease, including, growing older, having a personal or family history, or genetic predisposition of one or more Ataxin 2 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting Ataxin 2" means reducing the level or expression of an Ataxin 2 mRNA and/or protein. In certain embodiments, Ataxin 2 mRNA and/or protein levels are inhibited in the presence of an antisense compound targeting Ataxin 2, including an antisense oligonucleotide targeting Ataxin 2, as compared to expression of Ataxin 2 mRNA and/or protein levels in the absence of an Ataxin 2 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-$CH_2$—O-2) LNA, (B) β-D-Methyleneoxy (4'-$CH_2$—O-2') LNA, (C) Ethyleneoxy (4'-$(CH_2)_2$—O-2') LNA, (D) Aminooxy (4'-$CH_2$—O—N(R)-2') LNA and (E) Oxyamino (4'-$CH_2$—N(R)—O-2') LNA, as depicted below.

(A)

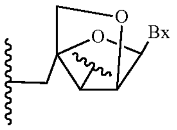

(B)

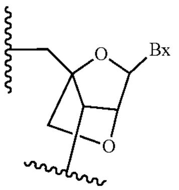

(C)

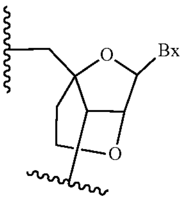

(D)

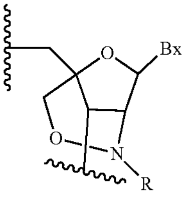

(E)

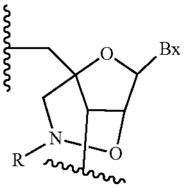

As used herein, LNA compounds include, but are not limited to, compounds having at least one bridge between the 4' and the 2' position of the sugar wherein each of the bridges independently comprises 1 or from 2 to 4 linked groups independently selected from —$[C(R_1)(R_2)]_n$—, —$C(R_1)$═$C(R_2)$—, —$C(R_1)$═N—, —C(═$NR_1$)—, —C(═O)—, —C(═S)—, —O—, —$Si(R_1)_2$—, —$S(═O)_x$— and —$N(R_1)$—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl ($S(═O)_2$-$J_1$), or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: —$[C(R_1)(R_2)]_n$—, —$[C(R_1)(R_2)]_n$—O—, —$C(R_1R_2)$—$N(R_1)$—O— or —$C(R_1R_2)$—O—$N(R_1)$—. Furthermore, other bridging groups encompassed with the definition of LNA are 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—$N(R_1)$-2' and 4'-$CH_2$—$N(R_1)$—O-2'- bridges, wherein each $R_1$ and $R_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-$CH_2$—O-2') bridge to form the bicyclic sugar moiety. The bridge can also be a methylene (—$CH_2$—) group connecting the 2' oxygen atom and the 4' carbon atom, for which the term methyleneoxy (4'-$CH_2$—O-2') LNA is used. Furthermore; in the case of the bicylic sugar moiety having an ethylene bridging group in this position, the term ethyleneoxy (4+—$CH_2CH_2$—O-2') LNA is used. α-L-methyleneoxy (4'-$CH_2$—O-2'), an isomer of methyleneoxy (4'-$CH_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

A "modified nucleoside" means a nucleoside having, independently, a modified sugar moiety and/or modified nucleobase.

"Modified nucleotide" means a nucleotide having, independently, a modified sugar moicty, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to Ataxin 2 is a pharmaceutical agent.

"Pharmaceutical composition" means a mixture of substances suitable for administering to a subject. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" refers administering a composition to effect an alteration or improvement of the disease or condition.

"Unmodified nucleobases" mean the purine bases adenine (A) and guanine (G), and the pyrimidine bases thymine (T), cytosine (C) and uracil (U).

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide methods, compounds, and compositions for inhibiting Ataxin 2 mRNA and protein expression. Certain embodiments provide methods, compounds, and composition for decreasing Ataxin 2 mRNA and protein levels.

Certain embodiments provide antisense compounds targeted to an Ataxin 2 nucleic acid. In certain embodiments, the Ataxin 2 nucleic acid is the sequence set forth in GENBANK Accession No. NM_002973.3 (incorporated herein as SEQ ID NO: 1), the complement of GENBANK Accession No. NT_009775.17 truncated from nucleotides 2465000 to 2616000 (incorporated herein as SEQ ID NO: 2) and GENBANK Accession No. BX410018.2 (incorporated herein as SEQ ID NO: 3).

Certain embodiments provide methods for the treatment, prevention, or amelioration of diseases, disorders, and conditions associated with Ataxin 2 in an individual in need thereof. Also contemplated are methods for the preparation of a medicament for the treatment, prevention, or amelioration of a disease, disorder, or condition associated with Ataxin 2. Ataxin 2 associated diseases, disorders, and conditions include neurodegenerative diseases. In certain embodiments, Ataxin 2 associated diseases include spinocerebellar ataxia type 2 (SCA2), amyotrophic lateral sclerosis (ALS), and parkinsonism.

Certain embodiments provide compounds, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 11-165.

In certain embodiments the nucleobase sequence of the modified oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1, SEQ ID NO: 2, or SEQ ID NO: 3.

In certain embodiments, the compound is a single-stranded modified oligonucleotide.

In certain embodiments, at least one internucleoside linkage of the modified oligonucleotide is a modified internucleoside linkage.

In certain embodiments, at least one modified internucleoside linkage is a phosphorothioate internucleoside linkage.

In certain embodiments, each modified internucleoside linkage is a phosphorothioate internucleoside linkage.

In certain embodiments, at least one internucleoside linkage is a phosphodiester internucleoside linkage.

In certain embodiments, at least one internucleoside linkage is a phosphorothioate linkage and at least one internucleoside linkage is a phosphodiester linkage.

In certain embodiments, at least one nucleoside comprises a modified nucleobase.

In certain embodiments, the modified nucleobase is a 5-methylcytosine.

In certain embodiments, at least one nucleoside of the modified oligonucleotide comprises a modified sugar.

In certain embodiments, at least one modified sugar is a bicyclic sugar.

In certain embodiments, the bicyclic sugar comprises a a chemical link between the 2' and 4' position of the sugar 4'-CH2-N(R)—O-2' bridge wherein R is, independently, H, C1-C12 alkyl, or a protecting group.

In certain embodiments, the bicyclic sugar comprises a 4'-CH2-N(R)—O-2' bridge wherein R is, independently, H, C1-C12 alkyl, or a protecting group.

In certain embodiments, at least one modified sugar comprises a 2'-O-methoxyethyl group.

In certain embodiments, the modified sugar comprises a 2'-$O(CH_2)_2$—$OCH_3$ group.

In certain embodiments, the modified oligonucleotide comprises:

a gap segment consisting of 10 linked deoxynucleosides;

a 5' wing segment consisting of 5 linked nucleosides; and a 3' wing segment consisting of 5 linked nucleosides;

wherein the gap segment is positioned between the 5' wing segment and the 3' wing segment and wherein each nucleoside of each wing segment comprises a modified sugar.

In certain embodiments, the modified oligonucleotide consists of 20 linked nucleosides.

Certain embodiments provide compositions comprising any compound described herein or salt thereof and at least one of a pharmaceutically acceptable carrier or diluent.

Certain embodiments provide methods comprising administering to an animal any compound or composition described herein.

In certain embodiments, the animal is a human.

In certain embodiments, administering the compound prevents, treats, ameliorates, or slows progression of an Ataxin 2 associated disease, disorder or condition.

In certain embodiments, the Ataxin 2 disease, disorder or condition spinocerebellar ataxia type 2 (SCA2), amyotrophic lateral sclerosis (ALS), and parkinsonism.

Certain embodiments provide use of any of the compounds or compositions of described herein for the manufacture of a medicament for treating a neurodegenerative disorder.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an Ataxin 2 nucleic acid is 12 to 30 subunits in length. In certain embodiments, an antisense compound targeted to an Ataxin 2 nucleic acid is 12 to 25 subunits in length. In certain embodiments, an antisense compound targeted to an Ataxin 2 nucleic acid is 12 to 22 subunits in length. In certain embodiments, an antisense compound targeted to an Ataxin 2 nucleic acid is 14 to 20 subunits in length. In certain embodiments, an antisense compound targeted to an Ataxin 2 nucleic acid is 15 to 25 subunits in length. In certain embodiments, an antisense compound targeted to an Ataxin 2 nucleic acid is 18 to 22 subunits in length. In certain embodiments, an antisense compound targeted to an Ataxin 2 nucleic acid is 19 to 21 subunits in length. In certain embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 30, 18 to 50, 19 to 30, 19 to 50, or 20 to 30 linked subunits in length.

In certain embodiments, an antisense compound targeted to an Ataxin 2 nucleic acid is 12 subunits in length. In certain embodiments, an antisense compound targeted to an Ataxin 2 nucleic acid is 13 subunits in length. In certain embodiments, an antisense compound targeted to an Ataxin 2 nucleic acid is 14 subunits in length. In certain embodiments, an antisense compound targeted to an Ataxin 2 nucleic acid is 15 subunits in length. In certain embodiments, an antisense compound targeted to an Ataxin 2 nucleic acid is 16 subunits in length. In certain embodiments, an antisense compound targeted to an Ataxin 2 nucleic acid is 17 subunits in length. In certain embodiments, an antisense compound targeted to an Ataxin 2 nucleic acid is 18 subunits in length. In certain embodiments, an antisense compound targeted to an Ataxin 2 nucleic acid is 19 subunits in length. In certain embodiments, an antisense compound targeted to an Ataxin 2 nucleic acid is 20 subunits in length. In certain embodiments, an antisense compound targeted to an Ataxin 2 nucleic acid is 21 subunits in length. In certain embodiments, an antisense compound targeted to an Ataxin 2 nucleic acid is 22 subunits in length. In certain embodiments, an antisense compound targeted to an Ataxin 2 nucleic acid is 23 subunits in length. In certain embodiments, an antisense compound targeted to an Ataxin 2 nucleic acid is 24 subunits in length. In certain embodiments, an antisense compound targeted to an Ataxin 2 nucleic acid is 25 subunits in length. In certain embodiments, an antisense compound targeted to an Ataxin 2 nucleic acid is 26 subunits in length. In certain embodiments, an antisense compound targeted to an Ataxin 2 nucleic acid is 27 subunits in length. In certain embodiments, an antisense compound targeted to an Ataxin 2 nucleic acid is 28 subunits in length. In certain embodiments, an antisense compound targeted to an Ataxin 2 nucleic acid is 29 subunits in length. In certain embodiments, an antisense compound targeted to an Ataxin 2 nucleic acid is 30 subunits in length. In certain embodiments, the antisense compound targeted to an Ataxin 2 nucleic acid is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments the antisense compound is an antisense oligonucleotide, and the linked subunits are nucleosides.

In certain embodiments antisense oligonucleotides targeted to an Ataxin 2 nucleic acid may be shortened or truncated. For example, a single subunit may be deleted from the 5' end (5' truncation), or alternatively from the 3' end (3' truncation). A shortened or truncated antisense compound targeted to an Ataxin 2 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an Ataxin 2 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)$n-O-2' bridge, where n=1 or n=2 and 4'-$CH_2$—O—$CH_2$-2'). In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X-Y-Z", where "X" represents the length of the 5' wing, "Y" represents the length of the gap, and "Z" represents the length of the 3' wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5' wing and the 3' wing. Thus, no intervening nucleotides exist between the 5' wing and gap, or the gap and the 3' wing. Any of the antisense compounds described herein can have a gapmer motif. In certain embodiments, "X" and "Z" are the same; in other embodiments they are different.

In certain embodiments, gapmers provided herein include, for example 20-mers having a motif of 5-10-5.

In certain embodiments, gapmers provided herein include, for example 19-mers having a motif of 5-9-5.

In certain embodiments, gapmers provided herein include, for example 18-mers having a motif of 5-8-5.

In certain embodiments, gapmers provided herein include, for example 18-mers having a motif of 4-8-6.

In certain embodiments, gapmers provided herein include, for example 18-mers having a motif of 6-8-4.

In certain embodiments, gapmers provided herein include, for example 18-mers having a motif of 5-7-6.

Target Nucleic Acids, Target Regions and Nucleotide Sequences

Nucleotide sequences that encode Ataxin 2 include, without limitation, the following: GENBANK Accession No. NM_002973.3 (incorporated herein as SEQ ID NO: 1), the complement of GENBANK Accession No. NT_009775.17 truncated from nucleotides 2465000 to 2616000 (incorporated herein as SEQ ID NO: 2) and GENBANK Accession No. BX410018.2 (incorporated herein as SEQ ID NO: 3).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Ataxin 2 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain emodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed hercin.

Suitable target segments may be found within a 5' UTR, a coding region, a 3' UTR, an intron, an exon, or an exon/intron junction. Target segments containing a start codon or a stop codon are also suitable target segments. A suitable target segment may specfcally exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Ataxin 2 mRNA levels are indicative of inhibition of Ataxin 2 expression. Reductions in levels of an Ataxin 2 protein are also indicative of inhibition of target mRNA expression. Phenotypic changes are indicative of inhibition of Ataxin 2 expression. Improvement in neurological function is indicative of inhibition of Ataxin 2 expression. Improved motor function and memory are indicative of inhibition of Ataxin 2 expression.

Hybridization

In some embodiments, hybridization occurs between an antisense compound disclosed herein and an Ataxin 2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an Ataxin 2 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Ataxin 2 nucleic acid).

Non-complementary nucleobases between an antisense compound and an Ataxin 2 nucleic acid may be tolerated provided that the antisense compound remains able to specifically hybridize to a target nucleic acid. Moreover, an antisense compound may hybridize over one or more segments of an Ataxin 2 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Ataxin 2 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul ct al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an Ataxin 2 nucleic acid, or a target region, or a target segment or target sequence thereof. As used herein, "fully complementary"

means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Ataxin 2 nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Ataxin 2 nucleic acid, or specified portion thereof.

The antisense compounds provided herein also include those which are complementary to a portion of a target nucleic acid. As used herein. "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e., non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Ataxin 2 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$, and O—$CH_2$—C(═O)—$N(R_l)$—$(CH_2)_2$—$N(R_m)(R_n)$, where each $R_l$, $R_m$ and $R_n$ is, independently. H or substituted or unsubstituted $C_1$-$C_{10}$ alkyl.

As used herein. "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4 to 2' bridge. Examples of such 4' to 2' bridged bicyclic nucleosides, include but are not limited to one of the formulae: 4'-$(CH_2)$—O-2' (LNA); 4'-$(CH_2)$—S—2'; 4'-$(CH_2)_2$—O-2' (ENA); 4'-$CH(CH_3)$—O-2' and 4'-$CH(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—$N(OCH_3)$-2' (and analogs thereof see published International Application WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—$C(H)(CH_3)$-2' (see Chattopadhyaya et al., *J. Org. Chem.,* 2009, 74, 118-134); and 4'-$CH_2$—C—(═$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2007, 129(26) 8362-8379; Elayadi et al., *Curr. Opinion Invest. Drugs.* 2001, 2, 558-561; Braasch et al., *Chem. Biol.,* 2001, 8, 1-7; and Orum et al., *Curr. Opinion Mol. Ther.,* 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$═$C(R_b)$—, —$C(R_a)$═N—, —C(═O)—, —C(═$NR_a$)—, —C(═S)—, —O—, —$Si(R_a)_2$—, —$S(═O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is $—[C(R_a)(R_b)]_n—$, $—[C(R_a)(R_b)]_n—O—$, $—C(R_aR_b)—N(R)—O—$ or $—C(R_aR_b)—O—N(R)—$. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-$CH(CH_3)$—O-2') BNA, (G) methylene-thio (4'-$CH_2$—S—2') BNA, (H) methylene-amino (4'-$CH_2$—N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

(A)

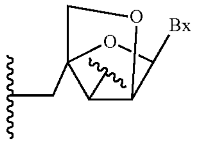

(B)

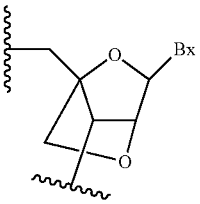

(C)

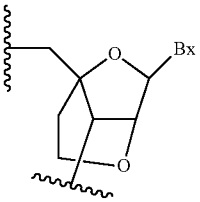

-continued (D)

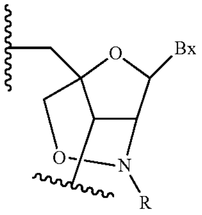

(E)

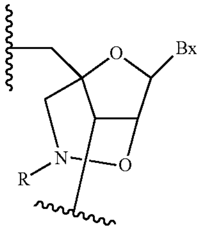

(F)

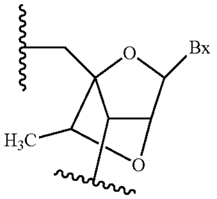

(G)

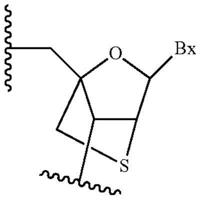

(H)

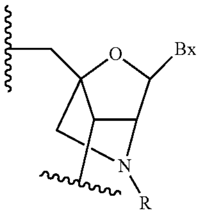

(I)

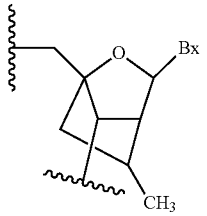

(J)

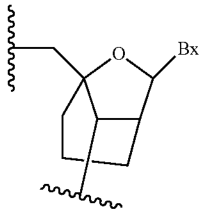

wherein Bx is the base moiety and R is independently H, a protecting group or $C_1$-$C_{12}$ alkyl.

In certain embodiments, bicyclic nucleosides are provided having Formula I:

I

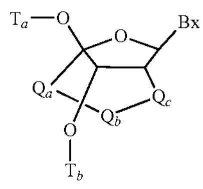

wherein:

Bx is a heterocyclic base moiety;

$-Q_a-Q_b-Q_c-$ is $—CH_2—N(R_c)—CH_2—$, $—C(=O)—N(R_c)—CH_2—$, $—CH_2—O—N(R_c)—$, $—CH_2—N(R_c)—O—$ or $—N(R_c)—O—CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II

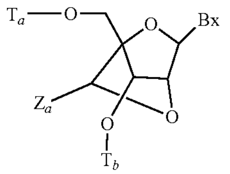

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

III

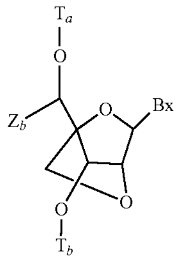

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl $(C(=O)—)$.

In certain embodiments, bicyclic nucleosides are provided having Formula IV:

IV

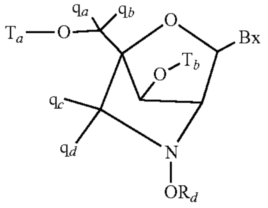

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

V

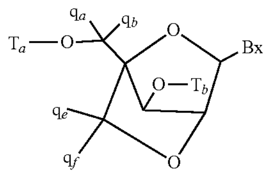

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O—C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

VI

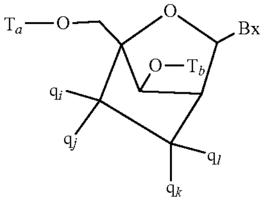

wherein:

Bx is a heterocyclic base moiety;

$T_a$ and $T_b$ are each, independently H, a hydroxyl protecting group, a conjugate group, a reactive phosphorus group, a phosphorus moicty or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(═O)$OJ_j$, C(═O)$NJ_jJ_k$, C(═O)$J_j$, O—C(═O)$NJ_jJ_k$, N(H)C(═NH)$NJ_jJ_k$, N(H)C(═O)$NJ_jJ_k$ or N(H)C(═S)$NJ_jJ_k$; and $q_i$ and $q_j$ or $q_l$ and $q_k$ together are ═C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH═CH—$CH_2$-2' have been described (Freier et al., *Nucleic Acids Research,* 1997, 25(22), 4429-4443 and Alback et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.,* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moicties that are not bicyclic sugar moieties. In certain embodiments, the sugar moicty, or sugar moicty analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C$(═O)N(H)$CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin. *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854), fluoro HNA (F-HNA) or those compounds having Formula VII:

VII

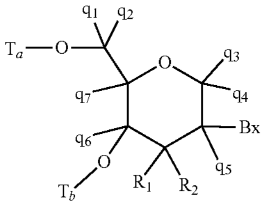

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an Ataxin 2 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an Ataxin 2 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Ataxin 2 nucleic acids can be tested in vitro in a variety of cell types. Cell types used for such analyses are available from commerical vendors (e.g. American Type Culture Collection, Manassus, VA; Zen-Bio, Inc., Research Triangle Park, NC; Clonetics Corporation, Walkersville, MD) and are cultured according to the vendor's instructions using commercially available reagents (e.g. Invitrogen Life Technologies, Carlsbad, CA). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, CA). Antisense oligonucleotides may be mixed with LIPOFECTIN in OPTI-MEM 1 (Invitrogen, Carlsbad, CA) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, CA). Antisense oligonucleotide is mixed with LIPOFECTAMINE in OPTI-MEM 1 reduced serum medium (Invitrogen, Carlsbad, CA) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, CA) according to the manufacturer's recommended protocols.

Analysis of Inhibition of Target Levels or Expression

Inhibition of levels or expression of an Ataxin 2 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, CA). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, CA). Cyclophilin A expression is quantified by real time PCR, by being run simultaneously with the target, multiplexing, or separately. Total RNA is quantified using RIBOGREEN RNA quantification reagent (Invetrogen, Inc. Eugene, OR). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to an Ataxin 2 nucleic acid. Methods for designing real-time PCR probes and primers are well known in the art, and may include the use of software such as PRIMER EXPRESS Software (Applied Biosystems, Foster City, CA).

Analysis of Protein Levels

Antisense inhibition of Ataxin 2 nucleic acids can be assessed by measuring Ataxin 2 protein levels. Protein levels of Ataxin 2 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of Ataxin 2 and produce phenotypic changes, such as, improved motor function and cognition. In certain embodiments, motor function is measured by walking initiation analysis, rotarod, grip strength, pole climb, open field performance, balance beam, hindpaw footprint testing in the animal.

Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in Ataxin 2 nucleic acid expression are measured.

Certain Indications

In certain embodiments, provided herein are methods, compounds, and compositions of treating an individual comprising administering one or more pharmaceutical compositions described herein. In certain embodiments, the individual has a neurodegenerative disease. In certain embodiments, the individual is at risk for developing a neurodegenerative disease, including, but not limited to, spinocerebellar ataxia type 2 (SCA2), amyotrophic lateral sclerosis (ALS), and parkinsonism. In certain embodiments, the individual has been identified as having an Ataxin 2 associated disease. In certain embodiments, provided herein are methods for prophylactically reducing Ataxin 2 expression in an individual. Certain embodiments include treating an individual in need thereof by administering to an individual a therapeutically effective amount of an antisense compound targeted to an Ataxin 2 nucleic acid.

In one embodiment, administration of a therapeutically effective amount of an antisense compound targeted to an Ataxin 2 nucleic acid is accompanied by monitoring of Ataxin 2 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to an Ataxin 2 nucleic acid results in reduction of Ataxin 2 expression by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values. In certain embodiments, administration of an antisense compound targeted to an Ataxin 2 nucleic acid results in improved motor function in an animal. In certain embodiments, administration of an Ataxin 2 antisense compound improves motor function by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, pharmaceutical compositions comprising an antisense compound targeted to Ataxin 2 are used for the preparation of a medicament for treating a patient suffering or susceptible to a neurodegenerative disease including spinocerebellar ataxia type 2 (SCA2), amyotrophic lateral sclerosis (ALS), and parkinsonism.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Ataxin 2 in HepG2 Cells by MOE Gapmers

Antisense oligonucleotides were designed targeting an ataxin 2 nucleic acid and were tested for their effects on ataxin 2 mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 4,500 nM antisense oligonucleotide. After a treatment period of approximately 24 hours, RNA was isolated from the cells and ataxin 2 mRNA levels were measured by quantitative real-time PCR. Human primer probe set RTS3642 (forward sequence ACCAAAGAGTAGTTAATGGAGGTGTTC, designated herein as SEQ ID NO: 5; reverse sequence AGAAGGTGGGCGAGAGGAA, designated herein as SEQ ID NO: 6; probe sequence CTGGCCATCGCCTTGCCCA, designated herein as SEQ ID NO: 7) was used to measure mRNA levels. Ataxin 2 mRNA levels were adjusted according to total RNA content, as measured by RIBOGREEN®. Results are presented as percent inhibition of ataxin 2, relative to untreated control cells.

The chimeric antisense oligonucleotides in the Tables below were designed as 5-10-5 MOE gapmers. The gapmers are 20 nucleosides in length, wherein the central gap segment is comprised of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human ataxin 2 mRNA, designated herein as SEQ ID NO: 1 (GENBANK Accession No. NM_002973.3) or the human ataxin 2 genomic sequence, designated herein as SEQ ID NO: 2 (the complement of GENBANK Accession No. NT_009775.17 truncated from nucleotides 2465000 to 2616000). Some oligonucleotides do not target either SEQ ID NO: 1 or SEQ ID NO: 2, but instead target a variant gene sequence, SEQ ID NO: 3 (GENBANK Accession No. BX410018.2). 'n/a' indicates that the antisense oligonucleotide does not target that particular gene sequence with 100% complementarity.

TABLE 1

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564118 | 606 | 625 | CCGGCTCGCACGCCGGGCGG | 57 | 2596 | 2615 | 11 |
| 564119 | 612 | 631 | CATACACCGGCTCGCACGCC | 63 | 2602 | 2621 | 12 |
| 564120 | 637 | 656 | GGCTTCAGCGACATGGTGAG | 78 | 2627 | 2646 | 13 |
| 564121 | 880 | 899 | CGACCTCTGCCCAGGCCGGG | 67 | n/a | n/a | 14 |
| 564122 | 935 | 954 | TGCATAGATTCCATCAAAAG | 90 | 47454 | 47473 | 15 |
| 564123 | 959 | 978 | AAGTATATGAACCATCCTCA | 67 | 47478 | 47497 | 16 |
| 564124 | 997 | 1016 | TTCACTTGTACTTCACATTT | 85 | 48696 | 48715 | 17 |
| 564125 | 1084 | 1103 | TCTGTACTTTTCTCATGTGC | 88 | 49258 | 49277 | 18 |
| 564126 | 1090 | 1109 | CTGGATTCTGTACTTTTCTC | 89 | 49264 | 49283 | 19 |
| 564127 | 1123 | 1142 | CTCTCCATTATTTCTTCACG | 92 | 49297 | 49316 | 20 |
| 564128 | 1168 | 1187 | TCTTTAAACTGTACCACAAC | 86 | 49342 | 49361 | 21 |
| 564129 | 1210 | 1229 | GAGTCAGTAAAAGCATCTCT | 84 | n/a | n/a | 22 |
| 564130 | 1264 | 1283 | CAGGGCTCCAGGTCCTTCTC | 83 | 76401 | 76420 | 23 |
| 564131 | 1270 | 1289 | GCATCCCAGGGCTCCAGGTC | 86 | 76407 | 76426 | 24 |
| 564132 | 1363 | 1382 | TCTTCATTATATCGAAACAT | 84 | 80718 | 80737 | 25 |
| 564133 | 1477 | 1496 | GCTAACTGGTTTGCCCTTGC | 98 | 81637 | 81656 | 26 |
| 564134 | 1556 | 1575 | GTATTTTTCTTCCTCACTCC | 82 | 81716 | 81735 | 27 |
| 564135 | 1562 | 1581 | TGCTGTGTATTTTTCTTCCT | 89 | 81722 | 81741 | 28 |
| 564136 | 1748 | 1767 | GAAATCTGAAGTGTGAGAAG | 61 | 83359 | 83378 | 29 |
| 564137 | 1789 | 1808 | CCTCCATTAACTACTCTTTG | 90 | 83400 | 83419 | 30 |
| 564138 | 1795 | 1814 | GGAACACCTCCATTAACTAC | 66 | n/a | n/a | 31 |
| 564139 | 1807 | 1826 | GGCGATGGCCAGGGAACACC | 95 | 85303 | 85322 | 32 |
| 564140 | 1844 | 1863 | GTAGCGAGAAGGTGGGCGAG | 88 | 85340 | 85359 | 33 |
| 564141 | 1862 | 1881 | AGAGTTGGGACCTGACTGGT | 84 | 85358 | 85377 | 34 |
| 564142 | 1868 | 1887 | TGGAAGAGAGTTGGGACCTG | 84 | 85364 | 85383 | 35 |
| 564143 | 1963 | 1982 | GGAGCTGGAGAACCATGAGC | 91 | 85459 | 85478 | 36 |
| 564144 | 1969 | 1988 | GAGACAGGAGCTGGAGAACC | 86 | 85465 | 85484 | 37 |
| 564145 | 2101 | 2120 | TTGTGGGATACAAATTCTAG | 56 | 88211 | 88230 | 38 |
| 564146 | 2185 | 2204 | GGAACCCCACTGACCACTGA | 70 | n/a | n/a | 39 |
| 564147 | 2401 | 2420 | TCTTGAAGCCTGGAATCTTT | 61 | 91671 | 91690 | 40 |
| 564148 | 2560 | 2579 | AACCTAAAATCATTCTTAAA | 21 | n/a | n/a | 41 |
| 564149 | 2596 | 2615 | AGTTGATCCATAGATTCAGA | 74 | 112905 | 112924 | 42 |
| 564150 | 2704 | 2723 | CTGGTACAGTTGCTGCTGCT | 91 | 113013 | 113032 | 43 |
| 564151 | 2710 | 2729 | CTGCCACTGGTACAGTTGCT | 85 | 113019 | 113038 | 44 |
| 564152 | 2899 | 2918 | TTTGCATTGGGATTCAATGT | 76 | 114859 | 114878 | 45 |
| 564153 | 2938 | 2957 | GAAGGCTTTGGCTGAGAGAA | 66 | n/a | n/a | 46 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564154 | 2944 | 2963 | GTAGTAGAAGGCTTTGGCTG | 71 | n/a | n/a | 47 |
| 564155 | 2995 | 3014 | TGACCCACCATAGATGGGCT | 38 | 115850 | 115869 | 48 |
| 564156 | 3097 | 3116 | GGTATTGGGTATAAAGGTTG | 57 | n/a | n/a | 49 |
| 564157 | 3103 | 3122 | GTCATAGGTATTGGGTATAA | 76 | 116339 | 116358 | 50 |
| 564158 | 3331 | 3350 | GGATGCTGAGACTGATAATG | 54 | n/a | n/a | 51 |
| 564159 | 3337 | 3356 | ACATGAGGATGCTGAGACTG | 63 | n/a | n/a | 52 |
| 564160 | 3472 | 3491 | AATTTGGGACATGCATACAT | 23 | n/a | n/a | 53 |
| 564161 | 3490 | 3509 | GTCTCCTTGTTGTATGGTAA | 76 | 136963 | 136982 | 54 |
| 564162 | 3658 | 3677 | TGAACAGGACTGGGTGCAGG | 41 | 144433 | 144452 | 55 |
| 564163 | 3715 | 3734 | GACTGCTGCTGTGGACTGGC | 69 | 145447 | 145466 | 56 |
| 564164 | 3903 | 3922 | CTGACTGTACATGAGCCTGA | 50 | 147818 | 147837 | 57 |
| 564165 | 3909 | 3928 | CCATTCCTGACTGTACATGA | 69 | 147824 | 147843 | 58 |
| 564166 | 3927 | 3946 | CAGTTGGATGAGAAGGAACC | 58 | 147842 | 147861 | 59 |
| 564167 | 3933 | 3952 | CATGGGCAGTTGGATGAGAA | 29 | 147848 | 147867 | 60 |
| 564168 | 3971 | 3990 | ACCGCCGGGTGGCTGTGTCG | 40 | 147886 | 147905 | 61 |
| 564169 | 3993 | 4012 | TTTGAGCGAGGGCGGCCTGG | 19 | 147908 | 147927 | 62 |
| 564170 | 4005 | 4024 | GCTGTAGTGCACTTTGAGCG | 73 | 147920 | 147939 | 63 |
| 564171 | 4017 | 4036 | AGACTGGAATGGGCTGTAGT | 58 | 147932 | 147951 | 64 |
| 564172 | 4029 | 4048 | GCGCTGTTGTCGAGACTGGA | 74 | 147944 | 147963 | 65 |
| 564173 | 4035 | 4054 | GGAAATGCGCTGTTGTCGAG | 69 | 147950 | 147969 | 66 |
| 564174 | 4064 | 4083 | GGCTTGTACTGAAGGGTGCG | 23 | n/a | n/a | 67 |
| 564175 | 4070 | 4089 | GTGGTGGGCTTGTACTGAAG | 35 | n/a | n/a | 68 |
| 564176 | 4076 | 4095 | CTGTTGGTGGTGGGCTTGTA | 22 | 148827 | 148846 | 69 |
| 564177 | 4082 | 4101 | CAACTGCTGTTGGTGGTGGG | 39 | 148833 | 148852 | 70 |
| 564178 | 4088 | 4107 | GCCTTACAACTGCTGTTGGT | 62 | 148839 | 148858 | 71 |
| 564179 | 4106 | 4125 | TTCGGTTCCTCCAGGGCAGC | 72 | 148857 | 148876 | 72 |
| 564180 | 4166 | 4185 | TTCTAGTTTTCTGTGCTTCC | 72 | 148917 | 148936 | 73 |
| 564181 | 4367 | 4386 | AATAAATAACTTCCAGTTTC | 59 | 149118 | 149137 | 74 |
| 564182 | 4429 | 4448 | GAATCACTCTTGTTACTTCT | 78 | 149180 | 149199 | 75 |
| 564183 | 4435 | 4454 | CAGCAAGAATCACTCTTGTT | 85 | 149186 | 149205 | 76 |
| 564184 | 4551 | 4570 | TTTATAAATAATAATCCGTC | 4 | 149302 | 149321 | 77 |
| 564185 | 4593 | 4612 | AAGTTGAACCACTGTAGACA | 60 | 149344 | 149363 | 78 |
| 564186 | n/a | n/a | ATCGGCCACCACCCGCGCGC | 55 | 3683 | 3702 | 79 |
| 564187 | n/a | n/a | CAAAGGGTTAATTAGGATCT | 66 | 85057 | 85076 | 80 |
| 564188 | n/a | n/a | CCCAAAGGGTTAATTAGGAT | 94 | 85059 | 85078 | 81 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564189 | n/a | n/a | AGGACAGTCATTTGATTTGT | 72 | 85166 | 85185 | 82 |
| 564190 | n/a | n/a | CTTTGAGGACAGTCATTTGA | 70 | 85171 | 85190 | 83 |
| 564191 | n/a | n/a | CTGACAGAACAAATGATATG | 17 | 85284 | 85303 | 84 |
| 564192 | n/a | n/a | TATTGGGTATAAAGGCTTGA | 31 | 116331 | 116350 | 85 |
| 564193 | n/a | n/a | GGTATTGGGTATAAAGGCTT | 78 | 116333 | 116352 | 86 |
| 564194 | n/a | n/a | CTCTTTTACGCATACAGGCA | 74 | 147789 | 147808 | 87 |
| 564195 | n/a | n/a | AGGAAGGCCAACTGAGTCCT | 70 | 148258 | 148277 | 88 |

TABLE 2

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564158 | 3331 | 3350 | GGATGCTGAGACTGATAATG | 61 | n/a | n/a | 51 |
| 564196 | 70 | 89 | GGTCAGACGGAAGCAGAACG | 9 | 2060 | 2079 | 89 |
| 564197 | 218 | 237 | CCACCTGGCTGCGGCGAAGC | 12 | 2208 | 2227 | 90 |
| 564198 | 392 | 411 | GCCGTTGCCGTTGCTACCAA | 80 | 2382 | 2401 | 91 |
| 564199 | 616 | 635 | GGCCCATACACCGGCTCGCA | 79 | 2606 | 2625 | 92 |
| 564200 | 636 | 655 | GCTTCAGCGACATGGTGAGG | 81 | 2626 | 2645 | 93 |
| 564201 | 732 | 751 | GGACATTGGCAGCCGCGGGC | 83 | 2722 | 2741 | 94 |
| 564202 | 929 | 948 | GATTCCATCAAAAGAAATCG | 67 | n/a | n/a | 95 |
| 564203 | 969 | 988 | CAACTGATGTAAGTATATGA | 45 | 47488 | 47507 | 96 |
| 564204 | 1053 | 1072 | CCAAATCACACTTCGGACTG | 74 | n/a | n/a | 97 |
| 564205 | 1073 | 1092 | CTCATGTGCGGCATCAAGTA | 79 | 49247 | 49266 | 98 |
| 564206 | 1138 | 1157 | CATTTGAACAAAATACTCTC | 71 | 49312 | 49331 | 99 |
| 564207 | 1219 | 1238 | CTGATAGCAGAGTCAGTAAA | 72 | 76356 | 76375 | 100 |
| 564208 | 1521 | 1540 | GGGCCACTCGAGCTTTGTAC | 88 | 81681 | 81700 | 101 |
| 564209 | 1628 | 1647 | AGGAATATATTTATTTTCCC | 52 | 83239 | 83258 | 102 |
| 564210 | 1693 | 1712 | CCCATACGCGGTGAATTCTG | 91 | 83304 | 83323 | 103 |
| 564211 | 1713 | 1732 | TGGAGCCCGATCCAGGCTGG | 77 | 83324 | 83343 | 104 |
| 564212 | 1733 | 1752 | AGAAGTGGATCTTGATGGCA | 54 | 83344 | 83363 | 105 |
| 564213 | 1957 | 1976 | GGAGAACCATGAGCAGAGGG | 83 | 85453 | 85472 | 106 |
| 564214 | 2002 | 2021 | GGCCCTTCTGAAGACATGCG | 85 | n/a | n/a | 107 |
| 564215 | 2079 | 2098 | CACTGGATATGGAACCCCTC | 84 | 88189 | 88208 | 108 |
| 564216 | 2099 | 2118 | GTGGGATACAAATTCTAGGC | 94 | 88209 | 88228 | 109 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564217 | 2177 | 2196 | ACTGACCACTGATGACCACG | 67 | 88287 | 88306 | 110 |
| 564218 | 2215 | 2234 | CTGGGTCTATGAGTTTTAGG | 67 | 91099 | 91118 | 111 |
| 564219 | 2291 | 2310 | TGGAATAATACCAGCTTGGG | 84 | 91175 | 91194 | 112 |
| 564220 | 2311 | 2330 | GGCATGGCAACAGCTTCAGT | 81 | 91195 | 91214 | 113 |
| 564221 | 2331 | 2350 | TAGGAGATGCAGCTGGAATA | 71 | 91215 | 91234 | 114 |
| 564222 | 2397 | 2416 | GAAGCCTGGAATCTTTAGCC | 69 | n/a | n/a | 115 |
| 564223 | 2426 | 2445 | CCCTGCAGGAGAGTTCTGCC | 75 | 91696 | 91715 | 116 |
| 564224 | 2582 | 2601 | TTCAGAAGTAGAACTTGGCT | 76 | 112891 | 112910 | 117 |
| 564225 | 2652 | 2671 | CAATTTTGTCTTTGATCAAA | 56 | 112961 | 112980 | 118 |
| 564226 | 2757 | 2776 | TGTTACTAAGTATTGAAGGG | 53 | 113066 | 113085 | 119 |
| 564227 | 2787 | 2806 | AAGTGACCTCAGGTCCCCTC | 83 | 113096 | 113115 | 120 |
| 564228 | 2883 | 2902 | ATGTTGATTTCCTAACTTGC | 53 | 114843 | 114862 | 121 |
| 564229 | 3019 | 3038 | GTATAAACTGGAGTTGGCTG | 75 | 115874 | 115893 | 122 |
| 564230 | 3039 | 3058 | GTGCAAAACAAACAGGCTGA | 79 | 115894 | 115913 | 123 |
| 564231 | 3059 | 3078 | GACTGGATACATCATATTTG | 18 | 115914 | 115933 | 124 |
| 564232 | 3082 | 3101 | GGTTGCACGCCTGGGCTCAC | 74 | n/a | n/a | 125 |
| 564233 | 3102 | 3121 | TCATAGGTATTGGGTATAAA | 50 | 116338 | 116357 | 126 |
| 564234 | 3122 | 3141 | TTGATTCACTGGCATGGGCG | 77 | 116358 | 116377 | 127 |
| 564235 | 3180 | 3199 | GATGATGCTGGTCTTGCCGC | 49 | 130944 | 130963 | 128 |
| 564236 | 3373 | 3392 | ATCATTCTAGCATTACCCTG | 61 | 131454 | 131473 | 129 |
| 564237 | 3408 | 3427 | ATACTAAACCAGGCTGGGCG | 71 | 131489 | 131508 | 130 |
| 564238 | 3464 | 3483 | ACATGCATACATCGCATGCG | 32 | n/a | n/a | 131 |
| 564239 | 3505 | 3524 | TAGAAAGAAGGGCTTGTCTC | 67 | 136978 | 136997 | 132 |
| 564240 | 3545 | 3564 | CGCATACTGCTGAGCAAGGG | 79 | 144320 | 144339 | 133 |
| 564241 | 3597 | 3616 | TAGCTGAAGGCTGAGGGTGT | 43 | 144372 | 144391 | 134 |
| 564242 | 3630 | 3649 | CACCATGTTGGCTTTGCTGC | 81 | 144405 | 144424 | 135 |
| 564243 | 3650 | 3669 | ACTGGGTGCAGGATGACTTC | 36 | 144425 | 144444 | 136 |
| 564244 | 3729 | 3748 | CGTGGTAAATGGCTGACTGC | 50 | 145461 | 145480 | 137 |
| 564245 | 3772 | 3791 | TTGGAGGCAGGTGTCATGGA | 36 | 145504 | 145523 | 138 |
| 564246 | 3938 | 3957 | TGGCGCATGGGCAGTTGGAT | 67 | 147853 | 147872 | 139 |
| 564247 | 3994 | 4013 | CTTTGAGCGAGGGCGGCCTG | 29 | 147909 | 147928 | 140 |
| 564248 | 4021 | 4040 | GTCGAGACTGGAATGGGCTG | 54 | 147936 | 147955 | 141 |
| 564249 | 4225 | 4244 | ATTCCTATTGGATGTTACAA | 65 | 148976 | 148995 | 142 |
| 564250 | 4252 | 4271 | ATCTTCCACTGCAAGTGAAC | 77 | 149003 | 149022 | 143 |
| 564251 | 4306 | 4325 | TATGGAATTATGGAATAGCC | 65 | 149057 | 149076 | 144 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564252 | 4433 | 4452 | GCAAGAATCACTCTTGTTAC | 77 | 149184 | 149203 | 145 |
| 564253 | 4581 | 4600 | TGTAGACAGTGATCACCTCA | 77 | 149332 | 149351 | 146 |
| 564254 | n/a | n/a | GGCCAAGGCCCACTTGTCTC | 54 | 3485 | 3504 | 147 |
| 564255 | n/a | n/a | CACTGCGGCCTCGAACAGCA | 81 | 3709 | 3728 | 148 |
| 564263 | n/a | n/a | AAATTCCTCATTTTCTTTTC | 68 | 26924<br>27239 | 26943<br>27258 | 149 |
| 564264 | n/a | n/a | GTTATAGTAATCTGTAATCA | 71 | 36133<br>36239 | 36152<br>36258 | 150 |
| 564265 | n/a | n/a | AGGATTGTAAAATGATACAG | 47 | 65107<br>65148 | 65126<br>65167 | 151 |
| 564266 | n/a | n/a | GTAGGATTGTAAAATGATAC | 64 | 65109<br>65150 | 65128<br>65169 | 152 |
| 564267 | n/a | n/a | TTATATATGTAAATTATATC | 9 | 95228<br>95288 | 95247<br>95307 | 153 |
| 564268 | n/a | n/a | AACCACTGATTTATACACTT | 88 | 95260<br>95320 | 95279<br>95339 | 154 |
| 564269 | n/a | n/a | TTAAAAACCACTGATTTATA | 17 | 95265<br>95325 | 95284<br>95344 | 155 |
| 564270 | n/a | n/a | ATATAGCACTCTGCTGTATT | 83 | 99282<br>99340 | 99301<br>99359 | 156 |
| 564271 | n/a | n/a | TACCAAGCTTGTGGCTTGGG | 32 | 137342<br>137420 | 137361<br>137439 | 157 |
| 564272 | n/a | n/a | TTATACCAAGCTTGTGGCTT | 52 | 137345<br>137423 | 137364<br>137442 | 158 |

TABLE 3

Inhibition of ataxin 2 mRNA by 5-10-5 MOE gapmers targeting SEQ ID NO: 3

| ISIS No | SEQ ID NO: 3 Start Site | SEQ ID NO: 3 Stop Site | Sequence | % inhibition | SEQ ID NO |
|---|---|---|---|---|---|
| 564256 | 311 | 330 | CCTCGATGTTCCACAGGCGC | 83 | 159 |
| 564257 | 715 | 734 | GAGTTCACCTGCATCCAGGG | 81 | 160 |
| 564258 | 736 | 755 | TCCAGTTCCCTCATTGGCTG | 27 | 161 |
| 564259 | 771 | 790 | GGTTCCATCCATTAGATACG | 52 | 162 |
| 564260 | 791 | 810 | TTAAACGAAACATATCTTTG | 10 | 163 |
| 564261 | 815 | 834 | GCCCCTGCGCCATAATTTTT | 3 | 164 |
| 564262 | 835 | 854 | ATAAACTGCTTTCAACGGTG | 2 | 165 |

Example 2: Dose-Dependent Antisense Inhibition of Human Ataxin 2 in HepG2 Cells by MOE Gapmers Gapmers from Example 1 exhibiting significant in vitro inhibition of ataxin 2 mRNA were selected and tested at various doses in HepG2 cells. Cells were plated at a density of 20,000 cells per well and transfected using electroporation with 0.625 μM, 1.250 μM, 2.500 μM, 5.000 μM and 10.000 μM concentrations of antisense oligonucleotide, as specified in the Table below. After a treatment period of approximately 16 hours, RNA was isolated from the cells and ataxin 2 mRNA levels were measured by quantitative real-time PCR. Human primer probe set RTS3642 was used to measure mRNA levels. Ataxin 2 mRNA levels were adjusted according to total RNA content, as measured by RIBOGREEN®. Results are presented as percent inhibition of ataxin 2, relative to untreated control cells.

The half maximal inhibitory concentration ($IC_{50}$) of each oligonucleotide is also presented. Ataxin 2 mRNA levels were significantly reduced in a dose-dependent manner in antisense oligonucleotide treated cells.

TABLE 4

| Dose response assay | | | | | | |
|---|---|---|---|---|---|---|
| ISIS No | 0.625 μM | 1.250 μM | 2.500 μM | 5.000 μM | 10.000 μM | $IC_{50}$ (μM) |
| 564133 | 89 | 95 | 98 | 98 | 97 | <0.6 |
| 564188 | 52 | 72 | 81 | 88 | 90 | <0.6 |
| 564127 | 42 | 62 | 65 | 85 | 91 | 0.8 |
| 564150 | 39 | 63 | 74 | 86 | 91 | 0.8 |
| 564143 | 37 | 60 | 76 | 84 | 94 | 0.9 |
| 564122 | 25 | 53 | 69 | 85 | 88 | 1.3 |
| 564126 | 23 | 48 | 61 | 78 | 89 | 1.7 |
| 564144 | 12 | 35 | 53 | 71 | 85 | 2.4 |
| 564135 | 22 | 35 | 53 | 73 | 86 | 2.1 |
| 564125 | 33 | 44 | 64 | 78 | 85 | 1.5 |
| 564129 | 31 | 42 | 54 | 71 | 77 | 1.9 |
| 564216 | 50 | 67 | 82 | 86 | 94 | <0.6 |
| 564210 | 33 | 48 | 72 | 80 | 94 | 1.3 |
| 564208 | 30 | 40 | 67 | 75 | 87 | 1.6 |
| 564268 | 35 | 52 | 69 | 81 | 85 | 1.2 |

Example 3: Antisense Inhibition of Human Ataxin 2 in a SCA2 BAC Mouse Model

Gapmers from Example 1 exhibiting significant in vitro inhibition of ataxin 2 mRNA were selected and tested in vivo in a SCA2[Q22]-BAC mouse model. This mouse model was created in the Pulst laboratory (University of Utah, Salt Lake City), using mice of FVB/B6 hybrid background, for the study of spinocerebella ataxia type 2 (SCA2). These mice possess the entire 176 kb human ATXN2 gene region, including the 16 kb upstream sequence and the 2.5 kb downstream sequence.

Treatment

Groups of 3 mice each were administered normal saline (0.9%) or antisense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 μL mark with either normal saline (0.9%) or antisense oligonucleotide (250 μg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 μL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen). cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 μL, consisting of 15 ng cDNA, 2 μL of each primer (0.3 μM final), and 10 μL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis.

The results from the RNA analysis for mouse and human ataxin 2 are presented in the Table below. As indicated, some of the ISIS oligonucleotides decreased human ataxin 2 mRNA in the brains of the mice.

TABLE 5

| Percent inhibition of ataxin 2 mRNA compared to the saline (0.9%) control in SCA[Q22]-BAC mice | | |
|---|---|---|
| ISIS No | Human ataxin 2 | Mouse ataxin 2 |
| 564122 | 10 | 15 |
| 564127 | 46 | 65 |
| 564133 | 60 | 62 |
| 564150 | 21 | 53 |
| 564188 | 9 | 23 |
| 564216 | 21 | 55 |

Example 4: Antisense Inhibition of Human Ataxin 2 in an ATXN2-Q127 Mouse Model Gapmers from Example 1 exhibiting significant in vitro inhibition of ataxin 2 mRNA were selected and tested in vivo in an ATXN2-Q127 mouse model. This mouse model (Hansen, S. T. et al., Human. Molecular Genetics 2012. 1-13) expresses the full-length-mutant ATXN20127 complementary DNA under the regulation of the Purkinje cell protein-2 (Pcp2) promoter. This model shows an early-onset progressive motor impairment phenotype accompanied by the formation of diffuse cytoplasmic aggregates in cerebellar Purkinje cells.

Treatment

Groups of 3 mice each were administered normal saline (0.9%) or antisense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 μL mark with either normal saline (0.9%) or antisense oligonucleotide (250 μg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 μL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen), cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 μL, consisting of 15 ng cDNA, 2 μL of each primer (0.3 μM final), and 10 μL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis. All mRNA levels were normalized to the housekeeping gene, actin.

The results from the RNA analysis for mouse and human ataxin 2 are presented in the Table below. As indicated, some of the ISIS oligonucleotides decreased human ataxin 2 mRNA in the brains of the mice.

qPCR analysis of the marker for microgliosis, AIF/Iba1, to measure inflammation, was also performed. The results are presented in the Table below.

TABLE 6

Percent inhibition of ataxin 2 mRNA compared to the saline (0.9%) control in ATXN2-Q127 mice

| ISIS No | Human | Mouse |
|---|---|---|
| 564133 | 64 | 52 |
| 564127 | 62 | 49 |
| 564216 | 46 | 40 |
| 564210 | 39 | 48 |

TABLE 7

Percent Iba1 mRNA level increase compared to the saline (0.9%) control in ATXN2-Q127 mice

| ISIS No | Iba1 |
|---|---|
| 564133 | 9 |
| 564127 | 49 |
| 564216 | 16 |
| 564210 | 96 |

Example 4: Dose-Dependent Antisense Inhibition of Human Ataxin 2 in an ATXN2-Q127 Mouse Model ISIS 564133 was tested in different doses in the ATXN2-Q127 mouse model.

Treatment

Groups of 3 mice each were administered normal saline (0.9%) or ISIS 564133 via intracerebroventricular injections dosed at 50 μg, 100 μg, 200 μg, 250 μg, or 300 μg. The mice were administered in the same manner as described in the studies above and monitored daily.

RNA Analysis

After 7 days, the mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for mouse and human ataxin 2 are presented in the Table below.

TABLE 8

Percent inhibition of ataxin 2 mRNA compared to the saline (0.9%) control in ATXN2-Q127 mice

| Dose (μg) | Human ataxin 2 | Mouse ataxin 2 |
|---|---|---|
| 50 | 60 | 47 |
| 100 | 84 | 35 |
| 200 | 85 | 67 |
| 250 | 79 | 62 |
| 300 | 73 | 41 |

Example 5: Time-Dependent Antisense Inhibition of Human Ataxin 2 in an ATXN2-Q127 Mouse Model ISIS 564133 was administered and mRNA level reduction was tested in different time points in the ATXN2-Q127 mouse model.

Treatment

Groups of 3 mice each were administered normal saline (0.9%) or ISIS 564133 via intracerebroventricular injections dosed at 200 μg. The mice were administered in the same manner as described in the studies above and monitored daily.

RNA Analysis

After 9 days, 18 days, 27 days, and 84 days, groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for human ataxin 2 are presented in the Table below. Western analysis of the corresponding protein samples was performed and confirmed the qPCR results.

TABLE 9

| Ataxin 2 mRNA levels in ATXN2-Q127 mice | |
|---|---|
| Time Point | ATXN2 expression relative to actin |
| saline (0.9%) control | 8.4 |
| 9 days | 2.9 |
| 18 days | 0.9 |
| 27 days | 1.4 |
| 84 days | 2.7 |

Immunohistochemical staining of cerebellar Purkinje cells on day 7 was performed using rabbit anti-oligonucleotide antibody generated in-house. The results demonstrated that ISIS oligonucleotide localized in cerebellar Purkinje cells of ATXN-Q127 mice.

Example 6: Effect of Antisense Inhibition of Human Ataxin 2 in an ATXN2-Q127 Mouse Model ISIS oligonucleotide was administered in the ATXN2-Q127 mouse model and wild-type mice. On day 3, motor performance was evaluated using the rotarod test.

Groups of ATXN2-Q127 mice were administered normal saline (0.9%) or ISIS 564133 at 50 μg, 100 μg, or 200 μg via intracerebroventricular injections in the same manner as described in the studies above. Groups of wild-type mice were administered normal saline (0.9%) or ISIS oligonucleotide at 200 μg via intracerebroventricular injections dosed in the same manner as described in the studies above. Groups of ATXN2-Q127 mice were administered normal saline (0.9%) or ISIS 546127 or ISIS 564216 at 200 μg via intracerebroventricular injections dosed in the same manner as described in the studies above. After 6 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20%.

TABLE 10

| Rotarod performance test in ATXN2-Q127 mice | | | |
|---|---|---|---|
| Strain of mice | Number of mice | Treatment | Latency to fall (seconds) |
| WT | 10 | saline (0.9%) control | 199 |
| | 10 | ISIS 564133 (200 μg) | 189 |
| ATXN-Q127 | 8 | saline (0.9%) control | 127 |
| | 15 | ISIS 564133 (50 μg) | 149 |
| | 16 | ISIS 564133 (100 μg) | 141 |
| | 9 | ISIS 564133 (200 μg) | 100 |
| ATXN-Q127 | 15 | saline (0.9%) control | 130 |
| | 13 | ISIS 564127 (200 μg) | 150 |
| | 15 | ISIS 564216 (200 μg) | 156 |

Example 7: Effect of Antisense Inhibition of Human Ataxin 2 in an ATXN2-Q127 Mouse Model ISIS oligonucleotide was administered in the ATXN2-Q127 mouse model and wild-type mice. Cerebellar expression of ataxin 2, as well as several Purkinje cell (PC) genes, was assessed.

Groups of ATXN2-Q127 mice were administered normal saline (0.9%) or ISIS 564133 at 200 μg via intracerebroventricular injections dosed in the same manner as described in the studies above. Groups of wild-type mice were administered normal saline (0.9%) or ISIS 564133 at 200 μg via intracerebroventricular injections dosed in the same manner as described in the studies above. After 5 weeks, the mice were euthanized and cerebellar expression of various gene mRNA levels was assessed.

RNA Analysis

Groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin. RNA levels of human ataxin 2, murine ataxin 2, Pcp2, Calb1, Rgs8, and Fam107b were measured. Transcription changes in several of these PC-specific genes have been demonstrated to progressively decrease in models of SCA2 (Hansen, S. T. et al., Hum. Mol. Genet. 2013. 22: 271-283).

The results from the RNA analysis are presented in the Table below and demonstrate that treatment with ISIS oligonucleotides targeting ataxin 2 increased the expression levels of all the PC-specific genes compared to the transgenic control group.

TABLE 11

| PC-specific mRNA levels in ATXN2-Q127 mice | | | |
|---|---|---|---|
| | WT | ATXN-Q127 | |
| | saline (0.9%) control | saline (0.9%) control | ISIS 564133 (200 μg) |
| human ataxin 2 | 0.21 | 3.57 | 1.31 |
| murine ataxin 2 | 0.79 | 0.84 | 0.6 |
| Pcp2 | 0.77 | 0.36 | 0.48 |
| Rgs8 | 1.45 | 0.25 | 0.35 |
| Calb1 | 1.14 | 0.5 | 0.71 |
| Fam107b | 1.41 | 0.7 | 0.9 |

Example 8: Effect of Antisense Inhibition of Human Ataxin 2 in an ATXN2-Q127 Mouse Model ISIS oligonucleotide was administered in the ATXN2-Q127 mouse model and wild-type mice. Motor performance was evaluated using the rotarod test.

Groups of ATXN2-Q127 mice (7.5 weeks of age) were administered normal saline (0.9%) or ISIS 546127 or ISIS 564216 at 200 μg via intracerebroventricular injections dosed in the same manner as described in the studies above. After 5 weeks and 9 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20% on week 5 and about 27% on week 9.

TABLE 12

| Weeks after injection | | ISIS 564127 | ISIS 564216 | Saline control |
|---|---|---|---|---|
| Week 5 | DAY 3 | 137 | 145 | 123 |
| | DAY 4 | 140 | 141 | 119 |
| | DAY 5 | 155 | 154 | 131 |
| Week 9 | DAY 3 | 131 | 149 | 104 |
| | DAY 4 | 125 | 139 | 104 |
| | DAY 5 | 134 | 139 | 112 |

Rotarod performance test in ATXN2-Q127 mice. (mean latency to fall, in seconds)

TABLE 12-continued

Example 9: Effect of Antisense Inhibition of Human Ataxin 2 in an ATXN2-Q127 Mouse Model ISIS oligonucleotide was administered in the ATXN2-Q127 mouse model. Motor performance was evaluated using the rotarod test.

Seven week old ATXN2-Q127 mice were subjected to the rotarod test, then divided into two groups of 30 mice each, such that average rotarod performance, average weights, and sex composition were equal across both groups. At 8 weeks of age, one group of mice received normal saline via intracerebroventricular (ICV) injection and one group rceived ISIS 564216 at 210 μg via ICV injection, dosed in the same manner as described in the studies above. Five weeks later (13 weeks of age), the mice were again subjected to the rotarod test. Six weeks post injection (14 weeks of age), the mice received a second ICV injection, identical to the injection received at 8 weeks of age. Five weeks later (19 weeks of age, 11 weeks after the first ICV injection), the mice were subjected to a third rotarod test.

Rotarod Test

The accelerating rotarod test was performed on the Rotamex rotarod. Rotarod testing was conducted over five days. On the first day, mice were acclimated to the technician by being handled by the technician three times, 5 minutes each time. On the second day, mice were introduced to the rotarod three times, 10 minutes each time at a speed ranging from 0 to 10 RPM. On each of days 3-5, mice were placed on the rotarod at a speed of 0 RPM, then the rotarod was accelerated to 40 RPM over 6 minutes, and this was done for each mouse three times. The three total trials per day were used to calculate a mean value of "latency to fall" per day, in seconds. Latency to fall is defined as the amount of time before the animal falls from the rotarod. It was recorded automatically, when the mouse no longer interrupted infrared beams directed above the rotarod. The time to first passive rotation (when mice stop walking and hold on and revolve with the rod) is also automatically recorded, and generally reflects the latency to fall time.

The results from the rotarod test are presented as the average for each treatment group in the Table below. As shown in the Table below, treatment with ASO improved rotarod performance.

TABLE 13

| Rotarod performance test in ATXN2-Q127 mice | | | | |
|---|---|---|---|---|
| Treatment | Weeks after $1^{st}$ injection | Weeks after $2^{nd}$ injection | Testing day | Latency to fall (s) |
| Saline | 5 | n/a | 3 | 218.5 |
| | | | 4 | 240.9 |
| | | | 5 | 236.5 |

TABLE 13-continued

| Rotarod performance test in ATXN2-Q127 mice | | | | |
|---|---|---|---|---|
| Treatment | Weeks after 1st injection | Weeks after 2nd injection | Testing day | Latency to fall (s) |
| Isis No. 564216 | 5 | n/a | 3 | 240.6 |
| | | | 4 | 257.9 |
| | | | 5 | 259.6 |
| Saline | 11 | 5 | 3 | 216.2 |
| | | | 4 | 198.7 |
| | | | 5 | 212.1 |
| Isis No. 564216 | 11 | 5 | 3 | 194.4 |
| | | | 4 | 226.0 |
| | | | 5 | 242.8 |

What is claimed is:

1. An oligomeric compound comprising a modified oligonucleotide consisting of 12 to 30 linked nucleosides, wherein the nucleobase sequence of the modified oligonucleotide comprises a portion of at least 12 contiguous nucleobases, wherein the portion is complementary to an equal length portion of nucleobases 4581-4612 of SEQ ID NO: 1, wherein the modified oligonucleotide comprises at least one modification selected from a modified sugar moiety and a modified internucleoside linkage.

2. An oligomeric compound comprising a modified oligonucleotide consisting of 12 to 30 linked nucleosides and having a nucleobase sequence comprising at least 12 contiguous nucleobases of the nucleobase sequence of SEQ ID NO: 78 or 146, wherein the modified oligonucleotide comprises at least one modification selected from a modified sugar moiety and a modified internucleoside linkage.

3. The oligomeric compound of claim 1, wherein the modified oligonucleotide is at least 95% or is 100% complementary to an equal length portion of an Ataxin 2 RNA transcript.

4. The oligomeric compound of claim 3, wherein the Ataxin 2 RNA transcript has the nucleobase sequence of SEQ ID NO: 1, SEQ ID NO: 2, or SEQ ID NO: 3.

5. The oligomeric compound of claim 1, wherein the modified oligonucleotide consists of 12 to 25, 12 to 22, 13 to 30, 14 to 20, 14 to 30, 15 to 25, 15 to 30, 16 to 30, 17 to 30, 18 to 22, 18 to 30, 19 to 21, 19 to 30, or 20 to 30 linked nucleosides.

6. The oligomeric compound of claim 1, wherein the modified oligonucleotide consists of 20 linked nucleosides.

7. The oligomeric compound of claim 1, consisting of a single-stranded modified oligonucleotide.

8. The oligomeric compound of claim 1, wherein at least one internucleoside linkage of the modified oligonucleotide is a modified internucleoside linkage.

9. The oligomeric compound of claim 8, wherein at least one modified internucleoside linkage is a phosphorothioate internucleoside linkage.

10. The oligomeric compound of claim 9, wherein at least one internucleoside linkage of the modified oligonucleotide is a phosphodiester internucleoside linkage.

11. The oligomeric compound of claim 9, wherein each modified internucleoside linkage is a phosphorothioate internucleoside linkage.

12. The oligomeric compound of claim 1, wherein at least one nucleoside of the modified oligonucleotide comprises a modified nucleobase.

13. The oligomeric compound of claim 12, wherein the modified nucleobase is a 5-methylcytosine.

14. The oligomeric compound of claim 1, wherein at least one nucleoside of the modified oligonucleotide comprises a modified sugar moiety.

15. The oligomeric compound of claim 14, wherein the modified sugar moiety is a 2'-substituted sugar moiety.

16. The oligomeric compound of claim 14, wherein the modified sugar moiety is a bicyclic sugar moiety.

17. The oligomeric compound of claim 16, wherein the bicyclic sugar moiety comprises a 4'-CH(R)—O-2' bridge wherein R is H, C1-C12 alkyl, or a protecting group.

18. The oligomeric compound of claim 17, wherein R is methyl.

19. The oligomeric compound of claim 17, wherein R is H.

20. The oligomeric compound of claim 15, wherein the modified sugar moiety is a 2'-O-methoxyethyl group.

21. The oligomeric compound of claim 1, wherein the modified oligonucleotide comprises:

a gap segment consisting of 10 linked deoxyribonucleosides;

a 5' wing segment consisting of 5 linked nucleosides; and a 3' wing segment consisting of 5 linked nucleosides;

wherein the gap segment is positioned between the 5' wing segment and the 3' wing segment and wherein each nucleoside of each wing segment comprises a modified sugar moiety.

22. A pharmaceutical composition comprising the oligomeric compound of claim 1 or a salt thereof, and a pharmaceutically acceptable diluent.

23. The pharmaceutical composition of claim 22, wherein the pharmaceutically acceptable diluent is phosphate-buffered saline (PBS).

* * * * *

SEQUENCE LISTING

```
Sequence total quantity: 165
SEQ ID NO: 1           moltype = RNA  length = 4712
FEATURE                Location/Qualifiers
source                 1..4712
                       mol_type = mRNA
                       organism = Homo sapiens
SEQUENCE: 1
acccccgaga aagcaaccca gcgcgccgcc cgctcctcac gtgtccctcc cggccccggg  60
gccacctcac gttctgcttc cgtctgaccc ctccgacttc cggtaaagag tccctatccg  120
cacctccgct cccacccggc gcctcggcgc gcccgccctc cgatgcgctc agcggccgca  180
gctcctcgga gtcccgcggt ggccaccgag tctcgccgct tcgccgcagc caggtggccc  240
gggtggcgct cgctccagcg gccggcgcgg cggagcgggc ggggcggcgg tggcgcggcc  300
ccgggaccgt atccctccgc cgcccctccc ccgcccggcc ccggcccccc tccctcccgg  360
cagagctcgc ctccctccgc ctcagactgt tttggtagca acggcaacgg cggcggcgcg  420
tttcggcccg gctcccggcg gctccttggt ctcggcgggc ctccccgccc cttcgtcgtc  480
ctccttctcc ccctcgccag cccgggcgcc cctccggccg cgccaacccg cgcctccccg  540
ctcggcgccc gcgcgtcccc gccgcgttcc ggcgtctcct tggcgcgccc ggctcccggc  600
tgtccccgcc cggcgtgcga gccggtgtat gggcccctca ccatgtcgct gaagccccag  660
cagcagcagc agcagcagca gcagcagcag cagcagcaac agcagcagca gcagcagcag  720
cagcagccgc cgcccgcggc tgccaatgtc cgcaagcccg gcggcagcgg ccttctagcg  780
tcgcccgccg ccgcgccttc gccgtcctcg tcctcggtct cctcgtcctc ggccacggct  840
ccctcctcgg tggtcgcggc gacctccggc ggcgggaggc ccggcctggg cagaggtcga  900
aacagtaaca aaggactgcc tcagtctacg atttcttttg atggaatcta tgcaaatatg  960
aggatggttc atatacttac atcagttgtt ggctccaaat gtgaagtaca agtgaaaaat  1020
ggaggtatat atgaaggagt ttttaaaact tacagtccga agtgtgattt ggtacttgat  1080
gccgcacatg agaaaagtac agaatccagt tcggggccga aacgtgaaga aataatggag  1140
agtattttgt tcaaatgttc agactttgtt gtggtacagt ttaaagatat ggactccagt  1200
tatgcaaaaa gagatgcttt tactgactct gctatcagtg ctaaagtgaa tggcgaacac  1260
aaagagaagg acctggagcc ctgggatgca ggtgaactca cagccaatga ggaacttgag  1320
gctttggaaa atgacgtatc taatggatgg gatcccaatg atatgtttcg atataatgaa  1380
gaaaattatg gtgtagtgtc tacgtatgat agcagtttat cttcgtatac agtgccctta  1440
gaaagagata actcagaaga atttttaaaa cgggaagcaa gggcaaacca gttagcagaa  1500
gaaattgagt caagtgccca gtacaaagct cgagtggccc tggaaaatga tgataggagt  1560
gaggaagaaa aatacacagc agttcagaga aattccagtg aacgtgaggg gcacagcata  1620
aacactaggg aaaataaata tattcctcct ggacaaagaa atagagaagt catatcctgg  1680
ggaagtggga gacagaattc accgcgtatg ggccagcctg gatcgggctc catgccatca  1740
agatccactt ctcacacttc agatttcaac ccgaattctg gttcagacca aagagtagtt  1800
aatggaggtg ttccctggcc atcgccttgc ccatctcctt cctctcgccc accttctcgc  1860
taccagtcag gtcccaactc tcttccacct cgggcagcca cccctacacg gccgccctcc  1920
aggccccccct cgcggccatc cagacccccg tctcacccct ctgctcatgg ttctccagct  1980
cctgtctcta ctatgcctaa acgcatgtct tcagaagggc ctccaaggat gtccccaaag  2040
gcccagcgac atcctcgaaa tcacagagtt tctgctggga ggggttccat atccagtggc  2100
ctagaatttg tatcccacaa cccacccagt gaagcagcta ctcctccagt agcaaggacc  2160
agtccctcgg ggggaacgtg gtcatcagtg gtcagtgggg ttccaagatt atcccctaaa  2220
actcatagac ccaggtctcc cagacagaac agtattggaa atacccccag tgggccagtt  2280
cttgcttctc cccaagctgg tattattcca actgaagctg ttgccatgcc tattccagct  2340
gcatctccta cgcctgctag tcctgcatcg aacagagctg ttacccccttc tagtgaggct  2400
aaagattcca ggcttcaaga tcagaggcag aactctcctg cagggaataa agaaaatatt  2460
aaacccaatg aaacatcacc tagcttctca aaagctgaaa acaaaggtat atcaccagtt  2520
gtttctgaac atagaaaaca gattgatgat ttaaagaaat ttaagaatga ttttaggtta  2580
cagccaagtt ctacttctga atctatggat caactactaa acaaaaatag agagggagaa  2640
aaatcaagag atttgatcaa agacaaaatt gaaccaagtg ctaaggattc tttcattgaa  2700
aatagcagca gcaactgtac cagtggcagc agcaagccga atagccccag catttcccct  2760
tcaatactta gtaacacgga gcacaagagg ggacctgagg tcacttccca aggggttcag  2820
acttccagcc cagcatgtaa acaagagaaa gacgataagg aagagaagaa agacgcagct  2880
gagcaagtta ggaaatcaac attgaatccc aatgcaaagg agttcaaccc acgttccttc  2940
tctcagccaa agccttctac taccccaact tcacctcggc ctcaagcaca acctagccca  3000
tctatggtgg gtcatcaaca gccaactcca gtttatactc agcctgtttg ttttgcacca  3060
```

-continued aatatgatgt atccagtccc agtgagccca ggcgtgcaac ctttataccc aatacctatg 3120
acgcccatgc cagtgaatca agccaagaca tatagagcag taccaaatat gccccaacag 3180
cggcaagacc agcatcatca gagtgccatg atgcacccag cgtcagcagc gggcccaccg 3240
attgcagcca ccccaccagc ttactccacg caatatgttg cctacagtcc tcagcagttc 3300
ccaaatcagc cccttgttca gcatgtgcca cattatcagt ctcagcatcc tcatgtctat 3360
agtcctgtaa tacagggtaa tgctagaatg atggcaccac caacacacgc ccagcctggt 3420
ttagtatctt cttcagcaac tcagtacggg gctcatgagc agacgcatgc gatgtatgca 3480
tgtcccaaat taccatacaa caaggagaca agcccttctt tctactttgc catttccacg 3540
ggctcccttg ctcagcagta tgcgcaccct aacgctaccc tgcacccaca tactccacac 3600
cctcagcctt cagctacccc cactggacag cagcaaagcc aacatggtgg aagtcatcct 3660
gcacccagtc ctgttcagca ccatcagcac caggccgccc aggctctcca tctggccagt 3720
ccacagcagc agtcagccat ttaccacgcg gggcttgcgc caactccacc ctccatgaca 3780
cctgcctcca acacgcagtc gccacagaat agtttcccag cagcacaaca gactgtcttt 3840
acgatccatc cttctcacgt tcagccggcg tataccaacc caccccacat ggcccacgta 3900
cctcaggctc atgtacagtc aggaatggtt ccttctcatc caactgccca tgcgccaatg 3960
atgctaatga cgacacagcc acccggcggt ccccaggccg ccctcgctca aagtgcacta 4020
cagcccattc cagtctcgac aacagcgcat ttcccctata tgacgcaccc ttcagtacaa 4080
gcccaccacc aacagcagtt gtaaggctgc cctggaggaa ccgaaaggcc aaattccctc 4140
ctcccttcta ctgcttctac caactggaag cacagaaaac tagaatttca tttattttgt 4200
ttttaaaata tatatgttga tttcttgtaa catccaatag gaatgctaac agttcacttg 4260
cagtggaaga tacttggacc gagtagaggc atttaggaac ttgggggcta ttccataatt 4320
ccatatgctg tttcagagtc ccgcaggtac cccagctctg cttgccgaaa ctggaagtta 4380
tttatttttt aataaccctt gaaagtcatg aacacatcag ctagcaaaag aagtaacaag 4440
agtgattctt gctgctatta ctgctaaaaa aaaaaaaaaa aaaaaatcaa gacttggaac 4500
gcccttttac taaacttgac aaagtttcag taaattctta ccgtcaaact gacggattat 4560
tatttataaa tcaagtttga tgaggtgatc actgtctaca gtggttcaac ttttaagtta 4620
agggaaaaac ttttactttg tagataatat aaaataaaaa cttaaaaaaa atttaaaaaa 4680
taaaaaaagt tttaaaaact gaaaaaaaaa aa 4712

SEQ ID NO: 2 moltype = DNA length = 151001
FEATURE Location/Qualifiers
source 1..151001
mol_type = genomic DNA
organism = Homo sapiens
SEQUENCE: 2
tcccaaagtg ctgggattac aggcgtgagc caccacactg gccaaaactt gttcttaaga 60
ttgtattctg ggaccttgat tccaatcaga gaaaagtgat tgtatttttt tatttttatt 120
tttttagat aaagtttcgc tcttgttgcc caggctggag tgcagtggtg ccctctttgg 180
tcactgtaac ctccgcctcc tgggttcaag cgattctcct gcctcagcat cctgcgtagc 240
tgagatcaca gatgcccacc accacgccca gctaattttt tcgtattttt agtagcgatg 300
gggtttcacc atgttggcca cgctggtctt gaactcctga cctcaggtga tccatccgcc 360
tcggcctccc agagtgctgg gattacaggt gtgagccacc gcgccaggcc aagtgtttgt 420
atttctatta aagaaagaat ataacgggac accattgacg acctgctcca ttgcaggcct 480
ccttgctgtt cctcagactc ccccctcaga gcctttgccc tcgctgtgcc ctccacctgg 540
agcgtttctc cccaggatcc tcatgcccat gctcatttgg gtccctgccc catgtcaccc 600
tctccaggag cttcccctca cagcagccct ggcctgtacc acagccgggt acaggtattt 660
ttttgtttca actggttttt tagttccagt ttcctttagg ttactttatt tatttattta 720
tttatttatt ttttgagacg gagtctcgct ctgtcgccca ggctggagtg catgatctcg 780
gctgactgca acctccacct cccggattca agcaattctc ctgtatcagc ctcccgagta 840
gctgggatta caggcgccca ccaccacacc cggctaattt ttatattttt ggtagagacg 900
gggtttcacc atgttggcta ggctaggtta atttttaaag ggttttgcaa tggtcccttg 960
atctactttt taccttagat gggaaataaa actgatttcc tacattggca gaatacaatg 1020
atcatttttg cctggactat ctaggaggtt aatttcagtt ggactactga aaactgctgg 1080
ttcaatcatt ctccacgttt atctaagtct ttaccttat ctggacagtt ctaggacatt 1140
gaggggaatt ttggtgtttc ttcccctatt atttcctgaa gtcatttcac tttaaaaaac 1200
aatagattca ctgctcaaaa aaaaaaaaaa aagttaccta ctttctactt gcttccagtt 1260
taactgcaac acattttaaa aagagtctac tgtgctggct gggtaagtta aattaaaact 1320
tctaaagggt ccaaggtcta aagttcgcac attgttttga ggtcggctct gtctctaccg 1380
agggagatcc cattatccgt agttctacca gtcccaatcc catatatttc ctttagaatc 1440
tcatgaatga ggaaaaagaa gttcaagtga gggaacatag gttcaaatga aggtcagata 1500
cctaaaagag ttttctggtg actgtgcgcg gctggggtgg aaaaagtggg gaaaaggtac 1560
ccagatgtgg gtggccccgg agggttgctc cactccagcc ccggcagggc aggacagcgc 1620
ggcctgcctg gtagatgccc cgagccactg gagcgcctac tgtgtggcgg gcgggggacg 1680
gcaggaaaac ggcaggatgc tgtgtcccct gaatctggca gggttctagg tgctttacac 1740
gtagcaagac acattctccg ccccaaggca ctcgcagtca gtccattttc tgggttgcat 1800
caggtggggg caaactaggt ccccgcagaa gtgaagatgc tgaaggaata cagtaggaga 1860
agaaatgctt ctctcctgtc ctccacacca ggcaggcccc agaggctgag accgacacgc 1920
cctccccgaa gggcagaccc gccttgagga aggcggatcc gggtagggac cgccgcctgg 1980
ccctcacccg acccccgaga aagcaaccca gcgcgccgcc cgctcctcac gtgtccctcc 2040
cggcccgggg gccacctcac gttctgcttc cgtctgaccc ctccgacttc cggtaaagag 2100
tccctatccg cacctccgct cccacccggc gcctcggcgc gcccgccctc cgatgcgctc 2160
agcggccgca gctcctcgga gtcccgcggt ggccaccgag tctcgccgct tcgccgcagc 2220
caggtggccc gggtggcgct cgctccagcg gccggcgcgg cggagcgggc ggggcggcgg 2280
tggcgcggcc ccgggaccgt atccctccgc cgcccctccc ccgcccggcc ccggcccccc 2340
tccctcccgg cagagctcgc ctccctccgc ctcagactgt tttggtagca acggcaacgg 2400
cggcggcgcg tttcggcccg gctcccggcg gctccttggt ctcggcgggc ctccccgccc 2460
cttcgtcgtc ctccttctcc ccctcgccag cccgggcgcc cctccggccg cgccaacccg 2520
cgcctccccg ctcggcgccc gcgcgtcccc gccgcgttcc ggcgtctcct tggcgcgccc 2580
ggctcccggc tgtccccgcc cggcgtgcga gccggtgtat gggcccctca ccatgtcgct 2640

-continued

```
gaagccccag cagcagcagc agcagcagca gcagcagcag cagcagcaac agcagcagca  2700
gcagcagcag cagcagccgc cgcccgcggc tgccaatgtc cgcaagcccg gcggcagcgg  2760
ccttctagcg tcgcccgccg ccgcgccttc gccgtcctcg tcctcggtct cctcgtcctc  2820
ggccacggct ccctcctcgg tggtcgcggc gacctccggc ggcgggaggc ccggcctggg  2880
caggtgggtg tcggcacccc agccccctcc gctccgggcc cggcgtcccc tcccccgcgg  2940
cccgcgccgc cgtccccgcc ccgtgacccg ccgggctacc cggggtgggc tgggggccgg  3000
cagcgcgggg gagactcgct cgggcctgag ccccgaggct cggccggtgg gcgcagccgg  3060
ggtcctctgg gattgtcagg cctgtccagc ctcccgcagc atccccgccc cctcccccgg  3120
cggtcaagat ggagggagcg ggcggcctcc cctccccacg cgtgttggga ggggttctcg  3180
ggtagcggcg atggtcagcc ccggctcccc cttccgcacg atcctccgcc cgcagcgtgg  3240
ggatgctcgg gcagctcctc cactcccggt ttaggtgtga acgttggagg ggtctggagg  3300
ctgtggtggc gttttccgga acatgtcccc ctccatgggg gacatctctg gaggggagaa  3360
gttagggccg cgtcccccgt gccggttaaa ggggtaggca ccgggctcct ccggaatcat  3420
cagggtctgt cggggctctc tccccgcccc ctccgagtcc tgggaaagat cggaggacgg  3480
ggtggagaca agtgggcctt ggcccccgca cccctctgcg ttcgtgtccg aggcggcggc  3540
gggggctccc gaactcccct gaaatcgtgg ggctccatgt ggcctccggc agcgttccac  3600
cctcccccac ctggggaagg gaaggggtgg ggagtgcccg gccccgtccc ggccttcctc  3660
cttcccccgc cagacctctc cggcgcgcgg gtggtggccg atccgcattg ctgttcgagg  3720
ccgcagtgga gaaggcgcct gtggaacatc ggtgggtgag ggctggaccc aggctggacc  3780
ctggagatcc ggggtggcgg tgctggtggc agggggcggg caccctgcgc acttatccca  3840
acccccgccc caatttcgga aatgctagga gagagagatt gcagcagggg acgtggtcgg  3900
gttcctgaag gcagaaaggc gggtgtttac tagcgtcttt ttccctccta agccggggtt  3960
gtagtagggg ctgggggctc agtgttgtcc cggctaactg ggtttgactc gagggtgtgt  4020
ttgtgcagga gggcctgttg ggggtggcgg gcggttgtca gttcgtattt cacgaactaa  4080
gaaaatgctt agtgttcaaa gggagaagga aacgtcaata gactccattc cattgtggcc  4140
ggtgtcctta acttcgggag tgccgccaga gcttaccaag ggcacgcaag tccatttccc  4200
ttgtgcctca agtccatccg tgttgtaggc actactgtgc cttctttagg cctaggccgc  4260
cggcttgacg gcgggtgacc ggcgtcctcc ttaaataggc atcttgggct ttggaaggtg  4320
gaataagagg atttttcatt cacccgagtt ttctttttga aaacacattt tcagcaaccc  4380
atttccaaag aatttttatt tacagcagaa attccccatc aagaggaatc agctggtttt  4440
taaggaattc tgctgccttc aaagggggcg gaaacagtcg gttatttgac tttacacgcc  4500
ccgccccccc ttccccttct ctgagtctga agcatcccaa acactactta gccaaactag  4560
ttcagatgaa gtgatcgttt ccccaagtag ggtaacttca gtttcccttt ttcgttggca  4620
tctagcgaaa aatgaaaaaa tttaaaatac aacttttata gaaaaggatg tattctgttt  4680
ttactttctt aggtattagg aagagatttg gcagataatt caacatgttc aaatatataa  4740
acattaaaac taaggttatt aagttgcatt gactactagg cttaaaaatt agattataag  4800
agaatttgct cctgagtagt ttgagtgatc aaagatattt ggaatgtttt agtaccacaa  4860
ggtctttttt ctgttccttg aggctttaca acaatttaag gttaatttag atttttcctt  4920
gctttaagtt cttttacttg agacctaaat ggcagccctt attctttctg atgaataggt  4980
gaaatttgt ttactgtgtt ggatttgtgt aatgtgaagt tttattcttg aacagatcgt  5040
taatgtactt gtagaattac tttgaatttg aatcactttc ctgcattcct tgtaaataag  5100
tttcagcttc tagaatctcc tcacttaggt ttgtgcgtat caacagtgaa aataagtctc  5160
tgagagcaag ggtgaaaaaa aatgcagcat tcggtttgac aagtttcgag atagcaaaat  5220
atgcttgaaa gtctggaaat tcacatctgc tttaagaaac atttcataat ttgactttgt  5280
gtgtgtgtgt gtgaatagtt tttcatgact ttcagaagtg atttattttg ttctttgtta  5340
tatatatttt tgaaggtggc tgttttagga aagataatgt aatcacaata ttagaacata  5400
attttactgt aatctaattt tgtgtgtgtg tgtgtgtgtg tgtgtgtgtg tgtgtgtgtg  5460
ttttggatgg aatctcactc tgtcgcccag gctggagtgc agtggcctga tctcagctta  5520
ctgcagtctc tgtctcctgg gttcatttaa gtgattctcc agcctcagcc tccccagtag  5580
ctgggattac aggttcgtgc taccacacct ggctaatttt tttgtatttt tagtgaggac  5640
gggattttgc catgttggcc aggctggtct cgaactcctg acctcaagtg atccgcctgc  5700
cttggcctcc caaagtgctg ggattacagg cgtgagctac tgcccctggc caatttttgt  5760
atttttagta gagatggggt ttcaccatgt tggccaggct ggtctcgaac tcctcctgac  5820
ctcaagtgat tcgccagcct cggcctccca aagtgccagg attacaggca ggaatgagcc  5880
actgccccca accatcagtc taattcttat ttttgctttt taccttttca tttttatgta  5940
gtagaggtga ttgtgtatgt tattttgtag ttagcttttt tcccctgaac gttgtattgt  6000
aaatgtaaat tttttttttt tttttgaga cagagtctcg gtgtttgccc agtctgaagt  6060
gcagtggtac gatctcagct cactgcagcc tctgactcct gggttcaagc gattctccca  6120
cctcagcctc ttgagtagct ggggctacag gaatgttcca ccacgcttgg ctaatttttg  6180
tatttttggt agagacaagg tttcaccatg ttggccagtt tggtctcgta ctaccgacct  6240
caggtgatgc gcccgcctcg gcctcccaaa gtgctgggat tgcaggcgtg agccactgcg  6300
cccggctgta aggtttttac ttaaccattc tattgttggg aattgggttt ccactttttt  6360
gttatagata gtggtgcagt gaacattttt aaatagcttt ttgcttcagt gtaattattt  6420
ccttagagaa agttaccaag agtggtttta ctagttcaga gggcttcagg atttttatgg  6480
ctcttgctag cggtgctcta ttattcttta gaagacttgt attacttcca gtgtcaagaa  6540
ggttgctctt ccatggaatg gtttctttgt agtttgtcaa atattgtggg gaatttttaa  6600
aggaaaaatt gcatttttac tgtcaagtgc atatattatt aagtgctttt gttagttact  6660
ggattattga tatttgagtt taatttggtt cctctgagga tttaataagg taatatatgt  6720
gaagatgttt tgaaacctgt aaccattatt attaatgagg gtacttggtt tatctgtcgt  6780
gctgatagta ctgagtaaag tgcaggaatg aaattcctga ggaactgttc taaagctttg  6840
ttgttgttgt taacctttct ttttcatctg aaagtgtttt ttattagctg ctagcctatg  6900
accaagttat ttttggtaac ttttttgtaa tttcatggca ctattgggaa ttttcgctgg  6960
ttgactcttc ttcttctaca ttcccttccc cattaaaaat aaaaatatgg atttacaatt  7020
gttactctat tcctaaacct aaataatatg acattagaat tgcttgggat acaggattca  7080
gtctgaataa aatattttc ttttagtgat tttcagctta gtatttttac tgcttctttc  7140
tcttgaggca ttgcaactta aaaattgtgc tgtttagcca ggcgcctgta atcccagcta  7200
cttgggaggc tgaggcagga gcatcacttg agcccaggag gcggaggttg cagtcagctg  7260
agattgtgcc actgcactcc agcctgggag acagagtgag actctatctc aaaaaaaaaa  7320
aaaatgtgct gtgatttaat gtagttgttc atcatgcttc catttaaatt tcagtgagac  7380
```

-continued

```
tgttcatctt ttgcagttaa atatcttgta gaagggccta aaatatctac gttgaataca  7440
gctttattga agcatctatg tacatggggt ttttgggatg aatcagtgaa taaagcaaac  7500
atattgtcct tttggagttt acattctaat gtgactaggc agacaatgag acattaaatt  7560
accagcctat gtataatagt gtataagagc tatggaatta gaagaaagca gattaaaggt  7620
atagggagtg tggggagggg aatgagttac aattttaaat ggattggggg aacttaattg  7680
aggagctaac atttgagcaa agatttgaag gttgggtatt tagccgtttg ctttttatct  7740
aggttaatta gtcatgtggc ttcattagta atttataagg tttaaatggc atcatccttt  7800
gttattcttt tatgtgcaca ttgatactaa ccatctctga agttagacca aaaaagttaa  7860
ttgacattga gggtcattag aggtaaattg tagatggcta ttactaacca aagagacatg  7920
ttttgttttt cttttgggct tacgtatttt acctaattag tttagttttt gtttcaagta  7980
tgtggagaaa ataaactttt taagtttggg ccaaaacttg ctttggtttt ctttttcttt  8040
ttcttttttt tttttaaga gaaaaatgta agcctgtagt tgcttaaaga ttccacattc  8100
tgaaacagtg aaaacatggg atcagtcatg gtgttccttt ttttggttaa atgtaaactt  8160
gtattttcag tgttactcta attagcaatg gtttatactt ctacataagg gatgttaact  8220
catattgtag ctatttaata gccatatatt ttgacttaaa ggaggatctc aaggccaggc  8280
gcggtggctc atacctgtaa tcccagcact ttaggaggct gaggcgggtg gatcacctgg  8340
ggtcaggagt ttgagactag tctggccaac atggtgaaac cccatctct actaaaaata  8400
caaaaattag ccgggcatgg tggtgggcgc ctgtaatccc agcttcttgg gaggctgagg  8460
gaagagaatt gcttgatccc ggaggttgca atgagtgcgg aggttgcagt gagctgagat  8520
catgccatta cactccagcc tgggcaacag agcgagactc tgtctcaaaa caaacaaaca  8580
aacaaaaaaa ggaggatctc atttttttgt cctaaatagc tacagccgtg ttagaactgt  8640
caccttagca aagtattgtt tttttacttt gaaacgaatt ttaaggtttt agaagattgt  8700
tctctagaat tacaatttc tgttttgact agtgatagta ttttgatgtt gtgtaaatag  8760
ttgagcatga acaaaaccct attttttttt ttagctattt caagtgattg tgacaacttc  8820
aacggagatg taaacagttt attaacagtc acacctatta tctttttttt tttttttttt  8880
ttttgagacg gagtcttgct ctgtcgccca ggctggagtg cagtggcacg atctctgctt  8940
actgcaacct ttgcctcccg ggttcaagtg attctcctgc ctcagcctcc tgagtagctg  9000
ggtctacatg cgcacaccac cacgcctggc taatttttgt atttttagta gagacagggt  9060
ttcaccatgt tggctagaat ggtctcaaac tcctgacctc aggtgatcca cctgcctcag  9120
cctcccaaag ttctgggatt acaggcatga gccaccgtgc ttggccgctg ccgtatcttt  9180
ttaaatgaaa gtacttgtgt ttttttgtt tttttccaaa ggatatctgg gtcatctatg  9240
atgttactgt taccatctaa gggttttttt gtttgttttt gagacagagt ctctgtcgcc  9300
caggctggag tgcagtggcg tgatcttggc tcactgcaac ctccgcctcc caggttcaag  9360
caattctcct gccttagccc tcccgaatag ctgggattac aggcacccgc caccatgcct  9420
ggctaagttt tgcattttta gtagatatgg agtttcacca tgttggccag gctgctcttg  9480
aactcctgac ctcaggtgat tcgcttgcct cggcctccca aagtgctggg attacaggcg  9540
tgagccaccc ccgcccagcc tcatgagcta aggtgttttt tttttttttg agacagtttt  9600
gctctttccc aggctggagt gcagtggtgc aatctcagct cactgcaacc tctgtttccc  9660
gggttcaagc gattctcctg cctcagcctt ctgagtagct gagattacag gtgcctgcta  9720
ccccactcag ctaattttg tatttttagc agagacaggg tttcaccatg ttggttaggc  9780
tcatctcgaa ctcctgacct taagcgatcc acctgccttg gcctcccaaa gtgctgggat  9840
tataggcatg agccaccgtg cgcagcctac cctgtctctt aaaaaacagt aacaacaaca  9900
acaacaacaa aaaatcctaa atcttaaaaa tggaaggcaa aaactctaag ctttgagaga  9960
ttaggggact tgcccaaagc aatatttgta ggattttatt acacctctcc ctttatttat  10020
tttttagag tcaaggtctc cctctgtcac ccaggctgga gtgcagcctc aatctatggg  10080
gccaagcatt tctcctgtct tagcctcctg agtagctgga actacaggtg tacaccagct  10140
ggctaacatt taaatttttt gtagagacag ggtcctgcca tgttgcccag attggtctca  10200
aactcctggg ctcaagtgat cctcctgcct cagcttccca aagtgctgag attacaggtg  10260
tgagccactg caccgagccc cctcccttta tttttatttt taaattttaa gttctggggc  10320
ccctcccttg aaataaatag aaacgtaata tatacacaag atcatgctgt gtattttaag  10380
gcaatggtcc tcaacctttt taacactagg gaccggtttt gtggaagatg gtttttccat  10440
aggggcaggg gatgattttg agatgaaact gttccaccgg ccgggcacgg tggctcacgc  10500
ctgtaatccc agcactttgg gaggccgagg cgggcagatc acgaggtcag gagatcgaga  10560
ccatcctggc taacatggtg aaaccccct ctactaaaaa tacaaaaaaa ttagctgggc  10620
gcggtggagg gcgcctgtag tcacagctac tccggaggcc gaggcaagag aatggcatga  10680
aacccgggag gcagagcttg cagtgagctg agatagcacc actgtacttc agcctggggg  10740
acaaagtgag actccgtcta aaaaaaaaaa aattgttcca cctcagatca ttatgcattt  10800
gttagattct cataaagagc atacaaccta catctcttgc tatatgcagt tcccagtagg  10860
gtttgtgctt ctataagaac ctaatgctgc acctgatcta acaggtgggg ctcaggtgct  10920
aatgctcaca cagctcctgt tgtgcagtct ggttcctaac aggcctgttt tttttttttt  10980
aattagatgg agtctcgctc tgtcaccagg ctggagtgca gtggcacgat ctcagctcac  11040
tgcaacctct gcctcccggg ttcaagcgat tctcctgcct tagcctccca tgtagttggt  11100
actacaggcg cacactgtga tgcccagcta atttttgtat ttttagtaga gacggggttt  11160
caccatgttg gccaggatgg tgtcgatctc ctgaccttgt gatccgccca acagcctccc  11220
aaagtgctgg aattacaggc gtgagctgct gcgtccggcc ccctaacagg cttgttttat  11280
ggaatacagt cacggacagt acttgccctt caggatatct ttttgtaacc ttgattttgg  11340
cttgctaaaa taggaggtct attttctttt ctttgttttt aatgtatgtg gttctgtact  11400
tacgtggtgt gaaatctaca taaatgttaa atccttggtt atttatttat tttgagacag  11460
agtctcactc tgtcacccag tctggaaagc agtggcataa tctcggctca ctgtaacctc  11520
cacttcccag gttccagtga ttctcctgcc tcagcctcct gagtagctgg gattacaggc  11580
atgcaccact acacctggca aatttttgta tttttttta gtagagatgg ggtttcacca  11640
tgttggccag gctcgtcttg aactcctgac cttaggtgat ctgcctgtct tggcctccca  11700
aagttttggg attacagcat gagccactgc gcctcgcctt attttttga gacaggttct  11760
agctctgtca cccaggcggg agtgcagtgg tgccatcatg gctcattgca acctcgagtt  11820
ctcaggccca agtgatcctc ctatctcagc ctcctgagta gctgggacca caggcatgcg  11880
ccactatgcc cagcaaaatt tttgtttcac tctgttgcct agggtggggt gcagtggcag  11940
gatatcggct cagtgcaacc tctgcctctt gcgttcaaat gattctcatg cctcagcctc  12000
ccgagtagct gggattatag gcatgcgcca ctacacctgg ctaattttg tattattggt  12060
agagatgggg ttttatcatg ttggccaggc tggtctcgaa ctcccgacct caggtgatcc  12120
```

-continued

```
atataccttg gcctcctgaa gtgctggaat tacaggcata agccactgcg cctagctttt  12180
ttgtttgttt ttattttgta gggacagaga ttttacctgt tgcccaggat ggccttgaat  12240
tcctgacctc aaacaatttg ccctccttgg cctcccaagg tgctgggatt acaggtgtga  12300
gccactatgc ctggctggtt ttttaaatta ttattattgt ttgtgtgtgt gtgttgcagg  12360
atcttaccct gtcacccagg ctggaatgca gtgatgtgat ctcggcttac tgcaacctcc  12420
gcctcctagg ttcaagtgat tgtcctgcct cagcctcctg agtagctggg ataacagctg  12480
tgtgccacca tgcctggcta atttttgtat ttttagtaga gatggggttt catcatgttg  12540
gccaggctgg tctcgaactc ctgaccttag atgatccacc cgcctcgtcc tcccaaagtg  12600
ctgggattac aggtgtgagc caccgtgacc agtttggttt agtttttttt tttttttttt  12660
tttttttttt tttttgagaa atctcgctct gtcgcccagg ctagagtgcg gtgacacaat  12720
ctcagctcac tgcaagctcc acctcccagg ttcatgccat tctcctgcct cagcctcccg  12780
agtagctggg actacatgcg cccgccacca tgcccggcta atttttttta tgcattttaa  12840
gtagagatgg ggtttcactg tgttagccag gattgtctca atctcccgac ctcttgatct  12900
gcccgcctcg gcttcccaaa gtgctgggat tataggcatg agccaccgcg tccggcctgg  12960
tttggtattt tttttatgag tctgggttgt ttatgaaaac ttgtcacagc tgttaacctt  13020
aacttttttt ttttcttttt tttccgagac ggagtctcgc tctgtcacct aggctggagt  13080
gcagtggtgc gatctcggct cattgcaacc tctgcctccc aggttaaagc gatttttctg  13140
cctcagcctc ctgagtagct gggactgcag gcacgcacca tctcgcctgg ctaatttttg  13200
tattttagta gagatggggt ttcaccatat tggccaggct ggtctggaac ttctggcctc  13260
aagtgatcca cctgccttgg cctcccatgc ctggcaacct taacttttta tttgctggta  13320
attatttgtg tttgcattca tgtgaaaatt tgaaattctc attaacattt aaagattctt  13380
acatagattg cttgtaattt taaccctgaa gttgtgtcaa gtgactttac aatgtcaatt  13440
tgttttattt atttatttat ttatttattt atttattttt gtgataggat ctggctctgt  13500
tgctaaggct ggagtgcagt gttgcaaata cggctcactg caacctctgt ctcccgggtt  13560
caagccatcc tcccacctca gcctcccaag tagttggaac tactggtgcg ccccacagtg  13620
cctgcctagt ttttttgtat tttcagtaga tgtggagttt tgccatgttg atcttgaact  13680
catggcctcg agtgatccac ccccacttagg cctcctaaca tgctggtgtt acaggtgtga  13740
gccactgtgt ccagcccgaa aatgtcagtt tcgtgccatg attaatagct aactacattt  13800
tgggaatgta ataaaatttc attctataat gaagtctttg taaaactcat tagttgtggt  13860
atgaggcttg tcggcaatat aagtgaacgt ggtttatttt tattaactgt atcagaactt  13920
tagaatgttg gtctcctgaa accattgcct tgagaggctt tattgaacag tgttgccaat  13980
gatcagtttt tttttaaatt tcctttttttt tgagactgag tcttaccctg ttggccaggt  14040
tggagtatag tggtatggtc atggctcact gcagcctcaa catcctgggc tcaagcagtc  14100
ctcctacctc agtctcccga gtagctggaa ctacaggtgt atgccaccat gcctggcttt  14160
tgtatatttt gtagagacag ggtttagcca tgttgcccag gctggtctca aactcttaaa  14220
ttcaaatgat ccacccacct agttttccca aagtgcttta attacatgtg tgaggcaccg  14280
tggctggcca ggtcaaatat ttttcattga cgtttttcat attgcttttt aaagtcatgt  14340
taaaatattc ttaataattt ttctaagtgg aattaatctt gattataatt ttagtttttt  14400
ataaagggcg ggttttgaaa caagtactgc atttttcttt tcgggtttat aaacatttgc  14460
tgtggacttt gtgcagttaa ctattttcat tcctgaaaca catttcgaaa tcaggaattg  14520
aagactaaat gtcttttcac tgaagcttga gcagatttta gaaaggggag ttcttttttt  14580
tttttttttt tttggtagaa atgggggtct tgttatgttg cccaggctgg cctccaactt  14640
ctgggcttaa actgtcctcc tgctttagcc tctggtctgg agagttcttt atggcctctt  14700
tgagaacttt tactttacac atgattctat ctagctttct tttctgatgt acatattggc  14760
agcaagtaga aaagcaatgt tttcagaggc agatatatta acagcaatga gaaataacag  14820
tagcgtgata gaaagttgaa agacttagct gggtgcggtg gctcacgctt gtaatcccag  14880
cactttggga ggccaaggag ggtggatcac ttgaggtcag gagttcgaga ccagtctggc  14940
caacatggtg aaaccctgtc tctactgaaa aacagaaaaa gggccgggcg tggtggctca  15000
cccctgtaat cccagcactt tgggaggttg aggagggcgg attacaaggt caagagattg  15060
agaccattct ggccaacagg gtgaaacccc atctctacta aaaatacaaa aaaattaaat  15120
gggcgtggtg atgtgtgcct gtagtcccag ctactcggga ggctgaggca ggagaattgc  15180
ttgaacccgg gaggcagagg ttgcagtgag ccgagatcgg gccactgcac tgacgacaga  15240
gggagactcc gtctaaaaaa aaaaaaaaaa aaaaaaaacc agacttgggg ctgggcgggc  15300
gcctgtaatc ccagctactt gggaggctga ggcaggagaa tcgcttgaac ccgggaggtg  15360
aaggttgcag tgagctcaga ttgtgccact gtgccccagc ctgggccaca gagcagagtg  15420
agactctgtc tcaaaaaaaa aaaaaaagtt tggaagactg gtggctgggc atggtggctc  15480
acacctgtaa tcccaacact ttgggaggct gaagcaggca gattacctga gcccaggagt  15540
tcaagtccag cctgggcaac acagggaaac cccatctcaa caaaaaatat taatacaaaa  15600
aatttagcca gtcatggtcg tgcacttctg tagtctcagc tacttgggag gctgaggcag  15660
gtggttcact taagtctgga tgtcgaggtg agccatgatt gcaccactgc actccagcct  15720
gggcgttaaa atgagacctt atctcaaaaa aacaaagcaa agagcctggg aactactaaa  15780
atgggaacta ctaaaaaaca gacacaagag ctcaacaagt ataccattct gggaggtttt  15840
tttttttttt tttttttttt tttttgagat ggagttttgc tcttgtcacc caggctggag  15900
tgcaatggcg ccatctctgc tcactgtagt tccgcctccc aggttcaagc agttctcctg  15960
cctgactcct gagtagctgg gagtacagat attggtcaca caccgggtta atttttgtat  16020
ttttagtaga gacggggttt ccccatttttg gccaggctgg tctcgaactc ctgacctcag  16080
gtgatccgcc tgcttcagcc tcccaaagtg ccgggaccac aggcgtgagc caccgcacct  16140
ggcttttttt ttttgacata gaatcttgtt ctgttgccca ggctggagtg caatggtaca  16200
atcttggccc actgcaacct ctgcctccca gcttctagcg attttcctgc ctctgactcc  16260
tgagtagctg ggattacggg tgcccgccac cacacccgga taatttttgt atttttagta  16320
gagatggggt tttgccatat tggccaggcc ggtcttgaac tcctgacctc agatgatcca  16380
cctgcctagg cctcccaaag tgccgggatt acaggcgtga gccaccactc ccggcctggg  16440
agttttgact gtaagtttat agctgtatat cttaggccct aagggcatta ctgttttata  16500
gcacagtgta gttagttaat gtgctcataa tggtgactca taacaccagg ttaaatgatt  16560
ttttatatct cccaaagaag tatttttcaa tctgcagatc atgacccctt agtagattgt  16620
gaaacacatt agtggattat gacaagcatt tttagaaaaa tgaaaaagaa taagaagtgt  16680
taggatgcat tgcattattg aaataattgt ttttgagatg gagtttcgct cttagttgcc  16740
gaggctggag tgcaatggcc cgatctgcct cccgggttca agtgattctc ctacctcagc  16800
ctcctgagta gctgggatta cagacatgct ccaccatgcc tggctaattt tgtatttagt  16860
```

-continued

```
tttagtagag atggggtttc tccatgttgg tcaggctggt cttgaactcc tgacctcagg  16920
tgatccactt gcctcggcct cccaaagtgc tggggataca ggcatgaacc cctgtgcccg  16980
gcctaatttt tgtattttta gtagagatgg ggtttcacca tgttggccag gatagtcttg  17040
atctcttgac ctcgtaatct gcccacctcg actcccaaag tgctgggatt acaggtgtga  17100
gccactgcac ccagctgcca agaattgttt taagctttgg tttgagttaa tgtatatata  17160
ccgcattgta attcaaaatg taatttttgg ccaactctgg gcacattgcc tatggactag  17220
tcctgctctg ccacgagcag caacagttca atgaattttt tttttttttt tttttttttt  17280
tttttttttg agacagggtc tctgtcacca aggctagaat gtagtggtgc agtctcggct  17340
cactgcaacc tctgtttcct gggctcaagc gatcctccca cctcagcctc ctgagtagct  17400
gggagtacag gagcacgcta ccatgcctgg ctaatttttg tatttttga agagatgagg  17460
ttttgccatg ttgttcaggc tagtcttgaa ctctggagct cagatgatcc acccaccttg  17520
gtgtccagaa atgctgggat tacagggatg agccaccgtg cctagccaaa aattttttt  17580
taagtaattt tttattgata tagtcaaaaa agttactgct ttagagccag agaaacgcag  17640
taaaaggatt gagaaagagt tttgaggtta tatctaagct agggttgtca gatttggcaa  17700
atagaaatac aggacactca gttaaatttg aatttttgat gaacattgac cagtttttta  17760
gtataattgt gtattaaatt gcatagaaaa aagttattta tctaaagttg aaatttaact  17820
gagcatcttg tattttatct ggcaactcca gtctaagctg gaatcatggt tcactgtttt  17880
tttttttttt tttttttttt gagtcggagt cttgctgtgt tgcccaggct ggagtgcaat  17940
ggtgcgatct tggctcactg caacctccac ctcctgtgtt caagtgattc tcctgcctca  18000
gcctcctgaa tagttgggat tacaggcacc caccaccatg cccagctaat ttttatattt  18060
ttagtagaga cggggtttc gccatgttgt tcaggctggt cttgaactcc tgacctcagg  18120
tggtccgccc acctgggcct cccaacgtgc tgggattaca ggcatgatct accgtgcctg  18180
gccatggttc actcttcagt aactaaaatt taagctctat gaaagcagga actttgtttt  18240
gttcactatt gattgtatcc ctatttcttg aatggttggc acttaactgc ttggtcacat  18300
gtttgaatgg gcaagttact cagccactct caggcttagt ttatttacct attaaaagag  18360
aaagaatatc ttccttggct gggcgcggtg gctcacgcct ataatcccag cactttggga  18420
ggctgaggcg ggtggatcac gaggtcagga gatcgagacc aacctgggca acattgtgaa  18480
acctcatctc tactaaaata gaaaaaatta gctgggcatg gtggtgcgca tctgtagtcc  18540
cagctactcg agaggctgag gcaggggaat cgcttgaacc caggaggtgg aggttgcagt  18600
gagccaagat tgtgccactg cactccagcc tgggcgacag aacgagactc tgtctccaaa  18660
aaaaaaaaaa aaacaaacaa aaaaaaaaac tgagatactg gccgggcgcg gtggctcgtg  18720
cctgtaatcc cagcactttg gaaggccgag gcgggtggat cacgaggtca ggagatcgag  18780
accgtcctgc ctaacatggg gaaaccctgt ctctactaaa aatacaaaaa attagccagg  18840
cgtggtggcg ggcgcctgta atcccagcta cttgggaggc tgaggcagga gaatggcgtg  18900
aacccgggag gcagagcttg cagtgagcgg agatggtgcc actgcactcc agcctgctgg  18960
gcgacagagc gagactccgt ctcaaacaaa caaacaaaca aacaaaaaaa ctgagatact  19020
aaagtcttaa tattttctgt ttttatgtat ttattttttg agatgggatc ttgctgtatt  19080
gcccaggttg gagtacagta ttgtgatcat ggcttattgc agcctttaac tcctgggttc  19140
aagtgatcct cccacctcag cctcctgagt agctgggacc acaggcacat gcaacatcac  19200
accctgcagt tcttttttt tttttgagac accgtctcgc tttgtcaccc aggctgcagt  19260
gcgtggtgca atttctgctc actctaacct ccacctcccg agttcaagca gttctgcctc  19320
agcctcctga gtagcttggg accacatgtg tgtgccatca tgcctggtta attttttgta  19380
tttttagtag tgacagggtc ttaccatgtt gcccaggttg gtctcaaact cctgagctca  19440
agtgatctgc ccgccttcgc ctcccaaagt gtctgcgccc tacaatttaa aaaaattttt  19500
gtagagacag tctcactgtt acccgggctg gttttgaact tctgccctca agtactcctc  19560
ttgccttggc ctcccaaagt attgaaatta aggccatgag gcagcacacc cagcctaaat  19620
tcttcttatg ttctgttctt ggcacatagt agatgttcaa caatgtagag tcaaacgcat  19680
ttggagttgg aatggctctg gtgtttttt tttttttta aaccagaaac acgtgcagtt  19740
tattgaatgc cattgtagaa aagtgtgtga ggataaacgg ctgatagaga acttggctct  19800
gggggcaggg cgaggaatgg agggtggatg gagtacatgg gaatcagatc acgggcagag  19860
ctcctggcct agataatgcc tcctgatctg ttgatagact tgaaagatca acactgggat  19920
gatgctgagc agaatggtcg taatgatgcg cacaatcagg gcccagatgt tcaggcactt  19980
ggcggtaaag gcataggcct gggccctgat caggtcgcca accatcttct tgtccctaga  20040
cttcacggag taggccaatg ctatgaagcc caggcagcag gagttcatga agtgggtgtt  20100
gaacagggac cagacgacat ggtcgggcac ggagttctcg ctgtggatgg ggatcacggt  20160
ggacattggg ggagcagggt tgtggggtgc cccccagcaca gccacctctt gctcctcctt  20220
gagcatctca tagttagggg gatggccgat gttggcagga gtgaagaggt ttggacattg  20280
tggttcatgg tgtccaggga agaccagctg tggtcgggtt gctggggtgg ttctcagtgg  20340
gcccctccct ttccctggta gtttggattt ctctggctct ggtggttttt tagtactcat  20400
tctatttacg ggtgaagaaa ttgagaccaa gagggttatt taccagagta tctcatcatt  20460
ggctgcataa ctggcattag aatctgatgt actttattt ctaatacatt tcttttttt  20520
tttttttttt tgagatggag tctcgctctg ttgccgagcc tagagtgcag tggggcaatc  20580
ttggctcctt gcaacctcca cctcctgggt tcaagctatt cctgtctcag cctcccaagt  20640
agctgggact acaggcacct gccaccacag ccggctaggt tttgtatttt agtagagatg  20700
gggtagcacc atgttggcca ggctggtctc gaactcatga cctcaggtga tccacctgcc  20760
tcggcctccc agtgctggga ttataggcat gagccaccat gcctggcctt tctttgtcgt  20820
ttcctttctt tctcttcatc cctcctctcc ttttttcccc tccccgctgc ctcctcctgt  20880
cttcccttct ttccttcctt tctctccttt ttatttttc ctttcttttt ctttctctgt  20940
ctctcccaac ccttcctctc tccctccctc cctccccttc tctctccccc cctccctccc  21000
cttctctctc cccctcccct tttgttccta agagacaggg tctccttatg ttgctgaggc  21060
tgaccttgaa ctcctgagcc cagatgattc tgcctcctta gtagctggga ctacacccac  21120
ctcccgttcc gttgtcatct tttttttttt tttcttttt ggagacagaa tcttcctctg  21180
ttgctcaggg tggagtgtag tggcacgatc atagcttact gtaactgtgt aacctcgaat  21240
tcttgggctc aagcaatcat cccatcatcc cacctcagct tgctgagtac ctggggctac  21300
aggtgtgtac caccatgtcc ggctaattac ttttcttatt tttaattttt cggagatagg  21360
atcttgctct gttgcccagg ctggtgtcaa actcctgggc tcaagtgaaa ctcttgcctt  21420
ggcctcccaa agtgttggga gggattacag gcatgagcca ctgcacccag cctcctcttt  21480
cttcccattt aactcctaac cacaccgaac tttctgtctg cagagaggag cattggtcag  21540
cagttcacaa aatggctagg tgtgatggcg tgcacccata gtcccagcta cttggggagc  21600
```

-continued

```
tgaggtggga ggatcgctgg agcccaggag ttcaaggccc tgggcaacac agcaagacct  21660
tatctctggc tgggcccagt ggctcacgcc tgtaatccca gcactttggg aggctgaggt  21720
gggtggatca cctgaggtca ggagttcgag accagcctgg ccaacatggt gagaccctgt  21780
gtctactaaa agtacaaaaa ttagccaggc acggtggcgc gctcctgtaa tcccagctac  21840
tcgggggggc tgagacagga gaatcacttg aacccaggag gaggaggttg cagtgaacca  21900
agaacacgcc actgcactcc agcctgggtg acatagtgag actcttatct caaaaaaaaa  21960
aaaaaaaggt cgtctgtact attgcatgtt agtagtttct ttctgcttat tgttgagtag  22020
tagtctattg tatgcatgta ccagtttgtt catctagtgg tggacattga gttagcaggt  22080
tttggctatt aaaaataaag ctggaggccg ggtgcgatgt ctcacgcctg taatcccagc  22140
attttggaag gccgaggcag gcggatcacc taaggttggg agtttgagac cagcctgacc  22200
aacatggaga aaccccatct ctactaaaaa tacaaaatta gccaggcgtg gtggcgcatg  22260
cctgtaatcc tagctactca ggaggctgag gcaggagaat cgcttgaacc cgggaggcag  22320
aggttgtggt gagccaagat tgcaccattg cactccagcc tgggcatcaa gagtgaaact  22380
ccgtctcaaa aaaataaata aataaagctg gtatgaatat ttatgtacag gttttgtgtg  22440
aacatatgat tttatttctc ttggttggaa tgcatagaaa tgagattgct gggttttgtg  22500
gcaagtgttt atttttccag ggtacatata atcctgtgag tgtttattta attttaaaag  22560
taattgctaa actgtttgct aaagtgactg ctatattttc tttccctagc agtgtatgaa  22620
tttttttttg aggcagggtc ttgctctgtc acccagggtg gagtgcagtg gtgcgatatt  22680
gtctgactgc aacattgacc tcctgggctc aagtgatcct cctgcctcag cctcctggct  22740
gggaccacag gcatgtacca ccacacctgg tagtttgctt tgatttttag tagagaagag  22800
gtctcactat gttgccctgg gtggtgttga actcctgggc tcaagtgatt catctacctc  22860
agcctcccaa agtgctggga ttatagatat gagcccctgt gcctggcctc attgtggttt  22920
taatttgcat ttccctaatg cccagtgata ttgagcattt tttcatgtgt ttatttgaca  22980
ttcataccat ctttggtgat gagaaactat gtttatgcat tgcttaatga tggggatgtg  23040
ttttgagaaa ttttttcggt gatcttatca ttgtacaaat atagagttta cttacacaag  23100
cctagatggt atacctacta gacacatagg ctgtcgtaca gagtattact cttaggctac  23160
aaatctgtat agcatgttgc ggtactgaac actgttggca gatgtaacat aatgttaagt  23220
atttgtgaat ctaaacatat ctaaacatag aaaaggtgag taaaaataca gcgtaaaaga  23280
taaaagtggt atatctgaat aggtcactta ccatgaatgg agcttgcagg acaggaagtt  23340
gcttgggatg agtcatttat cagtggtgtg tgaatgtgca ggcctaggac attactgtat  23400
gctactgtag acaaacactg aacagttagg atacactaaa ttgataaata tctttcttat  23460
tttgtttttt gagatggagt ctcgctctat cgcccaggct ggagtgtagt ggcgtgatgt  23520
tggctcactg cagtctctgc cttctgggtt caagcgattc tcctgcctca acctcctgaa  23580
tagctgggat tacaggtgcg tgccaccaca cctggctaat ttttgtattt ttagtagaga  23640
cgggggtttc accatgttgg ccaggctggt ctcgaactcc tgacctcagg tgatccaccc  23700
gcccgtggcct cccaaagtgc tgggattaca gatgtgagcc accgcacctg gccagagatg  23760
aggtcttgct gtattgccca gggcgttgaa ctcctgggct ccagcaatcc tcccacctca  23820
gcttcccacg tagctgggac tgtgggtgca cgccatcatg cctagccgtt ttgtgaactg  23880
ttgaccaatg ctcttttctg cagacagaaa gttcactgtg gttaggagtt aagactttta  23940
acctctgacc tcaagtgatc tgcccacctt gacctcccaa agtgctggga ttacaggtgt  24000
gagccatcac gcctggtcaa aaatatcttt ctttaagagt aaatttacct taacttactg  24060
gttgatcatt gtatataggt ctgttgttaa ttgaaacatg cgggccgggc ccggtggctc  24120
atgcctgtaa tcccagcact ttgggaggcc gaggcgggtg gatcacaagg tcaggagatc  24180
gagaccatcc tggctaacac ggtgaaaccc cgtctctact aaaaatacta aaaattaacc  24240
gggtgtggtg gcgggcgcct gtaatcccag ctactcggga ggctgaggca ggagaatggc  24300
gtgaacccgg gaggcggagc ttgcagtgag ccgagatcgt gccactgcac tccagcctgg  24360
gcaacagagc gagactctgt ctcaaaaataa ataaataaat aaataaataa ttgaaacatg  24420
cggtgcatgt gtttatttgc gatctgactt gtttggaaat atttgcatta tcttccttct  24480
agatttagag catcttgaca gtaggaacaa gtgttttgta caactttgta tgcttagtaa  24540
gttatcaatt aacttgtcgt ggccaggcgc agtggctcac gactgtaatc ccagcacttt  24600
gggaggccga ggcgggcaga tcacctgagg tcaggagttc gagaccagcg tggccaacgt  24660
ggtgaaaccc tgggtttgtt tgtttgttta tttatttatt tattttttgg agacggagtc  24720
tcgctctgtc gcccaggctg gagtgcagtg gcgtgatctc ggctcactgc aacctccgac  24780
tcccaggttc atgccattct cctgcctcag cctcccaagt agctgggact acaggagccc  24840
gccaccatgc ctggctaatt tttttatttt tagtagagat ggggtttcgc cgtgttatct  24900
gggatggtct cgaactcctg actttgtgat ccgcccgcct cggcctccca aagttctggg  24960
attacaggcg tgagccacca cacctggcct accctgtgtt tattacaaat acacaaattg  25020
gccatttgtg cgtggctcat ctacagtctc agtgactcag aaggctgagg caggagaatc  25080
tcttgaaccc gggaggcaga ggttgcagtg agcagagatc gtgccactgt acttcagcct  25140
gggtgacaga gtgagactgt gtctcaaaat aataataata atttgttgaa tatgtgactg  25200
ttggtttaat ttttattttt atgagatgga gtctcactct gttgcccagg ttggagtaca  25260
gtggcgtgca gtggcgcaat cttagctcac tgcaacctcc gcctcctgtg ttcaggtgat  25320
tcagcctccc aagtacctga gactacagac gtgcactacc gtgcctgact aatttttgta  25380
tttttagtag aaatggggtt tcaccatgtt ggtcagcctg gtctcaaact cctattctca  25440
agtgatccgc ctacctcgac cttccaaagt ggcggaatta taggtgtgag ccgtggtgcc  25500
cggccagact attggtttgg tttggtgtga tgttatgtta tgttatgtta tgttatgtta  25560
tgttatgtta tgttatgtta ttttaagaca gagtttgtct cttgtcgccc aggctggagt  25620
gcagcggcat gatctcggct tactgcaacc tccgcctccc aggttcaagt gattctcctg  25680
tcttagcctc ccaagtagct gggattacag gcgcccacca ccgtgcctgg ctaatttttg  25740
tatttttagt agagacaggg tttcaccatc ttggccaggc tgttctggaa ctcctgacct  25800
catgatccac ccgccttggc ctcccaaagt gctgggatta caggcgtgag ccactgcgcc  25860
tggctgacta ttggttttat tattaagcag tagtagttga ccctgtcatg tagaaagcat  25920
ggcatttata ggcataccac gtttaatttc ctccccttt tttatttttg gagtacctcc  25980
tgcttgtgag gcttgggaat acagtagtga ataagccaga tgaggtctct ctctttttgg  26040
agcttatgtg gtagtataga ctaggcagaa agttctcatt gcccctgcca ccttatggca  26100
ttgaggtgtt tgagatgctg atgtttactt ctgtctcata aaatcttgaa aggagttctt  26160
ttagatgaag aggaaaacaa aatcagaaga atgggcctgg gtcatgtctg taaacctccc  26220
cacgtcatgg ggaggctgaa atgggaaggg ccaggagttc aagaccaggc tgagaaacat  26280
aacaagaccc catctctaca aaaaatattt tttaattaat gggggatggc agcacacacc  26340
```

-continued

```
tgtagtcgca gctactacga ggctgaagcg agaggattgc ttgagctcag gagttaaaga  26400
ttgcaggagc tatgatcaca gcactgcgct ccagcccctc ttatcagcag tctggtatgt  26460
tgctaagggt cttgttcttt ttagtgcttc agggacagcc actggctatg cccagaaata  26520
agtatgtttg agaagctttc tgacctcagc ttgaaaaatt gattagggtc ataattaaaa  26580
agggagggaa acaggattga gtgaaccgga cgctaccgtg agtttattct cccagggcat  26640
acataatctc atgtgattac cacatagccc tgttagataa tctgttatcc tgtcctcatt  26700
ttacccatga ggaaatgaag gcccagagag gttaaatgac ctattcaaat tcactcagaa  26760
ggtggcagag atgagttact atcattgtat tttggatctc tggaaagaaa gaaaactagt  26820
gatggtatta aaaaatgtta ttaatagttt cttttaatca accaggaact tgagtcacta  26880
gcttctctgg gtgaaggact atacttcaac agtatgaaaa acggaaaaga aaatgaggaa  26940
ttttggctgg gcacagtggc tcacacctgt aattctagca ctttgggaag ccaagggagg  27000
agggtcgctt gagctcagga attcaagatc agcctaggca acatagtgag gccccatctc  27060
tacaaaaata aattagctgg gcatggtggt gcatgcgtat agtctcagct acttgggagg  27120
ctgactcagg agggtcactt aaacccagga attggaggtt gcagtgagct atgattgcgc  27180
cactgtatac catcccaggc gacagagtga gaccctatcc ccccaccgcc aaaaaaaaga  27240
aaagaaaatg aggaatttac atttgtgaca gatacggaat tcagggaatt tagttgttca  27300
tagtctataa atgctataag aagtctccat accttttttt tttttttttt tttttttttgg  27360
agacagagtc ttgctctgtc gcccaggctg gagtgcagtg gtgcgatctt ggctcactac  27420
aagctctgcc tctcgggttc acgccattct cctgcctcca cctcccgagt agctgggact  27480
acaggtgccc gccaccacgc ccggctaatt tttttgtatt tttggtagag atgaggtttc  27540
actgtgttag ccacagatcc cgacctcatg atctgtctgc ctcagcctcc caaagtgctg  27600
ggattgcagg cttgaatcac cgcacccggc cggaagtctc catacttttt aacccaatct  27660
aaaatggtaa ggaaatatat aagaatgtct atttattatt aaattttttc tatataaaac  27720
atttcagaaa ataaagacta gcatttctga gccaagtggt agtagtggcc atttttctg  27780
gaaaaaaaaa aaaaaagaaa gaaaaaacac atttagctat ctatgatgtg aaaagatgaa  27840
cattttattt aggtaataaa tgttatgtca taaaatacca tttattgtgt gcctattagg  27900
tttcaggaga gctgtgccaa gagcattact tgtatatctt ttaagcctta caacagccca  27960
gcctgtcagg ctggtagtgc catatctgtt ttacagatga ggaagtgatg gattggagaa  28020
attaaggaaa ttgcctttag gtcaaagaga taggaagtga caaagctgag atttttaacc  28080
ttgtgagatt tcaaagtctt tgctttttaa taactgttcc attgcttcta atatagagat  28140
atgacaaaaa caagtaaaaa tcagtgaaga aggctgggag cagtcgctta tgcctgtaat  28200
cccagcagtt tgggaggccg aggcgtgtgg atcgcctgag gtcaggaatt tgagaccagc  28260
ctggccaaca tgacaaaact ccgtctctac taaaaataca aaaaagttag ccaggcgtgg  28320
tgacaagcac ctgtaatccc agctactcag taggctgagg caaggagaat cgcttgaacc  28380
tgggaggtgg aggttgcagt gagctgagat cgctccattg cactccagcg taggcaacaa  28440
agcaagactc cgtctcaaaa aataaataaa taaataaata aaaataataa caataatgaa  28500
gaaaacaatc cggtgattat tgtcagcaat aaaatttctt caatcaacca tgctttagtc  28560
ctggcagttc tctatcagtg agtttcaatc aaaaagtttg tttataattt tttttttttt  28620
aaaattttga aatttggaaa caacatcata aatgatggtt agttttctgc agctccctat  28680
tttggcagat agtctgttgt tactcataat taatttgaac taaaaagtag tgttgtacga  28740
tatcatgggc tgtgaatgtg tttgtgactt gatctgagaa cccacacacc acttaggatg  28800
cttctgtagg aaaattagag tatggaactc acttgcccac gctttccctg tctcagtcca  28860
tgttggtagg ctgcaaagtc tggggctaga aggacactga acaagacttc agcagtacat  28920
gttagtcttc cagagggaag gaatataata gttgagagaa taattccttt cctctgtgac  28980
tttaggcaaa ttcttggcta tgctgttatt tatttgggcc aaacaatatc aggaggttgt  29040
acattttatt cttaattact gcgatacatt aattttatcc atgggtttaa cctagcctac  29100
cttttgctgt tagacttcaa ctctacttgt gttgggttac ccctctgctt aaaaatcacc  29160
ctattcccaa gcctgaggga gtctaccttc aaagctttct atgacctaat ccaaggcctg  29220
tcaaacttcg taaagggcca gatagtaaat ttgttttttt tttttgagat ggagttttgc  29280
tcttgtcacc caggctggag tgcaatggtg ccatcttggc tcactgcaac ctctgcctcc  29340
caggttcaag tgattctcct gcctcagcct ctcaagtagc tggggttata ggcatgtgcc  29400
accacgctcg gctaatttct ttgtatttag tagagatggg ggtttcacca ttttggtcag  29460
gctggtctcg aactcctgac ctcaggtgat ccacctgctg cggcctccca aagtgctggg  29520
attaccagtg tgaaccaccg tgcccagccc gatagtaaat attttaggct ttgcagtcca  29580
tatacagtcc cattttttg tgtatgtttg cacgttttct ttacatattt taaaagcccc  29640
tttttttttt tttttgagac agagtcttgc tgtgttgctc aggctggagt gcagtggtgc  29700
aatcttggct cactgcaacc tctgcctcct gggttcaggc gattctcctg tctcagcttc  29760
ccgagtaact gggattacag gcacatgctg ccacgcccag ctaatttttg tatttttagt  29820
aaagatgggg tttcgccaca ttggccaggc tggtctcctg atctcaggtg atctgcccac  29880
ctctgcctcc caaagtgctg ggattacagg tgtgagccac cgtgcctgac ctaaaagctc  29940
tttacagtgt aaaaaatatt ctgagcttta agccatgtga aaataggcca tgggcatttg  30000
ctgaccccta atagaactcc atttaccttt tctgatcatg tttcccatta actcttcaaa  30060
aatatgacct ccatttaaat caagatggtc tccttcctca ctgcttgtgg aggtccagtg  30120
cccagtgtct gcctcttgct tgctcctcca tcattgttct gccattcgag atcctcatac  30180
ttacccttta agatctagcc caaattttcc atgaaactaa ttctaataat taaaaacttc  30240
ctgtagaact taactttgtc tagtacaagt tagctttctt attcagtagt agcttactat  30300
aaattacaag aataaaaaga ttaccatttt ccctcacact gttttgtgga gaatgcctaa  30360
agttactttt tctttttaca ggtcagtatt cctatttggc atcctaatcc cctttcccaa  30420
atctgaattt tgggatttga agcttgcatt tgagattatg atttgtcttc cttgttgtac  30480
acaggagcag ggactttaca attagtattc gcatccctgc tccttcatac ttcgtgatgt  30540
aaggcaagtt attttcactt atgcttaagt ttcttcccct gtaaaaaggg gatggaagag  30600
gattaaatga attaaacatg taacacgctt aaagcaatgc ctggcaagta ataagtgctc  30660
agtaactttt agctgttctt attagcatgt ttggaaacca gtagaaacta caccagcaag  30720
ttaaggttga aaagtggtat tgatgggctt ggggtagtac agtatgaatg gctacagttt  30780
agcgtttcat taagtttgta tattcattaa ttcattacac atttgatgct gtcagactag  30840
gacagagaca aagatgaatg aaacattatc tctgcttcca ggttacccag tgtagtagag  30900
aaggcaggca tgcagatagt ttaaattggt agcactggga ggggactgcc atgggtgggc  30960
agtgaagaaa aagggcttca aaataatgag agttgagatg gatcttcaag gaagataagc  31020
agttttcagt aaggccatga agagaggagg aagttccagg cgggaagagt ttgtgctaaa  31080
```

-continued

```
gtacagggat tgctatacac atggtgtatg tagaaaaaat ttggttcaca gtgtgataga  31140
agaattggag gggtcctca ctgaaagtaa ggaaacacat ttggaagaat atgtttcagt  31200
tagaaaatga aatgagctta aagtaaacgc taataaggtt tttaaaatgt aaaatttcaa  31260
cgtatttaga aagagaacag ctggatgaat cttatgtacc tgtcactcag ctttagcagt  31320
tatcagtaaa tggccaacgt tgtttcagct atactcccct ctcctccact gatagtcttt  31380
tgaaggggaa tacaattgtt ttgtggcctc cagaaaggga taagtttatg agcaacgggt  31440
agatcgttgg gagagacttg agtttcctgt caggaagcat tcttggtgca taagtcagag  31500
gtgatatgaa tgccgtggaa gggggtggct tactgtctgg agaactcgag aagatgggaa  31560
tgggcactgt ccagtattgt ggctacttcc acacatggtt ctttaaattt aaaattatgt  31620
tgattaaaat ttaaatattt cagttcctca gccatactaa tcgtatttca agtgcttagc  31680
tgccacatgt gcctaatggc tgcaatattg gacagcatga cataggacat cttcatcatt  31740
gtacaaagtt ctcttggaca gcatgggact agagccctaa gatccttttc tacctgagtt  31800
gtttggattt tttggtgtgt ctaggttgga tctagttgtt catggcttca tgaccaagcc  31860
ttttatccct ttctctagag ggactcaagg ggtaaaggca ctgaaggggt aaaacttcat  31920
atgaagagtg tggtggtggt ggtggtgttt taagacaggg tctcgctctg tcactcaggc  31980
tggagtccag tggcatgatc ctggctcact gcagcctcga cttcctgggc ttaagtgatc  32040
ctcccacctc agctcccaag taactggaac tgtaggcatg agccaccaca cctgcctaat  32100
ttttaaaact ttctgtagag acgagatttc gccatgttgt ccaggctggt ctcaaattcc  32160
tggactcacc ttggcctccc agagtgctgg gattgcaggt gtgggccact gcgactggcc  32220
tttttttttct cctttactac tctagtgtat gctggaatat gaggaaataa ttatattagc  32280
tagcagttat taaacactta ataacatacc aggcactgtt ttaagctatg cgatctgtat  32340
ggaatattac ttaatttcca caaccttatg aaaagatact atttttttttc ttttgagaag  32400
gtactatttt catcttcatt tcatagatgt tgaaattgaa acacagagag ctgaagtcac  32460
aggattaagg ccacagagct gagaagtgat ggagccggaa tttgaaccca agcaattaat  32520
gctgatatta gttcttgtgt gaatggtaat tgttttgaaa caatgatcct agatgattat  32580
atgaccggat taatctggca gttgttctgt gtgaatttag agttgccttc ccacctcagt  32640
ttcctaaaaa caaaacaaaa caaaacaaaa caaaaaaaac tctagcttca ctgtgtttgg  32700
gttgtcatgg cctacccccct cttgccacct catttgactc aacttttttag ggagaaaata  32760
ttcaatacgt ggtataggat ttccctttct aataataatg taaacaacaa caagaagtct  32820
gaaattggaa gaacaaaatg actcacctaa gtgagttaac cttaagaggt ggaacttgat  32880
ttctagattt tagttaattg tctaactgat gtactaaata ttagttactt aagtattaaa  32940
acgggtagac ataatagttg gggagctgct gtagaggggg tagtttgaga aggcttcttt  33000
caggaggtga catttaagtt ggtaactaac aagaaagggg cagccatgtg aatagctgga  33060
gggaagagca ttcttacagt tttactggaa gggggttaga ggtatgtggt acccttatgc  33120
caaagaaaat tagttacttc tatacaacca gtctgattct agaaacctgg atcaatgaaa  33180
tattttgatt atataaaaaa atctgttacc caggtcttgt tgaaatagca ttagaaacta  33240
ctgaaggaca tatagaggag gagtgttgaa aaatggtgat ggatgagcag aatggtgaaa  33300
aataaaaaga catgaagctc tataattata ttgtatggtg acagtaccaa tagagattgc  33360
atgtttttttc tccccagttt ttttttttgt tttgtttttt gtttttgaga cagagtctca  33420
ctgtgtcact caggctggag tgcattgtcg tgatattggc ttactgcaac ctctgcttcc  33480
tgggttcaag cgattctcct gcctcagcct cctgagtagc tgggattaca ggcatgtgcc  33540
accacgcccg gctaattttt gtatttttat ttgagagggg atttcaccat gttggcaagg  33600
ctggtcttga gttcctgacc tcagataatc cacctgcctc agcctcccaa agtgccggga  33660
ttacaggtgt gagccactgc gcccggcctc ccccagttgt tgaaacaata atggaaggta  33720
attttattct tagattattt aatgtttttc agttatcagg atgtgttaga ttgtttgtgt  33780
atattgtttt gcttgttaat taagtaacac agtgaataag acagacaaac atacgaaaat  33840
gtacatttat tttatttttt tgagacagtc tgttgcccag gctggagtgc agtggcccaa  33900
tctcggccca ctgcaacctc tgcctcctga gttgaagcga ttctcttgtg tcagcctcat  33960
gagtagctgg ggccatgggt gcacgccacc atacccggct aatttttata tttttagtag  34020
agatggggtt tcaccatatt ggccaggctg gtctcgaatt cctgacctca ggtgatctgc  34080
ccgccttggt ctcccaaagt gctgggacta caggcatgag ccactgtgcc aggccatttc  34140
atttttggaa cgttcttttt tttttttgaa atggggtctc gctctgtctc ccaggctgga  34200
gtgcagtggc tcaatctcag cttactgcaa cctctgcctt ccgggttcaa gtgattctcc  34260
tgcctcagcc tcctgagtat ctgggactac aggtgcatgc caccacgcca ggctaatttt  34320
tgtattttta gtagagacgg ggtttcacca tattggtgag gctggtcttg aactcctggc  34380
ttcgtgatct gcccgcctca acttcgcaaa gtgctgggat tacaagtgtg agccaccacg  34440
cccggcctgt ttctggaata ttcataatct tttgttgtca tttcaacagt gctcacagca  34500
gcttcaccag gtgtagattc catcttaaga aaccactttc tttgcttatc catgagaagc  34560
aacacctcat ctattcaagt tttatcatga gattgcagca attcagttac atcttctgac  34620
cccacttcta attttagttc tcttgctttt ttaccacatc tgcagttact tgctctactg  34680
aagtcctgaa cccctcaaaa tcattcatga gtattagaag caatttcctg gttgggcacg  34740
gtggctcatg cctgtaatcc cagtactttg ggaggccaag gagggcggat cacctgaagt  34800
caggagttca agaccagtct ggcaaacgtg gtgaaacccc gtttctacta aaaatacaaa  34860
aattagcggg gatgtggtgg cgggcgccta taatcccagc tacttgggag actgaggcag  34920
gagaatcgct tgaacctggg aggtggaggt tgcagtgagt tgagattgtg cccttgcact  34980
ccagcctggg caacaggagc gaaactctat cttaaaaaaa aaaaaaaaga aaagcaattt  35040
cctctaaaac tcctgttaat gttgatgttt taacctcctc ccatgctcat ggatggcatt  35100
ctcagtggca tctagaatgg tgaatacttt ttagaaagtt ttcaatttat tttgccatca  35160
gagaatggct atgaatggca gtagtagcct tacagaatgt atttcttttt tttttttttct  35220
tttttttttga gatggagttt tttttgctct tgtcacccag gctggagtgc agtggcatgc  35280
tatctcggct caccgcaacc tccgcctccc gggttcaagc aattctcctg cctcagcctc  35340
ctgagtagct gggattacag gcatgcacca ccatgcccac ctaattttgt atttttagta  35400
gaggcggggt ttctccatgt tggtcaggct ggtcttgaac tcccgatctc aggtgatctg  35460
cctgcctcgg ccttccgaag tgttgagatt acaggcgtga gccaccgcgc ccggccgtat  35520
ttcttaaata aaatggctta aacgtcaaaa ttatcccttg atccctgggc tatggactga  35580
ttcttgtgtt agcagttatg aaaacattta tgtccttgta cattcccatc atagcttttt  35640
gtcaatgaga agtaattttt tttttttttt tgagacagaa tctcactctg tttcccagcg  35700
tggagtgcag tggcatgatc tcagctcagt gcatcctaca actctgaggt tcaagcaatt  35760
ctcgtgcctc agcttactga gtagctggga ttacaggcgc ccaccaccac gtctggctaa  35820
```

-continued

```
tttttgtatt tttagtagag atggggtttc acgatgttgg ccaggctggg ctcgaactcc  35880
tggcttcaag tgatccacct gccttggcct cccaaagtgc tgggattgta ggtgtgagcc  35940
actatgcctg gcctaattgg cctaatttca atattgttat atctcaggga atagagaggc  36000
acgaggagaa agagagacaa gctgactgct ggttcgtgga gtagtcataa cacacaacat  36060
ttattaagat tgctgtctta tatggaccgt ttgtggtgcc ttaaaagaaa tcagggtaac  36120
atcaacgatt actgattaca gattactata acagatacaa taataattgt aaattattat  36180
ttacaattgt aaaatacaat cttttcttta ttatttacaa ttattgtaaa atacaatctg  36240
attacagatt actataacgt atacaataat agtggaaaag tttgaaaata ttgtgagatt  36300
tatgagaatg tgacacaggc gcaaagagag cacatgttac tggaaatacg gcactaatgg  36360
acttgcccga ctcggggttt ccacagacgg tcagcttgtc aaaaatgcag catctgtgaa  36420
tttcaataaa gcaaagcaga ataaaatgag gtatgcatgt attgccatca catgtacact  36480
agtaaaatac gttttttttt tcagtaggtg gatcaacctc aaattttaat ataaagcatt  36540
acttaaagga gaatatgggg acattcatga catttcttat atgtacataa aacttcatga  36600
aaataattta atgctatcca gcagtttatt ttagaagtac tggaggctag gcatggtgtc  36660
ttatgcctgt aatcccagca ctttgggagg ctgaggtagg aggatcactt gagttcagga  36720
gctggagacc agcttgggca atatagtgcg accccatctc tacaaaagag aaaagaagta  36780
ctggagtgtt gcagctctta cagaatttgt ctagcaggtt ttccagtctt taccagaaat  36840
gcccccatgc agaagtagta aatactgatt catgtaaaat aataaacaac tttatctttc  36900
agtttttaaa agacagggtc ttgtaacgtt gcccagactg gcctttaatt cctgggctca  36960
agcgatcctc tcacctgagc cttttgagta gctgagacta caggctgcac ctctgcacct  37020
ggctctgctt gatttttaat tgttgtattg ctgttgcagc tatgtttttt tttttcttca  37080
gtgtgaggat gggcaaactt tttatgtaaa gtctcaggta ataagtattt taggctctag  37140
ggccatatag cttctctgtt gcatatcctt tttttttttt tccatttccc ctcaaattcc  37200
ttttaccata agcaactctt gaggaacata aaaatcattc ttagcccaga agccagacca  37260
aaacaggttg tgggctgtag tgtcctgacc cctgatttaa agattgatag ctttgaaatg  37320
gaaagtttta actttctttt tttttctttc ccttgttctg attgggctgt taattcatta  37380
ggtatttact cagtgtgtat catatgaggc atgattcctc tgctaatttt ggtagtggta  37440
gaaagatact tttgccaagc ttggttgtta ggttttcatt tgtccaagag ttcctgacca  37500
agtgtgaatg gatgttgaaa tcaaggtgtt tctttggcca cacaatgtgc ctttgggggc  37560
tatatctatg tgcttctggt accttctttt aattttcaca aagacactgc ttgccgacca  37620
cactgttttg tctaatgtgg ggctatgacc ccctggaaga ggcatcattt tctgattttc  37680
acagaagcat aatatggtca ggtgatggtc ctgagtagtg ggtatatgac agatacacta  37740
gtaattataa tacagatcta aactggagag ttgaaaacag catcgtatat ttgattgaga  37800
taatcgaagg aagacttcct gaaaagatgg catttgagtt tcaaggctga gtaggattaa  37860
gtattattat ttaaaaaatg ccttggacaa tgcattaaat agagttaaca aatcacatca  37920
cttatagtct ccaattaaaa acattttact taaacataat tttagacttt tagaaaaatt  37980
gcaaagatat tataaagaat tctcctatat atctcacctg tattcttcaa gtaacatttt  38040
accatattca ccttaacatt ttctctgtat tggtaattgt atatgtaaga tttaatataa  38100
aataaaaatt cttattaaac atatgagaga catgatgcct ctttagccct aaatacttca  38160
acttgtatgt actaataaca agggcattct atttcaaaac cacagtacag ttgtcaaaat  38220
aaggaaatta ataattgtgt caaactgtta ttctgtttat agaccttcta atgtccttta  38280
aaacaatcaa caaatcaaca tttttctggt caagaaccag taaatatgta tattctacat  38340
atatatatac acatatatat acacacatat attctacata tatatgtgga atatacgtat  38400
ttactccctc tgtccaagaa ccaatccagg attgttacct tcggttatca tgtatctttg  38460
gtctccttta atccaaagca gtttctttgt cttttatgac ttgacacttt tgaagattac  38520
aggttatttt gtagactgtc cctcaactag ggtttatctg aggtttcctt atgattagat  38580
tcagatattt atttttggca ggaatacaac agaaatgatt tgtgtgtttt tctcattgca  38640
tgatatcaga aagtgcattg tatatattta tcccattact ggggttgtta actttgatca  38700
cttggttaga gttgtgtcta ctaagtttct tcactataaa gttattttc acttggtcat  38760
ttcatcagta tcttgtgggg agttactttg tggttatata aatactctgt ttctactttc  38820
ccttactata tttagcttct gtggacactt ttgcctgaaa cagttattta ctatggtgtt  38880
accaagtagt gatgcccttt tcttccatca ttctgtctac attttttttt tttttttttt  38940
ttttttgaga tggagtttcg ctcttattgc ccaggctgga gtgcggtggc ctgatcttgg  39000
ctcactgcaa cctctgcctc ccgggttcaa gcagttctcc tgcgtcagcc tcccgagtag  39060
ctgggattac agacatgcgc caccactcct ggctaatttt gtatgttcag tagagacagg  39120
atttttccat gttggtcagg ctggtctcca actcccgacc tcaggtgatc cacccacctc  39180
agcctcccag agtgctagga ttacaggcgt gagctgccac accaggcctt ctttttctct  39240
tttaagagat agagtcctgc tttgtcacca aggctggagt gcagtggcat gatgatagtt  39300
cactgcagcc tcaaactcct gggctcaagt gaacctccca tctgtagctg ggactacagg  39360
cacctgcata acacctgact gtttttttaaa actattttag agatggggtc ttgcgaagtt  39420
gctcaggatg gtcttgaact ccgggtctta agtggtcctt ctgcctcagc ctctggatta  39480
gttggcatta caggcatgag ccattgtacc tggcaagtgc atatttttctt tttttttttt  39540
taaggtggag tctcgaggcc gggcgcagtg gctcacacct gtaatcccag cactttggaa  39600
ggccgaggtg ggtggatcaa gaggtcagga gatcgagacc atcctggcta acatggtgaa  39660
accctgtctc tactaaaaat acaaaaaatt aactgggcat ggtggcacac gcctgtagtc  39720
ccagctactc gggaggctga ggcaggagaa ttgcttgaac ccaggaggtg gaggttgcag  39780
tgagtcaaga tcatgccact gcactccagc ctgagcgaca gaggtagact ctgtctcaaa  39840
aaaaacagaa agacggagtc ttgctctgtc acccaggctg cattgcagtg gcatgaactc  39900
cgcctcctga gttcaagcaa ttcttgtgcc tcagcctccc aagtagctgg gattacagac  39960
atgtgccacc acacgtggct aatttttata gttttagtag aggtggagtt tcaccatgtt  40020
ggctaggctg gtcttgaact cctgacttca ggtgatccac ccgccttggc ctcttgaagt  40080
ggtgggatta tgagtgtgag ccactgtgcc cagccaagtg agtatttgct tatgtagtat  40140
tttaatttta tgattttttt ttctttgaga cggaggtttg ctcttgttgc ccaagctgga  40200
gtacagtggt gccatctcgg ctcactgcag cctccacctc ctgggttcaa gccgttctcc  40260
tccctcagcc acctcctcct gaatagttgg gattataggc gcctgccacc atgcctggct  40320
aattttttgt atatctagta gtgatggagt ttgagcatgt tgccaggctg gtcttgaacc  40380
tctgacctca ggtgatccac ctgccttggc ctcccaaagt gctgggatta aggcatgagc  40440
caccatgccc ggccagagac tgttcattta tttttttttt ttgaggcgga gtctcgctgt  40500
attgcccagg ctggagtgca gtggcacaat ctcggctcac tgcaagctcc gcctcccaag  40560
```

-continued

```
ttcacaccat tgtcctgcct tagcctcctg agtagctggg actacaggtg cctgccacca  40620
cgcctggcta attttgtttt tgtattttta gtagagatgg ggtttcagcc cgccttggcc  40680
tcctggagtg ctgggattac aggcgtgagt cagggcgcct ggccaatcat accttctttt  40740
actgcattaa ttatggtttt ctttcgttct taaaacatgt ttatagtgac cacttttgaa  40800
attcttatta agtcagacat ctggttatac aagcaatttc tattgcctac ttctttttcc  40860
agtgggtggg gttatacttt cctgtgtctt agcttgtcgt ttttttttt gttgttgaaa  40920
actggacatt ttaagtaatg tagtaactct ggatacctca ttagcctatg gttgggggtg  40980
gtggttgtta ctgttatttg cttatttgtc taatgactgg ctgaatgatt ttagtgttct  41040
atccttcttc cctccctgta cagtgtgaca cgtctgatgc tagttttctt gggatgcagc  41100
cttgggtatg cctaccatca ctctagaatc acagtgattt tggcatggct ttgtctcttt  41160
tcctgactgt acccagctgt taagctacac taattactag gtgatgctgt gtagtcattt  41220
cttggtgtcc ttgggggatt ggtcccagga cccccccgtt ggatataaaa atttatggat  41280
gctctagtcc ctcataaaat ggcacagtat ttgcatatac cggtgcacat cctcctgtat  41340
gctttgtcat ttctagatta cttataatac ctaatatggt gtaaacacta ggtaaatagt  41400
tgttatatat tttttatttg tcttattttt attgtattta tttttaagtg tttttaatct  41460
cgagtgattg aatctgagga tgtgaaatct gcagatatgg agggcctgca ttgttttccg  41520
tggagctttg ggcctaaact gctccacaga ctgatctgat caaatttgcg cttctttgaa  41580
gggatagttt ctgagatcag tgtttgaaat ttgttccaat ccacagagga gtcctcccag  41640
ctctctttcc ctagttctgg ccaccaaact agacaactac aatttagcac ttatctccaa  41700
tgattctcct cctaccaagt gcctttgaaa gcatcattaa ctctttcata ccttgttgca  41760
aatgaaattt ctttgggaag agattgtgag tttttttct cctaaattat ggtgcaatat  41820
aagtaatata ccattttaac aattttaagt gtattaagtg ttttttttt ttgtagtttt  41880
ttttttttg tttttgaga tagtcttgct ctgtcgccca ggctggagtg cagtggcacg  41940
atctcggctc actggaacct ccacttcccg ggttcaagtg attctctggt ctcagcctcc  42000
ccaaatatct gggattacag gtgtgcacca ccacgcctgg ctaatttttc tatttttagt  42060
agaaacgggg tttcaccata ttggtcaggc tggtcttgaa cttctgagct cgtgatccac  42120
ccacctcggc ctcccaaagt gctgggatta caggccttag ccaccacacc tggcctatgc  42180
attgctttta tatgtatttt aaaattcata agttctcctc ctatgatgtt tttgtcccat  42240
gtgatttatt tgttaaaccg tcatctttgg ccgggcgtgg tagctcacgc ctgtaatccc  42300
agcactttgg gaggctgagg tgggtggatc acaaggttaa gagatcaaga ccatcctggc  42360
caacatggtg aaaccccgtc tctactaaga atacaaaaat tatctgggca tggtgacgcg  42420
tacctgtagt cctagctacc tgggaggcgg aggttgcagt gagccaagat cgtgccactg  42480
cactccagcc tggcgacaga gtgagactct gtctcagaaa aaaaaaaaaa caaaaaactg  42540
tcatttttta tgttgcattt actgcattct ggatttaaac tgtgaggaac ctcatggtat  42600
cagttaatat attcttccat cttaatgttt ctcgtaaact ggtagatctg taaacttgat  42660
taggtctatc ctattgtatc acatcagaag cagaaggtgc ttttttttt ttttaaggga  42720
aattgtgtga aagtagacag aatggtaaag tgaacccctg cacacctatc acccagcttt  42780
aatagttatc agctcatacc attcttgttt gatttacaac cccattcatt tctcccttct  42840
gtattattat tatttagtta attatttttt gagacagggt tttgctctgt caccaatgct  42900
ggagtgcagt ggcataatca cagctcactg ctgtcttgac ctcctgggct caagtgatcc  42960
tcccacctca ccctaccaag tagcggggac cacaggcgtg tgccaccatg cctggctagt  43020
tttttatttt ttgtagaaac agggttttgc tttgttgccc agactgatct caaactccgg  43080
cactcaagtg atcctcctgc ctcagcctcc taaagtgctg ggattacaag catgagctac  43140
cacattcagc atgtaaattt ctttatatta atttgactgg cattttaagt cacacttgaa  43200
tttcatattt ggcaactatt aaaagcatag agtcctggat attagtgttt tgttaaacct  43260
gatctatcta atcataaata tacttaggtc taaaatatgc tcttggcctt tgtttattgc  43320
ggttcagtat ttgttactat attaaatagt aaaatatttg gtttgagata ctaatgaaaa  43380
gattaaaagt aaagcataac ttgaatggat acaaaaagaa acaagaattt agacttcagt  43440
ggatttcaga gaatactgct tcgatatgct aacattcctg ttgggtgtcc aaccgtgtca  43500
tagatcagtg gaaattagtg gtttctgcac tttactgtac tgttttttta tatgataata  43560
ttttcctggt tgaatgattc gttcttttga gtaaactcca tggtcaaaca attactttt  43620
attagtcaaa gatgtaacca cataatcact aaaaagaaca gtgtgactta tttaaagggg  43680
attatgtttt taagtctttt atatagcttt gtagggaggc catatgagtt taaggacagt  43740
tcgtggcatt tgttcaaggt tttgtaactt ggcatctcag cagccaccag gataccagat  43800
catcgttcta agtaagattt aggcatttta gccttcatgt acagactata agtacacccc  43860
cccacacccc taccaaaact gtaaattcaa atgatgtttg aaaaagcata gaatttttgt  43920
taggcgaggt agtttattcc ttgtgataca gttccagaga ggcagcataa cctaggaatg  43980
aaaaacttag acgtggaatc agatacacct ggtttaaata ccagctctac tgctcatgaa  44040
ctggatgatt ttggtcaaga tacttgactg ctgaggttca gtttcctcac ctgtaaagta  44100
gaggtgatag attagacatg ttgcatgtga agtacttagt atggtgtctg gttttgtagt  44160
aagatctata aaagataaat tattagtcat attccttaga cttcaggaat ttatctctgt  44220
gccatgtttg aggcaaacag ttacagaatt agaatgttag aaatgaaagg aatcctagat  44280
gtcatttaat tcaagtccat tgttttctgg atgagagaag aaagtgagga aaagtgacag  44340
agttggagac caagctagga ctggcctcag aatgttaaga gtactcttct agggatcgac  44400
cagtcgtgtt actagacttt ttggatctga attgtgcttt tccttgaatg ttttgaattt  44460
tggcttgagt gttgtgatta ttttattaaa atgagattcc agtcctattg tcatgactaa  44520
tgtttatgag aaatataaca tttcacttta atgatgtttt ttaattattc taaggggcct  44580
aatctttttc agtggaataa gctttaggtt gtattatatt ctataattca cttgaaaata  44640
gaattcatct ttacttgaca gccaaatttt gtgtactgca tcttttctga gggagagagt  44700
tggcaaggaa aggcacttgt tacaacgatc cacacatata gacgcatatt atttagaaat  44760
gaaagtgctt tgaatgattt agcttatttt cagttttttt ttttctgcag ttgtaatcat  44820
atgacctgtt tttctttctt ttttttttt tgagacagag tcttgctctg tcaccccggc  44880
tggagtacaa tggggcggtc tcagctcact gcaacctcca cctcccaggt tcaggcgatt  44940
cttctgcctc agcctcccta gtagctggga ctacaggcgc atgccaccac acctggctaa  45000
ttttttttatt cttagtagag atggggtttc actgtgttag ccaggatggt ctcgaactcc  45060
tgaccttgtg atctgcccac ctctgcctcc caaagtgctg ggattacagg catgagccac  45120
tgcgcccggc ccatatgacc tgtttttctt ttatagatgg gggagaaata tgggaagtga  45180
cttggtgtca gtcatctgtg ttggttaaat caagaatata atccgtgttt tgcttctgaa  45240
tagctcttta taacagtgat tggttacttt gggagtaaag attattattt agagacagag  45300
```

-continued

```
tcttgctttg tcgcccaggc tagactgcag tggaatgatc gtagcctact gcagcctcag  45360
actcctggac tctggtgatc ctgcctcagc ctcctgagta gctaggacta gaggtgcatg  45420
ccacatgcct ggctataatt attattaatt tacgtttagc attagttttt ttcttccagt  45480
aggctatttt actttattta tttgattttg atgaagtttg attatttcta gtttgcttcc  45540
ttctatgacc cctacctgtt gtgggtctcc aggcaagcag tgcataggta gagccatcct  45600
taggtagcct ttagacttaa tattaggtga gctctcccca cagatagcct ctcctttatt  45660
tgaatggaat tatattttaa gtttggaaat atttttcagc ttatttagcc tgttgaattt  45720
aataaaaata atatttaatc ttttcagagg tcgaaacagt aacaaaggac tgcctcagtc  45780
tacggtgagt aactttaatg ttacttattg gggaaaatta gtagctaaaa catgatctct  45840
aaccacagac caaatgccaa ggcaaaagat tcccttcttt tgaattttgt catagataac  45900
ttgactgttt aagtatgtta ttagcctata tgtgtttttt taatgactct gtataaaatg  45960
tacaattact tgttgtatta gtccattctt acactgctaa taaagatata cctaagactg  46020
ggtaatttat aaaggaaaga ggtttaattg actcatgctc tgcattgctg gggaggcctc  46080
aggaaactta caatcatggt ggaaggggaa gcaaacacat ccttcttcac atagcgacag  46140
gagagagaag tgctgagcaa agcagggaaa gccccttata aaaccatcag atctcctgag  46200
aactcactca ctatcatgag agcagcgtag gggaaactgc cccatgatt  cagttatctc  46260
cacctggtct tgcccttgac acacgagaat tattataatt aaagataaga tttgggtggg  46320
gacacagaac caaaccatat catttgtaaa tagtattttt gtcacgtgta ataacaagaa  46380
caagtcgctt gttcttttct aaatgactaa gtgcaaatct aagtgaaaaa cctccaaaag  46440
atacgtagaa caccaagagt ggagtctgca gagttcttta tgctttttat tttgaattaa  46500
tgtgcttttt ttctgctgct ttcatttttc tcctttggct ttctggtctt aaattttgga  46560
atgttatcaa tgaaattgaa ccggacatga agggcagaaa ctataagtcc cacatgatgg  46620
aagaaataaa tgagaagcta tcacaaattt ttgagacttt gcctttatta gattgtttta  46680
caagaatcag gaagatatac acgtatatgg tagtaatatg gagtagtgtg gttgatcaga  46740
cttaagcact gtcactgatg ctgatatgct gggagaacct agtcagggtt cttctatgaa  46800
ggtatgacct ggcttcctac cccatttatt tatacttcac ccttcttagg gtacatttct  46860
gtgagtttta acaattgcat acaatcagtg taactaccac cacaatcaag ttaatagaac  46920
agtttcattg cccaccaaaa tccctcaaat cacttttcag tgaaccctcc tctctctcca  46980
accattgatt tgtcttccat ccttacggtt tgtgtccttc ctcctctatg gaagtttact  47040
cttgcttttt tatgtcatgt ttagtcaaaa caccattagt tggtttgact gataacactt  47100
gaaaacctga ccttctgttc cttctgttct ctatggaagc aaaatattaa ataaacaaaa  47160
tcttccctta atacatgtaa gatatcataa acctaactaa acattttgca acaaataata  47220
aacgttagct ttatatgcaa atgtaaatac aggctgagca tccctaatcg gaaatgctcc  47280
aaaatttcat attttgaatt agggatgttc aagcactaag tataatgcaa atatccccaa  47340
atccgaaaaa aatccgcagt ctaaaatact tctggtccca agcattttag atgaggaaga  47400
ttcagtttgt actaatttct aatagttttt tttttttta atattccaga tttcttttga  47460
tggaatctat gcaaatatga ggatggttca tatacttaca tcagttgttg taagttatta  47520
gattattggg gataaactgc cttgggggta gaataaagta attccatgaa gttaaaatgt  47580
ggataaatga ttgtcaaagt aacattgctt agatcatgtt tagtcaggat gatttagaga  47640
aatagattag aactcctttt atccagtcta atataattca ttgtaaaagt acagttggtc  47700
ctctgcatct gtgggttcca tattcatgga ttcagccaac cttggatcaa aaatatttgt  47760
taaaaaggcc aggcacagtg actcacgcct gtaatcccag cactttggga gtttgaggtg  47820
ggcagatggc ttgagctcac aagtttaaga ccagcctggg caacatggca gaactccgtc  47880
tctacaaaaa gtaaaaaaac tagccgaacg tggtggtacg tgcctgtagt cctagtgact  47940
tgggaggctg acgtgggagg attgtttgag cctgggaggt ggaggtttca ctgagctgag  48000
ataatgcccc tgcactcagc ctggtcaaca gtgccagaca gaccccttct caaaaaaaaa  48060
aatttttttt tttttttttt tttttttttt ttttgagaaa aaagaggcat ggttgcgtct  48120
gaaccaaaga tgtacggacg tttttcttgt cattattcct aaaacaatac agtatgacaa  48180
tttacatagc atttacatta tattaggtat tacaagtaat ttagggatag tttaaagtat  48240
ttgggagaat gtgcttagtt atatgcaaat actattacat tttatgtaag tgacttaagt  48300
attatgtaat tcggtatctg aaggaggtcc tggaaccagt cccctaccaa taacaacaga  48360
tagctgtatt cttgttaacc ctgctgtgtg tgtaaaataa tgttagtagt tgattgtctt  48420
ttgtacatta ttttgtcact taaaatagct ggggtcagaa atgtttgact tcagtattaa  48480
aattcgtact gcaaactctg agtagagcct cctgaagaat ttcaagagtt cagtgtattg  48540
ttaatgtttt gaaatttttt tattgttttg ttagtgaata cctaatattg aatgaagcct  48600
gatgaggtat aaaaagtaaa atgaaaacaa atatccctgg tgaccgggta gtatactgtt  48660
tctttgataa ataaattata tgtttttagg gctccaaatg tgaagtacaa gtgaaaaatg  48720
gaggtatata tgaaggagtt tttaaaactt acagtccgaa ggtaattttt acttttttc   48780
tttttcttac aaagtaaaag aacattttca tagtcagtgt tttacctagt ttttaaagcc  48840
actttgaatg attttacttc tcagtttcaa atactgatta ttttatagac tggtttgtgt  48900
aatcagagag gcttcttgat gtgtgtgctt attaaaatat ttcaaccatt tttaagcatt  48960
gtgagctaat agagggatgt ggtggtttgt tttttcctct taaaaattat tattaatgta  49020
cttaagacaa accatagaaa caaaaaacat ttagatatga ggatttttaa atgatggaat  49080
ggataataga tcatatgcct gggaaaaagg gtatgattct cttgagatta tttttgtcaa  49140
aggcatataa gaactggtac cttgatgagc taaagaattc ctaacaaatt ttattttgta  49200
aaggtttgga gtacttactt gtgtttttca ttttagtgtg atttggtact tgatgccgca  49260
catgagaaaa gtacagaatc cagttcgggg ccgaaacgtg aagaaataat ggagagtatt  49320
ttgttcaaat gttcagactt tgttgtggta cagtttaaag atatggactc cagttatgca  49380
aaaagaggtg ggttttgatt tcctaaatat gcctcatggt ttattagatt tattcaagca  49440
aagattttca cagtgatctt acaaactttt tttaaagaaa tatctgggct gggtatggcg  49500
gctcattcct gtaatcttag cacttaggga ggctgaggcg ggtggatcac ctgaggtcag  49560
gagttcgaga ccagcctggc caacatggcg aaaccccgtc tctactaaaa atacaaaaat  49620
ttatttttgt gtgtggtggc gtgcgcctat agtcctagct actagggagg ctgagacaga  49680
attgcttgaa cccaggaggc agaggttgca gtgagctgat accgcaccac tgcactccag  49740
cctgggtgac agagcaagac tccgtttcaa aaaaaaaaag aaagaaaaaa gaaatatcta  49800
ctttctagaa tagcccaagt aaggtaattt tttagaaaaa tgagaatgtt aatgcatttt  49860
tgttggaaaa caattagaac tttagagaaa aattaaatag agtttttgtg atctcttaaa  49920
aaattagttt gtaaagcatt ttctacagtt ttgtggtcaa gaatgctact gattatattc  49980
aactgaaaat ttcttgtccc atttggccta caatgcttta gtttataagt gggcatgtgg  50040
```

-continued caaatctgga aagaaatcaa agtataaggc taaggaagaa aggtagagaa cggttggtag 50100
aaaacaattg tctaatgaaa atgaaaaagg gtgaagaagt agaacatacg tattttaaaa 50160
atattcagag tatgagacaa ggttttgaga atttaaaagc gattatgtag ttatattaaa 50220
aatttagtct ctttttaagt gtccattgat gaacaaagtg ggaattcctg ttactcattt 50280
gcaaggcatt attgagtgtt cagtaacacg ttgcaaggca cttctgggca atcctgaact 50340
tggttctcaa attctttttt tttttttttt tgagacggag tcttgttctg tcccctgggt 50400
ggagtgcagt ggcacgatct cggctcactg cagcctctgc ctcccaggtt caagcgattc 50460
tcctgcctca gcctcctgag tagctgggac tacaggcgtg tgccaccaca ccaagctaat 50520
ttttgtattt tttgtagaga cagggtttca ccatgttggc caggatggtc tcgattgttt 50580
gacctcgtga tccgcccgcc tcggcctccc aaagtgctgg aattacaggc atgagccact 50640
gcacccagcc ggttctaaaa ttcttttatt tatttgtata tgccaaattc tgtagtgaaa 50700
tacgtaattc tgttgtaaat tgtagttcag tacaatttga ttttcactat tcaaatctat 50760
accaaaagct gtttttattg ttgggctgat tcttctacac tgttacttgg aaataataat 50820
ataccaggat tctttctctt agacttagga gtctttctct ttgcttgctt tttcagaggc 50880
taacagtact gggtattctt taactgtctt gatatgctga tgaaagcaca gtgttctgtt 50940
tttgaatctt ctcaaatgtc cttgtctttg attcacaact ttttgtctta agaggccttc 51000
agcatcccat acaaggaaac aagtcttttt ttagctgcta cctttggagt tgattttgtt 51060
tatgtctagg agcactaaat tatttatact tatactattg aaatattcct ctgttataaa 51120
ttcaaaaatt gactttggaa gataaaattt tagttgaatt taatacatag cactctggaa 51180
agagtattgg ccacaacaaa aaaaaaggtt ccctactcta ttggatacca ggtcatttaa 51240
cagccattta cggtatgcat tgtctttttg tttttatgat gaattgatat ttcccaaatg 51300
tggaagagtg aatattactt tgagatgttt gtgatagtcc attccttgct cctcttcaaa 51360
attaatgtca ttaaattttt attactttat tagatcttca tttctcagat aattttagtt 51420
cattatagaa aggcaagaaa atacagatca gagtgacaac tttgaaaatc tcactctact 51480
cataagggga tgggtgtatt ttgctatata ttacaaaatt agtttcttgg atgaggacat 51540
ccactattgg agtaatttca ggtatcttat tttttctttt ctctctcttt tttttttttt 51600
ttttggagac ggagtttcgc tctgttgccc aggctggagt gcagtggcct gatctcggct 51660
caccgcaacc tctgcctcct gggttcaagc gattctcttg cctcagcctc ccgagtagct 51720
ggttactgag gcatgtgcca ccatgcccgg ctaatttttg tatttttagt agagacgggg 51780
tttcactatg ttggccaggc tggtcttgaa ctcctgacct tgtgatcctc ctgccttggc 51840
ctcccagagt gctgggatta taggcgtgag ccaccacgcc tgggcaggta tcttatttca 51900
aaacttacag tggtttagtg aattatacaa ttgcgtccag tgcgtagtat cctgaaaata 51960
gtattaagtc atgtgtttag gacatcaggt ctcttaagct aagactatcc aggcagaaat 52020
tgccctcttc tataaaagaa gaaaagtatt aattaggaag tactatcagt atggagaaaa 52080
ccattttaga attattaatt ggcatggttt ccttcttttt tttttttattt cgagatggag 52140
tctcactcta tttcccaggc tggagtgcag tggtgcgatc tcggctcact gcaacctctg 52200
cctcctgggt ttaagcgatt ctcctgcctc agcctcccga gtagctggga ttataggcac 52260
ataccaccat gccctgctaa tttttttttt tgtttgtatt cttagtacag actgggtttc 52320
accatgttgg ccaggccgca tggttttcct taataacaaa attaaggcat ttattactgc 52380
atctagattt tttttatttt ttattagaga cttactcaga ttactcccaa agtaaaggaa 52440
ggtatggttt aatcaatgct tcttaatgct gggttcacgt ttagtcacct ggggagtttt 52500
taaaaatgtt ctcacttcta gggatcctgg tttaattata attagcctgg gtgaggctct 52560
ggacagtcag ggtgtgagct atgggtttca tgtgatgaga tcccaggagt ggctctgttc 52620
tgtggccttg agaatttgtg ctttctaggc caggtgcggt ggctcactcc tgtaatctca 52680
ctttgggaga ccaaggtggg cagatcattt gaggtcagga gttcgagacc agcctggcca 52740
acatgttgaa accccgtctt tactaaaaaa gtaaaaaatt agcgggacgt gatggcacat 52800
gtctataatc ccagctactt ggggagaggc tgaggcagaa gaatcgcttg aacccgggag 52860
gcagagattg cgagatcatg ccactgcact ccagcctggg caacagaata aaaaaagaat 52920
ttgtgcttta ttttcttgcc tcacagtccc ctttctgtct cagaattggc aactgcctga 52980
aatagtctct gctgttatca tttgatagta cttttccaca tcttgaatgg atagatagag 53040
tgttttttat aatagaagtg gatgaatgat tagagtatac taatatgaca ttgtattttc 53100
ctaaaagata tgaattgatt tcatttctga gcttttataa ttctcttctg taatagtctg 53160
tcaaattatt aaggttgata atattaacta aaatttgagt gcatattcta tgtgccagac 53220
tctgtgctaa cagatttacc tacatttgtt cacataatca tcacaagttg tttctgtagt 53280
agatacagct attatccacg tcatagatga ggaaacaggc atatttagga aacttgctaa 53340
agtgaggaca caaatctagc ttttctactc taactcatgt tcttaacatt atactgcagt 53400
gacataaatt atgtggtttg gtttgttgtt tatctcagtt gtcataagtc gaattaatgt 53460
ttgtttgttt gttttgagac agagtcttgc tctgtcgccc aggctgggta cagtggcgtg 53520
atcttggcgc actgcaacct ccacctcctg ggttcaagca gttatcttgc ttcagcctcc 53580
ctaataactg ggattacagg cacgtaccac cacacccggg taatttttgt atttttagta 53640
gagatggggt tttaccatgt tggccaggct gatttcaagc tcctgacctt aggtgatcca 53700
cccacctggg cctcccaaat tgctgggatt gtaggcatga accactgtgc ccagccagta 53760
agttccatgg ttgttaaagg atttctccac aaataaagct aaaagtaaaa aaaaaaaaaa 53820
aaaaaaaaaa ttctcaagca atataagatg cagactatta tgttgttcaa gttttttttt 53880
ttttttttta atctttggct ttatttttgg ggaaaccttt tttttctttt ttgttttcct 53940
tgggacggag ttttgctctt gtcgcccagg ctggagtgca atggtgcaat cttcgctcac 54000
tgcaacctcc gccttctggg ttcaagcgat tctcctatct cagcctcccg agtagctggg 54060
attacaggca tgtgccacca tgcccggcta actttgtatt tttagtagag actgggtttc 54120
tccacgttgg tcaggctggt cttgaactcc tgacctcagg tgatccacct gcctaggcct 54180
cccaaagtgc tgggatcaca agcgtgagcc accgcgccca gccagggaaa cctttatttt 54240
gaggcggagt ctcgctctgt cacccaggct ggagtgcagt ggcgtgatct cagctcactg 54300
caacctctgc ttcctaggtt caagcaattc ttctgcctaa gcctcccgag gagctgggat 54360
tataggcgtc tgccaccatg cccagctaat ttttatattt ttagtagaga cggggtttca 54420
ccatattggc caggctcttc tcaaattcct gacctcatga tccacccacc ttggcctccc 54480
aaagtgctag gattacaggc gtgagccacc acactcggct gctggggaaa ccttttaaca 54540
tgagtaaggt cagtgtgact tttaagttct tgatgctaac atcattgatt tcaataaagt 54600
ttaaaagtta tattcatgca tatatgcaaa tgaataaaag gctttgaaat agtgacttct 54660
tacggtacag tgaataagtt tcctttggtc tcttgaatgt tatacatgtt ccagtttgat 54720
ttactgagaa actgaaagta cctttacgtc atatgagctg tgagtcacct tggcacattc 54780

-continued

```
ataattagaa gagaccatca gattatcatt ggaaaatcag tttgtattta tcctttattt  54840
gaattccagt gcagacagat ctgaggttct cttcatttg ctaaaacttc ttagggcctt  54900
cagtcgcttt tggctctgta ttcgtgtatc tttggaattg tcctgttatc tctgcttgtt  54960
ttttacttga ttttccatcc atttccagta ttcctttctc ctctattttt ttccttcatt  55020
ttctttctgc tcttcctgtt gcgccattat tcatgttttc ctctttactc caactcaact  55080
atggctttac ttctgtttcc ttattccatt gttcctcata ctttttccta ctgcttcatt  55140
ttctttgcag tattctcagc ctagatgata ggggtcagca aatctgctca tcagtaaata  55200
aattttattg tagcatagct atgcccatgc gtttgtgcat tgtctatggc tgttttgatg  55260
gctgtagcca tagagttgag tagttgtagc tgactgtagg acttgcaaag ccagaaaatt  55320
tgactgtctc tttacagaaa agtttgccag ctcttggcct aaatcatatt ttccgctgca  55380
tttagggctt tttaggactg atcaaaaata catgctatac tggctttggt gaagtaacag  55440
aatgtgctct gtcctttaaa cttacaacta attgcatgct ttgattctaa tactgtataa  55500
tatcctgcga ttcttattca tgaccattct aattggattt agtctgaaga attacttttg  55560
cttaacagat tctttgtcac atttagtgaa aaatcataaa aggggaaggt tggttaatgg  55620
aaaagatctc catcaactaa ccactacctt ccttatctac aaatttatct tcttcctccg  55680
tgccatcttt tttttttttt ttttcagatg atcttgctct gttgcccagg ctggagtgca  55740
gtgatgcaat cacagctcac tgcagcctcg acttcccagg ctcaggtgat cctctcacct  55800
caacctccta cataactggg actgtatgtg cacatcacta tgcctgacta atttttttata  55860
tttatatttt ttgtagagat ggggtttccc tgtattgcac aggctggtct caaactgctg  55920
ggcctaagag tcttcccacc ttggcctccc aaagtcctgg gattacatga gtcaccgcac  55980
ccggcctcat tattattttt cctctggttt tagtagagag gatttttaag ccaacttcaa  56040
tcatgccctt gactctctcc cttctactta cctccttgtt ctctttttct ttttcttttt  56100
ttttagatgg agtctcggtc tgtcacccag gctgaagtgc agtggcgtga tttcagctca  56160
ctgcagcctc agcctcctga gtagctgggg ctataggtgc ctgccaccac gcccggctaa  56220
tttttgtatt tttagtagag atggggtttc accatgttgg ccaggctggt ctcgaactcc  56280
tgacctcaag tgatcacctg cctcagcctc ccaaagtgct gggattacag gcgtgagcca  56340
ccacgcctgg ccatcttttt ttttctcctt gctcttttat accacttctc tgtttctggg  56400
ctcttcaaca tctgcctttc tagttaatct ttccctttag catgaaaacc tattcacttc  56460
ctgctcatcc taaaaaggat tctttttttgt tttgttttgt ttttgttttt gagacagagt  56520
ctcgctcttg cccaggctgg agtgcagtgg cactatcttg gctcactgca agctccgcct  56580
cccgggttca cgccattctc ctgcctcagc ctcccgagta gctgggacta caggcacctg  56640
ccaccacgcc cagctaaatt tttgtatttt tagtagagat ggggtttcac cgtgttagct  56700
aggatggtct cgatctcctg accttgtgat ccatctgcct cggcctccca aagtgctggg  56760
attacaggca tgagccaccg cactgggccc aaaaggattc tttttaatcc tgaattcttc  56820
tagccattat cctgcctaag gctacgatta acctctaact gccaggtcct ttggaatctt  56880
tttctgtctt tattgctgca cttgaatgtt ggtttcaccc tccttcagaa tttcctcttc  56940
tgtatttttt atgtttattg atcattcctt ccctgcctca ttcctgggct tcttttcctt  57000
cacacacccc ttagatgtgt gtccccagtg tttgtttctt tgcctgctgc tcttgccaca  57060
tgacacacac tgccagctac cacacacaag ttccctccta tcatgtgtgt atcattgccc  57120
ttataccatg ttgtattaaa attatatgct tgtctcccct gttacagttt gagctctttg  57180
tgctccaagt aaagacagtg atactgtctt tattatttat tctcatggtc tagtatagtg  57240
ctttggcaca tagtacaggc tcaatataaa tgtgtttgaa taaatgaaat tcagtgcctt  57300
aatacacttt tgtagaagca ttattttatg gaaagaatga aaaagctgta agtggtctta  57360
catatatagt catccagcag atacttagag agctctggga tgtgttcctt gctgtgcttg  57420
ttgctatgga cagtacggag aaatacaaga atctattttg ggtccctttt gagaacctag  57480
tgaaactgtg tacctagtga aactgtatac cctcacccta gaaaaattta cacacatgta  57540
gattttacat gtaattcttt taaaaattaa tttttttttct ttttttttaaa gaaacagggt  57600
catgctctgt cactcaggct ggaatgcagt ggtgtgatca tggcttactg tagcctcgac  57660
ctcctggctc aagcgactct cccacctcag cctcccaagt agctggggct acaggtgcac  57720
gccgctatgc ccggctaatt tttaaaaata ttttatagac actggttctc actatgtttc  57780
ccaggctggc ctttacctcc tgggttcaag caatcctcta ccttggcctt caaaagtgat  57840
gggattatag gtgcaagcca ctgtgcccac gctaatgtaa tttcatggtg ttcacagttt  57900
cttcagggag ttcatatacg ccatgtactc tattctaagc atttttagag ttagagatag  57960
caaagcacgt gaataaattc aagaaaaatg gaatgttgta ctgcatgaca ttgaatatca  58020
aatggagtca gcgatgcaaa taattgtcta gattttacaa aaaaaattag cctggtgtgc  58080
tggtgtgcgc ctctaatccc agctactcgg gaggctgaga caggagaatc atttgaaccc  58140
agaaggtgga ggttgcaatg agctgagatc gtaccactgc actccagcct gagtgacaga  58200
gcgagactcc atctcaaaaa taaaaaataa aagaattgtg tagattttag tagttggaag  58260
aagttggagt gttaatgtgt aattagagaa cagtgagaaa taaaattcta cagattgttt  58320
tattctggtg tgctgttgtg ttctcatatg gttgtctttt tggtcttgat agtgtatcag  58380
taacagagta cgagtaacaa acagggatct cttctgaacg gcgtgacatt agaaaagctg  58440
tttacggcct caactttgct gtggtttatt aagacacaga tatgtgttca ttctggggcc  58500
aagcagtaac tggagagtgg cacttattga ggccagtatg gaggcagtac agagattatt  58560
gagattaaaa gaaagaaaca ggtggaacgg atctatgtaa tggaaagcta aacagaatag  58620
ttcgtggtac acagtagaaa agcattacat gtttattaag atatggtcat cttccattta  58680
ttaaagttac atgttttata atttttagag tatatagaaa ttctctaccc tatcatgttt  58740
gccaaagtca gaacaataac ttcatttatt aaatataaaa aaaataaaaa cctctagcat  58800
aaaatagaat tttatttgga caaacgataa aaaaatactg tgtggtacta gtaagagtaa  58860
ggttgattca agatacatgg gagcagaatc caaagtgtag aaataggcca ggtgcagtgg  58920
ctcatgcctg taatttcaac acttttggag gctgaggcgg gaggatgagt tcaggagttc  58980
aagactcgcc ttggcaactt ggcaaaaccc catctctaca aaaagtacaa aaattagccg  59040
ggtgtggtgg tgtactcctg taaacccagc tacttggtgg gctgaggtga gaggttcact  59100
tgcagccagt aagtcaaggc tgcagtgagc tgtggttatg ccacggcact ccagctgggt  59160
gacaagcaag accttgtctc aaaaacaaac cagccaggcg tggcggatca cctgaggtaa  59220
ggagttggag accagcctgg ccgacatggc tctactaaaa atacaaaaat tagctgggcg  59280
aggtgacggg cacctgtaat cccagctact tgggaggctg aggcaggaga atcgcttgaa  59340
tccaggagac ggagtttgca atgagccgag atggtggtgc tgcactccag cctgggtgac  59400
agagccagac tctgtctcaa aaacaaaaat aagcatagga catggggata aattgaagat  59460
ttatgaagac acagctgaag gagacataaa agtagatttg gctaaatgga aacatgccat  59520
```

-continued

```
actttgaatg gaattattta atactacaac gttgtcaatt ttcctcaaat aaatctctaa  59580
agataatata ttcagttttg gccgggcacg ttggctcacg cctgtaatcc cagcactttg  59640
gaaggctgag gtgggccgat cacttgagga cgggagtttg agaccagcct ggccaacatg  59700
gtgaaaccct gtctctacta aaaatacaaa aatcatctgg acatggtggc aggtaccagc  59760
tacttgggaa gctgaggcag gagaattact cgaaccccgt aggtggaggt tgcagtgagc  59820
tgagattgca ctccagccgg gtgactccat ctcaaaaaaa aaaaaatttt tataatatat  59880
atatatatat ccgtttttgt agaaattgac aaaatgattc taaagcttat tagattatgt  59940
gtattaacag aagaactttg gaaatttttt tccacaagag tcataaagga ggacttgccc  60000
tacaaaatat gtcagaatta aaacataact tgtcagctgg gtgcggtggc tcacgcctat  60060
aattccagca ctttgggagg ctgaggcagg cagatcatga ccagcctgac caacatggag  60120
aaaccccgtc tctactaaaa atacaaaatt agccggtcat ggtggcgcat acctgtagtc  60180
ccagctactc gggaggctga ggcaggagaa tcgcttgaac tcgggaggtg gaggttgcag  60240
tgagccgaga tcgcgccatt gcactccagc ctgggcaaca agagtaaaac tctgtttcaa  60300
aaaaaaaaaa aaaaaaaaaa gaattataac tgtcacagtg gctacgtatg gagcatccaa  60360
aactgaattt atgtgggtat tttattaata tgcaatatag cactttaatt ctggaggaaa  60420
ggtggattat tcagtaaatg attctgggac attggggaca aattagatac ctacttcaca  60480
ctgataaata aaaccaaata gattaatgag aaaactgtga ttaaacaaaa caacacccag  60540
actacactgg agcaaatctg tgaatttgtt taattttgag tggagaagga ctttataagc  60600
atgactacca gagcaaaaaa atcatgaagt aaaagatcga tacctttgat tataaagaga  60660
ttaaagattt aggccgggtg tggtgctcac gcttgtaatc ccagcacttt gggaggccaa  60720
agcgggtgga tcacttgagg tcaggagttt gagaccaacc tggtcaacct ggtgaaaccc  60780
catctctact aaaaatacaa aaaaattagt caggcatggt agcacatgcc tgtaatccca  60840
gctactcagg aggctaaggc aggagaattg cttgaatttg ggaagtggag gttgcagtga  60900
gccgagattg tgccacatca ctccagcttg ggcgacagag tgactccatc tcaaaaaaaa  60960
aaaaaaaaaa gacttagacg tgtccaaaag taccatacat ttaaaaagac atgccacaaa  61020
ctgggaaaag tagaaaaata gttttaaaaa tgaccagtga atgtatgaaa aggtggccct  61080
cctcacttgt aatgatttaa gaaatgcagt ttatttttat tttattgtat ttttaaagaa  61140
attcagtttt aaagcagtgg aatatgattg tctatcagct tgcgctgaat ggtaaatgtg  61200
agaaagatta ctactactta gtggtactga gggagttgca aaacacttaa cactgctagt  61260
gggatggttt aagtaaaaca agtagcattc ttaaactctc tattaggtaa agaataggta  61320
agtaatgcat atgtttccag gacattttca gtaagactgt ttactgatag ggttgtgtaa  61380
tgctaatata cttactatct agttttagta ttattttttt ctcttgtctt ggatggtttc  61440
aatggagtct tatgcatgca gatatattaa aactagtaat aaagcaagag aaggaatgtg  61500
gataaattat ctctaatttc tattttgttc tatttctatt tcatactcct gggaaagaat  61560
attaagtggg catgtgtact tgaacagttg ttctgttttt tattagaaaa gaatccgaat  61620
ctataaaatg ttttacatat ttgccaggga aacagaaaag atatttgtac agctgtaaga  61680
attggaatta atttcatttt actgactttt ccttaaccta attctgaaca cttttgccat  61740
aggtttgaga ataagttgtt ataaaatgac tactattctt cactaatagt attggcattt  61800
caattcctaa attctgtttt ttgattcttg aacatttctg aatttacttt ttttgtctta  61860
gttcttctac agaatcattt tcttcttttt tcttttttta ttttatttt ttatttttga  61920
gacagagtct tgctctgttg cccaggctgg agtgcagtag cgcgatctcg gctcactgca  61980
agctccgcct cccgggttca tgccattttc tcctgcctca gcctcccggg tagctgggac  62040
tagaggtacc cgccacagcg cccggctaat tttttgtatt tttagtagag acggggtttc  62100
accgtgttag ccaaggtggt ctcaatctcc tgacctcgtg atccatccgc ctcggcctcc  62160
caaagtgctg ggattacagg catgagccat cgcacccggc cttctttttt tctttctctt  62220
taacttctga gctgaaaata gtacctttta taaagaagtg ctcaaacgat gattggactg  62280
atttctcctt atttctctct ttctctctgt ctctttcact ctcttttag aatttttctt  62340
ttttaagtag agacgaggtc ccactatgtt gcccaggctg tcttgaactc ctgagcccaa  62400
gcaatcctct ttgcctcagc ctcccaaagt gctcggatta caggcttaag ctatcacacc  62460
aggcctaggc taatttcata ttttgagatg gcacaaattt ctttcaggta gctagctttt  62520
cctcctcctc cccacttaaa atagatcctg atccagaagc ctaatggaga aaatgaaaac  62580
agaatgttca cccataaaca gtatctttgt attggaatct tttctaaaac ttcttttgat  62640
ctttttagga gatagtgtgg gaatcagcaa tctagtatta cgtacgtgga atctgtcacc  62700
ttgtttttttt aaatacagca aacctcatga agtgaatttc catatttttt cttgttcttg  62760
ttagttttgc accactcagg ctttgctgta gaatttgatg tatatttgat tctgtagagc  62820
atgggctatt gatcttcact cagctttcag aggaatctga ttagtaagtt tgagtttttt  62880
attatttttt agttgatttt gaagtaaaat acagcaccat tttaactgat accatttcta  62940
aacaattttc agttcaaatt ttaagttagc taatttagag cttaagaaaa ttgctttaaa  63000
aacataaaat tactggctgg gtacagtggc tcattcctgt aatctcagca ctttgggagg  63060
ccaaggcaga tgaattgctt gagcccagta gttcaagacc agcctgggca atatggtgga  63120
accccgtttc tacaaaaaaa atacaaaaag tagccagaca cggtggtatg tacctgtagt  63180
cccagctatt cgggtggcag aggtgagagg atcatctgag cgcagggaga ttgaggctgc  63240
agtgagccaa gtgagaccct ggtttcaaaa aaaaaaaggt tactaattgc agtgcctttt  63300
atcttattta atgggcttag tcaaactaag atgatgtatt ttatcttata aatgttttcc  63360
cttgaatttt aactgaagaa tccaatttgt acctctcaca aacagaatgt attagtaagg  63420
aaaataaata ctgcttttta ttacttaaat aggatatatt tttctcttag ggattttttt  63480
tctattttat ctcactttat cgtagtgcta gaaaatttaa tcattcattt gagataggga  63540
gaaaattagg ttttttttt tcttctattt tgagacaggg tctcattttg ttgtccaggc  63600
tggagtgcag tggcgccatc gtagctcacc ataacctcaa actcatgggt tcaggtgatt  63660
caccttagcc tcctgattaa gctgggactg cagatgtgta tcaccactcc tggctaattt  63720
ttgttgttat tttttgtttg atgaggtctc attatgttgc ccaggctggt ctcaaactct  63780
gggcctcaaa tgatcctcct gccccagcct cccaaagtgc tgggattaca ggcatgaacc  63840
tctgctccca gcccattttt taaaatatat tcacagcatt gtgcaaccat cactacaatc  63900
aatttacatt ttcatcaccc tgaaaagaaa ctctgaaccc cttagcagtt cctctctgtt  63960
tgtttcaatt ttccccagct ccaggcaact attgatttat tgtcttcata ggtttgccca  64020
ttctggacat tgcgtattaa tggaatcata taatatatag ccttttttttt tcttttttttt  64080
ttttgaaaca gagtctcact gtgtcgccca ggctggagcg cagtggcatg attgcagctc  64140
actgcatcct ctgcctccca ggttgaagcg attctcctgc ctcagcctct tgagtagctg  64200
ggactatagg cgcctgccac cacacctact aatttttatat ttttagtaaa gacggggttg  64260
```

```
caccatgttg gccaggctgg tctcgaattc ctgacctcaa gtgatctgcc cacctcggac  64320
tcccaaagtg ctgggattgc agccatgagc caccgcatct ggccatatat attatgatag  64380
gcttgtttca cttagtatgt ttcttccatg ctgtagcatg tattagtact tctttctttt  64440
tcatggccaa atattccatt atacagttac acaggtacac tacattttgt ttattcatca  64500
gttggtggac attttcattg tttccacctt ttgatttata cataatcctg ctgcgaacag  64560
tgacttttaa agtttttgtg tgggccgggt gtggtggctc atgcctctgt aatcccagca  64620
ctttgggagg ctggggctgg cagatcattt gaggccggga gttcgagacc agcctgccca  64680
acatggtgaa accctgtctc tactaaaaat acaaaaatga gctgggtgtg gtggcgtgca  64740
cctgtaatct cagctactag ggaggctgag gcagagaatc acttgaagct gggaagccga  64800
ggctacagtg agccgagatc acgccactgc actccagcct gggtgacaga gtgaaacttc  64860
atctcaaaaa aaaaaaaaaa aaaaaaaaac tgcgtgtgga cataggtttt caattctcat  64920
gggggtgtgt gtgtatgcat actcatacat acatacacat acctgcaaga taattgctgg  64980
ctcgtatgct aaatctatgt tgaacctttt acataactgt tgggctgttt tgttttcttt  65040
ttattatttt ttgaaaatag agttggggtc tcactgttgc acaggctgat ttcctgggca  65100
tagtggctgt atcattttac aatcctacat agctgtttcc aacgtagctg tatcatttta  65160
caatcctact agcagtgtct gaggtttctt atgtttttca catcctcacc agcatttgtt  65220
attgtctgtc tctttgatta tacccatcct agtgggagag taagaagtag tatctcactg  65280
tagatttttt ttttctgttt acaactttac tttaaaaatt atatatgcac acatggtaaa  65340
aagttcaaaa cgtgtgtacc aaaagattta acagtgaaaa tagaaaataa gtgtggtcct  65400
tgttttcttc caccaaggca aatattgtta taatctccta aacaacttgt cttccagatt  65460
tctcattttc agtcaatctt gggcattgac ataaagaaat tcttagacat tgcttttatt  65520
agatcatctc atcccttgct caaaatcttc agtggccact gttgtttaca gaataaagtt  65580
gggatgctat acagggccct tcccagtgga acttctcttt ttcaacctta tctctcatta  65640
tttcccaatg tttttttttt ttttttgag acggagtctc gctctgtcgc ccaggctgga  65700
gtgcagtggc gggatctcgg ctcactgcaa gctccgcctc ctgggttcac gccattctcc  65760
tgcctcagcc tcccaagtag ctgggactac aggcgcccgc cactacgccc ggctaatttt  65820
ttgtattttt agtagagacg gggtttcacc gttttagccg ggatggtctc gatctcctga  65880
cctcgtgatc cgcccacctc ggcctcccaa agtgctggga ttacaggcgt gagccaccgc  65940
gcccggccta tttcccaatg ttaatctact tattgaccta ctaagctggc atgttctgtg  66000
tgttagacat caccaacttt gtgccttctt tttttgtttg tttttgagtt ggagtctcac  66060
tctgttgccc aggttggagt gcagtggcgc gatcttggct caccacaacc tctgcctccc  66120
gggttccagt gattctcctg cctgagcctc ccgagaagct gagacgacag gcgcgcgcca  66180
ccatgccctg ctaacttttg tatttttagt agagatgggt ttcactgtgt ttcccaggct  66240
ggtctcgaac tcctgacctt gtgatccacc tgccttgggc tcccaaattg ctgggattac  66300
aggcgtgagc caccgcggcc ccctgtgcct tcttctttta ctcctggatt taatcccaac  66360
gtgaagaatc taccttacta actagagttt tagatacttt ttcaaaacca agcccacatc  66420
tgtccttttt agagtcttct ctgaccttcc ctgctcattg tggtttgttt ttattgcctg  66480
taacaatggc tgttaaactt tacattttaa attaatttat gtttgtatgt atttatttgt  66540
tgagaaaggg tctctctctg tcacccctac tagaatgcag tggcgccatc atggcttact  66600
gcttcctggg ctcaagctgt tctcccattt cagcctcccc atgcaccacc ctacctggct  66660
aatttttttg tttgtttttt ttagtttagt ttttgtagag acagatgtct cactgtgttg  66720
cacaggctga tcttgaactc ctgggctcac ttgatcctcc catctcagcc tccccaagtg  66780
ctgggattac aggtgtgagt caccatgccc agactttaac attttctttt tagtatagaa  66840
taggtcagtt tttttccctc tgatgagatc ccatgctgac tcttagttaa aacaaggctt  66900
tggttggaag aagagctagt gatgtcctag ctccctactt actccacttt cccttgcctt  66960
ctggggtgtc ctgaagacat catagggtgt catgaagtac agttggagaa ccagtggtct  67020
ccatcatgta ccaaacactc atcttcacga agcagtatgt agtgtctttt ttaccggtat  67080
attttctctc tcccaatgca ttaaactttt ctggagttca gaaaacaaat ttatagaatt  67140
aaggaaatgc gtcccccca accatggtgt ctagtatata tacagtgact tacagataac  67200
aggtgttcaa catatatata ttcctttgat tgatttttga aaagtttaca tgtatatatt  67260
ttttatatac ggggtctcac tctatcactg aggttggagt gtggtgatgc agatcttggc  67320
tcaccgcaac ctcctcctcc caggctcaag tgattctccc acctcagcct cccgagtacc  67380
tgggaccaca ggtgcgcatc accatgcctg gctaattttt tatatttttg gtagagacag  67440
gattttgccg tgttgcccag gttggtttcg aactcctgag ctcaggcagt ccacctgcct  67500
tggcttccca agtgtgagcc accactgaaa tacttatatt tttaaactta atttatttat  67560
atttattata tttttatgtt tttatatttt aaaaaatatt tttatactca ctagacccaa  67620
ttttatactc ctaaaccagg gaataactgt tttttttct cttacatagg catgatacca  67680
tagacaatga ttaaaattgt aattaccatt catttcttag ttttgtggct gggacactga  67740
tgtcttcaaa tgttagtttg caaatacagt cagccctctc tatccatggg ttacacagct  67800
gtgaattcaa ccaaccatgg atccaaaata tatgggaaat acgctggggc tgtgggtcac  67860
acctgtaatt ccagcactta gggaggctga ggcagatgga tcacctgagg tcaggagttc  67920
aagaccagcc tggccaacat ggcaaaaccc tagctctact ataagtacaa aaaattagct  67980
ggccatggta gtgcacatgt gtaatcccag ctactcgaga ggttgagaca agcaatttgc  68040
ttgaacctga gaagtagagg tttccatgag ctgagattgt gtcactgcac tccagcctgc  68100
gcaacagagt gtgagaagaa aagaaaaaaa actgtctgaa aagaaaaaaa aaaattatat  68160
gggaaatcaa aagcatctat actgaacatg tacagacttt ttttcttgtc attattcctt  68220
aagcagtacc acaactattt ccgtagcatt tactttgtat taggtattat aggtaaccta  68280
gaggtttaaa gtatgcgaga gtatgcaaat actacaccac tttgtatcag ggacttaagc  68340
atccctggat tttggtatcc ctagggggta ttagaaccaa tcccccatag atgctgaagg  68400
acaactgtag tgtgtgttgg aataatttat tttcaaatgg atcatttgga gaacactatt  68460
ctttaggaaa catagcctcc taagttctgt tccatacatc cctttcacct ccacggcgtt  68520
gtagcatcct gctttcatga ctgtgtcatc actcggaagg aactgcttct cttccagaat  68580
gcttttcaag atctactctg accacagcta taaactttac acttctattc tcttcttgcc  68640
cctcacagtg ttctctgttc ctctaagatc ttaaactctg tctactccta atccagcctg  68700
ctgggtgtgg ctggagaaag tcccactggg gggctgatta gttaggaatg tagggtttcc  68760
agctcttgct ggagcctcag aagagttcag cagacttttt tttttttttt tttccttaaa  68820
cctatttctg cagccttgat gaccactcct tccagtccct cacctatttg ctttattcat  68880
ggcagaggct ctttcttcct gcttgtcagt acaaagaggc aggattcttc acctggatct  68940
gtggattctc aaagaatttg tggagagaat tcagggcatt gatgaccttg gatgaagaga  69000
```

```
aatttacatc tttatttaca ctaaccttca agtgaaattt agcatttttt gccatttaaa  69060
aatatgggca acaaacaact agtagtatta gcagtattta tgacttaagc acctatagaa  69120
ctcagttaat ttcatatcgc ttgatgttat gggtatctca aattattatt ttatgtatat  69180
atatttttga gatggagtct cgctctgtct cccaggctga gtgcagtggt gcagtctcag  69240
cccattgcaa cctctgcctc ctgggttcaa acgattctcc tgcctcagcc tcctgagtag  69300
ctgggattac aggcgcacac caccacgcct agctaatgtt tgtattttca gtagagaagg  69360
ggtttcacca tattggccag gctggtcacc aactcctgac ctcaagtgat ccgcctgcct  69420
tggcttccaa agtgctggga ttacaggtgt gagccaccgc acccggcctc aaattatttt  69480
tagaaacaga atcttgatat ggtatccgct ctggccttga acttgtgggc tcaggcagtc  69540
ctcccacctc agcctcctga gtagctggga ttataggcat gtgccactgc accaggcttc  69600
aaattattat gtatgttcat cacctcttta aatttataat agttattaaa cctgttactg  69660
gatcttaata tttaatgctt taattaagaa catgtatgtt actatgccaa cagatttttt  69720
tagtttttga taactgcatt tcattgttac ttgttctcat ttgatttcct gtgtatttta  69780
cgaatttaag tacattctga atacggtttc ataggcttcc ctaaaatatt gaagggggccc  69840
atggattaag aaaaaggcta agaatcccta atctagaggc tccccacagt cctcttttgt  69900
catcataccc ctaccccatt ctagcctgag gagcgtggct ccacctgtgc ccttggtttt  69960
gttgttccag tccatacatc ctgcaccctt aactgtgttt cttatcccca acttgtttct  70020
ttgtgttatt cttcagtatt atagtcttta atataatctg tataatacat ggtgtagtag  70080
tatatgctcg tagtatacaa ttcagttaga acagatgagt attcaatgaa aagataatct  70140
cctctctaac ccccagtccc acttccctgg ggaagcctgt gttcttgtgt acaattcaga  70200
aaatgtttat acacatattt tttatttatt tattttttga gacggagtct cgctctcgcc  70260
aggttggagt gcagtggcgc aatcttggct cactacaacc tccgcctccc tagtagttca  70320
agcaattcaa ggttcaagca attcgcctgc ctcagcctcc cgagtagctg ggactatagg  70380
cgtgtaccac cacgcctacc taatttttgt atttttagta gagacagggt ttcaccatgt  70440
tggccaggat ggtctcgatc tcttgacctc atgatccacc cgcctcagcc tcccaaagtg  70500
ctgggattac agatgtgagc cactgtgccc agcctgttga tttaatttta aacagagttt  70560
cgctcttgtt acccaggctg gagtgcaatg gtgcgatctc ggctcaccgc agcctctgcc  70620
tcccaggttc aagtgattct cctgcttcag cctcccgagc agctgggatt acaggcatgc  70680
accaccatgc acagctatat ttagtagaga tgggggtttc tccatgttgg tcaggctggt  70740
ctcgaactcc ggacctcagg tgatccgccc gcctcggcct cccaaagtga tgggattaca  70800
ggcgtcagcc actgcacccc gcctatacac atttttttgt tttttgtttt tttgagatgg  70860
agtctcgctc tgttgtccag gctggagtgc agtggcgcga tctctgctca ctgcaagctc  70920
tgcctccctg gttcacacca ttctcctgcc tcagcctccc gagtagctgg gattacaggc  70980
gccggccact acgcccatct aactttttgt atttttagta gagatggggt ttcaccgtgt  71040
taaccaggat ggtcttgatc tcctgacctc gtgatctgcc tgactgggcc tcccaaaatg  71100
ctgagattac aggcgtgagc caccgctccc agctatacac gtatttttaa tgccactcca  71160
gtctatgttg gaaccatttt acttcccctt tcttattttc ttcttgtgtt cttgaaggcc  71220
tagatcagct gttgctgata ggctgtcact gtcactttag aaagcccaga gccttttgtt  71280
ccttagaact ttgtttttaa ttgtattgta gcactcattg tattcgattc taaaagattt  71340
gcttcatttc tgtaactagt ctcttacacc caggagctcc tagttcctac aggaaatgct  71400
gggaattgta tcagtcaaat gtgaatcccc acctcgtcca gacttatgag tgcattgtag  71460
gtactcagta agtgctaaaa atgactaaat agtcccactg ataccaatct atatactgat  71520
actttatata gtatatagat tggtccacat ataacgatga cacataatga gaaactgtct  71580
taaaaagttg ttgaaagtgc cgcaggaata ggaattgatc aaaacaatat gatttttttag  71640
gtttatatgg aactttgatg tttgagaaaa ggctgattta gttgagaaga aatggttagc  71700
tgaggatttt gatgacttct ctggaagcac atttgagggt ttgtgatgtt aaatctgatg  71760
ttaatgatta tttcatccag ttttatgtca ttttatagtt tttatacatt taagtatatt  71820
tatttctaat gtttaacact accattttag ttatttgacc attattctgg ccctttaaaa  71880
aatgctcaga caagtttgaa tgatttttca gaggcattat tggctcagag gtaaaagagg  71940
aaagattgag aagctgaata tgtactctgt ttcctgggta tggggctggg gatacccaga  72000
agaggttcac acgttggtcg agacatttct ttatgaccac cagcaggtgg catcaccggc  72060
ccaaaatgac taagtttctg cccagaatca gaagagaagg tgttgagagc ccactgctgt  72120
gggggtagca tggaggtggg atacaggggc tggaggtgat acaattttgt ttcttcctcc  72180
aacatcgcct gctagtctag aggcttttat aaattgaaaa actaattctt tatcatctca  72240
tctgatggtt tttatgtttt tcctttttttc tctctatacc tgtagttcct tcagaaacag  72300
gtaacacttt tctaatagtc acgttgtatt cttgcatctt gttgttacaa tgcttttgtt  72360
tctcaccata ggggatgatg gaaaattaat attctttgac ttatggcatt ggtaaaatct  72420
gcatgcaaat tcccacagtt gcctgtagat tagagccagt tgttttttttc tcaactttgc  72480
aggaatcctg gttacaacat tgtactattt actaccaaca gtgttttttt tttttaaaat  72540
ccagacttgc tgggcatagt ggctcatgcc tgtaatctca gcgacttggg aggctgaggt  72600
gggaggattg cttgagccca gggctgcagt gattgcggca ctacactcca gcatgagtga  72660
caaagacccc atctctgaaa aaacaaaaac aaaaacaaat ttttttttaaa gaaacagaaa  72720
caaaaatcca aacttgtaac cactgtaaaa caaatcagaa tttacgatag tggatattat  72780
taatagtgca gaatggatac ccagatcttg cttcctttct agctaatgat gcaatgttgg  72840
cctgaaatgc attacttata gccagggatt ttctcagcat cctgatgata tagcctcatt  72900
tcgtgctaac tctccacttc tgcacatctt cccctaagtc ctttactcat ctttagaaag  72960
agctactttt ggtgaaattt taaaaccaag gaatatcatt ctttatagaa tcacacttct  73020
gtgttttccc cttccccatt tctgtctcga aagcgacaga ctgctacata acctgtgaat  73080
actttttttt aaaaaaagtt tggtattgta aacagaagat ttaagattaa aatgtagcat  73140
tgagaaaaat agatttatta ataatgccct cttaacacaa cctaaattct ggtcagtgga  73200
ataaagcctg ggtcctaaag ttttagacgc ttgcttgctt ttccacactg gctcttactt  73260
ggggatcctt ttagaaattt gtttagaata atactgtaaa aacatattta agctactttg  73320
tgtgtacatt tgggatcttt tggtttgaag acggcttgac tcaagacttt ctaaatattt  73380
tcacacacac acacataccc tgtagtgaga aaaaaatccg tttatatggt tctataaaaa  73440
tctctagctg cttcgagctt taatttcttg aatcaaaaga gtattgtttt taatactgag  73500
cttctatcta aataaatgct ttatttactt aaatgtgtgc ttttcaaaaa ctagtatgat  73560
taagacatta acaggatctt agacgtaaag gaacagtcct gttgcttctt ccagaagata  73620
atatgactcg tttggaattt tcctatagtg tagttttttg tctagtgttg tgagaattaa  73680
agggatttca ggatcttaag gtaggttatt atttgatgtt ttcttggaac attttacatt  73740
```

-continued

```
cttgaaaata cacatggcta aattaatttt tgccagcaat ccacataact ttaagataat  73800
gtagagaaga acgtgattca ggttagtatc aaataaggtc agatttctag tgccatcagt  73860
agctttcagc aaagatgagg tgttggtaag atagcattag tctcttagaa tctcttagag  73920
agattttcca aaattcagcc atttctagtg aatgctccat tccaccccca gctgagtcct  73980
gctgctctgg ggaactccct cagcacactc ttggctctta gaattgctag caatgggagt  74040
agtgctgctg gtggagctgg cagctaagcc cagaggtgga ttaatgcttt tattccctga  74100
tgtacaggta cacacactca tacctaccca cacctagttt gggataagaa gaggttagaa  74160
ttagctaggc ttgaagttcc atgcttaaat ttgctggctc agatttctta ttttggcatc  74220
actttgccca ttagggagac aatgacagtt atagaagcat tgccaaataa aaaatccatc  74280
tggaataacc tcttttgtag gagtattgtg tgtttagttg ttgattcgtc ccttcctcct  74340
cttagtggca acttacagta ctgggaagga acagtggctg ggagcttata ttcctcagca  74400
gagccagatc agcagaagta ttactcctta gttcgtagta ggtggtaccc tatgggtcca  74460
gtcatttaaa tgcaagcctg tatctacaga gcgtttccta gtgccatcat tgcccagtgg  74520
gcctttattt agctgagtct aactcccaac tagagaaaat ttcctgtgcc agacagcagt  74580
atggtcagct aacatgtgga tgctacattt gctttcataa gtcagtactc ttcaataaca  74640
ttagtagaag agaagaggac acaaagtgag agtgtgttaa taggaagtcc aggtatgcct  74700
gctacctgaa ctttctgaga caggtaatac tgtagggcct gaactttgta gcagagtggt  74760
tatatatgaa gaagtgggtt ctgggagggg ttaaaccact tagaatggct tcatttacta  74820
atggcaagag tttgctggga tattgaccac tgtacataga catgaatatg gaaagttaaa  74880
aacaaaatcc acatatattt ggctgcaagt actccgaagg tatatctaat tagtgcatcc  74940
attaaacaaa agagatattt taggccgggc atggttgctc acacctgtaa tcccagcact  75000
ttgggaggcc aaggtgggtg gatcacctga ggtcaggagt tcgagaccag cctggccaac  75060
atggtgaaac cctgtctctg ctaaaaatac aaacattagc tgggcgtgtt ggtgggcgcc  75120
tgtaatctta gctacttggg aggctgaggc aggagattcc cttgaacctg gaaggtggat  75180
gttgcaggga gccgagatgg tgtcactgca ctccggtctg ggtgaaagag caagctccat  75240
ctcaaaaaag aaaaaaaaaa aaagagatat ttttgatgga ttgatagaaa ttttcttttt  75300
cttttttttt ttgagacagg gtctcactct gtcgccaggc tggagcacag tggcgtgatc  75360
tccattcatt gcaacctcca cctcccgggt tcaaacgatt ctccttcctc agcctcccga  75420
gtagctggga ctacaggcat gtgccaccat gcccaactaa tttttgtatt tttagtagag  75480
agagggtttc accatgttgg ccaggatggt ctcgatctct taacctcatg atccacctgc  75540
ctgggcctcc caaagtgctg gtattacagg catgagccac cacatctggc cagaaatttt  75600
cttggtcact tctgagacat gcagagtaat tacctgtaat ataatttaat gaattatgtc  75660
aatatattaa aatatgcttc atgtgggctg ggcatggtgg ctcatgcctg taatcccagc  75720
actttgggag gccaaggtgg gggtatcact aggtcaggag atcaagacca gcctggctaa  75780
cacggtgaaa ccccgtctac taaaaataca aaaaattatc cgggcgtggt ggtacacacc  75840
tgtagtccca gctactcggg agactgaggc aggagaatcg cttgaacccg ggaggcagag  75900
gttgcagtga gccgagatca cgccactgca ttccagcctg ggcaacagaa cgagactcta  75960
tctcaaaaaa aaaaaaaaaa tgcttcgtgt ggcttaaaat tatatgaaaa gaaaataoct  76020
ttactgatag tcatctgtga ttccatttgc taaattaaac gtgaaagcat acttttactg  76080
aatactatat attccgtatc agtttagata gcagtttatc ttcacataca taagttttaa  76140
gtttaccttt attatagtgc attggtcttt tgttttcatc aacctaaatt atgttcaata  76200
aatgtttctg ttagatttta agttaaacaa ttatgtgaaa ttcatttttc gtaattgttt  76260
tttaacatat gtctttgttg gtaattcacg tgtgtgagtg taactgattg ccagattata  76320
taaactttca accaaaacca ttctttgcag atgcttttac tgactctgct atcagtgcta  76380
aagtgaatgg cgaacacaaa gagaaggacc tggagccctg ggatgcaggt gaactcacag  76440
ccaatgagga acttgaggct ttggaaaatg acgtagtaag taacatcttt gtaattattg  76500
ctagactctg gtcagtatga catcctgtca cttggttgta atttaaatgt gcttttgttg  76560
ttgttgttat tgtagtgagt gtatttagag cagcaggttt gttgtataac tagagacttt  76620
ctcccaagca atatataaag aaaaatgttt gtcattttac ttgtaggggt taagcaggag  76680
tactgtctgt tcttgtggat gctcatgaat tacttctttg tgattaaaat aaataataag  76740
aagtagctta aattaaaatt agaaaccatg ggaaatgccg gtgtgttttg ctttaacacc  76800
cagccaaata aggtagccta aggaaagtgg tgtcttaatt gttgacttca cctagagaag  76860
aggttgaagt aggacatttt aagcctcttg tctgaagaaa aggttgtcat taagataaat  76920
aattaggtta cattggaatt aaagcattac ataaatttct tggtcttaaa tttggattat  76980
tctccacaaa attcttttat ttctaaaacg cctcttgtca catactagtt ttgtttctct  77040
ctttaatgca ttatctgtac ttgaagtgct tagctgggta tgctggcaca tgcctgcagt  77100
cccagctact tgggaggctg aagcaggagg atcacttgag cccaggagtt ggagtccagc  77160
ctgaatgaca taaggagacc ccttctctaa gaaataaaaa taaaaacaaa tacttaataa  77220
agactctgtc tttaggatag agagcataga gatataaagc aaagtgtctt gccaaaaatg  77280
agtgttatgg taccaatatt tgagtagaat gaagaatctt ccattgagta gaaagagaat  77340
ttgtaacata tctgtgtttg atgtttaagg cataacagct taataatgac actcttcctc  77400
agacaggaag cctgaaatgt cctactttga cctaaagtct agtaataaaa ctggacatac  77460
acaggcaaca tgtcattaat tctcaaactt taacaaatca tatataacct aatataatgg  77520
ttctcaagtc tgtacatcac gtcacctgta tgaaaaatat gaggaaacag agacttcttt  77580
tacactattg gtgaggtgga taaattgata gagtcttttct ggagagaatc tggcaatgct  77640
aatcaaaatt taaaatgcac atacactttg ttccagcagt tctatctcta gtaatttatt  77700
tttgccctca tatatccata agacatgcaa ataattatat gtgaagattt tttttttttc  77760
tttttctgca gagacagggt tttaccatgt tgcccagggt gatctggaac tcctgagctc  77820
aggtaatcca cccacctcag cctcccaaag tgctgggatt acaggtgtga gccatcatgc  77880
ctgaccagga tttttttttt tttcagcatt atttcttttg ttgttgttgc tgttgttttg  77940
agagatggag tctcactctg tcacccagac tggagtgcag tggtgcgatc tcggctccct  78000
gtaacctcca cctcctgggt tcaagtgatt ctactgcctc agctttccaa gcagctggga  78060
ctataggcgt gcgccaccac acccagctaa tttttgtatt tttagtagag acggggtttc  78120
accatatgtt ggccaggctg gtcttgaact cctgacctca ggtgatctgc ccacctcggc  78180
ctcccaaagt gctgagatta taggcgtgaa ccaccatgcc tggccatagc attatttcta  78240
atagtgaaaa attggaaaca tgctaagtgt ctatcaatat agcatgagtt agatttatga  78300
tgtcaccatt caattgaaac actacatatc tcccaaaaag aatggtgttc caatatggaa  78360
agatatctaa gatttattaa gagaaaaagc acattgcaga acactgggat cctatttgct  78420
tttttttttc ttttttgag acagagtctt gctctgtcac actgcaacct ccgcctcccg  78480
```

-continued

```
ggttcaagcg attctcctgc ctcagcctcc tgagtagctg ccaccatgcc cagctaattt  78540
ttgtgttttt agtagagaag gggtttcacc atgtttgtca ggctggtctt gaactcctga  78600
actcgtgatc cacctgcctc agcctcccaa agtgctgcga ttactggcat gagccaccgc  78660
acctggccat gaaatttttt ttttttttta aagagctgtt catattctta ttgcctagaa  78720
gatgtctgaa attacaccca agaaactctt tttgagacgg agtcttgctc tgttgtccag  78780
gctggagtgc aatggcgtga tcttggctca ctgaaacctc tgccttccag gttcaagcga  78840
ttctcctgct tcagccttct gagtagctgg gactacaagc gcccgccacc acatctggct  78900
aatttttgt atttttagta gagacagggt ttcaacatgt tggccaggct ggtcccgaac  78960
tcctaatctc aggtgatcca cccaccttgg cctctcaaag tgctgggatt acaggcatga  79020
gccactgcgc ccggctgaaa ctcttttttt ttcttttaag atggagtctc gctctgtcgc  79080
ccagacttga gtgcagtggt gtgatctcag ctcactgcaa gctctgcctc ccgggttcac  79140
accattctcc tgccctagcc tcccaagtag ctgggactac aggctcccgc caccacacct  79200
ggctaatttt ttgtattttt agtagagaca gggtttcacc atgttagcca gcatggtctc  79260
aatctcctga cttcgtgatc ctcctgcctc ggcctcccaa agtgctggga taccaggcat  79320
gagccaccgt gcccggccag aactcttaat agtagttatt tatgcacgct gggattggaa  79380
gacatttact ttttactgga tgtctttccg tattgtgtgc tttttttttt ttttttttat  79440
gtagggcata cattacttaa gtaattttaa agcctccata agtaagtgtg atttcctgcc  79500
catgtgtttg gcaaaaggaa ttgcattggt ggtagactta cattatagtc ttacctggag  79560
tagcacagga ggacccaagg ttaataggtg aacttcgagg caagccttag cattgaggtt  79620
gccatcagca ttgcttggtt gatgtgttca ttcttctggg atggattaca acctttactg  79680
gactttatac ttttcaccag taaggcttta aaaaaggagt tgaaacatta gagaataatt  79740
atccaggcag taatattcac tggtaaatag tcttccagcc tgtggcccaa ttggttgatt  79800
cttttacgtt aaagaatgca gcctcagctg ctctgcctat ggagtaggat tcttttattt  79860
actttcttaa taaacttgct tgcccctggc tcccccccac caaaaaaaga aggcagcctc  79920
ccttttgcga atggtaattt cctatagttt cctcgtagaa ttgtggagtt acctatgctg  79980
aggttatagg ttagggtatt gagatccaga gttgccactt ctgaggtgtc acaactgcta  80040
atggtaaaac catttctaaa gcccagttct tgtgactttg tccagtgatt gcctgttcac  80100
cgtttcatgc tgccttccca tttgagcatt cccaggagga aggggaggtt gccagggacc  80160
tagtaccata gtccgacctt ggaatcgttg aatatgaggg aaagcgttgg cttctccctt  80220
ctttctccca aacattggaa gtatttttgg ctgttaaaaa gcaccccttg ttccatgtgg  80280
aatcccttgt ttaaaagaag taaaatatgt acctcctgtc ctccacagac ctgaggacca  80340
gtgtgatctc aagaaggtta caggtaaatg tagatgtctc taactgaaag gtggctttta  80400
caggttagag aaaagagaga accctgatct gaaggctatt ttatgaagta attaaaatgt  80460
tctaaacttt aaaaataact gctcaaataa ttgtgttgta tagttactta tcaactggag  80520
gggctgataa gtatttttct aaaacatttt taaggaaatt ttttcctatt ttctaatttg  80580
ctaattttgc tcaagtagtt tgttagatat tgttaatata gatgttggtt ataactgaat  80640
gaaagggaac aactactttg acattttgaa aaacaagctt cattttcttc tagtctaatg  80700
gatgggatcc caatgatatg tttcgatata atgaagaaaa ttatggtgta gtgtctacgt  80760
atgatagcag tttatcttcg tatacgtaag tttgaaaagt ttgtttttat tttagtgcat  80820
ttgtctttga ttttcatcag cttaatttat gatgaataaa tgtttgttag tttttaagtt  80880
aaacaattac atgaaataat ttttctctta ttaccaactg tgataaattt ccattaaaaa  80940
aagggaataa atgtagtttg cctataccct gtttttatgc tctaaacaaa ttttggtttt  81000
gtcttttttt ttcttttgag agggaatctc gctgtgtctc caggctggag tgcagtggtg  81060
caatctcggc tcactgcaac ctctgcatcc cgggttcaag cgattctcct gcctcagcct  81120
cccgagtagc tgggactata ggcgcgtgct accatgccca tctaatttct gtatttttag  81180
tagagacggg gtttcaccat gttggccagg atagtctcga tctcttcacc tcgtgatcca  81240
cctgcctcgg cctcccaaag tgctgggatt acaggtgtga gccactgtgc ctggccggtt  81300
ttgtcttcta agttgttaaa aaatatctaa atttgcaagg gcagagatta tggtgaacag  81360
tttaaccagt ttttgaaata tgttcctctg gagaaaaggt aacagaaaaa aaagttagaa  81420
ttttgattta taaatacaca gatcactata acttttagtt ttagttttag ttttagtttc  81480
tgtttttacc agtattctaa actctaaact ttcttagtag ttgattatga cagatacata  81540
aactgtggct ttaaaggact cattttgctt ttcttttcct catgtttcag agtgccctta  81600
gaaagagata actcagaaga atttttaaaa cgggaagcaa gggcaaacca gttagcagaa  81660
gaaattgagt caagtgccca gtacaaagct cgagtggccc tggaaaatga tgataggagt  81720
gaggaagaaa aatacacagc agttcagaga aattccagtg aacgtgaggg gcacagcata  81780
aacactaggt atttaaagga aatcatgatg cagtattttg gatacacaac tcaaggtctg  81840
tgtgagacgg tgtattgtta ttatatttcc tcttccttta atatagctta ggtagagaat  81900
gcaagtagaa ttggtttaag atctgttaga gaaaaggtta tggtgatctt ggaaaatatg  81960
cttttgagag taagctctgt ggagccaagt gttggtatat cacggtgagc aatccaagat  82020
cttgaagagc ttgttaaaat agttatctgg tgggggacac gtgtaacaat cacagcagta  82080
caatatgatt tgcttggtta aaggcatgtt caaagtacta ggaacataca gaatgaggag  82140
gagctagcat aacctgtaga gtcagagaaa acctcattga ggaggtgaca ttttgtgata  82200
agataatagg gtctttgaca cttagagaag agttgggaga agagtttatc acctgatgaa  82260
aagccatgta caagcatggc tatgagaaaa tttggccagc tcaggagagg gctggttgtt  82320
gcatgtgtct ggaacacagg atctgtgtca ggtgcagcag tggcagttga tagtaggaac  82380
tgaggtcatt aaaggacttg gcatgtcatg ctaaagagca ccctgttgga aggagatggg  82440
gtgaataaac cctggggcat tgaggactgg ctgagacaca gagaacagtt agtgcactga  82500
aatagttcaa ctgtgagaat ttggtaacca cctagttaag ggatgagcct gaggtttatt  82560
tgataactaa gtgacttaat ggatgtactg gtaagagaga gaggaaacat ggagcaagtt  82620
tgaggggaaa aacagtgact ccgtttgtgc agctaattgc atatgtgggc ttgtgggtct  82680
ttcatttatt cataaacgtg ttgagaaata cctgctacct atctagtaaa gtaagagatg  82740
catcctctct taaaggcagt cagcttagag tctggtgatt tgaattgaca tgtccactga  82800
tagatgttga cactgtgaga ctggcggttc agtttgaggt ttcatcagca ttgccgatat  82860
tggagccatg aaaaaccaaa gaacagccag tgagagaaga gatctcagag aaaataaaat  82920
tgagaaagtg aaggacaaaa aatgttgtga agatagacca agattgatgg aatcagccat  82980
agagaggtca agtgggatga gaatgagcac gcatctgtta aactttgtgc ttaggagcag  83040
aatctaaggg aagggacagt ccagaggtta gaactcaggg taagatggaa gaacaggggc  83100
atctgggagt gaggcagttt ggtttagtgt agaacctttt tgtaacaagc attcccttct  83160
gtctagatga cttttagata tgtttcattg gcttggtacc ttttagaata aaatgattta  83220
```

-continued

```
gaggatctct catttcagg gaaaataaat atattcctcc tggacaaaga aatagagaag 83280
tcatatcctg gggaagtggg agacagaatt caccgcgtat gggccagcct ggatcgggct 83340
ccatgccatc aagatccact tctcacactt cagatttcaa cccgaattct ggttcagacc 83400
aaagagtagt taatggaggc aagtattttg accagacttg tcaatatcat tgataaaata 83460
gttttctaaa tacttaaaat acttaaaata gtttacataa ctgatatgaa tgtgcacttt 83520
aatgatttgg tgagtagctt tcacttcagc attacttaaa attggctttt gtggatatta 83580
aattagtaaa acattgtata tgtcattgac atatatatta tttagcatga tgaaatattc 83640
atgatgtact aagataaagt gctacattta acccaagaca atcacttggc caaaaacact 83700
tcacatataa agaaattgga aactttgggt aggttctcaa ttttaaaaac actggataat 83760
aaaatttttt agacataatt tatatggaaa attctaacct atgtgcaaca ctgtggttaa 83820
tatagatcaa ttttcattat ttgtttctat attatgctta cttcaagaaa ggatctgagg 83880
taacttataa tacaagacat gatcaagagt catgtgaaga aagtgactag agaaatttgc 83940
ttaaaaaaca acaaaaacaa cccttagtct aagggtggat gttacagttt agcaacttaa 84000
gtaaaagaaa cctgaatctt tagtaggaag acatttttta ctctacctct aaatctaggt 84060
tgaatatatc ttgtaggttg tggatctttt ccataaatca gggatactga acaacagttc 84120
tatggatggt atggaaatag taatagcaat agtatgttac taactttgtg ggaaaagagt 84180
ggacattcaa ttttagctat ttaaatttgg aaagttagat gaaaatagag aacactaagt 84240
ttccaatttc atttgttttc attgagtctt ttctccagaa ttcctctcca aatggacact 84300
cttgagtatt ttcagtactt aatattgggg gtgaaatttc tttgctcact gaggaaagat 84360
tttagttgtt tataaacaga attttaaagt taaaaaacct gaagggggct gagaaatata 84420
tgatacttaa gtgtgtggaa ccctatggag aggagacctg gactgtttga taagattaag 84480
gtaagtgata tgtaatgtta aatactagct gtatctttac ctaggcatat ccatcagtat 84540
aaatttattt ggtgatgact gctttgtagt tgcagtattt attaagcagt cgcttagata 84600
agtgtttaac tgtataaatt atttagaagg tctccctttt tctagtttaa tgaggtcaag 84660
actttttttt tgaaatagca atgaatatta tcatttgata ctcacaggag tcacaaactc 84720
tagaagagta atgttttatt tctacttaaa tgggacttgc ttaataagat tccaaactga 84780
gttctgggtt caagtgtaaa cctgatgaaa atcatagata attgtaagga accagcattt 84840
ctaattggat ataatagcta ctgcttattt tcgttatgcc tcagagttaa aactaataca 84900
gtaaataatc ttactcctga gtaggaatta ttgtgattta ttatgtgaaa ttatctagtg 84960
tatgttatat tcctttaaac aaccagttac tgagaaacag ttatagaagc aggattaata 85020
ggcaaagtct taactgtctt cttcaatagt gtgtatagat cctaattaac cctttgggaa 85080
cgtgtattca tttaaacaga cttaatctta aggaggttaa agtaaaatgt gaatttatgt 85140
cagttaagtt atgctaaaac ttatcacaaa tcaaatgact gtcctcaaag ggttaaaatg 85200
tacaagaaat catttttgtc atttttacttt ttttctgttt actttttttcc ctcatttttt 85260
tctttagttt ttatactttc cttcatatca tttgttctgt caggtgttcc ctggccatcg 85320
ccttgcccat ctccttcctc tcgcccacct tctcgctacc agtcaggtcc caactctctt 85380
ccacctcggg cagccacccc tacacggccg ccctccaggc ccccctcgcg gccatccaga 85440
cccccgtctc accccctctgc tcatggttct ccagctcctg tctctactat gcctaaacgc 85500
atgtcttcag aaggtacaat accacaattt gttcatgttt ttgtttgtct ttgtttaact 85560
cctatgtgag tttataatta caaaatagtt tcctcttcat tatttaataa cctataattt 85620
ctgtgtttta actttagttt attaaaacta tttctattaa ccttttgttc attagagaga 85680
aatttgataa atgtgtgaag ctataaactc tcttgaattg ttgttaaaaa ggggggtttat 85740
ctctgcctga taattatgct tctttacagc cccagaaggg tctgccccac agccttcccc 85800
ctccttattt gcactgtata cagtagttaa acaaatgaac tttcttcagc cagtcttgaa 85860
cttaggttca ttttacagct ctttggccaa ggtcctagtg aaccttccta ttggccataa 85920
gcagggatgg tgttttctgg gtcttttttg agagcgacag cccatgtagc tgactttgcg 85980
tgtctgccct tagattaaag tagttgattt ttagaatgcc agaagaattc taaatttaac 86040
tgagtaattt ttttaaagtt agctttgcaa tcttacatag tgaaaggctg ctttaatctg 86100
gaagaagtcc ttgatctgag ataaaattga taaaaacgac atatgaattt gaatatttag 86160
ctatttcttt cctcgtcaaa aataagaata aaatcttgta attcttattc agtatttggc 86220
gctaaatcca tcattgccac atatcaaata cagggatatg ttgtagaaag gtaacattct 86280
aatttaaatg ccacccatat attaaaaacc tgttttctga atcataatgt ccttttgata 86340
ctagttctga atatttgtgt taaaatttta atctgatttg ttcattaaaa ttagttaata 86400
ttgcttatgt tgggactaat aaagttttcc gcacaaaatg tgtttctcct gcttccctgg 86460
agaaaactgt attggctact tttaaataaa ttgttaccat ctaagcaggc aggtcatatg 86520
actttgactg aagcatctaa ccttgaagag caagttccac tgattttcaa ggtgacttct 86580
ttgctcaaaa gggccttaat agtggtcact aaatgcaaaa ttctgttgat atttttcttg 86640
tagtccatca tttgagtaag cgatgtttat ttaatgagaa tatattaaat aaaacatgat 86700
cattaatgac tgtgaacatc tttattacat taagatttaa ggactgctca tgtattaact 86760
tcacacagaa atatactttc tgtgtcattc agagatgttg aatatttcca tttgaaaatt 86820
atagtgtata acattagcat tcttctaaag atcatgttcg tgtttaaatt cctgttggaa 86880
gccaggcatg gtggctaacg cctgtaatct cagcactttg ggaggctgag gcaggtggat 86940
cacttgaggt caggagtttg agaccagcct ggccaacatg gtgaaacctc gtctctacta 87000
aaaataccca gctacttggg aggctgaggc aggagaatca cttgaacctg ggaggcagag 87060
gttgcagtga gttgagatcg taccactgca ctccagcctg ggcgacagag acagactctg 87120
tcttataaaa ataaaaataa aataataatt ctattggcaa catatattaa tttgaagttc 87180
taaagagttt ggcagccggg tgagagagtg aggagatttg gctttgacat tagggaagtt 87240
ttcgcttggt gttaacacca gtaggcttct ctgatgaggg ccattctgtc cactctttta 87300
cctgatagat tggtctaatg cacagtagac tgatttagaa agagtagtca ctagtggcat 87360
ggcagaatca ataatgtaga attttgacaa ttcatatagt gctgatttct cccccaaatg 87420
tcagttattt tggtcatcta ttaatagact aatacaagtc atccctttaa tagaattttc 87480
agctcacagc ctgctaagcc taagaaactg cttacaggtt actgcttact gttttaagcc 87540
gagttttaaa attgatgatc atgatagaag agataaataa actaaaattt tagagaaatt 87600
taagaagggt atgtacatat gttttagtgg tatcggggtg tatagggatt aatagtcttc 87660
tgtttaaatt tttttttct aattttagaa gtaatgtaga aaattcgggt cagggaaagg 87720
taaaatatat ggaaagttaa aaatatttta tcatgtagtc ataatttcta gtaacatatt 87780
tctttacaaa taagacatag ttgaaacaga ttgctacagt tcttttaaga gttgacatct 87840
tattgttgat ttcttaccac caacttcatc cctccctttc tttaaaaata aagggaaata 87900
ataaaattta tttataaaac tttgtggcat tccacaaaat aattctgaaa gaattagtat 87960
```

-continued

```
ggccaaaaaa atatgtatgg tgtttttttt ttttctattt ttaaccaagg aaaaactgta  88020
gagtgagtga gtgtgtgtgc atgtgtgtgt gaatgggtgt atttagcaga aaagtagtac  88080
tgatgaatat catggaattt atgtgatgtt cactgtttct tccttagggc ctccaaggat  88140
gtccccaaag gcccagcgac atcctcgaaa tcacagagtt tctgctggga ggggttccat  88200
atccagtggc ctagaatttg tatcccacaa cccacccagt gaagcagcta ctcctccagt  88260
agcaaggacc agtccctcgg ggggaacgtg gtcatcagtg gtcagtgggg gtaggtaaca  88320
cttgggcata atgatggtac tcattttgtc attacactag atataaagag ggctgagcta  88380
caactctgtt tgaggaagtg taagtatgta tatgttaaaa atagtagaat caccaggaat  88440
tgggaaaccc atatttttat tctgggctct accacttatt catcatatat taaagcaagt  88500
cagacactca ttctgaagtt gagatttcgc agtgagtaaa gtgttaataa ttcttgccta  88560
gtctacatta tgggattgtg atgagattcc tataaggttc ataaatacag atatattgta  88620
aaactataaa gttttgtaaa gtacctctct aatatgaggc aaacacagta tgtaacacta  88680
tttggaggga ccgtatttcc ttatcttttt agcagctttg tttatcagta cattctataa  88740
acatttattt ttggcttaca ttgtagtgtg tttctatagc atctgtatat ggcactaatt  88800
cccaactata tttccataat aaggaatatc aaatacaaat aaagggtcca agttttattt  88860
gtgattagca taaggaatat gctgacagca gctataaaag tataaaaatt aggctgggtg  88920
tggtggctca cgcctgtaat cccagcactt tgggaggctg aggtgggcgg atcacaaggt  88980
caggagatcg agaccatcct ggctaacacg gtgaaacccc gtccctacta aaagtacaaa  89040
aaaaattagc cgggcatggt ggcgggtgcc tgtagtccca gctacttggg aggctgaggc  89100
aggagaatgg catgaactcg ggaagcggag cttgcagtta gctgagatca cgccattgca  89160
ctccagcatg ggcaacagag caagactctg tctcaaaaaa aaaaaaaaaa aaaaagttta  89220
aaaactagac gttgacatga ttttacaata aggctgactg cttttgctac tttgccaatc  89280
agtccttagt gctttgttcc cataactgtg gtaagcaaga gcttacaaag aatacttaaa  89340
acaaacaaac aaacaaacaa aaaaaacact ttttctcttt taatcagtcc agagaacctt  89400
taaaagaaac aagatcggcc agttgctgtg gctcatgcct gtaatcccag cactttggga  89460
ggctgaggtg ggtggatcac ttgaggtcag gagttcaaga ctggcctgac caacatgatg  89520
aaaccccatc tctactaaaa atacaaaatt agctgagtgt ggtggctatt tgagaggctg  89580
aggcaggaga atcatttgaa cccaggaggt gaaggttgca gtgagccaag atcacaccat  89640
tgcactccag tctgggtgac aagagcgaaa ctctatctca aaaaaaagaa aaaagaaaca  89700
agatcttcaa gcttaaggaa acaaaaacaa aactcagctg tgttaaatct gtttttagtt  89760
gctatacatt tctgctcagc ttcatgtgat gcacattcat gtaattgtat cctaaattcc  89820
tttgtacttt ttattttctt ccttggtctt caattatctt aagactacca agaaaacaaa  89880
aattttaaaa atcttcttca gccggtcagg cgcagtggct cacggctgta atcccagcac  89940
ttggggaggc tgaggcgggt ggatcacgag gtcaggagtt caacaccagc ctggccaaca  90000
tggtgaaacg tcgtctctac taaaaataca aaaattagct gggcattgtg gcgcgttctt  90060
gtaatcccag ctgctcagga ggctgaggca ggagaattgc ttgaaccagg acccgggagg  90120
tgtaggttgc ggtgagcgga gatcgcgcca ctgcactcca gcctgggcta tagagtgaga  90180
ctccatttca aaaaaaaaaa aaaaaatctg cttcagctat tctgttaatc ttttgacatt  90240
acttagatgg tctggaaata aattttgaga ataacatgat tagaagtgag agagtataag  90300
catagttttg gagatacact cagaatagca ttatagattt tctcttttta ctaattggaa  90360
aaatggcagt tgttgaataa tagttttctt ccgtgaccct tgtgacttaa aaaaaaaaaa  90420
acactgaaat gaaataatcg aaccatttc tctaaacctt tgaatctgag ctctgcagtt  90480
aggtttataa tggtatatga aacctattag atatatactt ggaagtcata tgggatacaa  90540
accctgcttt tattatcttc ccctttgac taacttgggt ctcaagtttc cttaattact  90600
gcacagtgga ccttgatgtt gctataaaga atgtgtaggg ctgggcatgg tggctcatgc  90660
ctgtaatccc agcactttgg gaggccaagg taggcagatc acctgaggtc aggagtttga  90720
gaccagcctg gccagcatgg tgaaaccccg tctctactaa aaatacaaaa aaattagctg  90780
gttgtggtgg cgagtgcctt taatcccagc tactccagag gctgaggcag gagaatcact  90840
tgatacattt agttaggaga gaaaatcata cttatgttag taattgctgc tgttcttcat  90900
atacttgtgg ttttgattgc cagcaaattc ctaacatttt ggaaaagaaa acagtaatgg  90960
gataaagggt aagggctaga gaggacagtt ttatttacct agatcttcag agaagcctga  91020
agcctctttt aggaagtaac atttgaactg agaatgtaat aaatacattt tccctttctt  91080
ctagttccaa gattatcccc taaaactcat agacccaggt ctcccagaca gaacagtatt  91140
ggaaataccc ccagtgggcc agttcttgct tctccccaag ctggtattat tccaactgaa  91200
gctgttgcca tgcctattcc agctgcatct cctacgcctg ctagtcctgc atcgaacaga  91260
gctgttaccc cttctagtga gggtatgtaa caaagggctt ctggatccat aatctcagct  91320
gtgaaattga atgttagagg gtgatattat atgaaaaaat tctaggttat ttttattcat  91380
agacaagtat ttttagtgca catttaaaag tttatgtaaa ttttgatgtt gtttaatact  91440
actaatttaa tatagtgtct gtgttacaaa ggttaacatt cctgggtgtc aaatacctac  91500
ataaataaaa ttattggtgt ttcatatgac atctgcaaag gaaaaaaagc ctctgtttaa  91560
atgaaagcat tattttccaa aaacatagga aatcaaaatt attgttcagt gttttcttgt  91620
tttgcttttc taacttatct gaattttttt taaaaaattg ttttctagct aaagattcca  91680
ggcttcaaga tcagaggcag aactctcctg cagggaataa agaaaatatt aaacccaatg  91740
aaacatcacc tagcttctca aaagctgaaa acaaaggtta gagtttaaag agtcattaag  91800
cttaactgta ggaataggaa gaagtatgtc taatttcatg cccatacaga atatttttgt  91860
tcaacatttc ttcttactat tgtgatagat aaatgtattg cttgacaaat tccaaaatcc  91920
aaatttaata tttgaaatta ttttctgatc ttatatctta ttctaatttc tatcatctca  91980
tactaaaaag aatgtgatgt taaagtttaa aaataaacct gtgtcttaac agttcttaat  92040
tttacaggta tatcaccagt tgtttctgaa catagaaaac agattgatga tttaaagaaa  92100
tttaagaatg attttagggt aagtattgta ctaactgatg aatttgagtt ttagaaaata  92160
agcattacta aagatttatc tatttataaa aatgcgttat gtatacagtc agaaacatca  92220
aaccatatat gtagaaagca gaacattttt aaagtggtct ttgcctatcc tttaagtggg  92280
ataactaaaa tcatgagatt tggtaacaac aatatgtagg tatcaaatga gagtatagcc  92340
ctgacatttg aaaccaccat agcacagctt actatttgat ggtcatttgt actttgttca  92400
gtgaagctag atattagtag agcaaggcca agtcattaat aatctagtgt ggcaaatgga  92460
agatgtactg gactctggtg ttctgaggta gttggagatt tatactttgt acacaaatat  92520
attgtggtca aaatctttct gtaacattat ttctctgtct tagcacaggc tttacttaac  92580
atctctcctt gattgtcatt tcattctttt gcatgttatt tactataggt atcgaggtag  92640
attttgagac caaccaataa atcttcttga aacttagctt cttagaaagg aaaatctaaa  92700
```

-continued taccagcctt ttaaaaaaag tagctgaatt aaaggatgag tgaaccaaag gcaaaggtag 92760
cctttcctca gcctgtgttt tagctttcta aatgttaaca atagcttcat tcttgactta 92820
ttggtaacat tcaaaatact acttattatt tcatacttta gcacatgtat ctattcagct 92880
ttaatgctat taacagttgt taacctaagt tttcatttgt tggcgggcac ggtggctcac 92940
acctgtaatc ctagcacttt gggaggccga ggtgggcaga tcacctaagg tcaggagttc 93000
gagaccagcc tggtcaacat ggtgaaaccc tgtcttgacc aaaaatagaa aaattagcta 93060
ggcatggtgg cgcacacttg taatcccagc tacttggcag gctgaggcag gataatcgct 93120
tgaacccagg agacagaggt tgcagtgagc cgagatcaca ccactccact ccatcctggg 93180
cgacagagca agactgcatc tcaaaaaaaa aaaaaaaaaa aaaaagtttt tcaatttgtt 93240
aaacaatagt taacacatac aaatgataca aagaatattg aatatgatca tgtgcccact 93300
acccagctta gtaaataaag cattctaaca cagttaaact cctcttatgt atctgcccct 93360
cctcagctgc ttccccctgt ttccttccaa aaggaagggt ttcttttctg tgcagttctt 93420
tatatttata ctgcatatga atatatctgt gagcaataga tgatattttg cataatctta 93480
aatttgctat aaagtctttt tttttttttt aattgatcat tcttgggtgt ttctcgcaga 93540
gggggatttg gcagggtcat aggacaatag tggagggaag gtcagcagat aaaaagtgaa 93600
caaaggtctc tggttttcct aggcagagga ccctgcggcc ttccgcagtg tttgtgtccc 93660
tgggtacttg agattaggga gtggtgatga ctcttaacga gcatgctgcc ttcaagcatc 93720
tgtttaacaa agcacatctt gcaccgccct taatccattt aaccctgagt gacacagcac 93780
atgtttcaga gagcacaggg ttgggggtaa ggtcatagat caacaggatc ccaaggcaga 93840
agaatctttc ttagtacaga acaaaatgaa aagtctacca tgtctacttc tttctccaca 93900
gacgcagcaa ccatccgatt tctcaatctt ttccccacct ttccccccttt tctattccac 93960
aaagccgcca ttgtcatcat ggcccgttct caataagctg ttgggtacac ctcccagacg 94020
gggtggtggc cgggcagagg ggctcctcac ttcccagaag gggcggccgg gcagaggtgc 94080
cccccacctc ccggacgggg cggctggctg ggcgggggct gaccccccac ctccctcccg 94140
gatggggcgg ctggccgggc gggggctgac ccccacctcc ctcccggacg ggttggctgc 94200
cgggtggaga tgctcctcac ttcccagacg gggtggctgc caggcggagg ggcttctcac 94260
ttctcagacg gggcggctgc cgggcagagg ggctcctcac ttctcagacg gggcggccag 94320
gcagagacgc tcctcacctc ccagacgggg tcgcggccgg gcagaggcgc tcctcacatc 94380
ccagacgggg cagcggggca gaggcgctcc ccacatctca gacgacgggt ggccgggcag 94440
agacgctcct cacttcctag acgggatggc ggccgggaag aggtgctcct cacttcccag 94500
actgggcagc cgggcagagg ggctcctcac atcccagacg atgggtggcc aggcagagac 94560
gctcctcact tcccagacgg ggtggcggcc gggcagaggc tgcaatctcg gcactttggg 94620
aggccaaggc aggtggctgg gaggtggagg ttgtagcgag ccgagatcac gccactgcac 94680
tccagcctgg gcaccattga gcactgagtg aacgagactc cgtctgcaat cccggcacct 94740
cgggaggccg aggctggcag atcactcgcg gttaggagct ggagaccagc ccggccaaca 94800
cagcgaaacc ccgtctccac caaaaaaata cgaaaaccag tcaggcgtgg cggcgcgggc 94860
ctgcaatcac aggcactagg caggctgagg caggagaatc aggcagggag gttgcagtga 94920
gccgagatgg cagcagtaca gtctagcttc ggctcggcat cagagggaga ccgtggaaag 94980
agagggagag ggagaccgtg gggagaagga gaaggagggg gagggggagg gggggagagg 95040
gagagggaca atgatgtctt gctgtaggta ttcttcccca tttgaatttt ttcctcagca 95100
ttattttttt taacatcatt cagtctcctc ttatactaca cttggattga atttaatatc 95160
tcatgaagaa aaaacatttc tactttgaag catgtgaatt agcatgtttt tataacagct 95220
ttattgagat ataatttaca tatataaata aaccgtttaa agtgtataaa tcagtggttt 95280
ttaatgagat ataatttaca tatataaatc aaccatttaa agtgtataaa tcagtggttt 95340
ttaaaatatt cacaatgttg tacaaccgtc ttctcagttg attttaaaac atactcttca 95400
cccccaaaag aaaccccgtg cccagtttag cagtcgttcc acatttgcct ccagcccttc 95460
tctttcccct actcccaacc ctaagcaacc gttaatctac tttctgtctc tatggatggg 95520
cttatttggg gcaaattcca tttcatacaa atggaataat aaaatatgtg gcttttatga 95580
ctggcttctt tcactcagag tagtgttata aaagttcatc catgttggag catgtttcag 95640
tacttcattt ctttttgtga ctgactaata ttccttgatg tggataatac cacattttgt 95700
ttatccatta atcagtttgt agctatttgt ggtgttctca ctgtttgact attctgaata 95760
acactgccac aaacatgagt gtgcagtttt tttctcgtcc tatcttttca tttcttttgt 95820
gtacctacct aggagttgaa ttgctgggtc atatggcaac tgtgtttaac cttttgagga 95880
actaccaagc tatttgccaa gatatctaca ctattttaca ttcccaccag cagggtatga 95940
gggtttctgt ttctccacat ccttgctaac acttattgtc ttgtcttttt tgattatagt 96000
catccttgtg ggtgtgaagt gttaacctca ttgtggcttt aatgtgcagt tctttcatgg 96060
ctaatgatgt tgaacatctt ttgtgtttat tggccattta tatatcttct ttggattgat 96120
gtctgttcaa atctttaccc attttaaaaa ttgagttgtc tttttattat tgggttgtgg 96180
gagttcttta tatattgtgt gtacaagtcc ctgttagata catggtttgc aaatgttttc 96240
tcctgttctg ttggttgtct ttttactttt tcatcccttg aagcacaaaa atttttaatt 96300
ttgatgaagt ccaatttatc tgattttgaa gtaagctttt ggtgtcgtat ctaagaaaat 96360
actgtttcat caatcattaa ggtttattac tcttctgggt ttttttaaga attacattta 96420
gaggtgtgat ccatttggag caactttttt tttcttttga cacagaatct cgctcttttg 96480
cttaggctgg agggcagtgg tgcaatcttg gctcacagca gcctcagcct cctgggctca 96540
aatgagtagc tggtactaca ggtgtgcacc accacacctt gctattaata acttttgtat 96600
tttttgtag agacagaatt tcgccatgtt gcccaggctg gtctcaaaca cttggactca 96660
agtgacacgc ccacctcagc ctcccaaagt gaaaaattgc tttcaccttg cactgcggac 96720
tcgccctgaa ttctttcttg tgcaagatcc aagagccctc tctgggggtc tggatcggga 96780
cccctttcct ataacaatat tatgagaata acatttgatt ttttttaagt gaaacaaatt 96840
gttattaaaa aattaaaaaa ggtcatagga gagtgacttg gtgctcagcc cattttgagc 96900
agttatttaa tatagcataa ggtggggttc aaattcattc tttatattaa tttttttattt 96960
ctaattgaca cataaccata cacttataac catttttact gtgtaagttc agattcattc 97020
ttccgtatgt aggtattagt tgtcccagca ccatctgtta aaaagactat tcttggccag 97080
gcacagtggc tctcaacgcc tgtaatccca gcactttggg agtcccaagc aggcagatca 97140
catgaggtca ggagttcgaa accagtctga ccaaatggtg aaaccgcatg tctactaaaa 97200
atacaaaaat tacctgggtg tggtggcgca cacctgtagt ctagtcccac tactgtagtg 97260
gctgaggcag gagattcgct tgaacccagg aggtagaggt tgcagtgagc tgagatcatg 97320
cactccagtg tgggcgacag agtgagactc catctcaaaa aaaagactat tctttcctcc 97380
attgaattat cttcacatgc ttgttggaag tctgttgact acaaatgtga aagtttatta 97440

-continued

```
ctggactctg aattgtcctc cactgaatct ctatgtctta tccttatggc agtaccatac  97500
tgtcttgatt agagttactg tattttaaaa ggctgtactt tttcagttag cagaaaacat  97560
tttagctatc agcacaactt tctgtaaacc ttcattaatg cttgacttaa attccaagaa  97620
ggagcaacat aaaaagtctt atctctttag gagttttagt cttactactt ttaggtgcct  97680
gaataaccaa atgtattatt tagcctctta ctaataactc cttgatccat aggggcatac  97740
caggaagaaa agaagtggtt tttaaaaaat gagagtgggc cgggcacggt ggctgatacc  97800
tataatccta acactttggg aggctgaggc gggtggatca cttgaggtca ggagtttgag  97860
accagcctgg ataacatggc gaaaccctat ctttattaaa aatatataaa ttagccgggc  97920
atggtggcac atgcctgtaa tcccagctac tcaggaggct gaggcaggag aatcacttga  97980
atccaggagg tggaggttgc agtgatccga gattgcatca gtgggcgaca gagcgagaat  98040
ctgtctcaaa gaaaaaaaaa gagagtggaa aaaaaaaata tgtgtcccag aacttaaatt  98100
ttaattaaaa aaaaataaaa gagtgaactt tctaattgtt ctcttcagat aatataatgt  98160
tattctctta tgttttattg cgtatttcct gtgtaccaga tgctgttctt catgcttgta  98220
tgttaaatct tgtctaacat ctctgtcaag caagttctgt ttgtatctgc actgtgtata  98280
ttaggcagct tgggcaaaga gaagttaagt aatctgccca aactcacatg gctagtaagt  98340
aagagggctg accatctggt gtttaagctt ctagcagtgc tttgaatagt aactaatgca  98400
tagtgcatgc tgcactgtca gtcagtgatt cattagagct aacttcatga catgctcata  98460
gccccaaact gcatttgttc acaaatatct gtagtccttc atttaggcag aaatagaaat  98520
accttgtgtg tttgttgttc cttccctttt gagccatatg cagagtgctg atagctttat  98580
ttgtgtaaga attgctagta atttgatctg ttttgggtta ataatgtggg ttttagaggt  98640
aaatggacct aggtttgaat gttggcctct atacatcatg tgcgtaacat tgtggcatgc  98700
tatctacttc ccccaagcca aaatgggtta attttagaac ctgcttcata gtgttcctgt  98760
gagagctcga tgagatattg cctataaagt gtttagcata gtgcctagca catggtatgt  98820
attcaataca tgttcattct tactagcaaa atatagatga cccagtattg tacagagtat  98880
gtacaatggt gtcattgtac catttcatgt ggagtcacat aagaatttca gttttctgct  98940
gggcatgatg gctcactcct gtaatcccag cactttggga ggctgaggtg gatggatcag  99000
ctgaggtcag gagttccaga ccagcctggc cgacatgatg aaaccccatc tctactaaaa  99060
atacaaaaaa ttagccaggc gtggtggcag gtgcctgtaa tcccagctac tcgcaagact  99120
gaggcaggag aaatgcttga acccgggagg cggtggttgc catgagttaa gatcgtgccg  99180
ctgcactcca gcctgggcaa taagagcgaa actccgtctc caaaaaaaag aaaaaaaaag  99240
aacttaagtt ttccattaga tttagtatag tgcagagagg aaatacagca gagtgctata  99300
ttccatatat agcaatatag cattagaaca atatattcca atacagcaga gtgctatatt  99360
cagataccaa ctagtggact tgctatttgt aagatggcaa taatagtatc tacatcaaat  99420
agggctgttg tgaagactaa atgaataagt ctataaatag tttagaacag tgtctggaca  99480
ggtacagtgg ctcatgcctg aatcttagca ctttgggagg ctgagacagg tggatagctt  99540
gagctcaggc attaaagacc aacctgggta acatggtaaa accctgtttc tacaaaaaaa  99600
tacacacatt agccaggtgt ggtggcacat gctaatagta ccagctactc aggaggctga  99660
ggtgggagaa tcacttgagc ctgggagatg gaggttgcag tgaggtgagc ttgcaccact  99720
gcgctccagt ctgggcaacg gagtcagacc ctgtttggaa aaaaaaaaaa aagtgtccaa  99780
cccatagtaa gaaatgcaga tgtgtttgac attgtaagaa aaagcaacac caaaagtctg  99840
atttttgcct tcactcaaga actcttatga taattaaact ccgaagtcct tggcaatata  99900
tatagttggt ctgttatgtg gatcgcctct actaaagatt tttgtgaaca aatgaaagtt  99960
taagtagtaa gttcctacat cgtgacttaa attgccagtg tgcccacata aataccctgt  100020
caacatttgc ccttagccac ttgactcttt agctatattg gtaatgcagt aaagcttgcg  100080
atgcgccaga gttgcataat gctgtttgcc atgacaccaa gagccttggt aatgaaacca  100140
ttgaaattgg tttgcctata ctgaggctga agaggtatct tggctctcta attttaaggc  100200
aaccttttg gctgtgtagg tttctcttta gcttgtttct caccacctgg ggctgtggct  100260
taggtccgtt gtcctaacct gtggcttagg ttctgttttt gttgcttgta cttgctcccc  100320
ctttttcag ccattcctgt tttctttctt ttgtagagga tgccatctta aatcatcttc  100380
agccagtggt agcattttat tttttctggt ctgcaaactt aaaaacctca tcacttattt  100440
tgctaatatc tttgtcttct gttctttttg atggtccttg gttttgcagt ctactttaaa  100500
ggtttttatt tttttatggg tacatagtag acgtattatt catagggtct gtgagatatt  100560
tagataaagg catataatgt gtaataatca cattagggta aatggggtat ccatcaccat  100620
catcattcat catttctttg tgtaatgaac gttgcaattg tactccctca gttattctaa  100680
aaagtacaac aaattaatgc tgactgtagt caccctgctt tgttgtcaaa tactagatct  100740
tattcattct ttatttaact ttttaaattt taaacttatt ttatttattt atttttagac  100800
ggagtctcac tctgtcgcca ggctggagtg cggtggcgca gtctcaactc actgcaacct  100860
ccgcctccag ggttcaagtg attctcctgc ctcagcctcc tgactagctg gaactacagg  100920
cacgtgccac cacgcccagc taatttttgt atttttagta gagacggggt ttcactatgt  100980
tggctgggat ggtcttgatc tcttgacctt gtgatccggc tgccacagcc tcccaaagtg  101040
ctggggttgc aggcgtgagc caccgtgccc ggcctttaaa attattttaa atcattttaa  101100
tatctttttc atttctgcct ccggtcctgc agagttctta ttcgttcttt ctaaattttc  101160
tttgcaccca ctaatcacct catttccctt cttctcccca ttacccttcc caacttctgg  101220
taaccattct gctatctcca tgtgttcaat tgtttttatt tttagtgcct gcaaacgagt  101280
aagaatatgc aaagtttatc tttctgtccc tggcttattt tacttaacat aatgtcctcc  101340
agtgccatct acattgctgc aaatgacagg atctcattct tttttatggc tgaatggtaa  101400
tctattgtgt atatatacca cattttcttt ctccatttgt ctgtcagtgg acacgtaggt  101460
tgattccaaa tcttggctgt tgtgtatata gtgccgtagt aaacatggga gtgcagatat  101520
tccttcaata aactgatttc ctttctgagt atatacctag cagtgcaatt gctggatcat  101580
atggtagctc tatttttagt tttttgagga atttccatac tgttctccat agtggtttta  101640
ccaatttaca tgtccaccaa cagtgtgtga aggttcccct ttatccacat cgttaccagc  101700
atttgttatt gcctgtcttt tggataaaag ccattttaac tggggtgaga tgatatcttg  101760
ttgtagtttt aatttccatt tttctggtga tcagtagtat tgaatacctt tcatatacct  101820
gtttgccatt cataaataac gatgaggtct tgctgtttgg cccaggctgg tctcgaactc  101880
ctgggctcaa gcaatcctcc caccttggct tcccaaaatg ctgaaattat agttgtgagc  101940
cactgcacct ggccttgtat gtcttccttt ttttttgtt ttgttttgtt tttgagacag  102000
agtctcactt tgttgcccag gctggagcgt agtggtgtga tcttggctca ctgcgcccta  102060
cacctcccgg attcaagcaa ttctcctgcc tcctgccacc atgtctgcct aatttttgta  102120
tttttagtag agacgggatt tctccttgtt gcccaggctg gtcttgaact cctaacctca  102180
```

-continued

```
ggtgatttac ctgcctcagc ctcccaaagt gctaggatta caggcgtgag ctgctgcgcc  102240
cagcctgtat gtcgtctttt gagaaatgtc tattcagatc ttttgcccat ttttaattga  102300
gttactaaaa ttttccctat ggagttgctt gagtgccttt tatattctgg ttattgatcc  102360
cttgtcagat gagtagtttg caaatatttt ctcccattct gtgggctgtc tcttcacttt  102420
gttgatggtt tcctttgctg tgcagaagct ttttaacttg atgtgatccc atttgtccat  102480
ctttgctttg gttgcctgta cttttggggt attactcaag aaatctttgc ccagagtaat  102540
gtccctggga gtttaatgtt ttcttttagt agtttcatag tttgaggtct tagatttaaa  102600
tctttagtcc attttgattt gattttttttt taatatggtg ggacacaggg gtctggtttc  102660
attcttctgc atatggatat ccagttttcc cagcaccatt tattgaagag actgtccttt  102720
ccccagtgta tgttcatggc ttctttgtgg aaaatgagtt cacttagacg tatggattca  102780
tttctgagtt ctctgttctg tttcattgat ctatatcttt ttttatgcca gtaccatgcc  102840
attttggtta caataatttg aagtcagata atgattcctc ccgttttgtt cattttgctc  102900
agtatggctt ttgctctttt gggccttttg tggttcccta caaattttag aattattttt  102960
gtctacttct gtgaggaatg tcattggtat tttgataggg attgcactga atctgtagat  103020
tgctttgagt attatcaaca ttttagcaat attaattctt ctaatccata aacatggaat  103080
ctcttttcat gtttttctg tgtcatcaat ttcagtgttt taaagttgtc attatagaaa  103140
tcttttactc atttggttaa gtttattcct aagtatttta ttatatttgt agctattgta  103200
aatgggattg cgtttaaaaa atttttcaga ttgtttgctg ttaaatataa aaatgctcct  103260
gatttttgtg tgttgatttt tgtatcctgc aattttactg aatttgtttg tcagttctaa  103320
taggtttttc tttttggag tctaggtttt tccaaatgta agatcatatt atctgcaaac  103380
aaggataatt tgacttcttc cattccagtg tggatgcttt ttatttcttt ctgttgtctg  103440
attgctccaa ttaggacttc cgagtattat gttgaataac aatggtgaaa gtgggcatcc  103500
ttgtcttgtt ccagatctta gaggaaagcc tttcagtttt tccctttttca gtatggtact  103560
agttatgggt ctgtcatata tggcttctgt tttgttgagg tatattcctt ctatacccag  103620
ttctttgggg tttttttgtt tgtttgtttt tgagatggag tctcactctg tcacccaggc  103680
tggagtgcag tggcgcaatg ttggctcact gcaagctcca cctcctgggt tcatgccgtt  103740
ctcctgcctc agcctcccga gtagctggga ctacaggtgt ccgctaacac gcccggctaa  103800
tttttgtat ttttagtaga gacggggttt caccgtgtta gccaggatgg tctcgaactc  103860
ctgacctcat gatctgcccg tctcagcctc ccaaagtgct gggattacag gcgtgagcca  103920
ccacgcccgg ccaagggttt taatcataag gggatgtggc atttatgtg atataaaatta  103980
tatatttata tcatgtgata tatatttata tcatacacag tataaaataat atatatatat  104040
attttttagt ctttgtcttt tattctgtta agatgtacca tgtttattga tttgcgtatg  104100
tcgaaccatc cttgcatccc tgggatgaat cccacttagt catgatgaat gatcttttta  104160
atgtgttact gaattcggtt tgctagtatt atattgagga tttttgcata atgttcttca  104220
gagacactgg cttctagttt tccctttttg atgtgtcctt tggttttgta tagggtaata  104280
gtggccttgt agaatgagtt tagaagtatt ccctcttcct gtattgtgtt ggaatagttt  104340
gagtaggatt ggtattagtt cttctttaaa ggtttagtag aattcagcag tgaagccatc  104400
aggtccatgg cttttctttg ctgggagact atttcttata gctttgatct cgttacttgt  104460
tattggtctc gttacttgtt attgtatttg ggttttggat ttctttgtgg ttcagtcttg  104520
gtaggttgta tgtgtctagg aatttatcca tttcttcaag gttttccaat gtatcagcat  104580
atagatgctc atagtagtct ctaatgatcc tttgaatttc ggtggtaaca attataatgt  104640
ctcctttttc atctctcatt ttattatttg ggtttttctct ttttttctg agtctggcta  104700
aaggtttgtc agttttgttt atctcttcaa aacaatttac tgttttattg atcttttgta  104760
ttttcttcat ttcaatttta tttatttctg ctttgatttt ttttatttct tctactgatt  104820
ttaggttttg tccttgcttt tctagttctt taggatgtat tggcagatga agtttttcca  104880
ctttttgat gtaggcactt actgctgtaa acattcctct tattgttgct tttactgtat  104940
cctataggtt ttgataagct gtgtttccat tttcatttgt ttcaaggaat tttccagttt  105000
tcttcttaat ttcttcatgg acccactggt cattcaggag catattgctt aattttcatg  105060
tatttgtata ctttccaaag ttcctcttgt tatctagtgt tattttattt tatttttatt  105120
tttgtttttt tgagatggag tctcgctctg tcacccatgc tggagtgtag tggcgcgatc  105180
tcggcttact gcaacctctg cctccccagt tcaagtgatt cttctgcctc agcctcctga  105240
gtagctggga ttacaggcat gtaccaccac tcctggctaa ttttttttg tatttttagt  105300
agagaggggg tttcaccatg ttggtcaagc tgatctcgaa ctcctgacct cagatgatcc  105360
acccaccttg gcctcctaaa gtgctggaat tacaggcatg agccaccgtg cccggcctct  105420
agtgttatct tattgtgatc agagaagata gttgatatga ttttaacttt tttgaatttt  105480
tatttattta tttgtttgtt tgtttgtttg tttgtaacag agtctcactc tgttacccag  105540
gctggagtac atgtcatgat cttggctcac ctgcaacctc cgccttcctg gctcaagcaa  105600
tcctcccacc ttagccttcc aagtagctgg gactacaggc acatgccgtc acatatggct  105660
gatattttttg gatttttttt tttttgtag agatggggct ttgcgatgtg tcccagggtt  105720
gtttcgaact cctgagctca agcaatccac ctatttcggc ctcccaaggt gctgggatta  105780
cagacatgag ccactgtgcc acgtcaaatc tttagacttg ttttgtggct taacataggg  105840
tctatctttg agagcaatcc atatgttgag gagaagaatg tgtattctat agctgttgga  105900
cacaatgttc tgtaaatatg tattgggcct atttggtcta tagagcaaat taggtctaat  105960
gtttctttgt tgattttctg tctgaatgat ctgtccattg ctgagagtgg ggtgttgaag  106020
tttccgactg ttactgaggt ctgtttctct tttttgctct aataatgttt gctttatata  106080
tctggatgct ccagtattgg ttgcatatgt atttatactt gttataacct cttgccgaat  106140
tgatcccttt atcattatac aataatcttc tttgtctgtt tttatagact ttgtctcaaa  106200
atctatttta tctaagcata gctactcctg ttcttttctg gtttccattt gcatggaata  106260
ttgttttcca gctcttcaat tttagtctat gtgtgatttt ataggtaaag tgtgtttctt  106320
gtaggcaatg gatctttggt tttttttttt tttttttga gacagagttt tgctattgtt  106380
gcccaggctg gagggcaatg gcgctatctc agctcactgc aacctccgcc tcctgagttc  106440
aagcgattct cctgcctcag cctcccaagt agctgggatt acaggcgcct gccaccaagc  106500
ccagctaaat tttttgtatt ttcagtagag atggggtttc agtatgttcg tcaggctgtt  106560
cttgaactcc taacctcagg tgatttgcct gccttggcct cccaaagtcc tgggattaca  106620
ggcgtgagcc accgcaccca gcctttttttt taaatccatt tagccactct gtatcttttg  106680
attggagagt ttagtcgatt tacattcagt gttgttactg attagtgagg acttaactac  106740
taccatttttg ttacttatta tctggttgtt ttgtagtcct actccctccc ttcccccttc  106800
tttttacttt cctcttcgct cctttttcc ctccctccct tccttgtttt gaaagtgatt  106860
ttctctggtg gtatgtttta atttcctgct ttatattttt tgtgtatctg ttgtaggtgt  106920
```

-continued

```
ttttgattta agatcaccat gacagctggg tgcagtggtt cacacctgta atcccagcac  106980
tttgggaggc cgaggtgggt ggatcaagag gtcaggagat tgagaccagc ctggctaaca  107040
tggtgaaacc ccatctctac taaaaataca aaacttagcc aggcgtggag gcacgtgcct  107100
gtaatctcag atactcagga ggctgaggca ggagaattgc ttgaacccag gaggcagagg  107160
ttgcagtgag tcaatattgt gccactgcac cccagcctgg gcgacagagt gagactccgt  107220
ctcaaaaaaa aaaaaaaaaa agagatcaca taagggttgc aaataacatt ttataaccca  107280
ttattttaaa ccaatgacaa cttgaaactt tgattgcaaa aacaagcaag caaagagaaa  107340
actaataaaa actctacact tcatctgccc gctttttaac ttttgttgtt tttatttata  107400
tctttattat actatgtctt aaaaaactgt agttataagc caggcgcagt ggttcacgtg  107460
tgtaatccca gcactttggg aggctgaggt gggcggatca cctaaggtca ggagttcgag  107520
accagcctag ccaatatggc aaaacccccct ctctactaaa aatagaaaaa ttagccggac  107580
atggtggcgg gtgcctgtaa tcccagctac tcggaggctg aggcaggaga atcacttgaa  107640
cccaggaggc ccaggttgca gtgagccgag agtgcgccac tgcactccag tctgggcaac  107700
agagtaagac tgtctcaaaa aacaatacaa aacaaaacaa aaccctggcc tagtggctca  107760
cgcctaatcc cagcactttg gaaggcaaag gtggggcgaa tcacaaggtt aggagttcga  107820
gaccagcctg accaacgtgg tgaaactctg tctctactaa aaatacaaaa attagccagg  107880
cgtggtggca cgcacctgta atcctagcta ctcaggaggc tgaggcagga gaatcgcttg  107940
aacctgggag gcggaggttg cagttagccg agatcgcgcc actgccgtcc agcctgggca  108000
gcagagcaag actctgtctc acaaaaaaaa aaaaaaattgt agttcttatt tttgaaaggt  108060
tcatttttta ttcttcctgc tcaaaatatg agtagtagtt tatacaccac aattacagtg  108120
ttacaatatt ctgtattttt ctgtgtactt gttaccagtg agtttttgca ccttcaggtg  108180
atttattatt gtttgttaac atccttttct tgcagattga agaacttttt tttttttttt  108240
ttttttttga gacagagtca tgctctgtta ccagcctgga gtgcagtggt gccatcttgg  108300
ctcactacaa cctccaactc ccaggttcaa gcgattcttc tgcctcagcc tcccaagtag  108360
ctgggattac aagcatgtgc caccacgccc agctactttt tgtattttta gtaaagacgg  108420
ggttttgcca tatttgccag gctggtcttg agctcctgac ctcagggtga tccgcccgcc  108480
ttggcatcct aaagtgctag gattataagc gtgagtcatc gtgcccaact tggttgttta  108540
ttttcaaata gcctgaattc aagctcacta atgttttctg ctgcttgata catttctgct  108600
attgagagac tgatgcattt ttcagtttgt caattgaatt tttccacttt gggatttctg  108660
cttgattctt tttactaata attattgcag tctctttttt aaatttatag gattctgaat  108720
ttgttctctg tattatcttg gatttcgttg aactttctca aagcattcag cttgaattct  108780
gtctgaaagt tcacatatct cttatcactt gggaattggt cactggtgtc ctttattttt  108840
agttcatttg gtgaggtcat gttttctcag atggccttga tgcttgtgga tgttcatcag  108900
tgtctgggca ttgaagagtt gggtattctg ttctttgtag tctggttttg tttgtacgca  108960
ttcttttttt tttttttctg tttttgagac agagtctcgc tctgtcgccc aggctggagt  109020
gcagtggcac agtctttgct caccgcaacc tccgtctccc ggattcaagc aattctcctg  109080
cctcagcctc ctgagtagct gggattacag gtgcgtgcca ccacgcctgg ctaatttttg  109140
tatttttagt aaatatggtg tttcaccatg ttggtcaggc tggtctcgaa ctcctaacct  109200
cgtgatctgt ccgccttggc ctctcagagt gttgggatta caggcgttag ccactgcatc  109260
cggctcccat tcttcttgag aaggtttttc aagtattcaa agggaattaa gtgttgtcat  109320
ctaagtcttc gctcactgca gccatacatg cattagaggg caccccaaga ctagtaatgt  109380
tgtgactctg tagaggtatc accttggtag tcttggggaa gatctgggag aattccctgt  109440
attaccaggc agtctcttgt cctcttacat ttctccaaac aaatggagtc tctctttgtg  109500
ctgagctgct tggagtttgg ggaagggtga cacaagcact gccatggcca ccgtcactgg  109560
aactgtactt ggtctcaccc aaggcctgtg gcagctattt tctggccacc actgatgtta  109620
atttaaggcc caagggtgct ttagtcagta ggtgaagaat cctgcaagaa ctgggtcttt  109680
actttcagtg cagcaggttc ccttctggcc cagggtgtgt ctagaaatgc tgcccaggag  109740
ccagggcctg ggatcgggag ctttaggaat ctgctttatt gtactggggc tgagctggca  109800
cccacttgca agataaagtc ctttttactc ttctctcacc tcaagcaggt gggtctcccc  109860
atggacacca cagctgtgaa tgtgcggggt catatctgaa gctggcacaa tacgacatgg  109920
caccttgttt tttattcaag gcacaagggc tctttagtca gctggtggtg aatcctacta  109980
ggactaggta tttcccttca aggcaatggg ttcccttctg gtccagaata tgtctagaaa  110040
tgtcatctgg gagctatggc ctagaattga ggcttcagaa ctatgcttgg tgctttattt  110100
tactgtggct gaactagtat ccacattgca agacaaagtc ctccctactc ttccctctcc  110160
tcccagagct gtgagctgtg gtacctggag ttgggggaag gctggcacaa gcactccctt  110220
ggccacccta gctggtgtct cagtgggtca catgtacccc aagtccactg actatgagcc  110280
cagcacagta ccatgacttg tccaggaatt gcagtccttc tggtctagac tgcctttcaa  110340
gtttatttag gaccccagag gactttaccc acggtggtgg ggcttaccaa aattaagatt  110400
cttttggttt tttttggcag agtttcgctc ttattgccca ggctggagta tagtgacgca  110460
atctcagctc accacaacct ccgcctcccg ggttcaaata attctcctac ctcagcctcc  110520
tgagtagctg ggattaccgg catgcgctac cacctctggc taattttttt gtttttttagt  110580
agagatgagg tttctccatg ttggtcaggc tggtcttgaa ctcccgacct caggttatcc  110640
gtccgcctcg gcctcccaaa gtgctgggat tacagaccat agtgcccagc ccgaaattca  110700
gattctaatc actgggatgg acaattcccc tctgactagg gctagtctaa atactccctc  110760
tgtgggtgct ggctgaattc tgtcctatgc tgctttccac tgtgacaggg cagcactgag  110820
tttcaatgca aaatcccaca gtcatttctc tctctctccc ccgagcacac agattctttc  110880
tccaccccac actgcattgt gggggaatgt caggggtgtt ggaggggcag ttcaagacta  110940
tcttccttat ctttttttggt gtctttttcc ttgataggat gtcaaaactg ggtactgtga  111000
tcgcttacct aatttttggt tcttatgaag gtgctttctt gtgtggatag ttgttcaatt  111060
tggtgctcct tgttggggat gatcactgga aggttctgtt tggccaccat gctctgtctc  111120
ttctcccctg ccatctcctt tttttactta ggggtttaga atgtctaact gaccaatatg  111180
tacagtcagg tctcattctg aattcaccta cttaatgacc ttccaagctg actaggccca  111240
gcgcttagtc cagcctccat gacggtccct ccacatccta attagcctcc ctccagttca  111300
tttcacacaa agctgctgtg ttcacctttc tgaactataa atctgcccag tactctaccc  111360
tacttaaaat tccgtataga ctgcccattt gccctgagaa ttaaaagcca aagtcctaaa  111420
cgtagctttt taaaactttt tttttttttt ttttaatttt tagatggagt cttgctctgt  111480
cacccaggct ggagtgcagt ggtgtgatct tggctcactg caacctccgc ctcctgggtt  111540
caagcaattc tcatatgtca gcctcccaag tagctgggat ttacacgtgt gccatcacgc  111600
ctggctaatt tttttttttt atctttagta gagacggagt ttcaccatgt tggccagtct  111660
```

-continued

```
ggtcttaaac tcctgacctc aagtgatcca cctgccttgg cttcccaaag tgctaggatg  111720
ataggtgtta gccactgcac gcagccctga acatagcttt taagttcctt tattgtcata  111780
ttcctttga cgagtctatc attttctgac tcacttgtac atgtgtgtct caccccttggt  111840
ccagccattg gtgcttttct ttacttcttt atttttgtta ttttatttta ttttattatt  111900
attttttaaa tgagacaggg tatcactatg ttgcccaggc tggtcttgaa ctcctgagct  111960
taagcagtct gcttgtctca gcctcccaaa gggctggaat tacagtgatg agctactgtg  112020
cccagctcat tggtgctatc tttttttttt tttttgagac ggagtctcgc tctgtcaccc  112080
aggctggagt gcagtggcgt gatcttggct cactgcagct ccacttccca ggttcacacc  112140
attctcctac ctcagcctcc cgagtagcag ggactatagg cgcctgccac catgcctggc  112200
taatttttgt atttttagta gagatggggt ttcagcgtgt gagccaagat ggtctcgatc  112260
tcctgacctc gtgatccgcc tgccttggcc tcccaaagtg ctgggattac aggcgtgagc  112320
caccgtgccc ggcccccatt ggtgctattg ttttatgtga tagagccagc ttctcccttt  112380
tctttggatt tttaaacata ctcttccttt tacttagact attctccatc ccaacacctt  112440
tcctaaactt ctttcacacc ttagactagc tgacacttta ctgagaaacc tttctttttt  112500
ataggttgct ttttctatag actctcttag catttactca ttttattgtg aagtgtctga  112560
tcttatttaa atgacaagta taagaggata gaaactattt catatttttc tcacccagca  112620
ggcacaattt ctgacatgtg gtaagcactc agtaaatatt gaactttaga ggctaggaca  112680
tttgagtgct ttggtgactg tggttgtgct atataggtac tctgttattg ttagtttata  112740
gtaaaagcat tactcttaaa gtatgaaaaa agccttattc agaacatttc atgcgtatag  112800
ttaatattac gtagcttgtg ctcatggcaa aaatgtatta ctaaagttat ttaagatatt  112860
taagtataat tgtttccttt atttagttac agccaagttc tacttctgaa tctatggatc  112920
aactactaaa caaaaataga gagggagaaa aatcaagaga tttgatcaaa gacaaaattg  112980
aaccaagtgc taaggattct ttcattgaaa atagcagcag caactgtacc agtggcagca  113040
gcaagccgaa tagccccagc atttcccctt caatacttag taacacggag cacaagaggg  113100
gacctgaggt cacttcccaa ggggttcaga cttccagccc agcatgtaaa caagagaaag  113160
acgataagga agagaagaaa gacgcagctg agtgagtaaa cctggaactt agaccatcct  113220
gttactcaat taacttttttt tttttaaag gcatttaggt ccttccaact gtgaagaatc  113280
catctggact tttagactac tttatacatt gcccttagtt tacaaacagc tagtccaaac  113340
aaatgacatc ttaagtaaat gaggttattg caccctgtgc tactcttctg ttcttcccct  113400
tttttgtacc ccagggctag aaaaacaagg cataaattaa gaaaagtttt tctgtaaatg  113460
aacaggagtt gaaaaattat caattcaggg gacctatctt tactggattc cactcattag  113520
tcaccctcac tgtgctgcta ggttgaaaaa ctgccactgt caaggagaga agcatgcggt  113580
gcttctactt ggaattcaaa atatttttca tcagaaactg tgttttagtt aatgtttaga  113640
tttgttaaga tagacttaat tctgcacatt cagtatatta attaaatgga cttttagggg  113700
ctaacctcag aacttaacta ccattgactt aggtgtttgg gtaccaaaca atccagttaa  113760
agctgaagtt ttggaatgca gcttattgat aaattgggga ctgcttattc ttgatttgag  113820
gcaatttttt tttacagcca tgactttttc caggtatgtc atgtaaaata tcttctcaca  113880
taagaattac tgcatgctag aatattggta tgttgactgg tagctcatac ctataatccc  113940
agcactctgg gaggtccaag caggtagatt acttgaggtt aggagttgaa gaccagcctg  114000
gccaacatgt gaaaccctgt ctgtactaaa aatacaaaaa ttagccaggc atggtggtag  114060
gtgcctgtat cccagctact cgggaggctg aggcaggaga attgcttgaa cccagaaggt  114120
ggaggctgca gtgagccgag atcatgccac tgcactccag cctgggtgac agagcgagac  114180
tctgtctcaa aaataaataa ataaataaat aaaaggatac tgttatgtta agaattgctt  114240
ttaaggatat ttcataagta gctactgtct tttcagctca agtgtttgtt gattggccag  114300
gcgtggtagc tcatacctgt aatcccagca ctttgggagg ctgagtcagg cagatcactt  114360
aaggtcagcg tggccaaaat ggtgaaaccc catctttact aaaaataaat attaaaaaaa  114420
attagctggg cgtggtggca gtctcctgta atcccagcta atcaggaggc taaggcaaga  114480
gaatggctta aactcgggag gcagaggttg cagtgagcca agattgcact gctgcactcc  114540
aacctgagca acagagtggg actctgtgaa ggaaaaaaaa aaagtatttt ttgattgcct  114600
ttgagaggaa cggttgtata ttactcagat ttttaaaaaa ttgttctttt atggctgtat  114660
tctttaaggg attaaggaat gggcaatata agtgtatatg tttcaataaa aacgattagt  114720
gatcttctag tgagaacagt ttaaatctat atttagcaat ttttttaaa ttgtcaggta  114780
tggaagattt tagagcaacg taaagtccat gtagatttca ctggccttta tatttttttt  114840
aggcaagtta ggaaatcaac attgaatccc aatgcaaagg agttcaaccc acgttccttc  114900
tctcaggtag gtttattact ttctttgagg ttatctagtc ccaaaaaaag aaaaattatt  114960
agtaatagtc cttcttccat acctgccatc tgaattttgt tttagtgtgc tgaaccaacc  115020
ttctttcttt tttttacatg gccattaatg aatactttttt aaacattaaa aaaaggtctt  115080
tgttttgtca tcaattagat gtgatcttgg gcaaatcttt gaatttctct gacccagaat  115140
ttgacgatgg ttggctagct aggctgtcag gtttatagat acgtcctctg cacctgaggg  115200
ttttgcatca ctggattcaa ccaaccatgg atcaaaaaca tagttaggat aatctatact  115260
gaacacatgc agacgtttcc ttgtcattat tccaaaacaa tacagtaaag catttacctt  115320
gttttaggta ttataaataa tctagagatg atgtaaagta tataggagga tatgcatagg  115380
ttgtatgcga atactacatg attttatgta agggacttga gcattccaag actttggtat  115440
cttcacaggg tactgtaacc aatcccccac agatactaag agatgactgt actattgtta  115500
ttattcgact gagatcataa gaagatatat ttatttttaa tttttaaaaa cacttccatc  115560
agtttcttaa aaatagctgc cactgttttt aatatttttt aattgacaaa gttttaagtt  115620
cctactgaaa cattttttct tttattgaaa tgtgaaaatt tatgtgctgt gtttttgttt  115680
tcaataaaag ggacatagtt aaagcaagta aaattagaaa gactgggaaa atccgtcttt  115740
aaattgcaat aatagttcat ctgttacctt gagataattg aatttattgt tgtttttgta  115800
gccaaagcct tctactaccc caacttcacc tcggcctcaa gcacaaccta gcccatctat  115860
ggtgggtcat caacagccaa ctccagttta tactcagcct gtttgttttg caccaaatat  115920
gatgtatcca gtcccagtga gcccaggcgt gcaagtaagt catagaattt gatgttcact  115980
tagcctcccc aattgtttgt atctgacacc aagcactctt taggttttca gtgacttgag  116040
ggtgtgatgg ttatgcatat gcatttgaaa cagacaggca tgcagagatt cagtgtgttg  116100
ttaagtatga ggacctaaat ctgagaatgt tttctgtgaa aaagatggtt tagatttact  116160
gtagtttggg gtttgttcct tttagctgtg ggtatgatct aattttttaa tgactaatgg  116220
agaatcagga aaccttctca tgcctagctc tctagcaata taaaactaag agtgacagaa  116280
taccttgtta ttatcatagg tgcctaatgt taattttttt tttaattctc tcaagccttt  116340
atacccaata cctatgacgc ccatgccagt gaatcaagcc aagacatata gagcaggtaa  116400
```

-continued

```
aggtgagaat aatcctgcct gtgtttgctt gtagtttgca tgctgcatga attgagtaac  116460
taagtttata atgaataaat agttgtagtt tagctctgac tttttgatga ggctatgcat  116520
tggcttttga tgaacaacat tacatagata ttcacatgga ttttatgaag aaaaacaggg  116580
gagaaaaaat gcccatcagt tgtgattata tagtatcctc ttcaaaaaga gtaattggag  116640
gcctggtgtg atggctcaca cctgtaattt tagcactttg ggaggccaag gcaggaggat  116700
tgcttgagct caggagccca agatcagcct ggacaacaga gactttgtct ctactaaaat  116760
tcaaaaaaat tagctgggca tggtggcata tgcctgtagc cccagctgtt tgggggactg  116820
aggcgagagg atcacttgag cccaggaagt agaggctgca gtgagctgtg attatgccac  116880
tgccctccag cctgggcgac agagtgagac cccgtctcaa acataaatac tggctgggca  116940
tggtggctta tgcctgtaat cccagcactt tgggaggccg aggtgggtgt atcacctgag  117000
gtcagtagtt tgagaccagc ctggccaaca tggcgaaacc ccatctctac taaaatacaa  117060
aaattagccg gacatggtgg cacctgccgc ctgtaatccc agctactagg tggggctgag  117120
gcaggagaat tgcttgaacc cgggaggcag gggttgcagt gagccaagat cgtgccactg  117180
cacttcagcc tgggcaacag agtgagactc catctcaaaa caaacaaaca aacaaaaaac  117240
aaacaaacaa aaaaaccaga ctaattggct ggacacagtg gctccatgcc tgatatccca  117300
gctggaggat gacttgaacc catgagttcg agagcagcat gggcaatata gtgagaccct  117360
atctcaaaaa aaaaaaaaaa agttaattcc aaagcttttt gatctgaaat ctgatttaaa  117420
tctgaactta aatttgaaga agagggtttg ctagattaat ttactagatt gctaaccttg  117480
ctttatatat acctacagtt atttccccaa agccagaatt tcttttgaag cagaggggca  117540
actaacttca accaatgtta agatcctatt agaaggatgt ttcggctagg cttggtggct  117600
cacgtgtaat tccagcactt tgagaggctg aggtgggcag atcacatgac cgggagtttt  117660
aagaccagcc tgggcaacat ggcaaaaacc tatctctgca aaaaaaaaat agaaatctta  117720
gccagccgtc atggtgtgct cctgtagtcc tagctacttg ggagactgag gtgggaggat  117780
caattgaaac cagaaggtcc aggctgcagg gaactgtgac tgcaccactg ggctccagct  117840
tgggtgaaag agcgaaaccc tgcctcaaaa agaaaaataa gatggatgtt tctgcattaa  117900
aattagggag ttgtcgtata atgtagttgc ataaactagt attctgtgct tgtgtggtta  117960
aagagccttc gtagaaaaaa tcccacattt ttcttaaaag gaaatctttt ggccaggtgt  118020
ggtggctcac atctgtaagc ccaacactct gggaagccga ggtgggcaga tcacttgagg  118080
tcaggagtac aaaaccatcc tggccaacat ggtgaaaacc cgtctctact aaaaatacaa  118140
agatcagctg ggcatggtgg tgcgtgcctg ggtgacagag cgagactccg tccaaaaaaa  118200
aaaaaaaaaa aaaagagttc ttttaatgtt ggaaaatgct aaagggtttt ttttttgcca  118260
accagttaat ttagagtgat taactgctat cagttgagaa actatagaaa gtagaataat  118320
ttatacagaa aagacatttc tcagtgccca ataattgcct ttctgacata aagttttcat  118380
ttttcctgaa ttaataagat ttcctcaatg tgttttttttg ggtgttttgt gtgtgtgtgt  118440
gtgtgtgtgt gtgtgtgtgt gtgtgtgtgt gtatgtgttt gatacagggt cttgctttgc  118500
tgctgaggct ggaacgcagt ggcgctatca tggctcaatg cagccttgac ctcctgggct  118560
caagcgatcc tcccttctca gtcccctgga tagcgggggc tacaggtgca caccaccaca  118620
cctagctaat ttttgtattt tttgtagaga tgggttttgc catgttgcct aggctggtct  118680
caaactcctg ggctcaagcg atctgcctgg ctctgcttcc caaagtgcct gcgcccagcc  118740
aatttttctcc atgtttgacc taattgtgat ttcatagatg ttaactaaaa ctcttaattt  118800
tcgttttctc agtatgctat tttttttttt tttagccttg gaacatatga acctgttgaa  118860
agaactctgc ctgaaataat gtaatcaaat tatagagttt aatcttattt tgagggcctt  118920
tagaaattct gagaagaaag tgggtttttt tttttactgc cattttaatg tagtgttaag  118980
gtgttcatgt atcaccagca ggtgtagctg ttttcaatga ttacttaaaa caatgcaatg  119040
ggaacttttt gttgtcatta aaatataaaa ggttactgta gtaagagcaa gcatgacagt  119100
ttggctatct gatgggagag tcacattcta acttcaggag gtactgtctt tttaatagaa  119160
atgatatact cagagtctgg gcacggtggc tcacgcctgt aatccagcac tttgggaggc  119220
cgaggtgggc agatcacgag gtcaggagat caagaccatc ctggctaata cagtgaaacc  119280
gtgtctctac taaaaataca aacaattagc tgagcgtggt ggcaggtgcc tatagtccca  119340
gctactcggg aggctgaggc aggagaatgg catgaacctg ggaggcagag ctggcagtga  119400
gctgagatgg tgccactgca ctccagcctg ggtgacagag cgagactccg tctcaaaaaa  119460
aaaaaaaaaa aaaaaatagt agagaaaggg ctttgccatg ttggccgggc tggtcttgaa  119520
ctcctggcct caagtgatcc acctccctcg gcctcccaaa gtgctgggat tacaggtgtg  119580
agccactgct cctggcctga atataccact tttacctatc atcagttgat gaacatttgg  119640
attatttcct ttttctggca atgagtaatg cttttgtgga ttttcatgta caaattttca  119700
tatgaggctg ggagcagtgg ctcatgccta taatcccagc agtctgggag gctgaggtgg  119760
gcagatgact tgaggtcagg agtttgagac cagcctggcc aacatggtga aatcccatct  119820
ctactaaaaa tacaaaaatt acactggcat ggtagcgtgc acctataatc ccagctattc  119880
aggaggctga ggcaggagca tcagaatcgc ttgaacctgg gaggcggagg ctgcagtgag  119940
ctgagatcac accactgcac cccagcctga gtgaaagagt gagtctcaaa aaataaaaaa  120000
taaaattttt tttcatgtgg ccttagattt tcatttctcc taaagtagaa atgctgtgat  120060
ggaactgcca aacttttcca aagcagctgc atcattttgt atttctacca gtaatgtaca  120120
agtgttccag tttctccaca tcctcataaa taaccgatat gtctttggtt tgggttatgt  120180
ccattctagt ggttatgaag tgtcattgtg gttttttgtt tttttgtatt gttttgagat  120240
cgtgcccagg ctggagcaca gtggcacaat ctcggctcac tgcagccttc gcttcctggg  120300
ttcaagcaat tctcctgcct caccctccca gatagctggg gctgcaggca tacgccacca  120360
caccaggcta atttttatat tttttgtaga gatggagctt ctccgtgctt cccaggctgg  120420
tctcgaattc ctgagctcaa gcgatccccc tgcgtcagcc tccagagtag ctggggttat  120480
aggcgtgcac caccgcgctc ggcccatttt tgtattttta gtagagatgg aatttcacca  120540
tgttggccag gctggtcttg aactcctgac ctcaaatgat ccgcctgcct caccttccca  120600
aagtgctgag attttagacg cgaaccacca tgccctgact ataggttatc tttttacttg  120660
cttgatggtg ttctttgtaa cacagttttt aattttgatg aagttcaatt tatctgtttg  120720
ttttttcttt tgttgctgtt gctcctgatg tcatatcaga caaagcattg cctaactcaa  120780
ggccacagag atttactcct atgaaacgcc tataaaactc ctatgatttt tatagtttag  120840
ctcttaacat ttaagtctac aatctctttt gagttaattt ttgtgtatga gatgagagta  120900
gtggtccagg tttttccttt tgcttgtgga tatccgttgt ccccacctca tttgttgaaa  120960
agactattct ttcctcttaa attgtttgtt tgtttattta tttttgagat ggagtgtcgc  121020
tctgatggag tggcgctaac ttagcttcac tgcaacctcc gcctctcaga ttcaagcgat  121080
tcccctgcct cagcctcctg agtagctgga attacagggg tgcgccacca cacccagcta  121140
```

-continued

```
atttttgtat ttttagtaga gacggggttt taccgtgttg gtcaggctgg tctcgaactc  121200
ctgatctcgt gatctgcctg tctcctggca ccctgggagg ctgagaggct gaggtgggag  121260
gatcacttga gctcaggagt ttgagaccag cctgtaccat tatgcctggc taattttaga  121320
atttatctta aagtataaaa tgtgaatcca atttatcttg ttctaaatga ctatccaaaa  121380
tgttttaacc agttttatta gtctgtaatt tacatacaag aaaatgctca tctttttatg  121440
tttacatttt aatgagtttt gacaaatata tttgctcatg taactacttg cttcatcagt  121500
gaagatggaa aacattgtgc ctgttcctct tctctgtcca actgtacttt attaccacta  121560
gctccagtta accagtaatc tgccttcttt tactatagat tagatttatc ctctttagat  121620
ttctttttct ttttttttt ttgattaggt ttttttttt cttttttttac gtaaaaaaat  121680
cttttttttgg agacgtctca ttatattgcc caggttggtc tcgaactctt gagctcacct  121740
cagcctccca gagtgctagg attacagatg tgagccacct cagccagccc ctagattttt  121800
tttttttttt taataaatgg aatcaaacag cgtgtaacag aggtgttcaa tcttttggct  121860
tccctgggtc atattggaag aagaattgtg ttgggccaca cataaaatac agtaacacta  121920
atgatagctg atgaacaaaa caaaaaaaaa tagcaaaact tataatgttt taagaaagtt  121980
tatgaatttg tgttgggcca cattcaaagc cgtcccagga cgcaagttgg acaagcttgg  122040
tatataattt catatgtgtg tcctaaacag tgtagtaatt tgaatttcat gttagtatca  122100
gcttattcct ttttgtttgt ttgtttgttt ttgagatgga gtcttgttct gtgtcccaga  122160
attggtctgc aattccactg cctcagcctc ccaagtagct gggattacag gcacgtgcca  122220
ccacacctgg ctaattttttg tctctctctc ttttttttt ttttttttt tttttagca  122280
gagacgggat ttcaccatgt tggccaggct ggtctcaaac tcctgacccc aaatgatcca  122340
cctgccttgg cctcccaaag tgctgggatt acaggtgtga gtcaccgtgc ccagccagct  122400
tattcctttt tattgctggg tagcatttca ttttatgatt ataccacagt taatttaccc  122460
attactagtc gatgggcatt tgagttattg ccagcttttg gctattatga atgaagctgc  122520
tgtgagcatt tgtgtacaag tgtttgtgtt tttatttctt ttagttaaat acctagaatt  122580
ggaattgctg aggtatggta agtgcatatt tcattttttt aaaaaattta ttttattttt  122640
tatttattta ttttttttga gatgaagtct cactctgttg cccaggctgg agttcagtgg  122700
cgtgatttca gctcatggca acctccctgt cccgggttca agcaattctc ccgcctcagc  122760
ctcccaagta gctgggatta caggcgcgca ccaccatgcc tggctaattt ttttgtattt  122820
ttagtagaga cggggtttca ccacgttggc caggctggtc tcgaactcct gaccacaagt  122880
gatccacccg ccccagcctc ccaaagtgtt gggattacag atgtgagcca ccacacactg  122940
cctggtaaat acatatttca attaataaga aactagcaat cttctaaagt gattgtgtca  123000
ttttacattc caactgatca ggtacatgtg taggttccat gtgttctgca tccttgccaa  123060
cacttggtat tgtgttatct ttttaatttc aacaggtcta atgggtgtct tatggtatct  123120
cattgtgatc ttaaatgtac atttctctga tgatgactga tccaggagca cctcatcatg  123180
tgtgtgtttg ttttcagctg tcaacctttt tttagtaaat ggttcaaatc ttttttccat  123240
tttatttatt tatttattta tttgatggaa tctcactcta ttgcccaggc tggaacgcag  123300
tggtgccatc ttggctcact gcaacctccg cctcccaggt tcaagcaatt cttacgcctt  123360
agcctcccaa gtagctggga ttacaggcat gcgccaccat gcctggctaa ttttgtattt  123420
ttagtgtagg tggggtttca ccatgttggt catgctggtc tctaactcct gacctcaggt  123480
gatctacctg cctcggcctc ccaaagtgct gagattacag gtgtgagcca ctgcgcctgt  123540
cctaataatt tctttttgtc tcaatgtttc tgcctgggtg cactggctca cgcctgtaat  123600
tccagcactt tgggaggcca acctggatgg atcatttgag ccaacagttt gagaccagcc  123660
tgaggaacat gacaaaaccc tgtctttgca aaaaaaaaaa agaaaaaaga aaaattagcc  123720
aggcacagaa gcgcattcct atggtcccag ctacttgggg ggctgaggtg ggacaatcgc  123780
ttgagcgagg ttgcgggggt ttggagggcg atggaggggt gatcgaggtt gcagtgagct  123840
gagattgcac tactgcactc cagcctgggc aatagagcca gaccctgtct cacaaaaaaa  123900
agaaaaaaaa gtcatgtttc ttttcttact gtgaaaataa agttactact tttagtaaat  123960
tattttaagt tatttatata ttctggttac aagtcctttc tcagaatatt gtgaatattt  124020
tctcccagtc tgcggttttt tttgaagagc cagtattgtt aattttaatg aagccttatt  124080
tatcaagctt ttctcttaag gttcatgctt ttttgtatca taataagaaa tcttttacgt  124140
accctaggtt atgaatgttt ttatggttag gtatatggtt gatttcaggt taggttttgt  124200
gtagggtgtg atgtaaaggt ctagcttcat tttctccacc ataaatattt actcggtttc  124260
tctggcacca gcctctgttt tccattggtg gctttatttt ttttctgttc ttgaaacaag  124320
agtctcgatc ttgttaccca ggctggagtg cagtagtgtg accttggctc actgcaacct  124380
ccacttccca gggtcaagcg attctgcctc agcctctcga gtagctagga ttacaggtgc  124440
ccgccactac acccagctaa tttgtatttt ttttttttt tttttagta gagacagggt  124500
ctcaccatgt tggccaggct agtctcgaac tcctgacctc aggtgatctg ctcatctcag  124560
cctcccaaag ttctgggatt acaggcatga gccactgcgc ccagccatag tagctttatt  124620
gaattcagtt gactgtattg tatgtgtgtc tatttgtgaa ctgttttgtt gtattgatct  124680
ttgtatatat ccttatgcca attctctctt tattgctgtt actttgtaac caacctttaa  124740
gttcatatga gtctcccagt tttattctcg tcaaaattac tcttattctg cgttctttga  124800
atttgcaaat aaattttaga atcagcttgg gattgtgcac tgaatcttta tatcagttct  124860
gggagaaata tcttaacaat atggaatctt cattgaggtc atcatatact gctccattta  124920
tttaagtctt aagtttcacc agtgttttct agtttttcttt gtatcagttt tgtgcctgct  124980
ttcttaaatt tatcccttaa tatttcatct gttttgtgct gttgtgagtt atattttaaa  125040
aactttcaac gtttgtttat tcgtaaatag agatgcactt gatttttgaa tattgacctt  125100
gtgtcttgat gtgttggtaa acccactgtt tctggcagcc ctttaagact taaacataca  125160
atcatgatct aatcaccatg ttggtgtttt tgggtttttt ttttttgtct tattgtactg  125220
gtgcattact gaaaaaggca tgagattttg ccatgctccc atttttaggg gtgagacatt  125280
gtctttcact attaagcata cagttaggtg ttacttcagt tcctaatttg cagaggtggg  125340
tttgttttct ttttaatcat gaatggttgt tggattatgt tcaaatactt atcatctact  125400
aagtatatca tattgaccag gaacagtggc tcatacctgt aacctcagag ctttgggagg  125460
ccaaggcagg aggatcgctt gaggccagga gttcaagacc aacctgggtg atgtaggaaa  125520
accccatatc tacaaaacaa tttaaaaatt tgctgggtgt ggtggcacac acctgtagtc  125580
ctaactactt gagaggctga ggaaggagaa ttgcttgagc ccagtagttt aaagcagcag  125640
tgagctgtga ttgtaccact gtactccagc ctgggtgaca gaaggagacc ctgtatttaa  125700
agtgtgtgtg tatgcgtgcg catagatgga tagataataa tgtaattcca ttatggtcat  125760
acaaactgat atgaaatgcc attttatcat ataacaagtg tctttttgtg gttgaatttg  125820
tttctggatt tttcactctg cttcactaat ctaataggac taccttctca tccactcact  125880
```

-continued

```
gccaacattg attttttttt tcagattacc ttgaattttc tgtttatttt tccatatgaa  125940
ctctataatt aacttactac taaaaaaatc agttgccttt ttaaaaccaa ctgatcttta  126000
aaatatatct tggctgggcc cggtggcagg cacctgtaat tctagctact tgggagactg  126060
aggcagaaga attgcttgaa cccaggaggc ggaagttgta gttgagttga gattgcgcac  126120
ctgtactcca gcctgggtga cagagcaaga ttccctctta aaaaaaaaaa aaaaaaaaag  126180
aaacagaaaa gataaatctt tttacaataa tttgttccaa ttagggtcca agtcaggctt  126240
gcaatttgga tttgtttata tgttgaagtc tttttttttt tttaattgtt tcatattgtg  126300
gtaacttttt tttttttttt ttgagatgga atcttggctc tgtcacctag gctggagtac  126360
agtggcacaa tctcaactca ctgcaacctc cccctctggg gttcaagcaa ttctcctgcc  126420
tcagcctccc aagtagccca gccttttttt tttgagacag agtctcgctc tgttgcccag  126480
gctggagtgc agtgatgcga tctcggctca ctgcaagctc cgcctcttgg gttcatgcca  126540
ttctcctgcc tcagcctcct gagtagctgg gactacattc gcccgccacc acacccggct  126600
aatttttttg tatttttagt agagacaggg tttcaccgtg ttagccagga tggtatcgat  126660
ctcctgacct cgtgatccgc ccgcctcggc ctcccaaagt gctgggatta caggtgtgag  126720
ccactgcgcc cggccttgta tttttaatag agatggggtt tcaccatgtt ggccagcccg  126780
gtcttgaact cctgacctca aatgatccac ccgcctcggc ctcccaaagt gctgggatta  126840
caggtgtgag ccatcgctct cagccttgcg gtaacttttt attacgaatg tattgagaca  126900
ttaataacct aggccagtca tgtttcatcc ctacccattg tctcttaaaa gctttgagtc  126960
cactggatta ttctgaagca aattctagac attgcatcag tttatccacc aacattttag  127020
tgtgtatctt taagttggtt ttggttttgt tttttgtttt tgagatgggg tctggctttg  127080
ttgcccaggc ttggagtgca gtagtgcaat catagctcac tgctgctgcg aattcctggt  127140
ctcaaaggat cctccctcct cagcctctca agtaactgtg actacaggca catgccacct  127200
tgccagcttt tcttttcttg tcttgtcttt cttcttcttt gtttttttgt ttgtttttttg  127260
tttttttttg agacagagtc tcaccatctt tctatcttgc ccaggctagt cctaaattcc  127320
agggcttaag ttatcttttct acctcagcct cctaaagtgc taggattaca ggccagcact  127380
ttaggaggtg ctggatgagc catcacaccc agccaagtca taggtttttt tgtttgtttg  127440
ttttttgaga cagtgtctaa ctctgtcacc caagctggag tgcagtggca tgatttcagc  127500
tcagtgcagt ctctaccaat tgggcttagg tggtcctccc acctcaacct cccaagtagc  127560
tgggactaaa ggtgcgcgcc accatacctg gctaattttt gtattttttg tagagacagg  127620
gtttcgaatt cctgagctca agcagtctgc ctgccttgac tcccaaggtg ccaggattac  127680
aggcatgagc cactgcactc agccctcaca gttttaatta cagtttttcc cttagttttt  127740
gtcttgttca tatccagctt gtcttgtatt tttttcccac gatctgaatt ttgctgactg  127800
tatccctgtg ttgatattta aagtagactt ctgtcccctg taatctttgt aaactgatag  127860
taaataatga aggcttgatc agattgggtt tttttttttt ttccccaatg tttcacagat  127920
gtgtgtactt tcagtgagga gtcatgtaat cagtcttttt cctgatagga gtagtcagtg  127980
agttcctaga tgttttatct atccaggaga taatatgtcc ctttagcgcc ttaatttttt  128040
tggtgtgttt tttagcagcc attgatgata attgtctagc ccaagatcag ttatttcctt  128100
aggggttgta aaatggtgac attcttttcc tttcatccct tcttcaatta ttgcctggaa  128160
tatttctata aagaaaaact ttcccatatc cagctgtttg gttaccctga ggtatagctt  128220
tcttaggaaa agtaatttaa aatgttaatc atttcccttt ttaaggcagt cttcaaaata  128280
atgagttggt tttctgttat cctccaaagg taaccagtga ggtggttttt ttgtcgttgg  128340
ttcttactat cagtataaac ttctggaatt tttttttttt ttttaatttt ttggagacaa  128400
ggtctggctc tgttacctag gctggagtgc agtgggatga tctgggcata ctgcagcctc  128460
aacttcccga gctaaggcaa tccccccacc tcagcctccc aagtagctgg gactacaggc  128520
aagcaccacc gtgcctggct taatttttgt atattttgca gagacagggt ttcaccatgt  128580
tgcccaggct ggtgtcgaac tcctgagctc aagcagtctg cctgtgtcag cctcacaaag  128640
tggtgggact acaggcatga gccaccatgg caggccagaa tcacaataaa cttataaatt  128700
aacttgagaa gaaatgattg atgtcttcat gatgttgagt cttcctgttc aagaacaaag  128760
tataccttca atagcatatt aaagtttatc cttggctgga tgcagtggct gacgcctgta  128820
atcccacctc tttgggaggc agaggtgggc agatcacctg aggtctggag ttcgagacca  128880
gcctggccaa catggtgaaa ccccgtctct actaaaaata ttttaaaaaa agtattagct  128940
gggtgtggtg tgcacctgta gtcccagcta ctctggaggc tgaggtagga gaatcgcttg  129000
aacccaggag gcagagagtg cagtgagtca agattgcacc actgcactcc agcttgggca  129060
accgagcgac actctgtctc aaagaaaata aataaataaa aataaagttt atctttaagg  129120
ttttgtacat ttttttcagt gtatgcctta ggtaggttct tttttaatgt tagtgtaacc  129180
cagggacttc tcttccattg catcttctaa gtaattactt atgaagtacc atatatgaag  129240
gctattgctg tttatatgtt agtttttacc ctgctccttt actaaattcc aatcctttga  129300
ggtattggat aaaaatattt ttagcatttt tcaaataaca ggcagagtca agggcttggt  129360
ttcttttctt cccctcctgt cccctaccct ccccttttttt gagacagggt ctcacttctt  129420
cgccgaggct ggagtgcagt ggtgcagtta cggcttaccg cggcatctgc ctccctggct  129480
gaaaagttcc tcccacctca gcctcctgag tagctgggac catagatgca cagcaccgca  129540
gctggctaat atttttgtat tttttgtgga ggcagtgtct ccccatgttg cccagggtgg  129600
tcccaaactc atgagctcaa gcagtccgct cgccctggcc tcctaaagtg tagggattat  129660
aagcgtgagc cactgcgcct ggcctgggga tcatgtttta acatgagaat tagtggagac  129720
aaacacatga tatctaaata atagcaccat agtatacttg actagctttt taattatttt  129780
ttaaatatac aggaaggtaa taagtaacaa agtaataata gtgaatagtt taagctcagt  129840
tagcataatc gggcaaactt tcatttgata aaagtgataa gtagttttca gtggcttttt  129900
tgtttaccag aaggaggtgg tttttaaata cgtgcatcca agataaaata taaaaaaatg  129960
ttcaggtttg ctttcctaca tagataaaat aatatgtaac tagctctccc aaatttcagc  130020
aacagttagt gaatgtttag ccacaaattt gcagttaatt atataatcag ttcttaggat  130080
tttatgaaca agttctatat tctttgtgcc ttatacctag ttgtaagcag tcattccaca  130140
attattttcc tgaagtggct tggttaatgc cacaccagaa acaggtcaca gacaatagtg  130200
ctgtaagaaa tgtgtgagga aagaggcaca tgggaagtag ctagctcgtg ctggaggaac  130260
tggaaaaaaa cctcacatgg gagatgacag ttgagctgaa ttcttaacta gagttgtaac  130320
agggcgaggc ccttacatgc agaccacctg tgtggattaa gataagacat aaagtaatct  130380
tttaaaagaa ctattattta gaaacctggt atatgctaca tggtgctgtg ttatactggg  130440
tttgagaaag aatgggaagt gttacaagga ttcagtggtt ggaaattaag gaagatagaa  130500
agttagtgtt ggatctgttt tggctctttg gtcatgcctt tgtttttctc aaaatgaatg  130560
cagtgcccgt cccagaaaat accatatgag aagcgatttc ataatgctgt gagagtctgt  130620
```

-continued

```
tacagggact tgatcaagtc tgagggccat gagagaaagt ccctctgagg aagttgcttt  130680
caagctgaca cctgaaggat gaagcagaat tatcccagct gggatttggg aactggtgtt  130740
tgaggctgag gactagcatg catgatagga aaataaccca gagtggcaga agtgggagtg  130800
gtatgagatg gcatcagaga cgcagattca gggtcaaatc attcagagcc tcctagacca  130860
tgtgaacaca tgtattatgc tgtggagata ctgtttaata ggcagtctgc tttttttttct  130920
gcagtaccaa atatgcccca acagcggcaa gaccagcatc atcagagtgc catgatgcac  130980
ccagcgtcag cagcgggccc accgattgca gccaccccac cagcttactc cacgcaatat  131040
gttgcctaca gtcctcagca gttcccaaat cagccccttg ttcagcatgt gccacattat  131100
cagtctcagg taaggctggt aaggcctaac tcttaatttt tgtaccatat aaaaaaactt  131160
ttaatatggt aaagggattt tcctttataa tttttgcttt tgtgtgatgg tagggtagat  131220
agctaaggac ttggggaccc ttttcaatat atattcgaag gttactgatg attgtaagag  131280
gttcagagga aacagccaag aaagatttga gagtttacag ctgtttctgg aaatctggaa  131340
accatggagt taaaaatctt aactaaagtc tgcttggctc tatttgcagt gttaatgtgc  131400
tttctttatt ttttgtttga acacagcatc ctcatgtcta tagtcctgta atacagggta  131460
atgctagaat gatggcacca ccaacacacg cccagcctgg tttagtatct tcttcagcaa  131520
ctcagtacgg ggctcatgag cagacgcatg cgatgtatgg taggaagcac tttgtttgtc  131580
tcttccagtg tgtgtgactc ttcttaattt aagtttctga aaacatactc tatctaagaa  131640
taacctgacc ttttatgaca ttgagggtca agaatctgaa ggaaaagatg aacccatttc  131700
tttgcctgac ttgctttata acttttggca aatagtttct acttctgtac ctggtcttca  131760
gatctctttc ctgctttaac taaaatgtaa tgatgtatat aatggcaaag catctttgtg  131820
gagaaaggta cctttctcct cttcctcatc aatattatgc tttggtatat cctgcctacg  131880
acatgcaaga gaattttata ataataaaag cataaaggtg ttctccagca tgaaaacatt  131940
ttgcttcact acttgatctg agggtcactg gcattacata tttttttttgc tgtttgttat  132000
aatgataata ctatgtttct acatcatgct gtattttaat ggttgaatat tatgtcatat  132060
tagatatatt ttagacatga gtcacacttt aaatataacc aatgtgaaca gaatgctgaa  132120
atgaaaatga gaagtatttt atgtaaaact aagcagtatt tatatgtgag aataataagc  132180
aaaaaaaccc atcttcgttt tgtgactaaa cagagaaatt tgtgtagatc aacttagcag  132240
ctgtctaaag taccaaaata atagattttt cactgttgat aatttaaaat aaaatgtcca  132300
tttgtatatc ttatgataca gaattaatgg attgcttcaa atgtttttca gaatatgttt  132360
ttaaatagta ctgatttcat taagatgttt tgttctgaat atttctgaga actaccgtag  132420
tgtcgtttag ttttcctatt tgcgtttttg gttgtttgga gtaggggata attttggttt  132480
attcatacag ttgaaaagtg tactgctatg agaatgagat tatggttaca tgtaactaca  132540
tgggcatttc atttttaaag cctctttgaa ctttttgaaa tactaagaat ataaaatttt  132600
tattttttaa gtttagatgt cctgaacgag tatgtttagg caaaattgag ttatttaaga  132660
atttataggc tgggcgcagt ggctcacgcc tgtaatccca gcactttggg aggccaaggc  132720
tggcggatca tgaggtcagg agatcgagac cagcctggcc aacatggtga aaccccatct  132780
ctactaaaaa tccaaaaaat tggccgggtg tggtggcatg tgcctgtagt cccggctact  132840
tcggaggctg aggcaacaga attgcttgaa cccgggaggc agaggttgca gtgagccgag  132900
atcgcgccac tacactctag cctgagcgac agagtgagac tccatctcca aaaaaaaaaa  132960
aaaaaaaaaa gaatttacag atttctggca aaccttcttc ttgagacatt actacttttc  133020
ataccacctc tgtccttttt gaagaataaa agttttaaca ttccgtaggt taatgagaat  133080
aggacttggg cagcagcaat catccttcct gtcacctgta acccacagct tatgctttct  133140
tcctggaggt tcttgtctgc cacaaaggct cactgctgat aggaatttgt atatgatcaa  133200
aggtgtttag ttttataaaa cagttaagtc cagtcttaat tttccacatt atcactttca  133260
attttgtatt gtggattacg cattttaaat aaaaaattgt gtgattgcta cattttggaa  133320
aacatttttt tcaagaggcc catccgtaat ttaattgtaa aagatactga caaactaact  133380
tggtttatta ttttggttat gaccccgtca tttgacttgt ctttagttgt cttaacgggg  133440
actgaatatg cgtgcaaagg cacgattgat ttatcatgct ggcttttatg caacttgtat  133500
atattttaac aattttcctg tttgctaaag gcttaggtta aaagttcatt atgattgttt  133560
atacatttct ggtgaataca tcatgattta acaagtggaa agaacatctc tttccttcca  133620
ttttctggca tactcccctt ggaatcagat ctgaaacttt taagctaaaa tttccattgc  133680
atttggagag tagttatttg tgtatgcatg cttttgagac attgtagcaa taatactgta  133740
atgttgagcc gaatctttct cctcattgtg ttcattcact gccaacatct ggcttcatct  133800
tttggatgaa tgttcattgg ttttgaaaca gcctataggg taaatactgt gtttgaggta  133860
cagatgattt tcataactac ttcctagaac atgtccattt gaagagcagt ggggccttag  133920
accccaaagt ccatttatgt gtgggcaaat aggaaatgtt gcaaacaaaa caaagcacta  133980
gatctaatgt ccagtgaaat ctggaatgaa ctagtcatta gagccggttc tttcatgcca  134040
ggaaaaagtt actcagccaa atctgaacta ctctcctgca gtttacacag gtggtattta  134100
attgctgtct gtatggaggc aggctaggag caaggctgtg gacttgttgt gattgtcact  134160
agttaatcaa gattcccttt gtggtgctta agaccctaaa aaggacacta ggagctgggc  134220
atggtggctg acacctgtaa tccaagaact tggggaggct gaagtggagg atcgcttagc  134280
ccaggtgttc aagaccagtc taggcaagat ggcgagatcc catctctacc aaaaaaaaaa  134340
aaaaaaaaaa aaaaaaaaag cccagtcatg gtggcacatg cctgtagtcc cacctacaca  134400
ggaagctgag atgggaggat cacttgagtc caggactttg aggctacagt gagctatcat  134460
ggcaccactg taatccagcc tgggtgacag agcaagaccc tgtctctatt taaaaaaaag  134520
aaaacataag aaagaattgt tttgttctat gccatcataa gccataattt aatctgctta  134580
agcatgttct tcattaaatc tgcagtgatt tatttgaatt attagacttt caaagcctta  134640
ttatatcaaa tataaacaaa atttgaagta cattcttata aactacaaca aacttacata  134700
gaagtgttaa ttttatactc atcttccctg aacaatttat attttataaa tatattaaat  134760
atattgtaat aaattttctc aaaggaacca aatactttga gtatgaattg tgcttttctt  134820
tttaagctac atcatatcta ggtttttaaa acatttaatg caaacagaag aacatgcacc  134880
cagatgttgg tgacaatttt atgtcacctt ttctcattca ttaattgtta tagccatagc  134940
caaaggcatt gaaaacatag gaccactaat gactgcaaaa tgaaatcctg attattgttt  135000
ttaaattttt agtatgttta atacacatat gctaacatta ctgaacagtt aaatgataaa  135060
ataggataat tattttattc taaaaaagta ttgaccttga cctctttcta gctatcttag  135120
aaagggcttt tgtcaaaaac cttatctctt tgatgtctct ttttttgaga tggagtctct  135180
ccctgtcgcc caggctggag tgcagtggcg tgatctcagc tcactgcacg ctccgcctcc  135240
tgcgttcacg ccattctcct acctcagcct cccgagtagc taggactaca ggcgcccgcc  135300
accatgcccg gctaattttt tgtattttgt ttagtagaga tggggtttca ctgtgttagc  135360
```

-continued

```
caggatggtc ttgatctcct gacctcgtga tccgcctgcc tcagcctccc aaagtgctgg  135420
gattacaggc gtgagccact gtgcccagcc tctttttttt tttttatttt ttatttattt  135480
tttatttttt ttttaatttt tgagaaggag tctccctctg ccacccaggc tggagtgcag  135540
tggcgcgatc tcagctccct gcaaactccg cctcctgggt tcaagcagtt ctcctgcctc  135600
agcctcctga gtagctggga ctacaggtgc ccgccaccac acctggctaa tttttgtgtt  135660
tttagtagag acagggtttc accatgttgg tcaggctggt cttgaattcc cgacctcagg  135720
tgatccaccc acctcagcct cccaaagtgc tgggattaca ggcgtgagcc actgccccgg  135780
cctctttgat gtctcttaat ctaacttcca tcattgcctc taccccatcc cttctaagaa  135840
gttactttaa ttttttttcc tctcacatct actctttttt tttttttttt ttttttttg  135900
aggtagtctc actctgtcac ccattctgaa gtgcagcggt gcgatctcag ctcactgcaa  135960
catctgcctc ccaggttcaa gcggtttttc tgcctcagcc tcccgagtag gtgggactac  136020
aggtgtgcgc caccacgacc ggccaatttt tgtattttta gtagagacgg ggtttcaccg  136080
tcttggccag gctgatctcg aacttctgac cttgtgattt gtctgcctag gcctcccaaa  136140
gtgctgggat tacagatgtg agccaccacg cccagcctca catctactct tctaatccat  136200
ctaattttgt tttatggtga tgcttttacc tttcagaaac agtaataata caactttcc  136260
gactaactag agccattagg aagaattaga tccagaatcc ttttttgatt tgtttttggt  136320
agtttaatgc agataagtaa gaaaatatag ttaagttaaa aaaaaaaaaa atgaaaagca  136380
tccataatcc ctccacctga caactgcctt ttaacatttt gatgtgtatc cttccaggtg  136440
tatttaaata cactcaaata ccctacccct ttatgtagac atgttttaat aagaaataat  136500
attcatgttt atattcttgc tatgatccta aatttttgga tccattacta gataatcttt  136560
caggataatg acatttccat tagtaatgtt tttgcaaaat tgtgtgtcta ttgaattaaa  136620
cttgtaaaat agttttattt tggtacatga tttatatcaa ggttgttcag tagaatgcca  136680
tgttggtgtt tttattagat aatgatttta ttccttttac ttttaagcaa gtcagcatga  136740
caacttgaca cctaagtaca gaagaacagt gtcttccggt ttagtccttt cttttaaaat  136800
tctgtagcag tgtttaaagt gcttgtcatc tcttatgaaa atgaattatg catgaataca  136860
aaaagaaatt actaatatgt caacctttcc agaaaatttg gaaaatgcac acctcaaaag  136920
gctaatttac ctttctattt cccaaattca gcatgtccca aattaccata caacaaggag  136980
acaagccctt ctttctactt tgccagtgag ttgggttttt tatactaatt tttaattgta  137040
cagtaaaaca ctttttaaag gatacatgtt aagggagtag acttgttgaa caatattttc  137100
cttgtgccag tcaaattatt gaaagtactt atatatataa ataattcagt ttttaaaatg  137160
gaaataccca atttaagaag gctggagtta atgaaaaatg gagttgtttc agaaatcaat  137220
ttttgcatac caagcaaatg tgactgggaa atgcctaata ttttccttgt tagagaaact  137280
tcctaaacag ctttatacac acacacacac acacacacac acacacacac aaacacacac  137340
acccaagcca caagcttggt ataaatttaa aatgtttatt tatacacaca cacacacaca  137400
cacacacaca cacacacacc ccaagccaca agcttggtat aaacttaaaa tgtttattta  137460
tattctgata agatgaaatt tatgcctacc aggattttta attgaatagg attgatgaaa  137520
tactaaggga aaaacttttc agtcctgtgc atggctaaag gtttaaaata ctcaggaagg  137580
gccaggcacg gtggctcaca cctgtaatcc cagtgctttg ggaggctgag gcgggtggat  137640
catctgaggt cagcagttca agaccagcct agccaacatg gtaaaactcc atctctacta  137700
aaaaatacaa aaatcagcca tgcatgctgg catgcgccta taatctcagc tactagggag  137760
gctgagacag gagaattgct tgaacttggg aggcagaggt tgcagtgagc cgaagtcgtg  137820
ccactccact ccagcctggg tggcagagcg aaattctgtc tcaaaaaata aaatattcag  137880
gaagcagacc cctcaggata tcttgagctt aagcaagaga tcatgacctc tcaggtcatt  137940
atcttggaca gcacaggtcc cctctcccca cctggcaaaa agtacagaaa tagttgctcc  138000
ttcatggaga aagtctgggc agagctttct tctggaaatg aacttttaag gtacattttt  138060
cctatttgta gggcaatttg taaaaataag ggccggacgt ggtggctcac gcctgtaatc  138120
ccagtacttt gggaggccga ggtgggtgga ttgcttgagg ccaggagttc gagaacagcc  138180
tggccaacat ggtgaaaccc tatctctacc aaagcatggt ggcacgcacc tgtagtccca  138240
gctacttggg aggcggaggc acaagagttc catgaaccct ggaggtggag gttgcagtga  138300
gctgagattg taccactgca ctcaggcctg ggcaacagag agagactctg tctcaaaata  138360
aaaaataaaa ataaggctag tcttggactt tggtatttaa ataggaagga gtactaatat  138420
ttgtagaaat cctttagaaa tttgtgccat taatattgtc accttgtatg aaatgttgtg  138480
ttctagagga tattaaggat tcaaatttta tgttaggcac attttgagtt attttggggt  138540
gactcaatgt ctgactctac taaatgccat attagcattt aaaatgcatt tgaccttaaa  138600
tctttgttaa ttatgccatg acttggtatc caaaaataag ctgatacata catacataca  138660
tatatgtgtg tgtgtgtgtg tgtgtgtgta tatatatata tatgtatgtg tgtatatata  138720
atttatttgg tgctaggaaa tgttaaattt aatcctttaa tagatgctct ttaaaaagga  138780
gtcttgctgt atgtatatac tattaaaggg gaaactatgt ctgtgattgt agtgtgtaaa  138840
agatagtagg tgattttatt atgtactcaa tttgaggtct caaatgtagt tatcctcacc  138900
atcttactgt ctctgttagt agtttggtgt tgttttcctg gtaagtagct aaggtcctta  138960
atcattaaca cctaagcctt aattgcctta gcacaacttc ccctaaaagg gagtatcagt  139020
actttttaaa agaaactaac agttgggctg ctaatttaat ctgctgcttc atttcccccct  139080
gttctaagcc attttatgat ggtttggtca agttgccttt tattcccctt ttagagtttt  139140
caactttcct tcacttccct ttttctgaat ttaacatcag atttacaagt tggaagattt  139200
tgttttgttt tataagtttt gcaatgctgg tgatctctta tgacttgtgc atccaaagtc  139260
aaaatgacaa aacctagtta caaattaaac acacagcttt ctgtacttaa tttgcttcag  139320
tgagatcaca gctgaggaaa ctagttctgg aatgtggtta gtgttattaa ggatttttga  139380
ctgatcatat gtttagaatc ttaaatattt atgtcaagga acactgagtg ggaaacttct  139440
ggactaggtc tggaccaaag aagcatatgt ctttgattat ctttaatcta aaagatttta  139500
tgaagactaa agttttataa atagaagttt aactgatgaa taaatcagta ttacaaataa  139560
aattaacttt atttttaacc tctctgggat ctttagccag aatgagcata tataacaaaa  139620
gcagtgaaat aatatgtgtg ggtcagaacc cactgccctt cccactccac tctccttttc  139680
cctgattctc ctgtgttttt tccttcttta ccttatcttg gttccttttt tttttttttt  139740
cttttgagat ggagtctcac tctgtcgtcc aggctggagt gcagtggtgc gatctcggct  139800
cactgcaacc tccgcctcct aggttcaagc aattctctgc ctcagcttcc agagtagctg  139860
ggattacagg cgcctgctgc cacacccagc taatttttt tgtattttta gtagagacag  139920
ggtttcacca tcttggccag gctggtcttg aactcctgac ctcgtgatca cctacctcgg  139980
cccctggttc ctttttttgtc tctcttgtct tccaagctat ttttttcctt ggcttttaaa  140040
ttttcttcct accctgcttt gtgtcactgt cacttaactg gcctatcaag gaaccgaact  140100
```

-continued

```
gtatttttgt tactagtatt gatttaaagt ataagtttca catttctccc aatttattat  140160
tattatttat ttatttattt gtttatttta ttttttgaga cggagtttcg ctcttgttgc  140220
ccaagctgga gtgcaatggt gtgatgtcgg ttcactgcaa cctccacctc ccgggttcaa  140280
gctattctcc ttccccactc tccctagtag ctgtgattac aggtgcctgc caccacgccc  140340
agctaatttt tgtattttta gtagagacag ggtttcgccg tgttggccaa gctggtctcg  140400
aactcctaac ctcaggtgat ccgcccgcct cggcctccca aaatgctggg attacaagcg  140460
tgagccaccg tgcccggctc catttctccc aatttcaaat tcaaggagga aaagaattcc  140520
tgattaaggt acttctttca gatcttttga gctagaacaa aaaaacaaag ggaaatattt  140580
ctaattaact ctttttaaat tttgtttaca acgtatgata catattttac acatcctttg  140640
tggtttttgt tcgtcttgtt tttaatcaat gccttgcaag tttaccggta tttaggtagg  140700
gaaaggattt tgtttttgtt tttttaaaca aagcctatgt acattcactc agcttgggta  140760
tttgtgctat gcatgcaaat tagctataga ttagaaaacc gtattatagt ctttaaatac  140820
tggtaaactt aaattgcaga gatgcctttt aaaaatgcat agtaaaaata tttcatcttt  140880
acttttctct tcaaatgatt ttaagatttt tacatttttc cagttgatga ataacttaaa  140940
ttatgagatt tcatgggcat aattattttc tatatttatt gttacttttt aatattctta  141000
atactttgct tagaaggtat ttaaaagtga aatttcaaac tttttagtac aaaatttctt  141060
gaataaaataa agttacaaaa aaaaaacaaa aacctctgag attccgtact gtatctttat  141120
gaacctccat gaacagaatt tgggatttgg gaattgcttt tccttagaca gatttagatt  141180
gttacaaatg acatttttaa gaggctgggg tggcggtagg ggttagtgct aatggtttaa  141240
cagtagggga ccatggacaa ctgtagacat cactatccag tagaacattt tgtggctggg  141300
cgcggtggct cacgcctgta gtcccagcac tttgggaggc caagacaagt ggatcacctg  141360
aggtcaggag ttcaagacca gccagaccaa catggtgaaa ccctgtctct actaaaaata  141420
caaaaaagtt agccaggcgc gcctgtagtc ctagctactc aggaggctga cacaggagaa  141480
tcgcttgaac ccgggaggca gaggttgcgg tgagctgata tcacgccact gcactccacc  141540
ctgggcaaca gagcgagact ccgtctcaaa acaacaacaa aactgcactg tccaccgtat  141600
tagctactta gctacatgtg gctttttttat tattcaaaaa taaattttta ggccgggtgc  141660
agttgctcac acctgtaatc ccaacacttt gggaggccga gatggacgga tcacttgagg  141720
ccaggagttt gagaccagcc tggccaacat ggtgaaaccc cgtctctact aaaaatacaa  141780
aaattagcca ggtaatccca gctactcaga ggctgaagca ggagtatcac tttaacccag  141840
gaggcggagg ctgcagtgag ccgagatcgc tccactgcac tccagcctgg gtgacagcaa  141900
gactgggtct caaaaataaa caaacatggc cgggcgcagt ggctcatgcc tgtaatccca  141960
gcactttggg aggccgaggc ggatggatca cttgaggcca gtagttcgag accagcctgg  142020
ccaacatggt gaaacccgtc tctactaaaa atacaaaaat cagccaggca tggtgatgct  142080
tgcctatagt tccagctact cggcaggctg aggcaggaga atcgcttgaa cccgggaggc  142140
ggaggttgca gtgagccgag atggtgcccc tgcactccag cctgggcaac agagcgagac  142200
tctgtcaaaa attaaacaaa taaatacatt tttaaaatga acgtaagatt tttacaagta  142260
caacaaactc aggttcgaaa tttacatcaa atcttttaga ccaagtcagt gcctatacaa  142320
cttggaggag ctggaagtaa acttaatgag tatgatgatg atggagggcc tgttaataag  142380
ccaccaagtt agaaaaaaag gactgtctta tagacttatg ggactgtgaa gctcaggaag  142440
gcttcatcgt ttgtacatca tttgttctag ctcccagaag acgttcacta ctcttaaaaa  142500
cattcagaga ctatgttgcc acagttttct tgttaaaata ttctggcata tgttaattcc  142560
tacagtctgg aaaatttttcc cagtgtataa acaaagctgc tgtatccagt ctaaactgga  142620
tatgaaggaa tattaatgcc agctgtggca ttggcagtgg atgcacaggt gatcctagaa  142680
ctggctcttt gccttgccct ttcccctgct aagagatagc tttgcagctg gagacgtaac  142740
tgttagggct ggagagttgg tggcccttag ccctacaaca cctaggatta tagaactgct  142800
ccatgtgcct agcctaaccc tctgcacacc atttacgtgg aatataccca gagccgtcta  142860
tgctggtgac tcggcagcct tgcctaccag actgctggaa ctagggtgcc tcttcccaaa  142920
gctgtgcttg cttctctcac caatcagtcc tgcatatgtc tgtgtttgct aacacgttat  142980
atgaagaatg tggggaacta ttttggaatc atttctgtgt atgggcttat tatcttgagg  143040
gattttagga tttgtttctc aagagagggc tgggaactat accttgctag agttgtcttg  143100
agaacgctct attctcagct cattgcctcg tggaggttag ttttttatca tcggtgtgct  143160
gtccatagtc actggaagca gtgaacacat cctactctgc ttctgattct caacttactg  143220
tttttgaagc acatgaacag gccaggcacg gtggctcacg tctgtaatcc cagcactttg  143280
ggaggctgaa gtgggcggat catttgaggt caggagtttg agatcagcct ggccagcatg  143340
gcgaaacccc atctctacta aaaatacaaa aattagctgg gcgtggtggc acatgcctgt  143400
aatctcagct actcgggagg ctgaggcagg agaattgctt gaacctggga ggcagaggtt  143460
gcagtgagcc tgggcaacag agtgagtgag acttatatct caaaaaaaaa caaaaaacaa  143520
aaaactgaaa gacatgaaga aatggttttt gtaccaaggt ttggcccacg ctgagattca  143580
caaagaactg gctttcagtt cttatcttta ttttgattta aactggccca tcatgttgtc  143640
ctttgaagtt agtctagtaa atttctttcc aaagggctgg ggcactcaga agggagttta  143700
cttttctata tttatttcat aaagcaaaga tgggagatcc tccattaggg cttgggaaag  143760
taaactgagt ggcagaaggg ctcctgtgat tagctgagag agactgtggt ccttcggccc  143820
tgatgataga tccctggcct tgccacatac catacacagt gcccgcaccc ccatccccca  143880
ccacacccaa tatagtctgt gccctcagga cattgctcca gggcagtagc atggtgaggt  143940
tagcctgatg atggccttga gctaaagagt gtgcacctaa aatgcacttg tttgagtagt  144000
ttctgcctat gccttcaagt tgccttttttg ggaaaaccta gtgaccgtta agagtaaatg  144060
caaactaatt tgattttaat atcatatgta gagctgtatt atatgaacca aatgctagtc  144120
tgttaagcaa tagctacact tattttttca agacaatgga tggtttaaat ggagtcatct  144180
atagaaattg gtagtggcgt gagttatgca ttgtaaccat caagaaagtt cagttgatga  144240
agtgtagagg agcgatggag gttgtcagac atcggttgtg tacatgctcc tttttctttc  144300
actttagttt ccacgggctc ccttgctcag cagtatgcgc accctaacgc taccctgcac  144360
ccacatactc cacaccctca gccttcagct acccccactg gacagcagca aagccaacat  144420
ggtggaagtc atcctgcacc cagtcctgtt caggtaaggg caactcagag gtctgcatgg  144480
agtggcttct ttatcctagt atctgagtgc tttcttcagg tgccaggtat cgcatcgtca  144540
gaacacatgg catgtccacc ctcgtgaaga tggatacagc tgtgcccctg gggtggtggt  144600
tttaagaatc acatttaaag gctgggcgca gtggctcacg cctgtaatcc caccactttg  144660
ggaggccgag gcgggtggat cacgaggtca ggagattgag accatcctgg cgaacactgt  144720
gaaactccgt ctctaataaa aatacaaaaa aattagccgg gcgtggtggt gggcgcctgt  144780
agtcccagct tctcgggagg ctgaggaagg agaatggcgt gaacccggga ggcggagctt  144840
```

-continued

```
gcagtgagca gagatcgcgc cactgcactc cagcttggac aacagcgaga ctctgtctca  144900
aaaaaataaa aaattaaaaa aaatcacatt taagatacat gttgataata aggtgattgg  144960
ataagctctg gaaacttgca gtaatgaaaa atcaaattta acataaagtt cataaggcaa  145020
attcctattt gcttgggact ttttaatttc taaggtttat gtgatgaggt tattttccta  145080
tgagcttctt gaattatgtt tgctaatgga ggcagttaaa gatgtctttg atatctatca  145140
gttccctggg gcagtagtct tttttgactt tagtatgtat gctcagaagt ttctaactgc  145200
cagactgaga atcaggcttc tgtaccctag aaaggagttg tccagatggg aggcacctcc  145260
agccttgctc ttaccaccct gtacattctc ctgtactttc cagtgaccct catcataggc  145320
ccaagtgtgc aaagcttagc tttgtgggta tcccttggct gcttttcatt aaagaagttt  145380
tcctctcaat tctttcctgt cgctttgcag caccatcagc accaggccgc ccaggctctc  145440
catctggcca gtccacagca gcagtcagcc atttaccacg cggggcttgc gccaactcca  145500
ccctccatga cacctgcctc caacacgcag tcgccacaga atagtttccc agcagcacaa  145560
cagactgtct ttacgatcca tccttctcac gttcagccgg cgtataccaa cccaccccac  145620
atggcccacg tacctcaggt aataccagct ttagccaact ttctgtgaag gccaagtaga  145680
atgtgaaggt tatcagtaag cagctagagg ctctcccagc taggaaaccc tgtgtgtcat  145740
gccatttgcc tgtctccctt tccctctcaa atacacgtga tctggcccta agggaatgtt  145800
tgtgtggttt tgtcatggga tcagtgaagg tgctgattgg tcagtccttt agttttccaa  145860
ctgagacctt aaaaatatct ttgactctgg aatgcaaccc agtccttctt tcctttctgt  145920
gtctgctttg ctatgtctat atagcctcac tactatatat atgtgtacat atatattccc  145980
ctacacactt accttggaag ccaggcaggg atgatggcct tcacagagtc tcagctctcc  146040
gaagtgacta ccggggcctg tcaacttgat tgttactcac atgagttcca gacacatctc  146100
tccaattgtt ttccctggtt atccatatat ctgctttgac cataagttgt actcttgaga  146160
gggcttggcc ttggacattg gtgcagtgta actagaagct ggaagcaccc aggtggtccc  146220
atttttcttt aagagcagcc ctggaagcac tttggagctc acctccagtg taagctgcta  146280
caggtgaaag gtgtgcttgc catctcagtg gttgctgtct gcatcagctg ctgacaaagg  146340
tccctgcact ccagggccca ggggattgtc ttaatgagga gaaggagctg cactgaagtt  146400
gggctctaac gctggccttg aggccctccc tggggctgtt acgggtgaat tggctgtatt  146460
agatgtctct gctactttca taacagaact ctctgaggcg ggtctaagtg agacctgcca  146520
caatgaattc catttcctgt taaatagtgc gccagtgagg ctctggcaag gtgtgggcta  146580
gagatgcgac tcagttggat ctatctctca gaaggctacc ttgtaagtag agttccacag  146640
ctctgggaag tttgggcgtc ctcaccctgc aaagtttagg ttctgtggtg tagcgcactg  146700
cagttgattt gctttttgat agtggggagg gaagccggtt tggtccgtgt gggccagcgt  146760
ggtttggtgg agtcagcttc ataagagctg gggtcctgta ggtgtctacc agaggctggt  146820
ggctaagtag gcatgtgaac ttacatgtaa gtcagggatc cctaaaacct cactctgttt  146880
ttgtgctgaa agggcaaaaa ggttaacaca gggaagctca aatttgccat gtgcccgttt  146940
gaatatgtga gagtaaaaac ggcatttcat ccaaggctta tcgtagtcta gaacagtgca  147000
cagtgtggga aaaaggaaac aagggctctt cctggccctg ccaacccccct gcagagctgg  147060
aatccagctg tttgggctga ctaaaatcac ctttccaact tgacagtgag tgagaccagg  147120
ttgaacttgg tacagagacg ctgggctggc ccagatgact tcaggttact cctttccatc  147180
tcactggagc cattaaaaac tccaactcct cctcctcctc ctgctccatc agcatatctc  147240
tgagagagtc acgggggcct aagagtctct tttcactgcc tggtgagcag accagaagca  147300
gagggagaga ggcaaatgaa cagaggtcca agtaattcac atacttgact gtgacagtct  147360
ctgcttatta atgtaatctg ttttcctatt tgaaagggat gttatctgca aaactacctc  147420
aggccccaca tggcagcctg attctgaagc atcattgaat cttgtatgat attaagttga  147480
gaaagctgcc cttggatcca gtgtctaatc tttgtgaaga tcttacccca tacatagaat  147540
acaatgatca gaaatgtcaa gggttaggac agcacagccc tgacttctac ccaggctcac  147600
ttgttgcctg ctccctgacc cttgcaggat ctgcccaaag gtgaagcgcg tcttcaggtc  147660
aatagataat ctactagaga ttgtccccag agaacagaac tgggccctga ggcccaccgt  147720
tgccctttcc tgagagtccc agcccagtga aaggaacaca gttgacatgt tgttgaagcc  147780
ggagatgttg cctgtatgcg taaaagagct ctctgtttca ggctcatgta cagtcaggaa  147840
tggttccttc tcatccaact gcccatgcgc caatgatgct aatgacgaca cagccacccg  147900
gcggtcccca ggccgccctc gctcaaagtg cactacagcc cattccagtc tcgacaacag  147960
cgcatttccc ctatatgacg caccccttcag gtgaggcgtg tgtgtgcagg ggccgccggg  148020
gcaccccaaa gcattctgct cgcacaggtg gaatggcagg cagggccagt gcttcaagcc  148080
ccgcatttga gaactagcaa gacccgtcca ggagtgtgca caggagggac tgtgacgatc  148140
agttcagcat cagggcctga ggcttccggg agccgagtct gtgtgtgttc tgatggtata  148200
caggatttgg cttgatgaga agcagcagca gcagcaacag cagcctgatg catgcctagg  148260
actcagttgg ccttccttgt tatgacaggc tggacagggc agtgttttcc ttcctgagtc  148320
ccaaaagtct gacatgtggg gggttattac catggcagag tttgattgta gctctggaga  148380
agatactgct gagaaagcgc tgtggatgga ctggctttga gtgtagcgtt agccccagcc  148440
cctgaacagg ggagagcgcc ctgtgattgt gctctactac ttgatggctg ccatggcgat  148500
acttcacagt ctgacctgtt attctgaaag caatactggt gcttggctaa tatttgggga  148560
gggggtttgt taaggccttt ttttctaccc catgaacaag tcttctggga gttttatctg  148620
aagtggtttt acgtctgact ggtttgtttc tacccaccca cccaaccctc cccactttgg  148680
tgcagatggg agggggaaaa gcgaattcaa ttttgagttt tgttcagcta gcacgaggat  148740
agtttacaat catgtgctgc agagacacta ggctgatgtg tggtgttgcc agtttctgt  148800
ttcaatgttc gcttttcttt ttacagtaca agcccaccac caacagcagt tgtaaggctg  148860
ccctggagga accgaaaggc caaattccct cctcccttct actgcttcta ccaactggaa  148920
gcacagaaaa ctagaatttc atttattttg tttttaaaat atatatgttg atttcttgta  148980
acatccaata ggaatgctaa cagttcactt gcagtggaag atacttggac cgagtagagg  149040
catttaggaa cttggggggct attccataat tccatatgct gtttcagagt cccgcaggta  149100
ccccagctct gcttgccgaa actggaagtt atttattttt taataaccct tgaaagtcat  149160
gaacacatca gctagcaaaa gaagtaacaa gagtgattct tgctgctatt actgctaaaa  149220
aaaaaaaaaa aaaaaaatca agacttggaa cgccctttta ctaaacttga caaagtttca  149280
gtaaattctt accgtcaaac tgacggatta ttatttataa atcaagtttg atgaggtgat  149340
cactgtctac agtggttcaa cttttaagtt aagggaaaaa cttttacttt gtagataata  149400
taaaataaaa acttaaaaaa aatttaaaaa ataaaaaaag ttttaaaaac tgatcaagtt  149460
agtgtgtgtc tgtataagct acttctttgt aggatactta atatcaaagc aggtgtgcta  149520
agggtgcatt ttgaatatcc cggaaggtag ctgtgaaatg atttttcttc ttcaccctta  149580
```

```
gttctggttc aaggtatctc tagaaaaaga caagactgag ctattctctt tggtggatta  149640
gagatctgct tcaggaggag gaaggttggc cagagttggg cagcactgaa attccacatc  149700
ctcgggctga caccgattct gtaagcttcc tttttaatat ctcctgaacc aaaatgagtg  149760
tcattagctg gaagttccca attcgggcat ttttctactt taccagtagg gggcaggaga  149820
cactcagaaa aaaattgcaa taaagaaatc cagagggcat gaaggctgaa aagatacaaa  149880
gatgtacaaa gctgcttatt gacatggatg gactcataag catttgttag tattcccaga  149940
ttgcaacggg gaggacaaag ggaagagcga gtatttgggc agggcaagga ttttgtagag  150000
acaccatggt cttaatagag cctttaaata ttatgacagc aaatcaagat tctgaaaact  150060
ttttaattca catatagcaa tttgtacatt atagcaaaat ttgcattatt caagaataag  150120
ttacttgtac agtacataaa acaatacata aaaatttgcc aaataccttc tgcctataat  150180
gatacaagat gaatccactt tatgttatca caatgtgctg tatattctaa ccaaacacag  150240
gatgtcagat gtgtccttgt taatatactc gcaagttcct ctagcttgtg ggagatgtta  150300
gagctaacac atttgcagta agggacttag tcctgaatag aaagcatgaa ggaatctcag  150360
gcaaccctca gggaagagtc caaggccttg actttaggtt aagaaactgt tatgtaaaaa  150420
tagtgttctc tggcccaaga ttttaatgat tgctattcct ttttcctacg gtccagaaat  150480
gatcaaaggc agaagattta taccagataa agccatatgg attgctggtc taaaattcaa  150540
ggcaggttag ttgacttaat tctttggtgc tggtgactgt tagtttgtaa aagttcaata  150600
agtcagatga aggaagggat ggtgccggga gctgtcaagc tgtactggtg gggtctgtaa  150660
ttagagctaa ctggagggat catgatgtct actgtccagt ttggtgttga gccatggctc  150720
tcggtagaag ttgccggctg gggcctggtc aggactggaa ggagagtggt gggatgtgct  150780
gtgcctatgg tgggctagct gcagccagtg gggtgcctgc cccacactgc tgcccacccc  150840
ttcatcagct gattctgctc ccacataaag aaaggtgttg gcttagtgtc acttcttcct  150900
agagccatgg gagttttctg tcagcatgtt tttgagctgt cctggtaact tggacgggaa  150960
gcagtctgga ggtgggtgcc ttccaaatct ctgccacaga a                      151001

SEQ ID NO: 3            moltype = RNA  length = 863
FEATURE                 Location/Qualifiers
source                  1..863
                        mol_type = mRNA
                        organism = Homo sapiens
SEQUENCE: 3
gtctgtcggg gctctctccc cgccccctcc ggatcctggg naagnacggn ggacggggtg  60
gagacaagtg ggccttggcc cccgcacccc tctgcgttcg tgtccgaggc ggcggcgggg  120
gctcccgaac tcccctgaaa tcgtggggct ccatgtggcc tccggcagcg ttccaccctc  180
ccccacctgg ggaagggaag gggtggggag tgcccggccc cgtcccggcc ttcctccttc  240
ccccgccaga cctctccggc gcgcgggtgg tggccgatcc gcattgctgt tcgaggccgc  300
agtggagaag gcgcctgtgg aacatcgagg tcgaaacagt aacaaaggac tgcctcagtc  360
tacgatttct tttgatggaa tctatgcaaa tatgaggatg gttcatatac ttacatcagt  420
tgttggctcc aaatgtgaag tacaagtgaa aaatggaggt atatatgaag gagtttttaa  480
aacttacagt ccgaagtgtg atttggtact tgatgccgca catgagaaaa gtacagaatc  540
cagttcgggg ccgaaacgtg aagaaataat ggagagtatt ttgttcaaat gttcagactt  600
tgttgtggta cagtttaaag atatggactc cagttatgca aaaagagatg cttttactga  660
ctctgctatc agtgctaaag tgaatggcga acacaaagag aaggaccctg cagcccctgg  720
atgcaggtga actcacagcc aatgagggaa ctggaggctt tgnaaaatga cgtatctaat  780
ggatggaacc caaagatatg tttcgtttaa tgaaaaaaat tatggcgcag gggccaccgt  840
tgaaagcagt ttatttcgga tac                                         863

SEQ ID NO: 4            moltype =   length =
SEQUENCE: 4
000

SEQ ID NO: 5            moltype = DNA  length = 27
FEATURE                 Location/Qualifiers
source                  1..27
                        mol_type = other DNA
                        organism = Synthetic construct
SEQUENCE: 5
accaaagagt agttaatgga ggtgttc                                     27

SEQ ID NO: 6            moltype = DNA  length = 19
FEATURE                 Location/Qualifiers
source                  1..19
                        mol_type = other DNA
                        organism = Synthetic construct
SEQUENCE: 6
agaaggtggg cgagaggaa                                              19

SEQ ID NO: 7            moltype = DNA  length = 19
FEATURE                 Location/Qualifiers
source                  1..19
                        mol_type = other DNA
                        organism = Synthetic construct
SEQUENCE: 7
ctggccatcg ccttgccca                                              19

SEQ ID NO: 8            moltype =   length =
SEQUENCE: 8
000
```

```
SEQ ID NO: 9           moltype =   length =
SEQUENCE: 9
000

SEQ ID NO: 10          moltype =   length =
SEQUENCE: 10
000

SEQ ID NO: 11          moltype = DNA  length = 20
FEATURE                Location/Qualifiers
source                 1..20
                       mol_type = other DNA
                       organism = Synthetic construct
SEQUENCE: 11
ccggctcgca cgccgggcgg                                        20

SEQ ID NO: 12          moltype = DNA  length = 20
FEATURE                Location/Qualifiers
source                 1..20
                       mol_type = other DNA
                       organism = Synthetic construct
SEQUENCE: 12
catacaccgg ctcgcacgcc                                        20

SEQ ID NO: 13          moltype = DNA  length = 20
FEATURE                Location/Qualifiers
source                 1..20
                       mol_type = other DNA
                       organism = Synthetic construct
SEQUENCE: 13
ggcttcagcg acatggtgag                                        20

SEQ ID NO: 14          moltype = DNA  length = 20
FEATURE                Location/Qualifiers
source                 1..20
                       mol_type = other DNA
                       organism = Synthetic construct
SEQUENCE: 14
cgacctctgc ccaggccggg                                        20

SEQ ID NO: 15          moltype = DNA  length = 20
FEATURE                Location/Qualifiers
source                 1..20
                       mol_type = other DNA
                       organism = Synthetic construct
SEQUENCE: 15
tgcatagatt ccatcaaaag                                        20

SEQ ID NO: 16          moltype = DNA  length = 20
FEATURE                Location/Qualifiers
source                 1..20
                       mol_type = other DNA
                       organism = Synthetic construct
SEQUENCE: 16
aagtatatga accatcctca                                        20

SEQ ID NO: 17          moltype = DNA  length = 20
FEATURE                Location/Qualifiers
source                 1..20
                       mol_type = other DNA
                       organism = Synthetic construct
SEQUENCE: 17
ttcacttgta cttcacattt                                        20

SEQ ID NO: 18          moltype = DNA  length = 20
FEATURE                Location/Qualifiers
source                 1..20
                       mol_type = other DNA
                       organism = Synthetic construct
SEQUENCE: 18
tctgtacttt tctcatgtgc                                        20

SEQ ID NO: 19          moltype = DNA  length = 20
FEATURE                Location/Qualifiers
source                 1..20
                       mol_type = other DNA
                       organism = Synthetic construct
SEQUENCE: 19
ctggattctg tacttttctc                                        20
```

```
SEQ ID NO: 20           moltype = DNA  length = 20
FEATURE                 Location/Qualifiers
source                  1..20
                        mol_type = other DNA
                        organism = Synthetic construct
SEQUENCE: 20
ctctccatta tttcttcacg                                              20

SEQ ID NO: 21           moltype = DNA  length = 20
FEATURE                 Location/Qualifiers
source                  1..20
                        mol_type = other DNA
                        organism = Synthetic construct
SEQUENCE: 21
tctttaaact gtaccacaac                                              20

SEQ ID NO: 22           moltype = DNA  length = 20
FEATURE                 Location/Qualifiers
source                  1..20
                        mol_type = other DNA
                        organism = Synthetic construct
SEQUENCE: 22
gagtcagtaa aagcatctct                                              20

SEQ ID NO: 23           moltype = DNA  length = 20
FEATURE                 Location/Qualifiers
source                  1..20
                        mol_type = other DNA
                        organism = Synthetic construct
SEQUENCE: 23
cagggctcca ggtccttctc                                              20

SEQ ID NO: 24           moltype = DNA  length = 20
FEATURE                 Location/Qualifiers
source                  1..20
                        mol_type = other DNA
                        organism = Synthetic construct
SEQUENCE: 24
gcatcccagg gctccaggtc                                              20

SEQ ID NO: 25           moltype = DNA  length = 20
FEATURE                 Location/Qualifiers
source                  1..20
                        mol_type = other DNA
                        organism = Synthetic construct
SEQUENCE: 25
tcttcattat atcgaaacat                                              20

SEQ ID NO: 26           moltype = DNA  length = 20
FEATURE                 Location/Qualifiers
source                  1..20
                        mol_type = other DNA
                        organism = Synthetic construct
SEQUENCE: 26
gctaactggt ttgcccttgc                                              20

SEQ ID NO: 27           moltype = DNA  length = 20
FEATURE                 Location/Qualifiers
source                  1..20
                        mol_type = other DNA
                        organism = Synthetic construct
SEQUENCE: 27
gtatttttct tcctcactcc                                              20

SEQ ID NO: 28           moltype = DNA  length = 20
FEATURE                 Location/Qualifiers
source                  1..20
                        mol_type = other DNA
                        organism = Synthetic construct
SEQUENCE: 28
tgctgtgtat ttttcttcct                                              20

SEQ ID NO: 29           moltype = DNA  length = 20
FEATURE                 Location/Qualifiers
source                  1..20
                        mol_type = other DNA
                        organism = Synthetic construct
SEQUENCE: 29
```

```
gaaatctgaa gtgtgagaag                                              20

SEQ ID NO: 30           moltype = DNA  length = 20
FEATURE                 Location/Qualifiers
source                  1..20
                        mol_type = other DNA
                        organism = Synthetic construct
SEQUENCE: 30
cctccattaa ctactctttg                                              20

SEQ ID NO: 31           moltype = DNA  length = 20
FEATURE                 Location/Qualifiers
source                  1..20
                        mol_type = other DNA
                        organism = Synthetic construct
SEQUENCE: 31
ggaacacctc cattaactac                                              20

SEQ ID NO: 32           moltype = DNA  length = 20
FEATURE                 Location/Qualifiers
source                  1..20
                        mol_type = other DNA
                        organism = Synthetic construct
SEQUENCE: 32
ggcgatggcc agggaacacc                                              20

SEQ ID NO: 33           moltype = DNA  length = 20
FEATURE                 Location/Qualifiers
source                  1..20
                        mol_type = other DNA
                        organism = Synthetic construct
SEQUENCE: 33
gtagcgagaa ggtgggcgag                                              20

SEQ ID NO: 34           moltype = DNA  length = 20
FEATURE                 Location/Qualifiers
source                  1..20
                        mol_type = other DNA
                        organism = Synthetic construct
SEQUENCE: 34
agagttggga cctgactggt                                              20

SEQ ID NO: 35           moltype = DNA  length = 20
FEATURE                 Location/Qualifiers
source                  1..20
                        mol_type = other DNA
                        organism = Synthetic construct
SEQUENCE: 35
tggaagagag ttgggacctg                                              20

SEQ ID NO: 36           moltype = DNA  length = 20
FEATURE                 Location/Qualifiers
source                  1..20
                        mol_type = other DNA
                        organism = Synthetic construct
SEQUENCE: 36
ggagctggag aaccatgagc                                              20

SEQ ID NO: 37           moltype = DNA  length = 20
FEATURE                 Location/Qualifiers
source                  1..20
                        mol_type = other DNA
                        organism = Synthetic construct
SEQUENCE: 37
gagacaggag ctggagaacc                                              20

SEQ ID NO: 38           moltype = DNA  length = 20
FEATURE                 Location/Qualifiers
source                  1..20
                        mol_type = other DNA
                        organism = Synthetic construct
SEQUENCE: 38
ttgtgggata caaattctag                                              20

SEQ ID NO: 39           moltype = DNA  length = 20
FEATURE                 Location/Qualifiers
source                  1..20
                        mol_type = other DNA
                        organism = Synthetic construct
```

-continued

```
SEQUENCE: 39
ggaaccccac tgaccactga                                              20

SEQ ID NO: 40          moltype = DNA  length = 20
FEATURE                Location/Qualifiers
source                 1..20
                       mol_type = other DNA
                       organism = Synthetic construct
SEQUENCE: 40
tcttgaagcc tggaatcttt                                              20

SEQ ID NO: 41          moltype = DNA  length = 20
FEATURE                Location/Qualifiers
source                 1..20
                       mol_type = other DNA
                       organism = Synthetic construct
SEQUENCE: 41
aacctaaaat cattcttaaa                                              20

SEQ ID NO: 42          moltype = DNA  length = 20
FEATURE                Location/Qualifiers
source                 1..20
                       mol_type = other DNA
                       organism = Synthetic construct
SEQUENCE: 42
agttgatcca tagattcaga                                              20

SEQ ID NO: 43          moltype = DNA  length = 20
FEATURE                Location/Qualifiers
source                 1..20
                       mol_type = other DNA
                       organism = Synthetic construct
SEQUENCE: 43
ctggtacagt tgctgctgct                                              20

SEQ ID NO: 44          moltype = DNA  length = 20
FEATURE                Location/Qualifiers
source                 1..20
                       mol_type = other DNA
                       organism = Synthetic construct
SEQUENCE: 44
ctgccactgg tacagttgct                                              20

SEQ ID NO: 45          moltype = DNA  length = 20
FEATURE                Location/Qualifiers
source                 1..20
                       mol_type = other DNA
                       organism = Synthetic construct
SEQUENCE: 45
tttgcattgg gattcaatgt                                              20

SEQ ID NO: 46          moltype = DNA  length = 20
FEATURE                Location/Qualifiers
source                 1..20
                       mol_type = other DNA
                       organism = Synthetic construct
SEQUENCE: 46
gaaggctttg gctgagagaa                                              20

SEQ ID NO: 47          moltype = DNA  length = 20
FEATURE                Location/Qualifiers
source                 1..20
                       mol_type = other DNA
                       organism = Synthetic construct
SEQUENCE: 47
gtagtagaag gctttggctg                                              20

SEQ ID NO: 48          moltype = DNA  length = 20
FEATURE                Location/Qualifiers
source                 1..20
                       mol_type = other DNA
                       organism = Synthetic construct
SEQUENCE: 48
tgacccacca tagatgggct                                              20

SEQ ID NO: 49          moltype = DNA  length = 20
FEATURE                Location/Qualifiers
source                 1..20
                       mol_type = other DNA
```

```
                      organism = Synthetic construct
SEQUENCE: 49
ggtattgggt ataaaggttg                                              20

SEQ ID NO: 50         moltype = DNA  length = 20
FEATURE               Location/Qualifiers
source                1..20
                      mol_type = other DNA
                      organism = Synthetic construct
SEQUENCE: 50
gtcataggta ttgggtataa                                              20

SEQ ID NO: 51         moltype = DNA  length = 20
FEATURE               Location/Qualifiers
source                1..20
                      mol_type = other DNA
                      organism = Synthetic construct
SEQUENCE: 51
ggatgctgag actgataatg                                              20

SEQ ID NO: 52         moltype = DNA  length = 20
FEATURE               Location/Qualifiers
source                1..20
                      mol_type = other DNA
                      organism = Synthetic construct
SEQUENCE: 52
acatgaggat gctgagactg                                              20

SEQ ID NO: 53         moltype = DNA  length = 20
FEATURE               Location/Qualifiers
source                1..20
                      mol_type = other DNA
                      organism = Synthetic construct
SEQUENCE: 53
aatttgggac atgcatacat                                              20

SEQ ID NO: 54         moltype = DNA  length = 20
FEATURE               Location/Qualifiers
source                1..20
                      mol_type = other DNA
                      organism = Synthetic construct
SEQUENCE: 54
gtctccttgt tgtatggtaa                                              20

SEQ ID NO: 55         moltype = DNA  length = 20
FEATURE               Location/Qualifiers
source                1..20
                      mol_type = other DNA
                      organism = Synthetic construct
SEQUENCE: 55
tgaacaggac tgggtgcagg                                              20

SEQ ID NO: 56         moltype = DNA  length = 20
FEATURE               Location/Qualifiers
source                1..20
                      mol_type = other DNA
                      organism = Synthetic construct
SEQUENCE: 56
gactgctgct gtggactggc                                              20

SEQ ID NO: 57         moltype = DNA  length = 20
FEATURE               Location/Qualifiers
source                1..20
                      mol_type = other DNA
                      organism = Synthetic construct
SEQUENCE: 57
ctgactgtac atgagcctga                                              20

SEQ ID NO: 58         moltype = DNA  length = 20
FEATURE               Location/Qualifiers
source                1..20
                      mol_type = other DNA
                      organism = Synthetic construct
SEQUENCE: 58
ccattcctga ctgtacatga                                              20

SEQ ID NO: 59         moltype = DNA  length = 20
FEATURE               Location/Qualifiers
source                1..20
```

-continued

```
                      mol_type = other DNA
                      organism = Synthetic construct
SEQUENCE: 59
cagttggatg agaaggaacc                                            20

SEQ ID NO: 60         moltype = DNA  length = 20
FEATURE               Location/Qualifiers
source                1..20
                      mol_type = other DNA
                      organism = Synthetic construct
SEQUENCE: 60
catgggcagt tggatgagaa                                            20

SEQ ID NO: 61         moltype = DNA  length = 20
FEATURE               Location/Qualifiers
source                1..20
                      mol_type = other DNA
                      organism = Synthetic construct
SEQUENCE: 61
accgccgggt ggctgtgtcg                                            20

SEQ ID NO: 62         moltype = DNA  length = 20
FEATURE               Location/Qualifiers
source                1..20
                      mol_type = other DNA
                      organism = Synthetic construct
SEQUENCE: 62
tttgagcgag ggcggcctgg                                            20

SEQ ID NO: 63         moltype = DNA  length = 20
FEATURE               Location/Qualifiers
source                1..20
                      mol_type = other DNA
                      organism = Synthetic construct
SEQUENCE: 63
gctgtagtgc actttgagcg                                            20

SEQ ID NO: 64         moltype = DNA  length = 20
FEATURE               Location/Qualifiers
source                1..20
                      mol_type = other DNA
                      organism = Synthetic construct
SEQUENCE: 64
agactggaat gggctgtagt                                            20

SEQ ID NO: 65         moltype = DNA  length = 20
FEATURE               Location/Qualifiers
source                1..20
                      mol_type = other DNA
                      organism = Synthetic construct
SEQUENCE: 65
gcgctgttgt cgagactgga                                            20

SEQ ID NO: 66         moltype = DNA  length = 20
FEATURE               Location/Qualifiers
source                1..20
                      mol_type = other DNA
                      organism = Synthetic construct
SEQUENCE: 66
ggaaatgcgc tgttgtcgag                                            20

SEQ ID NO: 67         moltype = DNA  length = 20
FEATURE               Location/Qualifiers
source                1..20
                      mol_type = other DNA
                      organism = Synthetic construct
SEQUENCE: 67
ggcttgtact gaagggtgcg                                            20

SEQ ID NO: 68         moltype = DNA  length = 20
FEATURE               Location/Qualifiers
source                1..20
                      mol_type = other DNA
                      organism = Synthetic construct
SEQUENCE: 68
gtggtgggct tgtactgaag                                            20

SEQ ID NO: 69         moltype = DNA  length = 20
FEATURE               Location/Qualifiers
```

-continued

```
source                  1..20
                        mol_type = other DNA
                        organism = Synthetic construct
SEQUENCE: 69
ctgttggtgg tgggcttgta                                                  20

SEQ ID NO: 70           moltype = DNA  length = 20
FEATURE                 Location/Qualifiers
source                  1..20
                        mol_type = other DNA
                        organism = Synthetic construct
SEQUENCE: 70
caactgctgt tggtggtggg                                                  20

SEQ ID NO: 71           moltype = DNA  length = 20
FEATURE                 Location/Qualifiers
source                  1..20
                        mol_type = other DNA
                        organism = Synthetic construct
SEQUENCE: 71
gccttacaac tgctgttggt                                                  20

SEQ ID NO: 72           moltype = DNA  length = 20
FEATURE                 Location/Qualifiers
source                  1..20
                        mol_type = other DNA
                        organism = Synthetic construct
SEQUENCE: 72
ttcggttcct ccagggcagc                                                  20

SEQ ID NO: 73           moltype = DNA  length = 20
FEATURE                 Location/Qualifiers
source                  1..20
                        mol_type = other DNA
                        organism = Synthetic construct
SEQUENCE: 73
ttctagtttt ctgtgcttcc                                                  20

SEQ ID NO: 74           moltype = DNA  length = 20
FEATURE                 Location/Qualifiers
source                  1..20
                        mol_type = other DNA
                        organism = Synthetic construct
SEQUENCE: 74
aataaataac ttccagtttc                                                  20

SEQ ID NO: 75           moltype = DNA  length = 20
FEATURE                 Location/Qualifiers
source                  1..20
                        mol_type = other DNA
                        organism = Synthetic construct
SEQUENCE: 75
gaatcactct tgttacttct                                                  20

SEQ ID NO: 76           moltype = DNA  length = 20
FEATURE                 Location/Qualifiers
source                  1..20
                        mol_type = other DNA
                        organism = Synthetic construct
SEQUENCE: 76
cagcaagaat cactcttgtt                                                  20

SEQ ID NO: 77           moltype = DNA  length = 20
FEATURE                 Location/Qualifiers
source                  1..20
                        mol_type = other DNA
                        organism = Synthetic construct
SEQUENCE: 77
tttataaata ataatccgtc                                                  20

SEQ ID NO: 78           moltype = DNA  length = 20
FEATURE                 Location/Qualifiers
source                  1..20
                        mol_type = other DNA
                        organism = Synthetic construct
SEQUENCE: 78
aagttgaacc actgtagaca                                                  20

SEQ ID NO: 79           moltype = DNA  length = 20
```

-continued

```
FEATURE               Location/Qualifiers
source                1..20
                      mol_type = other DNA
                      organism = Synthetic construct
SEQUENCE: 79
atcggccacc acccgcgcgc                                                  20

SEQ ID NO: 80         moltype = DNA  length = 20
FEATURE               Location/Qualifiers
source                1..20
                      mol_type = other DNA
                      organism = Synthetic construct
SEQUENCE: 80
caaagggtta attaggatct                                                  20

SEQ ID NO: 81         moltype = DNA  length = 20
FEATURE               Location/Qualifiers
source                1..20
                      mol_type = other DNA
                      organism = Synthetic construct
SEQUENCE: 81
cccaaagggt taattaggat                                                  20

SEQ ID NO: 82         moltype = DNA  length = 20
FEATURE               Location/Qualifiers
source                1..20
                      mol_type = other DNA
                      organism = Synthetic construct
SEQUENCE: 82
aggacagtca tttgatttgt                                                  20

SEQ ID NO: 83         moltype = DNA  length = 20
FEATURE               Location/Qualifiers
source                1..20
                      mol_type = other DNA
                      organism = Synthetic construct
SEQUENCE: 83
ctttgaggac agtcatttga                                                  20

SEQ ID NO: 84         moltype = DNA  length = 20
FEATURE               Location/Qualifiers
source                1..20
                      mol_type = other DNA
                      organism = Synthetic construct
SEQUENCE: 84
ctgacagaac aaatgatatg                                                  20

SEQ ID NO: 85         moltype = DNA  length = 20
FEATURE               Location/Qualifiers
source                1..20
                      mol_type = other DNA
                      organism = Synthetic construct
SEQUENCE: 85
tattgggtat aaaggcttga                                                  20

SEQ ID NO: 86         moltype = DNA  length = 20
FEATURE               Location/Qualifiers
source                1..20
                      mol_type = other DNA
                      organism = Synthetic construct
SEQUENCE: 86
ggtattgggt ataaaggctt                                                  20

SEQ ID NO: 87         moltype = DNA  length = 20
FEATURE               Location/Qualifiers
source                1..20
                      mol_type = other DNA
                      organism = Synthetic construct
SEQUENCE: 87
ctcttttacg catacaggca                                                  20

SEQ ID NO: 88         moltype = DNA  length = 20
FEATURE               Location/Qualifiers
source                1..20
                      mol_type = other DNA
                      organism = Synthetic construct
SEQUENCE: 88
aggaaggcca actgagtcct                                                  20
```

-continued

```
SEQ ID NO: 89           moltype = DNA  length = 20
FEATURE                 Location/Qualifiers
source                  1..20
                        mol_type = other DNA
                        organism = Synthetic construct
SEQUENCE: 89
ggtcagacgg aagcagaacg                                        20

SEQ ID NO: 90           moltype = DNA  length = 20
FEATURE                 Location/Qualifiers
source                  1..20
                        mol_type = other DNA
                        organism = Synthetic construct
SEQUENCE: 90
ccacctggct gcggcgaagc                                        20

SEQ ID NO: 91           moltype = DNA  length = 20
FEATURE                 Location/Qualifiers
source                  1..20
                        mol_type = other DNA
                        organism = Synthetic construct
SEQUENCE: 91
gccgttgccg ttgctaccaa                                        20

SEQ ID NO: 92           moltype = DNA  length = 20
FEATURE                 Location/Qualifiers
source                  1..20
                        mol_type = other DNA
                        organism = Synthetic construct
SEQUENCE: 92
ggcccataca ccggctcgca                                        20

SEQ ID NO: 93           moltype = DNA  length = 20
FEATURE                 Location/Qualifiers
source                  1..20
                        mol_type = other DNA
                        organism = Synthetic construct
SEQUENCE: 93
gcttcagcga catggtgagg                                        20

SEQ ID NO: 94           moltype = DNA  length = 20
FEATURE                 Location/Qualifiers
source                  1..20
                        mol_type = other DNA
                        organism = Synthetic construct
SEQUENCE: 94
ggacattggc agccgcgggc                                        20

SEQ ID NO: 95           moltype = DNA  length = 20
FEATURE                 Location/Qualifiers
source                  1..20
                        mol_type = other DNA
                        organism = Synthetic construct
SEQUENCE: 95
gattccatca aaagaaatcg                                        20

SEQ ID NO: 96           moltype = DNA  length = 20
FEATURE                 Location/Qualifiers
source                  1..20
                        mol_type = other DNA
                        organism = Synthetic construct
SEQUENCE: 96
caactgatgt aagtatatga                                        20

SEQ ID NO: 97           moltype = DNA  length = 20
FEATURE                 Location/Qualifiers
source                  1..20
                        mol_type = other DNA
                        organism = Synthetic construct
SEQUENCE: 97
ccaaatcaca cttcggactg                                        20

SEQ ID NO: 98           moltype = DNA  length = 20
FEATURE                 Location/Qualifiers
source                  1..20
                        mol_type = other DNA
                        organism = Synthetic construct
SEQUENCE: 98
ctcatgtgcg gcatcaagta                                        20
```

-continued

```
SEQ ID NO: 99           moltype = DNA  length = 20
FEATURE                 Location/Qualifiers
source                  1..20
                        mol_type = other DNA
                        organism = Synthetic construct
SEQUENCE: 99
catttgaaca aaatactctc                                             20

SEQ ID NO: 100          moltype = DNA  length = 20
FEATURE                 Location/Qualifiers
source                  1..20
                        mol_type = other DNA
                        organism = Synthetic construct
SEQUENCE: 100
ctgatagcag agtcagtaaa                                             20

SEQ ID NO: 101          moltype = DNA  length = 20
FEATURE                 Location/Qualifiers
source                  1..20
                        mol_type = other DNA
                        organism = Synthetic construct
SEQUENCE: 101
gggccactcg agctttgtac                                             20

SEQ ID NO: 102          moltype = DNA  length = 20
FEATURE                 Location/Qualifiers
source                  1..20
                        mol_type = other DNA
                        organism = Synthetic construct
SEQUENCE: 102
aggaatatat ttattttccc                                             20

SEQ ID NO: 103          moltype = DNA  length = 20
FEATURE                 Location/Qualifiers
source                  1..20
                        mol_type = other DNA
                        organism = Synthetic construct
SEQUENCE: 103
cccatacgcg gtgaattctg                                             20

SEQ ID NO: 104          moltype = DNA  length = 20
FEATURE                 Location/Qualifiers
source                  1..20
                        mol_type = other DNA
                        organism = Synthetic construct
SEQUENCE: 104
tggagcccga tccaggctgg                                             20

SEQ ID NO: 105          moltype = DNA  length = 20
FEATURE                 Location/Qualifiers
source                  1..20
                        mol_type = other DNA
                        organism = Synthetic construct
SEQUENCE: 105
agaagtggat cttgatggca                                             20

SEQ ID NO: 106          moltype = DNA  length = 20
FEATURE                 Location/Qualifiers
source                  1..20
                        mol_type = other DNA
                        organism = Synthetic construct
SEQUENCE: 106
ggagaaccat gagcagaggg                                             20

SEQ ID NO: 107          moltype = DNA  length = 20
FEATURE                 Location/Qualifiers
source                  1..20
                        mol_type = other DNA
                        organism = Synthetic construct
SEQUENCE: 107
ggcccttctg aagacatgcg                                             20

SEQ ID NO: 108          moltype = DNA  length = 20
FEATURE                 Location/Qualifiers
source                  1..20
                        mol_type = other DNA
                        organism = Synthetic construct
SEQUENCE: 108
```

```
cactggatat ggaacccctc                                                 20

SEQ ID NO: 109          moltype = DNA  length = 20
FEATURE                 Location/Qualifiers
source                  1..20
                        mol_type = other DNA
                        organism = Synthetic construct
SEQUENCE: 109
gtgggataca aattctaggc                                                 20

SEQ ID NO: 110          moltype = DNA  length = 20
FEATURE                 Location/Qualifiers
source                  1..20
                        mol_type = other DNA
                        organism = Synthetic construct
SEQUENCE: 110
actgaccact gatgaccacg                                                 20

SEQ ID NO: 111          moltype = DNA  length = 20
FEATURE                 Location/Qualifiers
source                  1..20
                        mol_type = other DNA
                        organism = Synthetic construct
SEQUENCE: 111
ctgggtctat gagttttagg                                                 20

SEQ ID NO: 112          moltype = DNA  length = 20
FEATURE                 Location/Qualifiers
source                  1..20
                        mol_type = other DNA
                        organism = Synthetic construct
SEQUENCE: 112
tggaataata ccagcttggg                                                 20

SEQ ID NO: 113          moltype = DNA  length = 20
FEATURE                 Location/Qualifiers
source                  1..20
                        mol_type = other DNA
                        organism = Synthetic construct
SEQUENCE: 113
ggcatggcaa cagcttcagt                                                 20

SEQ ID NO: 114          moltype = DNA  length = 20
FEATURE                 Location/Qualifiers
source                  1..20
                        mol_type = other DNA
                        organism = Synthetic construct
SEQUENCE: 114
taggagatgc agctggaata                                                 20

SEQ ID NO: 115          moltype = DNA  length = 20
FEATURE                 Location/Qualifiers
source                  1..20
                        mol_type = other DNA
                        organism = Synthetic construct
SEQUENCE: 115
gaagcctgga atctttagcc                                                 20

SEQ ID NO: 116          moltype = DNA  length = 20
FEATURE                 Location/Qualifiers
source                  1..20
                        mol_type = other DNA
                        organism = Synthetic construct
SEQUENCE: 116
ccctgcagga gagttctgcc                                                 20

SEQ ID NO: 117          moltype = DNA  length = 20
FEATURE                 Location/Qualifiers
source                  1..20
                        mol_type = other DNA
                        organism = Synthetic construct
SEQUENCE: 117
ttcagaagta gaacttggct                                                 20

SEQ ID NO: 118          moltype = DNA  length = 20
FEATURE                 Location/Qualifiers
source                  1..20
                        mol_type = other DNA
                        organism = Synthetic construct
```

-continued

```
SEQUENCE: 118
caattttgtc tttgatcaaa                                              20

SEQ ID NO: 119          moltype = DNA  length = 20
FEATURE                 Location/Qualifiers
source                  1..20
                        mol_type = other DNA
                        organism = Synthetic construct
SEQUENCE: 119
tgttactaag tattgaaggg                                              20

SEQ ID NO: 120          moltype = DNA  length = 20
FEATURE                 Location/Qualifiers
source                  1..20
                        mol_type = other DNA
                        organism = Synthetic construct
SEQUENCE: 120
aagtgacctc aggtcccctc                                              20

SEQ ID NO: 121          moltype = DNA  length = 20
FEATURE                 Location/Qualifiers
source                  1..20
                        mol_type = other DNA
                        organism = Synthetic construct
SEQUENCE: 121
atgttgattt cctaacttgc                                              20

SEQ ID NO: 122          moltype = DNA  length = 20
FEATURE                 Location/Qualifiers
source                  1..20
                        mol_type = other DNA
                        organism = Synthetic construct
SEQUENCE: 122
gtataaactg gagttggctg                                              20

SEQ ID NO: 123          moltype = DNA  length = 20
FEATURE                 Location/Qualifiers
source                  1..20
                        mol_type = other DNA
                        organism = Synthetic construct
SEQUENCE: 123
gtgcaaaaca aacaggctga                                              20

SEQ ID NO: 124          moltype = DNA  length = 20
FEATURE                 Location/Qualifiers
source                  1..20
                        mol_type = other DNA
                        organism = Synthetic construct
SEQUENCE: 124
gactggatac atcatatttg                                              20

SEQ ID NO: 125          moltype = DNA  length = 20
FEATURE                 Location/Qualifiers
source                  1..20
                        mol_type = other DNA
                        organism = Synthetic construct
SEQUENCE: 125
ggttgcacgc ctgggctcac                                              20

SEQ ID NO: 126          moltype = DNA  length = 20
FEATURE                 Location/Qualifiers
source                  1..20
                        mol_type = other DNA
                        organism = Synthetic construct
SEQUENCE: 126
tcataggtat tgggtataaa                                              20

SEQ ID NO: 127          moltype = DNA  length = 20
FEATURE                 Location/Qualifiers
source                  1..20
                        mol_type = other DNA
                        organism = Synthetic construct
SEQUENCE: 127
ttgattcact ggcatgggcg                                              20

SEQ ID NO: 128          moltype = DNA  length = 20
FEATURE                 Location/Qualifiers
source                  1..20
                        mol_type = other DNA
```

```
                      organism = Synthetic construct
SEQUENCE: 128
gatgatgctg gtcttgccgc                                              20

SEQ ID NO: 129        moltype = DNA  length = 20
FEATURE               Location/Qualifiers
source                1..20
                      mol_type = other DNA
                      organism = Synthetic construct
SEQUENCE: 129
atcattctag cattaccctg                                              20

SEQ ID NO: 130        moltype = DNA  length = 20
FEATURE               Location/Qualifiers
source                1..20
                      mol_type = other DNA
                      organism = Synthetic construct
SEQUENCE: 130
atactaaacc aggctgggcg                                              20

SEQ ID NO: 131        moltype = DNA  length = 20
FEATURE               Location/Qualifiers
source                1..20
                      mol_type = other DNA
                      organism = Synthetic construct
SEQUENCE: 131
acatgcatac atcgcatgcg                                              20

SEQ ID NO: 132        moltype = DNA  length = 20
FEATURE               Location/Qualifiers
source                1..20
                      mol_type = other DNA
                      organism = Synthetic construct
SEQUENCE: 132
tagaaagaag ggcttgtctc                                              20

SEQ ID NO: 133        moltype = DNA  length = 20
FEATURE               Location/Qualifiers
source                1..20
                      mol_type = other DNA
                      organism = Synthetic construct
SEQUENCE: 133
cgcatactgc tgagcaaggg                                              20

SEQ ID NO: 134        moltype = DNA  length = 20
FEATURE               Location/Qualifiers
source                1..20
                      mol_type = other DNA
                      organism = Synthetic construct
SEQUENCE: 134
tagctgaagg ctgagggtgt                                              20

SEQ ID NO: 135        moltype = DNA  length = 20
FEATURE               Location/Qualifiers
source                1..20
                      mol_type = other DNA
                      organism = Synthetic construct
SEQUENCE: 135
caccatgttg gctttgctgc                                              20

SEQ ID NO: 136        moltype = DNA  length = 20
FEATURE               Location/Qualifiers
source                1..20
                      mol_type = other DNA
                      organism = Synthetic construct
SEQUENCE: 136
actgggtgca ggatgacttc                                              20

SEQ ID NO: 137        moltype = DNA  length = 20
FEATURE               Location/Qualifiers
source                1..20
                      mol_type = other DNA
                      organism = Synthetic construct
SEQUENCE: 137
cgtggtaaat ggctgactgc                                              20

SEQ ID NO: 138        moltype = DNA  length = 20
FEATURE               Location/Qualifiers
source                1..20
```

-continued

```
                          mol_type = other DNA
                          organism = Synthetic construct
SEQUENCE: 138
ttggaggcag gtgtcatgga                                                      20

SEQ ID NO: 139            moltype = DNA  length = 20
FEATURE                   Location/Qualifiers
source                    1..20
                          mol_type = other DNA
                          organism = Synthetic construct
SEQUENCE: 139
tggcgcatgg gcagttggat                                                      20

SEQ ID NO: 140            moltype = DNA  length = 20
FEATURE                   Location/Qualifiers
source                    1..20
                          mol_type = other DNA
                          organism = Synthetic construct
SEQUENCE: 140
ctttgagcga gggcggcctg                                                      20

SEQ ID NO: 141            moltype = DNA  length = 20
FEATURE                   Location/Qualifiers
source                    1..20
                          mol_type = other DNA
                          organism = Synthetic construct
SEQUENCE: 141
gtcgagactg gaatgggctg                                                      20

SEQ ID NO: 142            moltype = DNA  length = 20
FEATURE                   Location/Qualifiers
source                    1..20
                          mol_type = other DNA
                          organism = Synthetic construct
SEQUENCE: 142
attcctattg gatgttacaa                                                      20

SEQ ID NO: 143            moltype = DNA  length = 20
FEATURE                   Location/Qualifiers
source                    1..20
                          mol_type = other DNA
                          organism = Synthetic construct
SEQUENCE: 143
atcttccact gcaagtgaac                                                      20

SEQ ID NO: 144            moltype = DNA  length = 20
FEATURE                   Location/Qualifiers
source                    1..20
                          mol_type = other DNA
                          organism = Synthetic construct
SEQUENCE: 144
tatggaatta tggaatagcc                                                      20

SEQ ID NO: 145            moltype = DNA  length = 20
FEATURE                   Location/Qualifiers
source                    1..20
                          mol_type = other DNA
                          organism = Synthetic construct
SEQUENCE: 145
gcaagaatca ctcttgttac                                                      20

SEQ ID NO: 146            moltype = DNA  length = 20
FEATURE                   Location/Qualifiers
source                    1..20
                          mol_type = other DNA
                          organism = Synthetic construct
SEQUENCE: 146
tgtagacagt gatcacctca                                                      20

SEQ ID NO: 147            moltype = DNA  length = 20
FEATURE                   Location/Qualifiers
source                    1..20
                          mol_type = other DNA
                          organism = Synthetic construct
SEQUENCE: 147
ggccaaggcc cacttgtctc                                                      20

SEQ ID NO: 148            moltype = DNA  length = 20
FEATURE                   Location/Qualifiers
```

-continued

```
source                  1..20
                        mol_type = other DNA
                        organism = Synthetic construct
SEQUENCE: 148
cactgcggcc tcgaacagca                                              20

SEQ ID NO: 149          moltype = DNA  length = 20
FEATURE                 Location/Qualifiers
source                  1..20
                        mol_type = other DNA
                        organism = Synthetic construct
SEQUENCE: 149
aaattcctca ttttcttttc                                              20

SEQ ID NO: 150          moltype = DNA  length = 20
FEATURE                 Location/Qualifiers
source                  1..20
                        mol_type = other DNA
                        organism = Synthetic construct
SEQUENCE: 150
gttatagtaa tctgtaatca                                              20

SEQ ID NO: 151          moltype = DNA  length = 20
FEATURE                 Location/Qualifiers
source                  1..20
                        mol_type = other DNA
                        organism = Synthetic construct
SEQUENCE: 151
aggattgtaa aatgatacag                                              20

SEQ ID NO: 152          moltype = DNA  length = 20
FEATURE                 Location/Qualifiers
source                  1..20
                        mol_type = other DNA
                        organism = Synthetic construct
SEQUENCE: 152
gtaggattgt aaaatgatac                                              20

SEQ ID NO: 153          moltype = DNA  length = 20
FEATURE                 Location/Qualifiers
source                  1..20
                        mol_type = other DNA
                        organism = Synthetic construct
SEQUENCE: 153
ttatatatgt aaattatatc                                              20

SEQ ID NO: 154          moltype = DNA  length = 20
FEATURE                 Location/Qualifiers
source                  1..20
                        mol_type = other DNA
                        organism = Synthetic construct
SEQUENCE: 154
aaccactgat ttatacactt                                              20

SEQ ID NO: 155          moltype = DNA  length = 20
FEATURE                 Location/Qualifiers
source                  1..20
                        mol_type = other DNA
                        organism = Synthetic construct
SEQUENCE: 155
ttaaaaacca ctgatttata                                              20

SEQ ID NO: 156          moltype = DNA  length = 20
FEATURE                 Location/Qualifiers
source                  1..20
                        mol_type = other DNA
                        organism = Synthetic construct
SEQUENCE: 156
atatagcact ctgctgtatt                                              20

SEQ ID NO: 157          moltype = DNA  length = 20
FEATURE                 Location/Qualifiers
source                  1..20
                        mol_type = other DNA
                        organism = Synthetic construct
SEQUENCE: 157
taccaagctt gtggcttggg                                              20

SEQ ID NO: 158          moltype = DNA  length = 20
```

-continued

```
FEATURE                 Location/Qualifiers
source                  1..20
                        mol_type = other DNA
                        organism = Synthetic construct
SEQUENCE: 158
ttataccaag cttgtggctt                                              20

SEQ ID NO: 159          moltype = DNA  length = 20
FEATURE                 Location/Qualifiers
source                  1..20
                        mol_type = other DNA
                        organism = Synthetic construct
SEQUENCE: 159
cctcgatgtt ccacaggcgc                                              20

SEQ ID NO: 160          moltype = DNA  length = 20
FEATURE                 Location/Qualifiers
source                  1..20
                        mol_type = other DNA
                        organism = Synthetic construct
SEQUENCE: 160
gagttcacct gcatccaggg                                              20

SEQ ID NO: 161          moltype = DNA  length = 20
FEATURE                 Location/Qualifiers
source                  1..20
                        mol_type = other DNA
                        organism = Synthetic construct
SEQUENCE: 161
tccagttccc tcattggctg                                              20

SEQ ID NO: 162          moltype = DNA  length = 20
FEATURE                 Location/Qualifiers
source                  1..20
                        mol_type = other DNA
                        organism = Synthetic construct
SEQUENCE: 162
ggttccatcc attagatacg                                              20

SEQ ID NO: 163          moltype = DNA  length = 20
FEATURE                 Location/Qualifiers
source                  1..20
                        mol_type = other DNA
                        organism = Synthetic construct
SEQUENCE: 163
ttaaacgaaa catatctttg                                              20

SEQ ID NO: 164          moltype = DNA  length = 20
FEATURE                 Location/Qualifiers
source                  1..20
                        mol_type = other DNA
                        organism = Synthetic construct
SEQUENCE: 164
gcccctgcgc cataattttt                                              20

SEQ ID NO: 165          moltype = DNA  length = 20
FEATURE                 Location/Qualifiers
source                  1..20
                        mol_type = other DNA
                        organism = Synthetic construct
SEQUENCE: 165
ataaactgct ttcaacggtg                                              20
```